US012582457B2

(12) United States Patent
Yates et al.

(10) Patent No.: US 12,582,457 B2
(45) Date of Patent: Mar. 24, 2026

(54) BIPOLAR COMBINATION DEVICE THAT AUTOMATICALLY ADJUSTS PRESSURE BASED ON ENERGY MODALITY

(71) Applicant: Cilag GmbH International, Zug (CH)

(72) Inventors: David C. Yates, Morrow, OH (US); Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 261 days.

(21) Appl. No.: 17/132,156

(22) Filed: Dec. 23, 2020

(65) Prior Publication Data

US 2021/0177489 A1    Jun. 17, 2021

Related U.S. Application Data

(63) Continuation of application No. 16/115,223, filed on Aug. 28, 2018, now Pat. No. 11,147,607.

(Continued)

(51) Int. Cl.
*A61B 18/12*        (2006.01)
*A61B 17/00*        (2006.01)
(Continued)

(52) U.S. Cl.
CPC .. *A61B 18/1206* (2013.01); *A61B 17/320068* (2013.01); *A61B 17/320092* (2013.01);
(Continued)

(58) Field of Classification Search
CPC ........ A61B 17/320068; A61B 18/1206; A61B 34/30; A61B 34/76; A61B 2017/0011; A61B 2018/126
See application file for complete search history.

(56) References Cited

U.S. PATENT DOCUMENTS 1,853,416 A    4/1932  Hall
2,222,125 A    11/1940  Stehlik
(Continued)

FOREIGN PATENT DOCUMENTS

AU        2015201140 A1    3/2015
CA          2709634 A1     7/2009
(Continued)

OTHER PUBLICATIONS

US 10,504,709 B2, 12/2019, Karancsi et al. (withdrawn)
(Continued)

*Primary Examiner* — Joseph A Stoklosa
*Assistant Examiner* — Annie L Shoulders
(74) *Attorney, Agent, or Firm* — Vorys, Sater, Seymour and Pease LLP

(57)        ABSTRACT

A surgical instrument, system and method for adjusting a compression force applied by a surgical instrument are disclosed. The method includes determining tissue impedance of tissue in contact with an end effector of the surgical instrument, determining a tissue type based on the tissue impedance, selecting a first energy modality to deliver to the surgical instrument, generating a first signal waveform based on the first energy modality, selecting a second energy modality to deliver to the surgical instrument, generating a second signal waveform based on the second energy modality, outputting the first and second signal waveform to deliver energy to the end effector, and adjusting a compression force applied by the end effector by changing a size of a gap between the tissue and the clamp arm based on a proportion of the first signal waveform to the second signal waveform.

19 Claims, 47 Drawing Sheets

Related U.S. Application Data

(60) Provisional application No. 62/721,999, filed on Aug. 23, 2018, provisional application No. 62/721,995, filed on Aug. 23, 2018, provisional application No. 62/721,998, filed on Aug. 23, 2018, provisional application No. 62/721,994, filed on Aug. 23, 2018, provisional application No. 62/721,996, filed on Aug. 23, 2018, provisional application No. 62/692,748, filed on Jun. 30, 2018, provisional application No. 62/692,768, filed on Jun. 30, 2018, provisional application No. 62/692,747, filed on Jun. 30, 2018, provisional application No. 62/650,882, filed on Mar. 30, 2018, provisional application No. 62/650,898, filed on Mar. 30, 2018, provisional application No. 62/650,887, filed on Mar. 30, 2018, provisional application No. 62/650,877, filed on Mar. 30, 2018, provisional application No. 62/611,340, filed on Dec. 28, 2017, provisional application No. 62/611,339, filed on Dec. 28, 2017, provisional application No. 62/611,341, filed on Dec. 28, 2017.

(51) Int. Cl.

| | |
|---|---|
| *A61B 17/32* | (2006.01) |
| *A61B 18/14* | (2006.01) |
| *A61B 34/00* | (2016.01) |
| *A61B 34/30* | (2016.01) |
| *A61B 18/00* | (2006.01) |
| *A61B 90/00* | (2016.01) |

(52) U.S. Cl.

CPC .......... *A61B 18/1445* (2013.01); *A61B 34/30* (2016.02); *A61B 34/76* (2016.02); *A61B 2017/00017* (2013.01); *A61B 2017/00026* (2013.01); *A61B 2017/00084* (2013.01); *A61B 2017/0011* (2013.01); *A61B 2017/00199* (2013.01); *A61B 2017/00398* (2013.01); *A61B 2017/00871* (2013.01); *A61B 2018/00595* (2013.01); *A61B 2018/00601* (2013.01); *A61B 2018/00619* (2013.01); *A61B 2018/0063* (2013.01); *A61B 2018/00666* (2013.01); *A61B 2018/00702* (2013.01); *A61B 2018/00779* (2013.01); *A61B 2018/00827* (2013.01); *A61B 2018/00875* (2013.01); *A61B 2018/00892* (2013.01); *A61B 2018/00994* (2013.01); *A61B 2018/1226* (2013.01); *A61B 2018/1253* (2013.01); *A61B 2018/126* (2013.01); *A61B 2018/1467* (2013.01); *A61B 34/25* (2016.02); *A61B 2034/256* (2016.02); *A61B 2090/032* (2016.02)

(56) References Cited

U.S. PATENT DOCUMENTS

| | | | |
|---|---|---|---|
| 3,082,426 A | 3/1963 | Miles | |
| 3,503,396 A | 3/1970 | Pierie et al. | |
| 3,584,628 A | 6/1971 | Green | |
| 3,626,457 A | 12/1971 | Duerr et al. | |
| 3,633,584 A | 1/1972 | Farrell | |
| 3,759,017 A | 9/1973 | Young | |
| 3,863,118 A | 1/1975 | Lander et al. | |
| 3,898,545 A | 8/1975 | Coppa et al. | |
| 3,912,121 A | 10/1975 | Steffen | |
| 3,915,271 A | 10/1975 | Harper | |
| 3,932,812 A | 1/1976 | Milligan | |
| 4,041,362 A | 8/1977 | Ichiyanagi | |
| 4,052,649 A | 10/1977 | Greenwell et al. | |
| 4,087,730 A | 5/1978 | Goles | |
| 4,157,859 A | 6/1979 | Terry | |
| 4,171,700 A | 10/1979 | Farin | |
| 4,202,722 A | 5/1980 | Paquin | |
| 4,412,539 A | 11/1983 | Jarvik | |
| 4,448,193 A | 5/1984 | Ivanov | |
| 4,523,695 A | 6/1985 | Braun et al. | |
| 4,608,160 A | 8/1986 | Zoch | |
| 4,614,366 A | 9/1986 | North et al. | |
| 4,633,874 A | 1/1987 | Chow et al. | |
| 4,701,193 A | 10/1987 | Robertson et al. | |
| 4,735,603 A | 4/1988 | Goodson et al. | |
| 4,788,977 A | 12/1988 | Farin et al. | |
| 4,827,911 A | 5/1989 | Broadwin et al. | |
| 4,849,752 A | 7/1989 | Bryant | |
| D303,787 S | 10/1989 | Messenger et al. | |
| 4,892,244 A | 1/1990 | Fox et al. | |
| 4,962,681 A | 10/1990 | Yang | |
| 4,976,173 A | 12/1990 | Yang | |
| 5,010,341 A | 4/1991 | Huntley et al. | |
| 5,026,387 A | 6/1991 | Thomas | |
| 5,035,692 A | 7/1991 | Lyon et al. | |
| 5,042,460 A | 8/1991 | Sakurai et al. | |
| 5,047,043 A | 9/1991 | Kubota et al. | |
| 5,084,057 A | 1/1992 | Green et al. | |
| 5,100,402 A | 3/1992 | Fan | |
| D327,061 S | 6/1992 | Soren et al. | |
| 5,129,570 A | 7/1992 | Schulze et al. | |
| 5,151,102 A | 9/1992 | Kamiyama et al. | |
| 5,156,315 A | 10/1992 | Green et al. | |
| 5,158,585 A | 10/1992 | Saho et al. | |
| 5,160,334 A | 11/1992 | Billings et al. | |
| 5,171,247 A | 12/1992 | Hughett et al. | |
| 5,189,277 A | 2/1993 | Boisvert et al. | |
| 5,197,962 A | 3/1993 | Sansom et al. | |
| 5,204,669 A | 4/1993 | Dorfe et al. | |
| 5,217,003 A | 6/1993 | Wilk | |
| 5,242,474 A | 9/1993 | Herbst et al. | |
| 5,253,793 A | 10/1993 | Green et al. | |
| 5,271,543 A | 12/1993 | Grant et al. | |
| RE34,519 E | 1/1994 | Fox et al. | |
| 5,275,323 A | 1/1994 | Schulze et al. | |
| 5,318,516 A | 6/1994 | Cosmescu | |
| 5,318,563 A | 6/1994 | Malis et al. | |
| 5,322,055 A | 6/1994 | Davison et al. | |
| 5,342,349 A | 8/1994 | Kaufman | |
| 5,364,003 A | 11/1994 | Williamson, IV | |
| 5,383,880 A | 1/1995 | Hooven | |
| 5,385,544 A | 1/1995 | Edwards et al. | |
| 5,391,144 A | 2/1995 | Sakurai et al. | |
| 5,396,900 A | 3/1995 | Slater et al. | |
| 5,397,046 A | 3/1995 | Savage et al. | |
| 5,403,312 A | 4/1995 | Yates et al. | |
| 5,403,327 A | 4/1995 | Thornton et al. | |
| 5,413,267 A | 5/1995 | Solyntjes et al. | |
| 5,415,335 A | 5/1995 | Knodell, Jr. | |
| 5,417,699 A | 5/1995 | Klein et al. | |
| 5,439,468 A | 8/1995 | Schulze et al. | |
| 5,445,304 A | 8/1995 | Plyley et al. | |
| 5,462,545 A | 10/1995 | Wang et al. | |
| 5,465,895 A | 11/1995 | Knodel et al. | |
| 5,467,911 A | 11/1995 | Tsuruta et al. | |
| 5,474,566 A | 12/1995 | Alesi et al. | |
| 5,485,947 A | 1/1996 | Olson et al. | |
| 5,496,315 A | 3/1996 | Weaver et al. | |
| 5,496,317 A | 3/1996 | Goble et al. | |
| 5,503,320 A | 4/1996 | Webster et al. | |
| 5,507,773 A | 4/1996 | Huitema et al. | |
| 5,529,235 A | 6/1996 | Boiarski et al. | |
| 5,531,743 A | 7/1996 | Nettekoven et al. | |
| 5,545,148 A | 8/1996 | Wurster | |
| 5,552,685 A | 9/1996 | Young et al. | |
| 5,560,372 A | 10/1996 | Cory | |
| 5,584,425 A | 12/1996 | Savage et al. | |
| 5,610,379 A | 3/1997 | Muz et al. | |
| 5,610,811 A | 3/1997 | Honda | |
| 5,613,966 A | 3/1997 | Makower et al. | |
| 5,624,452 A | 4/1997 | Yates | |
| D379,346 S | 5/1997 | Mieki | |
| 5,626,587 A | 5/1997 | Bishop et al. | |
| 5,643,291 A | 7/1997 | Pier et al. | |

(56) References Cited

U.S. PATENT DOCUMENTS

| | | | |
|---|---|---|---|
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,720,287 A | 2/1998 | Chapelon et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,796,188 A | 8/1998 | Bays |
| 5,797,537 A | 8/1998 | Oberlin et al. |
| 5,800,350 A | 9/1998 | Coppleson et al. |
| 5,807,393 A | 9/1998 | Williamson, IV et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,139,561 A | 10/2000 | Shibata et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,482,217 B1 | 11/2002 | Pintor et al. |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,628,989 B1 | 9/2003 | Penner et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,695,199 B2 | 2/2004 | Whitman |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,071 B2 | 2/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,094,231 B1 | 8/2006 | Ellman et al. |
| 7,097,640 B2 | 8/2006 | Wang et al. |

(56) References Cited

U.S. PATENT DOCUMENTS

| | | | |
|---|---|---|---|
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,422,586 B2 | 9/2008 | Morris et al. |
| 7,423,972 B2 | 9/2008 | Shaham et al. |
| D579,876 S | 11/2008 | Novotney et al. |
| 7,445,620 B2 | 11/2008 | Kefer |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,772 B2 | 4/2010 | Pauker et al. |
| 7,699,860 B2 | 4/2010 | Huitema et al. |
| 7,717,312 B2 | 5/2010 | Beetel |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,722,603 B2 | 5/2010 | McPherson |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,922,063 B2 | 4/2011 | Zemlok et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,950,560 B2 | 5/2011 | Zemlok et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,993,954 B2 | 8/2011 | Wieting |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |

(56) References Cited

U.S. PATENT DOCUMENTS

| | | | |
|---|---|---|---|
| 8,062,306 | B2 | 11/2011 | Nobis et al. |
| 8,062,330 | B2 | 11/2011 | Prommersberger et al. |
| 8,066,721 | B2 | 11/2011 | Kortenbach et al. |
| 8,074,861 | B2 | 12/2011 | Ehrenfels et al. |
| 8,075,571 | B2 | 12/2011 | Vitali et al. |
| 8,095,327 | B2 | 1/2012 | Tahara et al. |
| 8,096,459 | B2 | 1/2012 | Ortiz et al. |
| 8,116,848 | B2 | 2/2012 | Shahidi |
| 8,118,206 | B2 | 2/2012 | Zand et al. |
| 8,120,301 | B2 | 2/2012 | Goldberg et al. |
| 8,123,764 | B2 | 2/2012 | Meade et al. |
| D655,678 | S | 3/2012 | Kobayashi et al. |
| 8,128,625 | B2 | 3/2012 | Odom |
| 8,131,565 | B2 | 3/2012 | Dicks et al. |
| 8,136,712 | B2 | 3/2012 | Zingman |
| 8,146,149 | B2 | 3/2012 | Steinkogler et al. |
| D657,368 | S | 4/2012 | Magee et al. |
| 8,147,486 | B2 | 4/2012 | Honour et al. |
| 8,155,479 | B2 | 4/2012 | Hoffman et al. |
| 8,157,145 | B2 | 4/2012 | Shelton, IV et al. |
| 8,157,150 | B2 | 4/2012 | Viola et al. |
| 8,157,151 | B2 | 4/2012 | Ingmanson et al. |
| 8,160,098 | B1 | 4/2012 | Yan et al. |
| 8,160,690 | B2 | 4/2012 | Wilfley et al. |
| 8,161,977 | B2 | 4/2012 | Shelton, IV et al. |
| 8,170,396 | B2 | 5/2012 | Kuspa et al. |
| 8,172,836 | B2 | 5/2012 | Ward |
| 8,181,839 | B2 | 5/2012 | Beetel |
| 8,185,409 | B2 | 5/2012 | Putnam et al. |
| 8,206,345 | B2 | 6/2012 | Abboud et al. |
| 8,208,707 | B2 | 6/2012 | Mendonca et al. |
| 8,210,411 | B2 | 7/2012 | Yates et al. |
| 8,211,100 | B2 | 7/2012 | Podhajsky et al. |
| 8,214,007 | B2 | 7/2012 | Baker et al. |
| 8,216,849 | B2 | 7/2012 | Petty |
| 8,220,688 | B2 | 7/2012 | Laurent et al. |
| 8,225,643 | B2 | 7/2012 | Abboud et al. |
| 8,225,979 | B2 | 7/2012 | Farascioni et al. |
| 8,229,549 | B2 | 7/2012 | Whitman et al. |
| 8,231,042 | B2 | 7/2012 | Hessler et al. |
| 8,239,066 | B2 | 8/2012 | Jennings et al. |
| 8,241,322 | B2 | 8/2012 | Whitman et al. |
| 8,255,045 | B2 | 8/2012 | Gharib et al. |
| D667,838 | S | 9/2012 | Magee et al. |
| 8,257,387 | B2 | 9/2012 | Cunningham |
| 8,260,016 | B2 | 9/2012 | Maeda et al. |
| 8,262,560 | B2 | 9/2012 | Whitman |
| 8,292,639 | B2 | 10/2012 | Achammer et al. |
| 8,292,888 | B2 | 10/2012 | Whitman |
| 8,295,902 | B2 | 10/2012 | Salahieh et al. |
| 8,308,040 | B2 | 11/2012 | Huang et al. |
| 8,321,581 | B2 | 11/2012 | Katis et al. |
| 8,322,590 | B2 | 12/2012 | Patel et al. |
| 8,328,065 | B2 | 12/2012 | Shah |
| 8,335,590 | B2 | 12/2012 | Costa et al. |
| D675,164 | S | 1/2013 | Kobayashi et al. |
| 8,343,065 | B2 | 1/2013 | Bartol et al. |
| 8,346,392 | B2 | 1/2013 | Walser et al. |
| 8,360,299 | B2 | 1/2013 | Zemlok et al. |
| 8,364,222 | B2 | 1/2013 | Cook et al. |
| D676,392 | S | 2/2013 | Gassauer |
| 8,365,975 | B1 | 2/2013 | Manoux et al. |
| D678,196 | S | 3/2013 | Miyauchi et al. |
| D678,304 | S | 3/2013 | Yakoub et al. |
| 8,388,652 | B2 | 3/2013 | Viola |
| 8,393,514 | B2 | 3/2013 | Shelton, IV et al. |
| 8,397,972 | B2 | 3/2013 | Kostrzewski |
| 8,398,541 | B2 | 3/2013 | DiMaio et al. |
| 8,403,944 | B2 | 3/2013 | Pain et al. |
| 8,403,945 | B2 | 3/2013 | Whitfield et al. |
| 8,403,946 | B2 | 3/2013 | Whitfield et al. |
| 8,406,859 | B2 | 3/2013 | Zuzak et al. |
| 8,411,034 | B2 | 4/2013 | Boillot et al. |
| 8,413,871 | B2 | 4/2013 | Racenet et al. |
| 8,422,035 | B2 | 4/2013 | Hinderling et al. |
| 8,423,182 | B2 | 4/2013 | Robinson et al. |
| 8,428,722 | B2 | 4/2013 | Verhoef et al. |
| 8,429,153 | B2 | 4/2013 | Birdwell et al. |
| 8,439,910 | B2 | 5/2013 | Greep et al. |
| 8,444,663 | B2 | 5/2013 | Houser et al. |
| 8,452,615 | B2 | 5/2013 | Abri |
| 8,453,906 | B2 | 6/2013 | Huang et al. |
| 8,454,506 | B2 | 6/2013 | Rothman et al. |
| 8,461,744 | B2 | 6/2013 | Wiener et al. |
| 8,468,030 | B2 | 6/2013 | Stroup et al. |
| 8,469,973 | B2 | 6/2013 | Meade et al. |
| 8,472,630 | B2 | 6/2013 | Konrad et al. |
| 8,473,066 | B2 | 6/2013 | Aghassian et al. |
| D687,146 | S | 7/2013 | Juzkiw et al. |
| 8,476,227 | B2 | 7/2013 | Kaplan et al. |
| 8,478,418 | B2 | 7/2013 | Fahey |
| 8,489,235 | B2 | 7/2013 | Moll et al. |
| 8,499,992 | B2 | 8/2013 | Whitman et al. |
| 8,500,728 | B2 | 8/2013 | Newton et al. |
| 8,500,756 | B2 | 8/2013 | Papa et al. |
| 8,503,759 | B2 | 8/2013 | Greer et al. |
| 8,505,801 | B2 | 8/2013 | Ehrenfels et al. |
| 8,506,478 | B2 | 8/2013 | Mizuyoshi |
| 8,512,325 | B2 | 8/2013 | Mathonnet |
| 8,512,365 | B2 | 8/2013 | Wiener et al. |
| 8,515,520 | B2 | 8/2013 | Brunnett et al. |
| 8,517,239 | B2 | 8/2013 | Scheib et al. |
| 8,521,331 | B2 | 8/2013 | Itkowitz |
| 8,523,043 | B2 | 9/2013 | Ullrich et al. |
| 8,533,475 | B2 | 9/2013 | Frikart et al. |
| 8,540,709 | B2 | 9/2013 | Allen |
| 8,546,996 | B2 | 10/2013 | Messerly et al. |
| 8,554,697 | B2 | 10/2013 | Claus et al. |
| 8,560,047 | B2 | 10/2013 | Haider et al. |
| 8,561,870 | B2 | 10/2013 | Baxter, III et al. |
| 8,562,598 | B2 | 10/2013 | Falkenstein et al. |
| 8,566,115 | B2 | 10/2013 | Moore |
| 8,567,393 | B2 | 10/2013 | Hickle et al. |
| 8,568,411 | B2 | 10/2013 | Falkenstein et al. |
| 8,571,598 | B2 | 10/2013 | Valavi |
| 8,573,459 | B2 | 11/2013 | Smith et al. |
| 8,573,465 | B2 | 11/2013 | Shelton, IV |
| 8,574,229 | B2 | 11/2013 | Eder et al. |
| 8,585,631 | B2 | 11/2013 | Dacquay |
| 8,585,694 | B2 | 11/2013 | Amoah et al. |
| 8,590,762 | B2 | 11/2013 | Hess et al. |
| 8,591,536 | B2 | 11/2013 | Robertson |
| 8,595,607 | B2 | 11/2013 | Nekoomaram et al. |
| 8,596,513 | B2 | 12/2013 | Olson et al. |
| 8,596,515 | B2 | 12/2013 | Okoniewski |
| 8,604,709 | B2 | 12/2013 | Jalbout et al. |
| 8,608,044 | B2 | 12/2013 | Hueil et al. |
| 8,608,045 | B2 | 12/2013 | Smith et al. |
| 8,616,431 | B2 | 12/2013 | Timm et al. |
| 8,617,155 | B2 | 12/2013 | Johnson et al. |
| 8,620,055 | B2 | 12/2013 | Barratt et al. |
| 8,620,473 | B2 | 12/2013 | Diolaiti et al. |
| 8,622,275 | B2 | 1/2014 | Baxter, III et al. |
| 8,623,027 | B2 | 1/2014 | Price et al. |
| 8,627,483 | B2 | 1/2014 | Rachlin et al. |
| 8,627,993 | B2 | 1/2014 | Smith et al. |
| 8,627,995 | B2 | 1/2014 | Smith et al. |
| 8,628,518 | B2 | 1/2014 | Blumenkranz et al. |
| 8,628,545 | B2 | 1/2014 | Cabrera et al. |
| 8,631,987 | B2 | 1/2014 | Shelton, IV et al. |
| 8,632,525 | B2 | 1/2014 | Kerr et al. |
| 8,636,190 | B2 | 1/2014 | Zemlok et al. |
| 8,636,736 | B2 | 1/2014 | Yates et al. |
| 8,641,621 | B2 | 2/2014 | Razzaque et al. |
| 8,652,086 | B2 | 2/2014 | Gerg et al. |
| 8,652,121 | B2 | 2/2014 | Quick et al. |
| 8,652,128 | B2 | 2/2014 | Ward |
| 8,657,176 | B2 | 2/2014 | Shelton, IV et al. |
| 8,657,177 | B2 | 2/2014 | Scirica et al. |
| 8,663,220 | B2 | 3/2014 | Wiener et al. |
| 8,663,222 | B2 | 3/2014 | Anderson et al. |
| 8,666,544 | B2 | 3/2014 | Moll et al. |
| 8,679,114 | B2 | 3/2014 | Chapman et al. |
| 8,682,049 | B2 | 3/2014 | Zhao et al. |

(56) References Cited

U.S. PATENT DOCUMENTS

| | | | |
|---|---|---|---|
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,708,213 B2 | 4/2014 | Shelton, IV et al. |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,607 B2 | 9/2014 | Marczyk |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,864,747 B2 | 10/2014 | Merchant et al. |
| 8,875,973 B2 | 11/2014 | Whitman |
| 8,876,857 B2 | 11/2014 | Burbank |
| 8,882,662 B2 | 11/2014 | Charles |
| 8,885,032 B2 | 11/2014 | Igarashi et al. |
| 8,886,790 B2 | 11/2014 | Harrang et al. |
| 8,893,946 B2 | 11/2014 | Boudreaux et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,934,684 B2 | 1/2015 | Mohamed |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,005,230 B2 | 4/2015 | Yates et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,023,079 B2 | 5/2015 | Boulnois et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,131,957 B2 | 9/2015 | Skarbnik et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,141,758 B2 | 9/2015 | Kress et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |

(56)          References Cited

U.S. PATENT DOCUMENTS

| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,198,835 B2 | 12/2015 | Swisher et al. |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,220,505 B2 | 12/2015 | Vasudevan et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,299,138 B2 | 3/2016 | Zellner et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,200 B2 | 6/2016 | Whitman et al. |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,404,868 B2 | 8/2016 | Yamanaka et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,219 B2 | 11/2016 | Moore et al. |
| 9,498,231 B2 | 11/2016 | Haider et al. |
| 9,498,291 B2 | 11/2016 | Balaji et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,580 B2 | 12/2016 | Humayun et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,545,216 B2 | 1/2017 | D'Angelo et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |

(56)                     References Cited

U.S. PATENT DOCUMENTS

| | | | |
|---|---|---|---|
| 9,579,099 | B2 | 2/2017 | Penna et al. |
| 9,579,503 | B2 | 2/2017 | McKinney et al. |
| 9,585,657 | B2 | 3/2017 | Shelton, IV et al. |
| 9,585,658 | B2 | 3/2017 | Shelton, IV |
| 9,592,095 | B2 | 3/2017 | Panescu et al. |
| 9,597,081 | B2 | 3/2017 | Swayze et al. |
| 9,600,031 | B2 | 3/2017 | Kaneko et al. |
| 9,600,138 | B2 | 3/2017 | Thomas et al. |
| 9,603,024 | B2 | 3/2017 | Wang et al. |
| 9,603,277 | B2 | 3/2017 | Morgan et al. |
| 9,603,609 | B2 | 3/2017 | Kawashima et al. |
| D783,675 | S | 4/2017 | Yagisawa et al. |
| D784,270 | S | 4/2017 | Bhattacharya |
| 9,610,114 | B2 | 4/2017 | Baxter, III et al. |
| 9,610,412 | B2 | 4/2017 | Zemlok et al. |
| 9,615,877 | B2 | 4/2017 | Tyrrell et al. |
| 9,622,684 | B2 | 4/2017 | Wybo |
| 9,622,808 | B2 | 4/2017 | Beller et al. |
| 9,628,501 | B2 | 4/2017 | Datta Ray et al. |
| 9,629,560 | B2 | 4/2017 | Joseph |
| 9,629,623 | B2 | 4/2017 | Lytle, IV et al. |
| 9,629,628 | B2 | 4/2017 | Aranyi |
| 9,629,629 | B2 | 4/2017 | Leimbach et al. |
| 9,630,318 | B2 | 4/2017 | Ibarz Gabardos et al. |
| 9,636,096 | B1 | 5/2017 | Heaton, II et al. |
| 9,636,112 | B2 | 5/2017 | Penna et al. |
| 9,636,188 | B2 | 5/2017 | Gattani et al. |
| 9,636,239 | B2 | 5/2017 | Durand et al. |
| 9,636,825 | B2 | 5/2017 | Penn et al. |
| 9,641,596 | B2 | 5/2017 | Unagami et al. |
| 9,641,815 | B2 | 5/2017 | Richardson et al. |
| 9,642,620 | B2 | 5/2017 | Baxter, III et al. |
| 9,643,022 | B2 | 5/2017 | Mashiach et al. |
| 9,649,089 | B2 | 5/2017 | Smith et al. |
| 9,649,110 | B2 | 5/2017 | Parihar et al. |
| 9,649,111 | B2 | 5/2017 | Shelton, IV et al. |
| 9,649,126 | B2 | 5/2017 | Robertson et al. |
| 9,649,169 | B2 | 5/2017 | Cinquin et al. |
| 9,652,655 | B2 | 5/2017 | Satish et al. |
| 9,655,614 | B2 | 5/2017 | Swensgard et al. |
| 9,655,616 | B2 | 5/2017 | Aranyi |
| 9,656,092 | B2 | 5/2017 | Golden |
| 9,662,116 | B2 | 5/2017 | Smith et al. |
| 9,662,177 | B2 | 5/2017 | Weir et al. |
| 9,668,729 | B2 | 6/2017 | Williams et al. |
| 9,668,732 | B2 | 6/2017 | Patel et al. |
| 9,668,765 | B2 | 6/2017 | Grace et al. |
| 9,671,860 | B2 | 6/2017 | Ogawa et al. |
| 9,675,264 | B2 | 6/2017 | Acquista et al. |
| 9,675,354 | B2 | 6/2017 | Weir et al. |
| 9,681,870 | B2 | 6/2017 | Baxter, III et al. |
| 9,686,306 | B2 | 6/2017 | Chizeck et al. |
| 9,687,230 | B2 | 6/2017 | Leimbach et al. |
| 9,690,362 | B2 | 6/2017 | Leimbach et al. |
| 9,700,292 | B2 | 7/2017 | Nawana et al. |
| 9,700,309 | B2 | 7/2017 | Jaworek et al. |
| 9,700,312 | B2 | 7/2017 | Kostrzewski et al. |
| 9,700,320 | B2 | 7/2017 | Dinardo et al. |
| 9,706,993 | B2 | 7/2017 | Hessler et al. |
| 9,710,214 | B2 | 7/2017 | Lin et al. |
| 9,710,644 | B2 | 7/2017 | Reybok et al. |
| 9,713,424 | B2 | 7/2017 | Spaide |
| 9,713,503 | B2 | 7/2017 | Goldschmidt |
| 9,717,141 | B1 | 7/2017 | Tegg |
| 9,717,498 | B2 | 8/2017 | Aranyi et al. |
| 9,717,525 | B2 | 8/2017 | Ahluwalia et al. |
| 9,717,548 | B2 | 8/2017 | Couture |
| 9,724,094 | B2 | 8/2017 | Baber et al. |
| 9,724,100 | B2 | 8/2017 | Scheib et al. |
| 9,724,118 | B2 | 8/2017 | Schulte et al. |
| 9,733,663 | B2 | 8/2017 | Leimbach et al. |
| 9,737,301 | B2 | 8/2017 | Baber et al. |
| 9,737,310 | B2 | 8/2017 | Whitfield et al. |
| 9,737,335 | B2 | 8/2017 | Butler et al. |
| 9,737,355 | B2 | 8/2017 | Yates et al. |
| 9,737,371 | B2 | 8/2017 | Romo et al. |
| 9,740,826 | B2 | 8/2017 | Raghavan et al. |
| 9,743,016 | B2 | 8/2017 | Nestares et al. |
| 9,743,929 | B2 | 8/2017 | Leimbach et al. |
| 9,743,946 | B2 | 8/2017 | Faller et al. |
| 9,743,947 | B2 | 8/2017 | Price et al. |
| 9,750,499 | B2 | 9/2017 | Leimbach et al. |
| 9,750,500 | B2 | 9/2017 | Malkowski |
| 9,750,522 | B2 | 9/2017 | Scheib et al. |
| 9,750,523 | B2 | 9/2017 | Tsubuku |
| 9,750,560 | B2 | 9/2017 | Ballakur et al. |
| 9,750,563 | B2 | 9/2017 | Shikhman et al. |
| 9,753,135 | B2 | 9/2017 | Bosch |
| 9,753,568 | B2 | 9/2017 | McMillen |
| 9,757,126 | B2 | 9/2017 | Cappola |
| 9,757,128 | B2 | 9/2017 | Baber et al. |
| 9,757,142 | B2 | 9/2017 | Shimizu |
| 9,757,152 | B2 | 9/2017 | Ogilvie et al. |
| 9,763,741 | B2 | 9/2017 | Alvarez et al. |
| 9,764,164 | B2 | 9/2017 | Wiener et al. |
| 9,770,541 | B2 | 9/2017 | Carr et al. |
| 9,775,611 | B2 | 10/2017 | Kostrzewski |
| 9,777,913 | B2 | 10/2017 | Talbert et al. |
| 9,782,164 | B2 | 10/2017 | Mumaw et al. |
| 9,782,169 | B2 | 10/2017 | Kimsey et al. |
| 9,782,212 | B2 | 10/2017 | Wham et al. |
| 9,782,214 | B2 | 10/2017 | Houser et al. |
| 9,788,835 | B2 | 10/2017 | Morgan et al. |
| 9,788,836 | B2 | 10/2017 | Overmyer et al. |
| 9,788,851 | B2 | 10/2017 | Dannaher et al. |
| 9,788,902 | B2 | 10/2017 | Inoue et al. |
| 9,788,907 | B1 | 10/2017 | Alvi et al. |
| 9,795,436 | B2 | 10/2017 | Yates et al. |
| 9,797,486 | B2 | 10/2017 | Zergiebel et al. |
| 9,801,531 | B2 | 10/2017 | Morita et al. |
| 9,801,626 | B2 | 10/2017 | Parihar et al. |
| 9,801,627 | B2 | 10/2017 | Harris et al. |
| 9,801,679 | B2 | 10/2017 | Trees et al. |
| 9,802,033 | B2 | 10/2017 | Hibner et al. |
| 9,804,618 | B2 | 10/2017 | Leimbach et al. |
| 9,805,472 | B2 | 10/2017 | Chou et al. |
| 9,808,244 | B2 | 11/2017 | Leimbach et al. |
| 9,808,245 | B2 | 11/2017 | Richard et al. |
| 9,808,246 | B2 | 11/2017 | Shelton, IV et al. |
| 9,808,248 | B2 | 11/2017 | Hoffman |
| 9,808,249 | B2 | 11/2017 | Shelton, IV |
| 9,808,305 | B2 | 11/2017 | Hareyama et al. |
| 9,814,457 | B2 | 11/2017 | Martin et al. |
| 9,814,460 | B2 | 11/2017 | Kimsey et al. |
| 9,814,462 | B2 | 11/2017 | Woodard, Jr. et al. |
| 9,814,463 | B2 | 11/2017 | Williams et al. |
| 9,820,699 | B2 | 11/2017 | Bingley et al. |
| 9,820,738 | B2 | 11/2017 | Lytle, IV et al. |
| 9,820,741 | B2 | 11/2017 | Kostrzewski |
| 9,820,768 | B2 | 11/2017 | Gee et al. |
| 9,826,976 | B2 | 11/2017 | Parihar et al. |
| 9,826,977 | B2 | 11/2017 | Leimbach et al. |
| 9,827,054 | B2 | 11/2017 | Richmond et al. |
| 9,827,059 | B2 | 11/2017 | Robinson et al. |
| 9,830,424 | B2 | 11/2017 | Dixon et al. |
| 9,833,241 | B2 | 12/2017 | Huitema et al. |
| 9,833,254 | B1 | 12/2017 | Barral et al. |
| 9,839,419 | B2 | 12/2017 | Deck et al. |
| 9,839,424 | B2 | 12/2017 | Zergiebel et al. |
| 9,839,428 | B2 | 12/2017 | Baxter, III et al. |
| 9,839,467 | B2 | 12/2017 | Harper et al. |
| 9,839,470 | B2 | 12/2017 | Gilbert et al. |
| 9,839,487 | B2 | 12/2017 | Dachs, II |
| 9,844,321 | B1 | 12/2017 | Ekvall et al. |
| 9,844,368 | B2 | 12/2017 | Boudreaux et al. |
| 9,844,369 | B2 | 12/2017 | Huitema et al. |
| 9,844,374 | B2 | 12/2017 | Lytle, IV et al. |
| 9,844,375 | B2 | 12/2017 | Overmyer et al. |
| 9,844,376 | B2 | 12/2017 | Baxter, III et al. |
| 9,844,379 | B2 | 12/2017 | Shelton, IV et al. |
| 9,848,058 | B2 | 12/2017 | Johnson et al. |
| 9,848,877 | B2 | 12/2017 | Shelton, IV et al. |
| 9,861,354 | B2 | 1/2018 | Saliman et al. |
| 9,861,363 | B2 | 1/2018 | Chen et al. |

(56) References Cited

U.S. PATENT DOCUMENTS

| | | | |
|---|---|---|---|
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,901,411 B2 | 2/2018 | Gombert et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 * | 4/2018 | Hares .................... A61B 34/32 |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,976,259 B2 | 5/2018 | Tan et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,016,538 B2 | 7/2018 | Locke et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,373 B2 | 11/2018 | Castro et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |

(56) References Cited

U.S. PATENT DOCUMENTS

| | | | |
|---|---|---|---|
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,187,742 B2 | 1/2019 | Dor et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,255,995 B2 | 4/2019 | Ingmanson |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,846 B2 | 4/2019 | Shelton, IV et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,282,963 B2 | 5/2019 | Fahey |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,610 B2 | 5/2019 | Srivastava |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,868 B2 | 5/2019 | Tsuboi et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,042 B2 | 7/2019 | Schoenle et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |

(56) References Cited

U.S. PATENT DOCUMENTS

| | | | |
|---|---|---|---|
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,281 B2 | 10/2019 | Shelton, IV et al. |
| 10,441,344 B2 | 10/2019 | Notz et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,684 B2 | 11/2019 | Toth et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,507,278 B2 | 12/2019 | Gao et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,537,396 B2 | 1/2020 | Zingaretti et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,565,170 B2 | 2/2020 | Walling et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,962 B2 | 3/2020 | Friedrichs et al. |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |

(56) References Cited

U.S. PATENT DOCUMENTS

| | | | |
|---|---|---|---|
| 10,639,027 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,039 | B2 | 5/2020 | Vendely et al. |
| 10,639,098 | B2 | 5/2020 | Cosman et al. |
| 10,639,111 | B2 | 5/2020 | Kopp |
| 10,639,185 | B2 | 5/2020 | Agrawal et al. |
| 10,653,413 | B2 | 5/2020 | Worthington et al. |
| 10,653,476 | B2 | 5/2020 | Ross |
| 10,653,489 | B2 | 5/2020 | Kopp |
| 10,656,720 | B1 | 5/2020 | Holz |
| 10,660,705 | B2 | 5/2020 | Piron et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,877 | B2 | 6/2020 | Kapadia |
| 10,674,897 | B2 | 6/2020 | Levy |
| 10,675,021 | B2 | 6/2020 | Harris et al. |
| 10,675,023 | B2 | 6/2020 | Cappola |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,035 | B2 | 6/2020 | Zingman |
| 10,675,100 | B2 | 6/2020 | Frushour |
| 10,675,104 | B2 | 6/2020 | Kapadia |
| 10,677,764 | B2 | 6/2020 | Ross et al. |
| 10,679,758 | B2 | 6/2020 | Fox et al. |
| 10,682,136 | B2 | 6/2020 | Harris et al. |
| 10,682,138 | B2 | 6/2020 | Shelton, IV et al. |
| 10,686,805 | B2 | 6/2020 | Reybok, Jr. et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,884 | B2 | 6/2020 | Wiener et al. |
| 10,687,905 | B2 | 6/2020 | Kostrzewski |
| 10,695,055 | B2 | 6/2020 | Shelton, IV et al. |
| 10,695,081 | B2 | 6/2020 | Shelton, IV et al. |
| 10,695,134 | B2 | 6/2020 | Barral et al. |
| 10,702,270 | B2 | 7/2020 | Shelton, IV et al. |
| 10,702,271 | B2 | 7/2020 | Aranyi et al. |
| 10,709,446 | B2 | 7/2020 | Harris et al. |
| 10,716,473 | B2 | 7/2020 | Greiner |
| 10,716,489 | B2 | 7/2020 | Kalvoy et al. |
| 10,716,583 | B2 | 7/2020 | Look et al. |
| 10,716,615 | B2 | 7/2020 | Shelton, IV et al. |
| 10,716,639 | B2 | 7/2020 | Kapadia et al. |
| 10,717,194 | B2 | 7/2020 | Griffiths et al. |
| 10,722,222 | B2 | 7/2020 | Aranyi |
| 10,722,233 | B2 | 7/2020 | Wellman |
| 10,722,292 | B2 | 7/2020 | Arya et al. |
| D893,717 | S | 8/2020 | Messerly et al. |
| 10,729,458 | B2 | 8/2020 | Stoddard et al. |
| 10,729,509 | B2 | 8/2020 | Shelton, IV et al. |
| 10,733,267 | B2 | 8/2020 | Pedersen |
| 10,736,219 | B2 | 8/2020 | Seow et al. |
| 10,736,498 | B2 | 8/2020 | Watanabe et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,636 | B2 | 8/2020 | Baxter, III et al. |
| 10,736,705 | B2 | 8/2020 | Scheib et al. |
| 10,743,872 | B2 | 8/2020 | Leimbach et al. |
| 10,748,115 | B2 | 8/2020 | Laster et al. |
| 10,751,052 | B2 | 8/2020 | Stokes et al. |
| 10,751,136 | B2 | 8/2020 | Farritor et al. |
| 10,751,239 | B2 | 8/2020 | Volek et al. |
| 10,751,768 | B2 | 8/2020 | Hersey et al. |
| 10,755,813 | B2 | 8/2020 | Shelton, IV et al. |
| D896,379 | S | 9/2020 | Shelton, IV et al. |
| 10,758,229 | B2 | 9/2020 | Shelton, IV et al. |
| 10,758,230 | B2 | 9/2020 | Shelton, IV et al. |
| 10,758,294 | B2 | 9/2020 | Jones |
| 10,758,310 | B2 | 9/2020 | Shelton, IV et al. |
| 10,765,376 | B2 | 9/2020 | Brown, III et al. |
| 10,765,424 | B2 | 9/2020 | Baxter, III et al. |
| 10,765,427 | B2 | 9/2020 | Shelton, IV et al. |
| 10,765,470 | B2 | 9/2020 | Yates et al. |
| 10,772,630 | B2 | 9/2020 | Wixey |
| 10,772,651 | B2 | 9/2020 | Shelton, IV et al. |
| 10,772,673 | B2 | 9/2020 | Allen, IV et al. |
| 10,772,688 | B2 | 9/2020 | Peine et al. |
| 10,779,818 | B2 | 9/2020 | Zemlok et al. |
| 10,779,821 | B2 | 9/2020 | Harris et al. |
| 10,779,823 | B2 | 9/2020 | Shelton, IV et al. |
| 10,779,897 | B2 | 9/2020 | Rockrohr |
| 10,779,900 | B2 | 9/2020 | Pedros et al. |
| 10,783,634 | B2 | 9/2020 | Nye et al. |
| 10,786,298 | B2 | 9/2020 | Johnson |
| 10,786,317 | B2 | 9/2020 | Zhou et al. |
| 10,786,327 | B2 | 9/2020 | Anderson et al. |
| 10,792,038 | B2 | 10/2020 | Becerra et al. |
| 10,792,118 | B2 | 10/2020 | Prpa et al. |
| 10,792,422 | B2 | 10/2020 | Douglas et al. |
| 10,799,304 | B2 | 10/2020 | Kapadia et al. |
| 10,803,977 | B2 | 10/2020 | Sanmugalingham |
| 10,806,445 | B2 | 10/2020 | Penna et al. |
| 10,806,453 | B2 | 10/2020 | Chen et al. |
| 10,806,454 | B2 | 10/2020 | Kopp |
| 10,806,499 | B2 | 10/2020 | Castaneda et al. |
| 10,806,506 | B2 | 10/2020 | Gaspredes et al. |
| 10,806,532 | B2 | 10/2020 | Grubbs et al. |
| 10,811,131 | B2 | 10/2020 | Schneider et al. |
| 10,813,638 | B2 | 10/2020 | Shelton, IV et al. |
| 10,813,703 | B2 | 10/2020 | Swayze et al. |
| 10,818,383 | B2 | 10/2020 | Sharifi Sedeh et al. |
| 10,828,028 | B2 | 11/2020 | Harris et al. |
| 10,828,030 | B2 | 11/2020 | Weir et al. |
| 10,835,206 | B2 | 11/2020 | Bell et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,842,473 | B2 | 11/2020 | Scheib et al. |
| 10,842,490 | B2 | 11/2020 | DiNardo et al. |
| 10,842,492 | B2 | 11/2020 | Shelton, IV et al. |
| 10,842,522 | B2 | 11/2020 | Messerly et al. |
| 10,842,523 | B2 | 11/2020 | Shelton, IV et al. |
| 10,842,575 | B2 | 11/2020 | Panescu et al. |
| 10,842,897 | B2 | 11/2020 | Schwartz et al. |
| D904,612 | S | 12/2020 | Wynn et al. |
| 10,849,697 | B2 | 12/2020 | Yates et al. |
| 10,849,700 | B2 | 12/2020 | Kopp et al. |
| 10,856,768 | B2 | 12/2020 | Osadchy et al. |
| 10,856,867 | B2 | 12/2020 | Shelton, IV et al. |
| 10,856,868 | B2 | 12/2020 | Shelton, IV et al. |
| 10,856,870 | B2 | 12/2020 | Harris et al. |
| 10,863,984 | B2 | 12/2020 | Shelton, IV et al. |
| 10,864,037 | B2 | 12/2020 | Mun et al. |
| 10,864,050 | B2 | 12/2020 | Tabandeh et al. |
| 10,872,684 | B2 | 12/2020 | McNutt et al. |
| 10,874,396 | B2 | 12/2020 | Moore et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,881,464 | B2 | 1/2021 | Odermatt et al. |
| 10,888,321 | B2 | 1/2021 | Shelton, IV et al. |
| 10,888,322 | B2 | 1/2021 | Morgan et al. |
| 10,892,899 | B2 | 1/2021 | Shelton, IV et al. |
| 10,892,995 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,884 | B2 | 1/2021 | Stoddard et al. |
| 10,898,105 | B2 | 1/2021 | Weprin et al. |
| 10,898,183 | B2 | 1/2021 | Shelton, IV et al. |
| 10,898,186 | B2 | 1/2021 | Bakos et al. |
| 10,898,189 | B2 | 1/2021 | McDonald, II |
| 10,898,256 | B2 | 1/2021 | Yates et al. |
| 10,898,280 | B2 | 1/2021 | Kopp |
| 10,898,622 | B2 | 1/2021 | Shelton, IV et al. |
| 10,902,944 | B1 | 1/2021 | Casey et al. |
| 10,903,685 | B2 | 1/2021 | Yates et al. |
| 10,905,415 | B2 | 2/2021 | DiNardo et al. |
| 10,905,418 | B2 | 2/2021 | Shelton, IV et al. |

(56) References Cited

U.S. PATENT DOCUMENTS

| | | | |
|---|---|---|---|
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,952,732 B2 | 3/2021 | Binmoeller et al. |
| 10,954,935 B2 | 3/2021 | O'Shea et al. |
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 10,962,449 B2 | 3/2021 | Unuma et al. |
| 10,966,590 B2 | 4/2021 | Takahashi et al. |
| 10,966,791 B2 | 4/2021 | Harris et al. |
| 10,966,798 B2 | 4/2021 | Tesar et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,973,682 B2 | 4/2021 | Vezzu et al. |
| 10,980,536 B2 | 4/2021 | Weaner et al. |
| 10,980,537 B2 | 4/2021 | Shelton, IV et al. |
| 10,980,560 B2 | 4/2021 | Shelton, IV et al. |
| 10,980,595 B2 | 4/2021 | Wham |
| 10,980,610 B2 | 4/2021 | Rosenberg et al. |
| 10,987,102 B2 | 4/2021 | Gonzalez et al. |
| 10,987,178 B2 | 4/2021 | Shelton, IV et al. |
| 10,992,698 B2 | 4/2021 | Patel et al. |
| 10,993,715 B2 | 5/2021 | Shelton, IV et al. |
| 10,998,098 B2 | 5/2021 | Greene et al. |
| 11,000,276 B2 | 5/2021 | Shelton, IV et al. |
| 11,000,278 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,563 B2 | 5/2021 | Shelton, IV et al. |
| 11,020,115 B2 | 6/2021 | Scheib et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,197 B2 | 6/2021 | Shelton, IV et al. |
| 11,045,591 B2 | 6/2021 | Shelton, IV et al. |
| 11,051,817 B2 | 7/2021 | Shelton, IV et al. |
| 11,051,836 B2 | 7/2021 | Shelton, IV et al. |
| 11,051,873 B2 | 7/2021 | Wiener et al. |
| 11,051,876 B2 | 7/2021 | Shelton, IV et al. |
| 11,051,902 B2 | 7/2021 | Kruecker et al. |
| 11,056,244 B2 | 7/2021 | Shelton, IV et al. |
| 11,058,423 B2 | 7/2021 | Shelton, IV et al. |
| 11,058,498 B2 | 7/2021 | Shelton, IV et al. |
| 11,058,501 B2 | 7/2021 | Tokarchuk et al. |
| 11,064,997 B2 | 7/2021 | Shelton, IV et al. |
| 11,069,012 B2 | 7/2021 | Shelton, IV et al. |
| 11,071,560 B2 | 7/2021 | Deck et al. |
| 11,071,595 B2 | 7/2021 | Johnson et al. |
| 11,076,921 B2 | 8/2021 | Shelton, IV et al. |
| 11,083,458 B2 | 8/2021 | Harris et al. |
| 11,090,047 B2 | 8/2021 | Shelton, IV et al. |
| 11,090,048 B2 | 8/2021 | Fanelli et al. |
| 11,090,075 B2 | 8/2021 | Hunter et al. |
| 11,096,688 B2 | 8/2021 | Shelton, IV et al. |
| 11,096,693 B2 | 8/2021 | Shelton, IV et al. |
| 11,100,631 B2 | 8/2021 | Yates et al. |
| 11,103,246 B2 | 8/2021 | Marczyk et al. |
| 11,103,268 B2 | 8/2021 | Shelton, IV et al. |
| 11,109,866 B2 | 9/2021 | Shelton, IV et al. |
| 11,109,878 B2 | 9/2021 | Shelton, IV et al. |
| 11,114,195 B2 | 9/2021 | Shelton, IV et al. |
| 11,116,485 B2 | 9/2021 | Scheib et al. |
| 11,123,070 B2 | 9/2021 | Shelton, IV et al. |
| 11,129,611 B2 | 9/2021 | Shelton, IV et al. |
| 11,129,634 B2 | 9/2021 | Scheib et al. |
| 11,129,636 B2 | 9/2021 | Shelton, IV et al. |
| 11,129,669 B2 | 9/2021 | Stulen et al. |
| 11,129,670 B2 | 9/2021 | Shelton, IV et al. |
| 11,132,462 B2 | 9/2021 | Shelton, IV et al. |
| 11,134,942 B2 | 10/2021 | Harris et al. |
| 11,141,160 B2 | 10/2021 | Shelton, IV et al. |
| 11,141,213 B2 | 10/2021 | Yates et al. |
| 11,147,607 B2 | 10/2021 | Yates et al. |
| 11,160,551 B2 | 11/2021 | Shelton, IV et al. |
| 11,160,605 B2 | 11/2021 | Shelton, IV et al. |
| 11,166,716 B2 | 11/2021 | Shelton, IV et al. |
| 11,166,772 B2 | 11/2021 | Shelton, IV et al. |
| 11,179,150 B2 | 11/2021 | Yates et al. |
| 11,179,151 B2 | 11/2021 | Shelton, IV et al. |
| 11,179,155 B2 | 11/2021 | Shelton, IV et al. |
| 11,179,175 B2 | 11/2021 | Houser et al. |
| 11,179,204 B2 | 11/2021 | Shelton, IV et al. |
| 11,179,208 B2 | 11/2021 | Yates et al. |
| 11,183,293 B2 | 11/2021 | Lu et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,197,731 B2 | 12/2021 | Hoffman et al. |
| 11,202,570 B2 | 12/2021 | Shelton, IV et al. |
| 11,207,065 B2 | 12/2021 | Harris et al. |
| 11,207,067 B2 | 12/2021 | Shelton, IV et al. |
| 11,207,090 B2 | 12/2021 | Shelton, IV et al. |
| 11,213,293 B2 | 1/2022 | Worthington et al. |
| 11,213,294 B2 | 1/2022 | Shelton, IV et al. |
| 11,213,359 B2 | 1/2022 | Shelton, IV et al. |
| 11,218,822 B2 | 1/2022 | Morgan et al. |
| 11,219,453 B2 | 1/2022 | Shelton, IV et al. |
| 11,224,426 B2 | 1/2022 | Shelton, IV et al. |
| 11,229,436 B2 | 1/2022 | Shelton, IV et al. |
| 11,229,471 B2 | 1/2022 | Shelton, IV et al. |
| 11,234,756 B2 | 2/2022 | Shelton, IV et al. |
| 11,241,230 B2 | 2/2022 | Shelton, IV et al. |
| 11,253,256 B2 | 2/2022 | Harris et al. |
| 11,253,315 B2 | 2/2022 | Yates et al. |
| 11,257,589 B2 | 2/2022 | Shelton, IV et al. |
| 11,259,806 B2 | 3/2022 | Shelton, IV et al. |
| 11,259,807 B2 | 3/2022 | Shelton, IV et al. |
| 11,259,830 B2 | 3/2022 | Nott et al. |
| 11,266,409 B2 | 3/2022 | Huitema et al. |
| 11,266,468 B2 | 3/2022 | Shelton, IV et al. |
| 11,272,931 B2 | 3/2022 | Boudreaux et al. |
| 11,273,001 B2 | 3/2022 | Shelton, IV et al. |
| 11,273,290 B2 | 3/2022 | Kowshik |
| 11,278,280 B2 | 3/2022 | Shelton, IV et al. |
| 11,278,281 B2 | 3/2022 | Shelton, IV et al. |
| 11,284,890 B2 | 3/2022 | Nalagatla et al. |
| 11,284,936 B2 | 3/2022 | Shelton, IV et al. |
| 11,289,188 B2 | 3/2022 | Mabotuwana et al. |
| 11,291,440 B2 | 4/2022 | Harris et al. |
| 11,291,441 B2 | 4/2022 | Giordano et al. |
| 11,291,444 B2 | 4/2022 | Boudreaux et al. |
| 11,291,445 B2 | 4/2022 | Shelton, IV et al. |
| 11,291,465 B2 | 4/2022 | Parihar et al. |
| 11,291,495 B2 | 4/2022 | Yates et al. |
| 11,291,510 B2 | 4/2022 | Shelton, IV et al. |
| 11,298,128 B2 | 4/2022 | Messerly et al. |

(56) References Cited

U.S. PATENT DOCUMENTS

| | | |
|---|---|---|
| 11,298,129 B2 | 4/2022 | Bakos et al. |
| 11,298,130 B2 | 4/2022 | Bakos et al. |
| 11,298,148 B2 | 4/2022 | Jayme et al. |
| 11,304,699 B2 | 4/2022 | Shelton, IV et al. |
| 11,304,720 B2 | 4/2022 | Kimball et al. |
| 11,304,745 B2 | 4/2022 | Shelton, IV et al. |
| 11,304,763 B2 | 4/2022 | Shelton, IV et al. |
| 11,308,075 B2 | 4/2022 | Shelton, IV et al. |
| 11,311,306 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,317,919 B2 | 5/2022 | Shelton, IV et al. |
| 11,317,937 B2 | 5/2022 | Nott et al. |
| 11,322,248 B2 | 5/2022 | Grantcharov et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,746 B2 | 5/2022 | Boudreaux |
| 11,344,326 B2 | 5/2022 | Faller et al. |
| 11,350,932 B2 | 6/2022 | Shelton, IV et al. |
| 11,350,959 B2 | 6/2022 | Messerly et al. |
| 11,350,978 B2 | 6/2022 | Henderson et al. |
| 11,357,503 B2 | 6/2022 | Bakos et al. |
| 11,364,075 B2 | 6/2022 | Yates et al. |
| 11,369,377 B2 | 6/2022 | Boudreaux et al. |
| 11,373,755 B2 | 6/2022 | Shelton, IV et al. |
| 11,376,002 B2 | 7/2022 | Shelton, IV et al. |
| 11,376,098 B2 | 7/2022 | Shelton, IV et al. |
| 11,382,697 B2 | 7/2022 | Shelton, IV et al. |
| 11,382,715 B2 | 7/2022 | Arai et al. |
| D964,564 S | 9/2022 | Boudreaux |
| 11,464,514 B2 | 10/2022 | Yates et al. |
| 11,504,191 B2 | 11/2022 | Mccloud et al. |
| 11,571,212 B2 | 2/2023 | Yates et al. |
| 11,701,139 B2 | 7/2023 | Nott et al. |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0144147 A1 | 10/2002 | Basson et al. |
| 2002/0169584 A1 | 11/2002 | Fu et al. |
| 2002/0194023 A1 | 12/2002 | Turley et al. |
| 2003/0009111 A1 | 1/2003 | Cory et al. |
| 2003/0009154 A1 | 1/2003 | Whitman |
| 2003/0018329 A1 | 1/2003 | Hooven |
| 2003/0028183 A1 | 2/2003 | Sanchez et al. |
| 2003/0046109 A1 | 3/2003 | Uchikubo |
| 2003/0050654 A1 | 3/2003 | Whitman et al. |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0120284 A1 | 6/2003 | Palacios et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0082850 A1 | 4/2004 | Bonner et al. |
| 2004/0092992 A1 | 5/2004 | Adams et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0215131 A1 | 10/2004 | Sakurai |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0033108 A1 | 2/2005 | Sawyer |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0148854 A1 | 7/2005 | Ito et al. |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0213832 A1 | 9/2005 | Schofield et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2005/0288425 A1 | 12/2005 | Lee et al. |
| 2006/0020272 A1 | 1/2006 | Gildenberg |
| 2006/0025816 A1 | 2/2006 | Shelton |
| 2006/0039105 A1 | 2/2006 | Smith et al. |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0122558 A1 | 6/2006 | Sherman et al. |
| 2006/0136622 A1 | 6/2006 | Rouvelin et al. |
| 2006/0142739 A1 | 6/2006 | DiSilestro et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2006/0287645 A1 | 12/2006 | Tashiro et al. |
| 2007/0005002 A1 | 1/2007 | Millman et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175951 A1 | 8/2007 | Shelton et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |
| 2008/0033404 A1 | 2/2008 | Romoda et al. |
| 2008/0039742 A1 | 2/2008 | Hashimshony et al. |
| 2008/0040151 A1 | 2/2008 | Moore |

(56)  References Cited

U.S. PATENT DOCUMENTS

| | | |
|---|---|---|
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0164296 A1 | 7/2008 | Shelton et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0223904 A1 | 9/2008 | Marczyk |
| 2008/0234708 A1 | 9/2008 | Houser et al. |
| 2008/0235052 A1 | 9/2008 | Node-Langlois et al. |
| 2008/0245841 A1 | 10/2008 | Smith et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048595 A1 | 2/2009 | Mihori et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0157072 A1 | 6/2009 | Wham et al. |
| 2009/0182577 A1 | 7/2009 | Squilla et al. |
| 2009/0188094 A1 | 7/2009 | Cunningham et al. |
| 2009/0192591 A1 | 7/2009 | Ryan et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0281541 A1 | 11/2009 | Ibrahim et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0194574 A1 | 8/2010 | Monk et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0280247 A1 | 11/2010 | Mutti et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0006876 A1 | 1/2011 | Moberg et al. |
| 2011/0015649 A1 | 1/2011 | Anvari et al. |
| 2011/0022032 A1 | 1/2011 | Zemlok et al. |
| 2011/0036890 A1 | 2/2011 | Ma |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125138 A1* | 5/2011 | Malinouskas .......... A61B 90/90 |
| | | 606/1 |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0209128 A1 | 8/2011 | Nikara et al. |
| 2011/0218526 A1 | 9/2011 | Mathur |
| 2011/0237883 A1 | 9/2011 | Chun |
| 2011/0238079 A1 | 9/2011 | Hannaford et al. |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0264086 A1 | 10/2011 | Ingle |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2011/0307284 A1 | 12/2011 | Thompson et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0232549 A1 | 9/2012 | Willyard et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |

(56)                    References Cited

U.S. PATENT DOCUMENTS

| | | |
|---|---|---|
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0131845 A1 | 5/2013 | Guilleminot |
| 2013/0144284 A1 | 6/2013 | Behnke, II et al. |
| 2013/0153635 A1 | 6/2013 | Hodgkinson |
| 2013/0165776 A1 | 6/2013 | Blomqvist |
| 2013/0168435 A1 | 7/2013 | Huang et al. |
| 2013/0178853 A1 | 7/2013 | Hyink et al. |
| 2013/0190755 A1 | 7/2013 | Deborski et al. |
| 2013/0191647 A1 | 7/2013 | Ferrara, Jr. et al. |
| 2013/0193188 A1 | 8/2013 | Shelton, IV et al. |
| 2013/0196703 A1 | 8/2013 | Masoud et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005661 A1* | 1/2014 | Shelton, IV ....... A61B 18/1445 |
| | | 606/41 |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0039491 A1 | 2/2014 | Bakos et al. |
| 2014/0058407 A1 | 2/2014 | Tsekos et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0117256 A1 | 5/2014 | Mueller et al. |
| 2014/0121669 A1 | 5/2014 | Claus |
| 2014/0142963 A1 | 5/2014 | Hill et al. |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0171787 A1 | 6/2014 | Garbey et al. |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276748 A1 | 9/2014 | Ku et al. |
| 2014/0276749 A1 | 9/2014 | Johnson |
| 2014/0278219 A1 | 9/2014 | Canavan et al. |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0012010 A1 | 1/2015 | Adler et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053749 A1 | 2/2015 | Shelton, IV et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0099458 A1 | 4/2015 | Weisner et al. |
| 2015/0105647 A1* | 4/2015 | Katra .................. A61B 5/1072 |
| | | 600/509 |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0141980 A1 | 5/2015 | Jadhav et al. |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0168126 A1 | 6/2015 | Nevet et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0201918 A1 | 7/2015 | Kumar et al. |
| 2015/0202014 A1 | 7/2015 | Kim et al. |
| 2015/0208934 A1 | 7/2015 | Sztrubel et al. |
| 2015/0209035 A1* | 7/2015 | Zemlok ............ A61B 17/07207 |
| | | 73/1.01 |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0257783 A1 | 9/2015 | Levine et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282733 A1 | 10/2015 | Fielden et al. |
| 2015/0282821 A1 | 10/2015 | Look et al. |
| 2015/0289925 A1 | 10/2015 | Voegele et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297311 A1 | 10/2015 | Tesar |

(56)　　　　　References Cited

U.S. PATENT DOCUMENTS

| | | |
|---|---|---|
| 2015/0302157 A1 | 10/2015 | Collar et al. |
| 2015/0305828 A1 | 10/2015 | Park et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0331995 A1 | 11/2015 | Zhao et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0005169 A1 | 1/2016 | Sela et al. |
| 2016/0015471 A1* | 1/2016 | Piron ..................... A61B 1/045 |
| | | 600/424 |
| 2016/0019346 A1 | 1/2016 | Boston et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0051315 A1 | 2/2016 | Boudreaux |
| 2016/0058439 A1 | 3/2016 | Shelton, IV et al. |
| 2016/0066913 A1 | 3/2016 | Swayze et al. |
| 2016/0100837 A1 | 4/2016 | Huang et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0143659 A1 | 5/2016 | Glutz et al. |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0270732 A1 | 9/2016 | Källbäck et al. |
| 2016/0270842 A1 | 9/2016 | Strobl et al. |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287337 A1 | 10/2016 | Aram et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | Mchenry et al. |
| 2016/0314716 A1 | 10/2016 | Grubbs |
| 2016/0314717 A1 | 10/2016 | Grubbs |
| 2016/0317172 A1 | 11/2016 | Kumada et al. |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0331473 A1 | 11/2016 | Yamamura |
| 2016/0331474 A1* | 11/2016 | Lacal ..................... B25J 9/1689 |
| 2016/0338685 A1 | 11/2016 | Nawana et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0005911 A1 | 1/2017 | Kasargod et al. |
| 2017/0007247 A1 | 1/2017 | Shelton, IV et al. |
| 2017/0027603 A1 | 2/2017 | Pandey |
| 2017/0042604 A1 | 2/2017 | McFarland et al. |
| 2017/0049522 A1 | 2/2017 | Kapadia |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086906 A1 | 3/2017 | Tsuruta |
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1 | 4/2017 | Lendvay et al. |
| 2017/0119477 A1 | 5/2017 | Amiot et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143366 A1 | 5/2017 | Groene et al. |
| 2017/0147759 A1 | 5/2017 | Iyer et al. |
| 2017/0154156 A1 | 6/2017 | Sevenster et al. |
| 2017/0164996 A1 | 6/2017 | Honda et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0185732 A1 | 6/2017 | Niklewski et al. |
| 2017/0196583 A1 | 7/2017 | Sugiyama |
| 2017/0202595 A1 | 7/2017 | Shelton, IV |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224428 A1 | 8/2017 | Kopp |
| 2017/0231553 A1 | 8/2017 | Igarashi et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281186 A1 | 10/2017 | Shelton, IV et al. |
| 2017/0289617 A1 | 10/2017 | Song et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0319268 A1 | 11/2017 | Akagane |
| 2017/0325876 A1 | 11/2017 | Nakadate et al. |
| 2017/0325878 A1 | 11/2017 | Messerly et al. |
| 2017/0333147 A1 | 11/2017 | Bernstein |

(56) References Cited

U.S. PATENT DOCUMENTS

| | | |
|---|---|---|
| 2017/0333152 A1 | 11/2017 | Wade |
| 2017/0337043 A1 | 11/2017 | Brincat et al. |
| 2017/0348047 A1 | 12/2017 | Reiter et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014764 A1 | 1/2018 | Bechtel et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0056496 A1 | 3/2018 | Rubens et al. |
| 2018/0065248 A1 | 3/2018 | Barral et al. |
| 2018/0078170 A1 | 3/2018 | Panescu et al. |
| 2018/0082480 A1 | 3/2018 | White et al. |
| 2018/0085102 A1 | 3/2018 | Kikuchi |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0132895 A1 | 5/2018 | Silver |
| 2018/0144243 A1 | 5/2018 | Hsieh et al. |
| 2018/0144314 A1 | 5/2018 | Miller |
| 2018/0153436 A1 | 6/2018 | Olson |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0233235 A1 | 8/2018 | Angelides |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0296289 A1 | 10/2018 | Rodriguez-Navarro et al. |
| 2018/0300506 A1 | 10/2018 | Kawakami et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0317916 A1 | 11/2018 | Wixey |
| 2018/0325619 A1 | 11/2018 | Rauniyar et al. |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0353186 A1 | 12/2018 | Mozdzierz et al. |
| 2018/0357383 A1 | 12/2018 | Allen et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0059997 A1 | 2/2019 | Frushour |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0099226 A1 | 4/2019 | Hallen |
| 2019/0104919 A1 | 4/2019 | Shelton, IV et al. |
| 2019/0105468 A1 | 4/2019 | Kato et al. |
| 2019/0110828 A1 | 4/2019 | Despatie |
| 2019/0110855 A1 | 4/2019 | Barral et al. |
| 2019/0110856 A1 | 4/2019 | Barral et al. |
| 2019/0115108 A1 | 4/2019 | Hegedus et al. |
| 2019/0122330 A1 | 4/2019 | Saget et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125358 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0163875 A1 | 5/2019 | Allen et al. |

(56) References Cited

U.S. PATENT DOCUMENTS

| | | |
|---|---|---|
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200997 A1 | 7/2019 | Shelton, IV et al. |
| 2019/0201021 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201075 A1 | 7/2019 | Shelton, IV et al. |
| 2019/0201076 A1 | 7/2019 | Honda et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201083 A1 | 7/2019 | Shelton, IV et al. |
| 2019/0201085 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201102 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201130 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274713 A1 | 9/2019 | Scoggins et al. |
| 2019/0274714 A1 | 9/2019 | Cuti et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0365569 A1 | 12/2019 | Skovgaard et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054321 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |

(56)  References Cited

U.S. PATENT DOCUMENTS

| | | |
|---|---|---|
| 2020/0214699 A1 | 7/2020 | Shelton, IV et al. |
| 2020/0222079 A1 | 7/2020 | Swaney et al. |
| 2020/0222149 A1 | 7/2020 | Valentine et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261078 A1 | 8/2020 | Bakos et al. |
| 2020/0261086 A1 | 8/2020 | Zeiner et al. |
| 2020/0261087 A1 | 8/2020 | Timm et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0352664 A1 | 11/2020 | King et al. |
| 2020/0388385 A1 | 12/2020 | De Los Reyes et al. |
| 2020/0405304 A1 | 12/2020 | Mozdzierz et al. |
| 2020/0405375 A1 | 12/2020 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0157306 A1 | 5/2022 | Albrecht et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0249097 A1 | 8/2022 | Shelton, IV et al. |
| 2022/0323092 A1 | 10/2022 | Shelton, IV et al. |
| 2022/0323150 A1 | 10/2022 | Yates et al. |
| 2022/0331011 A1 | 10/2022 | Shelton, IV et al. |
| 2022/0331018 A1 | 10/2022 | Parihar et al. |
| 2022/0346792 A1 | 11/2022 | Shelton, IV et al. |
| 2022/0370117 A1 | 11/2022 | Messerly et al. |
| 2022/0370126 A1 | 11/2022 | Shelton, IV et al. |
| 2022/0374414 A1 | 11/2022 | Shelton, IV et al. |
| 2022/0395276 A1 | 12/2022 | Yates et al. |
| 2022/0401099 A1 | 12/2022 | Shelton, IV et al. |
| 2022/0406452 A1 | 12/2022 | Shelton, IV |
| 2022/0409302 A1 | 12/2022 | Shelton, IV et al. |
| 2023/0000518 A1 | 1/2023 | Nott et al. |
| 2023/0037577 A1 | 2/2023 | Kimball et al. |
| 2023/0064821 A1 | 3/2023 | Shelton, IV |
| 2023/0092371 A1 | 3/2023 | Yates et al. |
| 2023/0098870 A1 | 3/2023 | Harris et al. |
| 2023/0116571 A1 | 4/2023 | Shelton, IV et al. |
| 2023/0146947 A1 | 5/2023 | Shelton, IV et al. |
| 2023/0165642 A1 | 6/2023 | Shelton, IV et al. |
| 2023/0171266 A1 | 6/2023 | Brunner et al. |
| 2023/0171304 A1 | 6/2023 | Shelton, IV et al. |
| 2023/0187060 A1 | 6/2023 | Morgan et al. |

FOREIGN PATENT DOCUMENTS

| | | |
|---|---|---|
| CA | 2795323 A1 | 5/2014 |
| CN | 101617950 A | 1/2010 |
| CN | 106027664 A | 10/2016 |
| CN | 106413578 A | 2/2017 |
| CN | 104490448 B | 3/2017 |
| CN | 206097107 U | 4/2017 |
| CN | 106777916 A | 5/2017 |
| CN | 107811710 A | 3/2018 |
| CN | 108652695 A | 10/2018 |
| DE | 2037167 A1 | 2/1972 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5191993 U | 7/1976 |
| JP | S5373315 A | 6/1978 |
| JP | S57185848 A | 11/1982 |
| JP | S58207752 A | 12/1983 |
| JP | S63315049 A | 12/1988 |
| JP | H06142113 A | 5/1994 |
| JP | H06178780 A | 6/1994 |
| JP | H06209902 A | 8/1994 |
| JP | H07132122 A | 5/1995 |
| JP | H08071072 A | 3/1996 |

(56) References Cited

FOREIGN PATENT DOCUMENTS

| | | |
|---|---|---|
| JP | H08332169 A | 12/1996 |
| JP | H0928663 A | 2/1997 |
| JP | H09154850 A | 6/1997 |
| JP | H11151247 A | 6/1999 |
| JP | H11197159 A | 7/1999 |
| JP | H11309156 A | 11/1999 |
| JP | 2000058355 A | 2/2000 |
| JP | 2001029353 A | 2/2001 |
| JP | 2001195686 A | 7/2001 |
| JP | 2001314411 A | 11/2001 |
| JP | 2001340350 A | 12/2001 |
| JP | 2002272758 A | 9/2002 |
| JP | 2003061975 A | 3/2003 |
| JP | 2003070921 A | 3/2003 |
| JP | 2003153918 A | 5/2003 |
| JP | 2004118664 A | 4/2004 |
| JP | 2005111080 A | 4/2005 |
| JP | 2005309702 A | 11/2005 |
| JP | 2005348797 A | 12/2005 |
| JP | 2006077626 A | 3/2006 |
| JP | 2006117143 A | 5/2006 |
| JP | 2006164251 A | 6/2006 |
| JP | 2006280804 A | 10/2006 |
| JP | 2006288431 A | 10/2006 |
| JP | 2007123394 A | 5/2007 |
| JP | 2007139822 A | 6/2007 |
| JP | 2007300312 A | 11/2007 |
| JP | 2009039515 A | 2/2009 |
| JP | 2010057642 A | 3/2010 |
| JP | 2010131265 A | 6/2010 |
| JP | 2010269067 A | 12/2010 |
| JP | 2012065698 A | 4/2012 |
| JP | 2012239669 A | 12/2012 |
| JP | 2012240158 A | 12/2012 |
| JP | 2012533346 A | 12/2012 |
| JP | 2013044303 A | 3/2013 |
| JP | 2013081282 A | 5/2013 |
| JP | 2013135738 A | 7/2013 |
| JP | 2013144057 A | 7/2013 |
| JP | 2014155207 A | 8/2014 |
| JP | 2015085454 A | 5/2015 |
| JP | 2016514017 A | 5/2016 |
| JP | 2016528010 A | 9/2016 |
| JP | 2016174836 A | 10/2016 |
| JP | 2016214553 A | 12/2016 |
| JP | 2017047022 A | 3/2017 |
| JP | 2017096359 A | 6/2017 |
| JP | 2017513561 A | 6/2017 |
| JP | 2017526510 A | 9/2017 |
| JP | 2017532168 A | 11/2017 |
| KR | 20140104587 A | 8/2014 |
| KR | 101587721 B1 | 1/2016 |
| WO | WO-9734533 A1 | 9/1997 |
| WO | WO-9808449 A1 | 3/1998 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2006001264 A1 | 1/2006 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008076079 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014116961 A1 | 7/2014 |
| WO | WO-2014134196 A1 | 9/2014 |
| WO | WO-2015030157 A1 | 3/2015 |
| WO | WO-2015054665 A1 | 4/2015 |
| WO | WO-2015129395 A1 | 9/2015 |
| WO | WO-2016093049 A1 | 6/2016 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017183353 A1 | 10/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Choi et al., A haptic augmented reality surgeon console for a laparoscopic surgery robot system, 2013, IEEE, p. 355-357 (Year: 2013).

"Surgical instrumentation: the true cost of instrument trays and a potential strategy for optimization"; Mhlaba et al.; Sep. 23, 2015 (Year: 2015).

Shi et al., An intuitive control console for robotic syrgery system, 2014, IEEE, p. 404-407 (Year: 2014).

Slocinski et al., "Distance measure for impedance spectra for quantified evaluations," Lecture Notes on Impedance Spectroscopy, vol. 3, Taylor and Francis Group (Jul. 2012)—Book Not Attached.

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Miksch et al., "Utilizing temporal data abstraction for data validation and therapy planning for artificially ventilated newborn infants," Artificial Intelligence in Medicine, vol. 8, No. 6, pp. 543-576 (1996).

(56) References Cited

OTHER PUBLICATIONS

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey, " Artificial Intelligence in Medicine, vol. 39, No. 1, pp. 1-24 (2006).

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Hsiao-Wei Tang, "ARCM", Video, Sep. 2012, YouTube, 5 screenshots, Retrieved from internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

IEEE Std No. 177, "Standard Definitions and Methods of Measurement for Piezoelectric Vibrators," published May 1966, The Institute of Electrical and Electronics Engineers, Inc., New York, N.Y.

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model- Based Detection and Mitigation," 2016 46th Annual IEEE/IFIP International Conference on Dependable Systems and Networks (DSN), IEEE, Jun. 28, 2016, pp. 395-406.

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Phumzile Malindi, "5. QOS in Telemedicine," "Telemedicine," Jun. 20, 2011, IntechOpen, pp. 119-138.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode," Article, Oct. 8, 2010, pp. 1-9, Microwave Journal.

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1755-1759 (Year: 2010).

Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

(56)  References Cited

OTHER PUBLICATIONS

Sorrells, P., "Application Note AN680. Passive RFID Basics," retrieved from http://ww1.microchip.com/downloads/en/AppNotes/00680b.pdf on Feb. 26/2020, Dec. 31, 1998, pp. 1-7.

Lalys, et al., "Automatic knowledge-based recognition of low-level tasks in ophthalmological procedures", Int J Cars, vol. 8, No. 1, pp. 1-49, Apr. 19, 2012.

Hu, Jinwen, Stimulations of adaptive temperature control with self-focused hyperthermia system for tumor treatment, Jan. 9, 2012, Ultrasonics 53, pp. 171-177, (Year: 2012).

Hussain et al., "A survey on resource allocation in high performance distributed computing systems", Parallel Computing, vol. 39, No. 11, pp. 709-736 (2013).

Anonymous: "Quality of service—Wikipedia", Dec. 7, 2017, Retrieved from the Internet: URL:https://en.wikipedia.org/w/index.php?title=Quality_of_service&oldid=814298744#Applications [retrieved on Feb. 14, 2023], pp. 1-12.

Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023], pp. 1-7.

Anonymous: "Cloud computing—Wikipedia", Dec. 19, 2017, Retrieved from the Internet: URL:https://en.wikipedia.org/w/index.php?title=Cloud_computing&oldid=816206558 [retrieved Feb. 14, 2023], pp. 1-21.

International Search Report and Written Opinion received in PCT Application No. PCT/US2019/020149, mailed on May 20, 2019, 18 Pages.

* cited by examiner

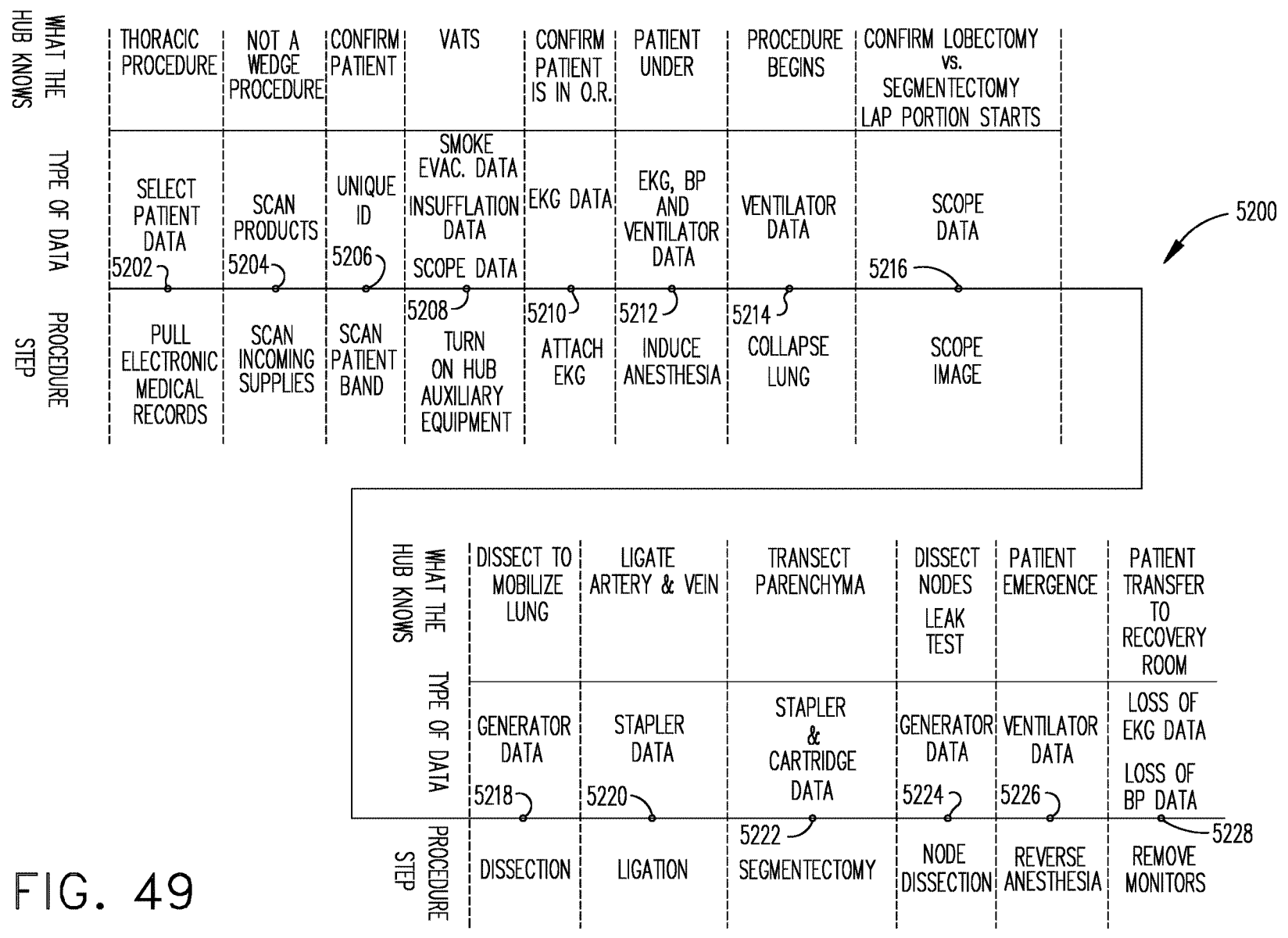

5200

| WHAT THE HUB KNOWS | TYPE OF DATA | PROCEDURE STEP |
|---|---|---|
| THORACIC PROCEDURE | | SELECT PATIENT DATA 5202 |
| NOT A WEDGE PROCEDURE | SCAN PRODUCTS 5204 | PULL ELECTRONIC MEDICAL RECORDS |
| CONFIRM PATIENT | UNIQUE ID 5206 | SCAN PATIENT BAND |
| VATS | SMOKE EVAC. DATA INSUFFLATION DATA SCOPE DATA 5208 | TURN ON HUB AUXILIARY EQUIPMENT |
| CONFIRM PATIENT IS IN O.R. | EKG DATA 5210 | ATTACH EKG |
| PATIENT UNDER | EKG, BP AND VENTILATOR DATA 5212 | INDUCE ANESTHESIA |
| PROCEDURE BEGINS | VENTILATOR DATA 5214 | COLLAPSE LUNG |
| CONFIRM LOBECTOMY vs. SEGMENTECTOMY LAP PORTION STARTS | SCOPE DATA 5216 | SCOPE IMAGE |

| WHAT THE HUB KNOWS | TYPE OF DATA | PROCEDURE STEP |
|---|---|---|
| DISSECT TO MOBILIZE LUNG | GENERATOR DATA 5218 | DISSECTION |
| LIGATE ARTERY & VEIN | STAPLER DATA 5220 | LIGATION |
| TRANSECT PARENCHYMA | STAPLER & CARTRIDGE DATA 5222 | SEGMENTECTOMY |
| DISSECT NODES | GENERATOR DATA 5224 | NODE DISSECTION |
| PATIENT EMERGENCE | VENTILATOR DATA 5226 | REVERSE ANESTHESIA |
| PATIENT TRANSFER TO RECOVERY ROOM | LOSS OF EKG DATA LOSS OF BP DATA 5228 | REMOVE MONITORS |

LEAK TEST

FIG. 49

BIPOLAR COMBINATION DEVICE THAT AUTOMATICALLY ADJUSTS PRESSURE BASED ON ENERGY MODALITY

CROSS-REFERENCE TO RELATED APPLICATIONS

The present application claims priority under 35 U.S.C. § 120 to U.S. patent application Ser. No. 16/115,223, titled BIPOLAR COMBINATION DEVICE THAT AUTOMATI-CALLY ADJUSTS PRESSURE BASED ON ENERGY MODALITY, filed on Aug. 28, 2018, the disclosure of which is herein incorporated by reference in its entirety.

U.S. patent application Ser. No. 16/115,223 claims priority under 35 U.S.C. § 119(e) to U.S. Provisional Patent Application No. 62/721,995, titled CONTROLLING AN ULTRASONIC SURGICAL INSTRUMENT ACCORD-ING TO TISSUE LOCATION, filed on Aug. 23, 2018, the disclosure of which is herein incorporated by reference in its entirety.

U.S. patent application Ser. No. 16/115,223 claims priority under 35 U.S.C. § 119(e) to U.S. Provisional Patent Application No. 62/721,998, titled SITUATIONAL AWARENESS OF ELECTROSURGICAL SYSTEMS, filed on Aug. 23, 2018, the disclosure of which is herein incorporated by reference in its entirety.

U.S. patent application Ser. No. 16/115,223 claims priority under 35 U.S.C. § 119(e) to U.S. Provisional Patent Application No. 62/721,999, titled INTERRUPTION OF ENERGY DUE TO INADVERTENT CAPACITIVE COU-PLING, filed on Aug. 23, 2018, the disclosure of which is herein incorporated by reference in its entirety.

U.S. patent application Ser. No. 16/115,223 claims priority under 35 U.S.C. § 119(e) to U.S. Provisional Patent Application No. 62/721,994, titled BIPOLAR COMBINA-TION DEVICE THAT AUTOMATICALLY ADJUSTS PRESSURE BASED ON ENERGY MODALITY, filed on Aug. 23, 2018, the disclosure of which is herein incorpo-rated by reference in its entirety.

U.S. patent application Ser. No. 16/115,223 claims priority under 35 U.S.C. § 119(e) to U.S. Provisional Patent Application No. 62/721,996, titled RADIO FREQUENCY ENERGY DEVICE FOR DELIVERING COMBINED ELECTRICAL SIGNALS, filed on Aug. 23, 2018, the disclosure of which is herein incorporated by reference in its entirety.

U.S. patent application Ser. No. 16/115,223 also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

U.S. patent application Ser. No. 16/115,223 also claims the benefit of priority under 35 U.S.C. § 119(e) to U.S. Provisional Patent Application No. 62/650,898 filed on Mar. 30, 2018, titled CAPACITIVE COUPLED RETURN PATH PAD WITH SEPARABLE ARRAY ELEMENTS, to U.S. Provisional Patent Application Ser. No. 62/650,887, titled SURGICAL SYSTEMS WITH OPTIMIZED SENSING CAPABILITIES, filed Mar. 30, 2018, to U.S. Provisional Patent Application Ser. No. 62/650,882, titled SMOKE EVACUATION MODULE FOR INTERACTIVE SURGI-CAL PLATFORM, filed Mar. 30, 2018, and to U.S. Provisional Patent Application Ser. No. 62/650,877, titled SUR-GICAL SMOKE EVACUATION SENSING AND CONTROLS, filed Mar. 30, 2018, the disclosure of each of which is herein incorporated by reference in its entirety.

U.S. patent application Ser. No. 16/115,223 also claims the benefit of priority under 35 U.S.C. § 119(e) to U.S. Provisional Patent Application Ser. No. 62/611,341, titled INTERACTIVE SURGICAL PLATFORM, filed Dec. 28, 2017, to U.S. Provisional Patent Application Ser. No. 62/611,340, titled CLOUD-BASED MEDICAL ANALYT-ICS, filed Dec. 28, 2017, and to U.S. Provisional Patent Application Ser. No. 62/611,339, titled ROBOT ASSISTED SURGICAL PLATFORM, filed Dec. 28, 2017, the disclo-sure of each of which is herein incorporated by reference in its entirety.

BACKGROUND

In a surgical environment, smart energy devices may be needed in a smart energy architecture environment.

SUMMARY

In one general aspect, a method of adjusting a compres-sion force applied by a surgical instrument is provided. The surgical instrument comprises an end effector and a clamp arm configured to receive energy modalities from a genera-tor configured to deliver a plurality of energy modalities to the surgical instrument. The method comprising: determin-ing, by a control circuit, tissue impedance of tissue in contact with an end effector of the surgical instrument; determining, by the control circuit, a tissue type based on the tissue impedance; selecting, by the control circuit, a first energy modality of the plurality of energy modalities to deliver to the surgical instrument; generating, by the control circuit, a first signal waveform based on the first energy modality; selecting, by the control circuit, a second energy modality of the plurality of energy modalities to deliver to the surgical instrument; generating, by the control circuit, a second signal waveform based on the second energy modality; outputting, by the generator, the first and second signal waveform to deliver energy to the end effector; and adjust-ing, by the control circuit, a compression force applied by the end effector by changing a size of a gap between the tissue and the clamp arm based on a proportion of the first signal waveform to the second signal waveform.

In another aspect, a surgical instrument is provided. The surgical instrument comprising: a control circuit configured to communicatively couple to a generator configured to deliver a plurality of energy modalities to an end effector of the surgical instrument, wherein the control circuit is further configured to: determine tissue impedance of tissue in contact with an end effector of the surgical instrument; determine a tissue type of based on the tissue impedance; select a first energy modality of the plurality of energy modalities; generate a first signal waveform based on the first energy modality; select a second energy modality of the plurality of energy modalities; generate a second signal waveform based on the second energy modality; and adjust a compression force applied by an end effector to tissue by changing a gap between tissue and an end effector based on a proportion of the first signal waveform to the second signal waveform.

In yet another aspect, a surgical system is provided. The surgical system comprising: a surgical hub configured to receive a tissue treatment algorithm transmitted from a cloud computing system, wherein the surgical hub is communicatively coupled to the cloud computing system; and a surgical instrument communicatively coupled to the surgical hub, wherein the surgical instrument comprises: an end effector comprising: a clamp arm; and a ultrasonic blade; a generator configured to deliver a plurality of energy modalities to the end effector; a control circuit communicatively coupled to the end effector and the generator, wherein the control circuit is configured to treat tissue, and wherein the control circuit is configured to: determine tissue impedance of tissue in contact with the end effector; determine tissue type based on the tissue impedance; select a first energy modality of the plurality of energy modalities; generating a first signal waveform based on the first energy modality; selecting a second energy modality of the plurality of energy modalities; generating a second signal waveform based on the second energy modality; applying the first and second signal waveform to the end effector; and adjusting a compression force applied by the end effector by changing a size of a gap between the tissue and the waveguide based on a proportion of the first signal waveform to the second signal waveform.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 49 is a timeline depicting situational awareness of a surgical hub, in accordance with at least one aspect of the present disclosure.

DESCRIPTION

Figure 1:
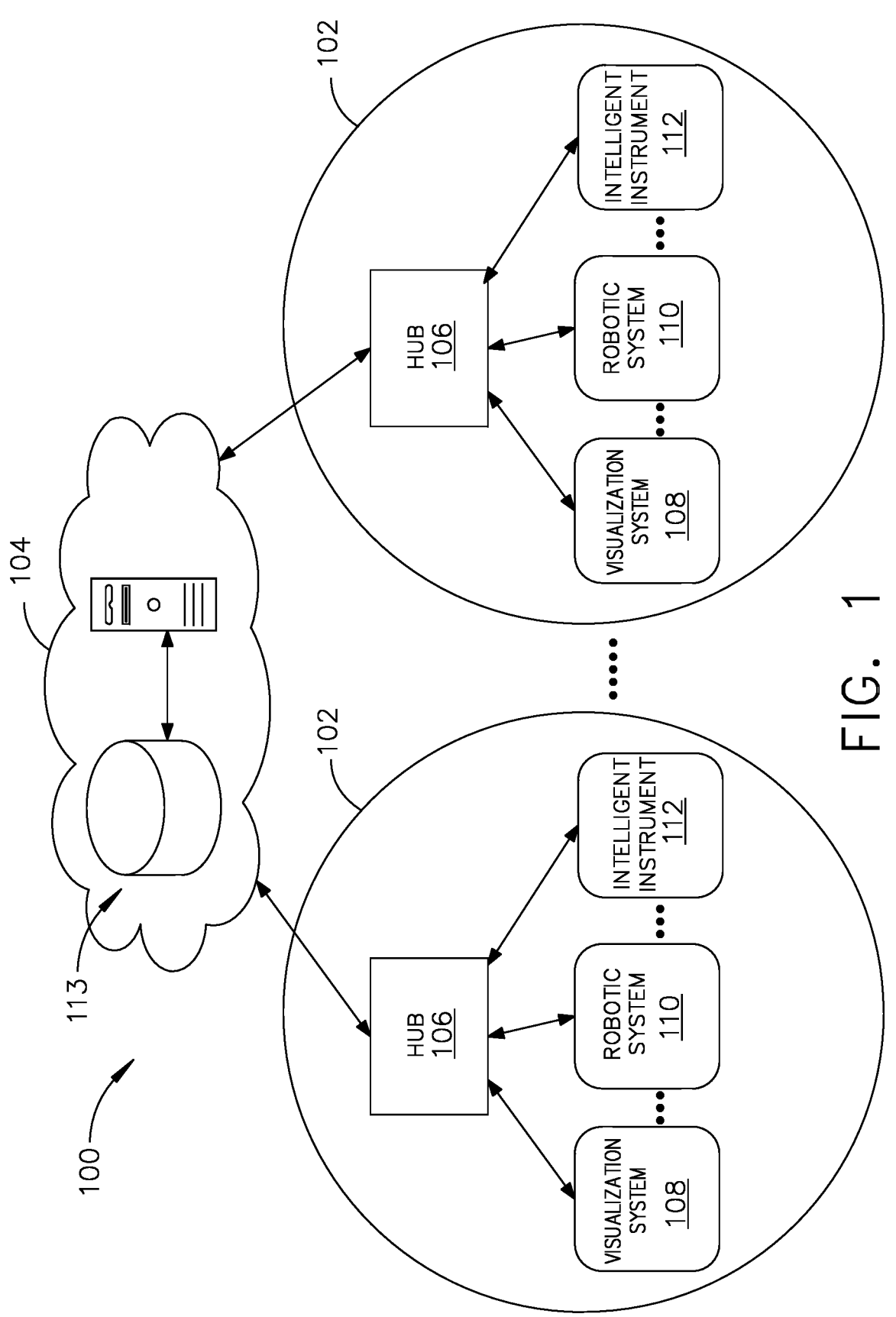
FIG. 1 is a block diagram of a computer-implemented interactive surgical system, in accordance with at least one aspect of the present disclosure.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR, now U.S. Patent Application Publication No. 2019/0201073;

U.S. patent application Ser. No. 16/115,205, titled TEMPERATURE CONTROL OF ULTRASONIC END EFFECTOR AND CONTROL SYSTEM THEREFOR, now U.S. Patent Application Publication No. 2019/0201036;

U.S. patent application Ser. No. 16/115,233, titled RADIO FREQUENCY ENERGY DEVICE FOR DELIVERING COMBINED ELECTRICAL SIGNALS, now U.S. Patent Application Publication No. 2019/0201091;

U.S. patent application Ser. No. 16/115,208, titled CONTROLLING AN ULTRASONIC SURGICAL INSTRUMENT ACCORDING TO TISSUE LOCATION, now U.S. Patent Application Publication No. 2019/0201037;

U.S. patent application Ser. No. 16/115,220, titled CONTROLLING ACTIVATION OF AN ULTRASONIC SURGICAL INSTRUMENT ACCORDING TO THE PRESENCE OF TISSUE, now U.S. Patent Application Publication No. 2019/0201040;

U.S. patent application Ser. No. 16/115,232, titled DETERMINING TISSUE COMPOSITION VIA AN ULTRASONIC SYSTEM, now U.S. Patent Application Publication No. 2019/0201038;

U.S. patent application Ser. No. 16/115,239, titled DETERMINING THE STATE OF AN ULTRASONIC ELECTROMECHANICAL SYSTEM ACCORDING TO FREQUENCY SHIFT, now U.S. Patent Application Publication No. 2019/0201042;

U.S. patent application Ser. No. 16/115,247, titled DETERMINING THE STATE OF AN ULTRASONIC END EFFECTOR, now U.S. Patent Application Publication No. 2019/0274716;

U.S. patent application Ser. No. 16/115,211, titled SITUATIONAL AWARENESS OF ELECTROSURGICAL SYSTEMS, now U.S. Patent Application Publication No. 2019/0201039;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT, now U.S. Patent Application Publication No. 2019/0201075;

U.S. patent application Ser. No. 16/115,240, titled DETECTION OF END EFFECTOR IMMERSION IN LIQUID, now U.S. Patent Application Publication No. 2019/0201043;

U.S. patent application Ser. No. 16/115,249, titled INTERRUPTION OF ENERGY DUE TO INADVERTENT CAPACITIVE COUPLING, now U.S. Patent Application Publication No. 2019/0201077;

U.S. patent application Ser. No. 16/115,256, titled INCREASING RADIO FREQUENCY TO CREATE PAD-LESS MONOPOLAR LOOP, now U.S. Patent Application Publication No. 2019/0201092; and U.S. patent application Ser. No. 16/115,238, titled ACTIVATION OF ENERGY DEVICES, now U.S. Patent Application Publication No. 2019/0201041.

Applicant of the present application owns the following U.S. patent applications, filed on Aug. 23, 2018, the disclosure of each of which is herein incorporated by reference in its entirety:

U.S. Provisional Patent Application No. 62/721,995, titled CONTROLLING AN ULTRASONIC SURGICAL INSTRUMENT ACCORDING TO TISSUE LOCATION;

U.S. Provisional Patent Application No. 62/721,998, titled SITUATIONAL AWARENESS OF ELECTROSURGICAL SYSTEMS;

U.S. Provisional Patent Application No. 62/721,999, titled INTERRUPTION OF ENERGY DUE TO INADVERTENT CAPACITIVE COUPLING;

U.S. Provisional Patent Application No. 62/721,994, titled BIPOLAR COMBINATION DEVICE THAT AUTOMATICALLY ADJUSTS PRESSURE BASED ON ENERGY MODALITY; and U.S. Provisional Patent Application No. 62/721,996, titled RADIO FREQUENCY ENERGY DEVICE FOR DELIVERING COMBINED ELECTRICAL SIGNALS.

Applicant of the present application owns the following U.S. patent applications, filed on Jun. 30, 2018, the disclosure of each of which is herein incorporated by reference in its entirety:

U.S. Provisional Patent Application No. 62/692,747, titled SMART ACTIVATION OF AN ENERGY DEVICE BY ANOTHER DEVICE;

U.S. Provisional Patent Application No. 62/692,748, titled SMART ENERGY ARCHITECTURE; and U.S. Provisional Patent Application No. 62/692,768, titled SMART ENERGY DEVICES.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS, now U.S. Patent Application Publication No. 2019/0201090;

U.S. patent application Ser. No. 16/024,057, titled CONTROLLING A SURGICAL INSTRUMENT ACCORDING TO SENSED CLOSURE PARAMETERS, now U.S. Pat. No. 10,695,081;

U.S. patent application Ser. No. 16/024,067, titled SYSTEMS FOR ADJUSTING END EFFECTOR PARAMETERS BASED ON PERIOPERATIVE INFORMATION, now U.S. Pat. No. 10,595,887;

U.S. patent application Ser. No. 16/024,075, titled SAFETY SYSTEMS FOR SMART POWERED SURGICAL STAPLING, now U.S. Patent Application Publication No. 2019/0201146;

U.S. patent application Ser. No. 16/024,083, titled SAFETY SYSTEMS FOR SMART POWERED SUR- GICAL STAPLING, now U.S. Patent Application Publication No. 2019/0200984;

U.S. patent application Ser. No. 16/024,094, titled SURGICAL SYSTEMS FOR DETECTING END EFFECTOR TISSUE DISTRIBUTION IRREGULARITIES, now U.S. Patent Application Publication No. 2019/0201020;

U.S. patent application Ser. No. 16/024,138, titled SYSTEMS FOR DETECTING PROXIMITY OF SURGICAL END EFFECTOR TO CANCEROUS TISSUE, now U.S. Patent Application Publication No. 2019/0200985;

U.S. patent application Ser. No. 16/024,150, titled SURGICAL INSTRUMENT CARTRIDGE SENSOR ASSEMBLIES, now U.S. Patent Application Publication No. 2019/0200986;

U.S. patent application Ser. No. 16/024,160, titled VARIABLE OUTPUT CARTRIDGE SENSOR ASSEMBLY, now U.S. Patent Application Publication No. 2019/0200987;

U.S. patent application Ser. No. 16/024,124, titled SURGICAL INSTRUMENT HAVING A FLEXIBLE ELECTRODE, now U.S. Patent Application Publication No. 2019/0201079;

U.S. patent application Ser. No. 16/024,132, titled SURGICAL INSTRUMENT HAVING A FLEXIBLE CIRCUIT, now U.S. Patent Application Publication No. 2019/0201021;

U.S. patent application Ser. No. 16/024,141, titled SURGICAL INSTRUMENT WITH A TISSUE MARKING ASSEMBLY, now U.S. Patent Application Publication No. 2019/0201159;

U.S. patent application Ser. No. 16/024,162, titled SURGICAL SYSTEMS WITH PRIORITIZED DATA TRANSMISSION CAPABILITIES, now U.S. Patent Application Publication No. 2019/0200988;

U.S. patent application Ser. No. 16/024,066, titled SURGICAL EVACUATION SENSING AND MOTOR CONTROL, now U.S. Patent Application Publication No. 2019/0201082;

U.S. patent application Ser. No. 16/024,096, titled SURGICAL EVACUATION SENSOR ARRANGEMENTS, now U.S. Patent Application Publication No. 2019/0201083;

U.S. patent application Ser. No. 16/024,116, titled SURGICAL EVACUATION FLOW PATHS, now U.S. Patent Application Publication No. 2019/0201084;

U.S. patent application Ser. No. 16/024,149, titled SURGICAL EVACUATION SENSING AND GENERATOR CONTROL, now U.S. Patent Application Publication No. 2019/0201085;

U.S. patent application Ser. No. 16/024,180, titled SURGICAL EVACUATION SENSING AND DISPLAY, now U.S. Patent Application Publication No. 2019/0201086;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, now U.S. Pat. No. 10,755,813;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM, now U.S. Patent Application Publication No. 2019/0201087;

9

U.S. patent application Ser. No. 16/024,265, titled SUR-
GICAL EVACUATION SYSTEM WITH A COMMU-
NICATION CIRCUIT FOR COMMUNICATION
BETWEEN A FILTER AND A SMOKE EVACUA-
TION DEVICE, now U.S. Patent Application Publica-
tion No. 2019/0201088; and U.S. patent application Ser. No. 16/024,273, titled DUAL
IN-SERIES LARGE AND SMALL DROPLET FIL-
TERS, now U.S. Patent Application Publication No.
2019/0201597.

Applicant of the present application owns the following
U.S. Provisional patent applications, filed on Jun. 28, 2018,
the disclosure of each of which is herein incorporated by
reference in its entirety:

U.S. Provisional Patent Application Ser. No. 62/691,228,
titled A METHOD OF USING REINFORCED FLEX
CIRCUITS WITH MULTIPLE SENSORS WITH
ELECTROSURGICAL DEVICES;

U.S. Provisional Patent Application Ser. No. 62/691,227,
titled CONTROLLING A SURGICAL INSTRUMENT
ACCORDING TO SENSED CLOSURE PARAM-
ETERS;

U.S. Provisional Patent Application Ser. No. 62/691,230,
titled SURGICAL INSTRUMENT HAVING A FLEX-
IBLE ELECTRODE;

U.S. Provisional Patent Application Ser. No. 62/691,219,
titled SURGICAL EVACUATION SENSING AND
MOTOR CONTROL;

U.S. Provisional Patent Application Ser. No. 62/691,257,
titled COMMUNICATION OF SMOKE EVACUA-
TION SYSTEM PARAMETERS TO HUB OR
CLOUD IN SMOKE EVACUATION MODULE FOR
INTERACTIVE SURGICAL PLATFORM;

U.S. Provisional Patent Application Ser. No. 62/691,262,
titled SURGICAL EVACUATION SYSTEM WITH A
COMMUNICATION CIRCUIT FOR COMMUNICA-
TION BETWEEN A FILTER AND A SMOKE
EVACUATION DEVICE; and U.S. Provisional Patent Application Ser. No. 62/691,251,
titled DUAL IN-SERIES LARGE AND SMALL
DROPLET FILTERS.

Applicant of the present application owns the following
U.S. Provisional patent application, filed on Apr. 19, 2018,
the disclosure of each of which is herein incorporated by
reference in its entirety:

U.S. Provisional Patent Application Ser. No. 62/659,900,
titled METHOD OF HUB COMMUNICATION.

Applicant of the present application owns the following
U.S. Provisional patent applications, filed on Mar. 30, 2018,
the disclosure of each of which is herein incorporated by
reference in its entirety:

U.S. Provisional Patent Application No. 62/650,898 filed
on Mar. 30, 2018, titled CAPACITIVE COUPLED
RETURN PATH PAD WITH SEPARABLE ARRAY
ELEMENTS;

U.S. Provisional Patent Application Ser. No. 62/650,887,
titled SURGICAL SYSTEMS WITH OPTIMIZED
SENSING CAPABILITIES;

U.S. Provisional Patent Application Ser. No. 62/650,882,
titled SMOKE EVACUATION MODULE FOR
INTERACTIVE SURGICAL PLATFORM; and U.S. Provisional Patent Application Ser. No. 62/650,877,
titled SURGICAL SMOKE EVACUATION SENSING
AND CONTROLS.

10

Applicant of the present application owns the following U.S.
patent applications, filed on Mar. 29, 2018, the disclosure of
each of which is herein incorporated by reference in its
entirety:

U.S. patent application Ser. No. 15/940,641, titled
INTERACTIVE SURGICAL SYSTEMS WITH
ENCRYPTED COMMUNICATION CAPABILITIES,
now U.S. Patent Application Publication No. 2019/
0207911;

U.S. patent application Ser. No. 15/940,648, titled
INTERACTIVE SURGICAL SYSTEMS WITH CON-
DITION HANDLING OF DEVICES AND DATA
CAPABILITIES, now U.S. Patent Application Publi-
cation No. 2019/0206004;

U.S. patent application Ser. No. 15/940,656, titled SUR-
GICAL HUB COORDINATION OF CONTROL AND
COMMUNICATION OF OPERATING ROOM
DEVICES, now U.S. Patent Application Publication
No. 2019/0201141;

U.S. patent application Ser. No. 15/940,666, titled SPA-
TIAL AWARENESS OF SURGICAL HUBS IN
OPERATING ROOMS, now U.S. Patent Application
Publication No. 2019/0206551;

U.S. patent application Ser. No. 15/940,670, titled COOP-
ERATIVE UTILIZATION OF DATA DERIVED
FROM SECONDARY SOURCES BY INTELLIGENT
SURGICAL HUBS, now U.S. Patent Application Pub-
lication No. 2019/0201116;

U.S. patent application Ser. No. 15/940,677, titled SUR-
GICAL HUB CONTROL ARRANGEMENTS, now
U.S. Patent Application Publication No. 2019/0201143;

U.S. patent application Ser. No. 15/940,632, titled DATA
STRIPPING METHOD TO INTERROGATE
PATIENT RECORDS AND CREATE ANONYMIZED
RECORD, now U.S. Patent Application Publication
No. 2019/0205566;

U.S. patent application Ser. No. 15/940,640, titled COM-
MUNICATION HUB AND STORAGE DEVICE FOR
STORING PARAMETERS AND STATUS OF A SUR-
GICAL DEVICE TO BE SHARED WITH CLOUD
BASED ANALYTICS SYSTEMS, now U.S. Patent
Application Publication No. 2019/0200863;

U.S. patent application Ser. No. 15/940,645, titled SELF
DESCRIBING DATA PACKETS GENERATED AT
AN ISSUING INSTRUMENT, now U.S. Patent Appli-
cation Publication No. 2019/0207773;

U.S. patent application Ser. No. 15/940,649, titled DATA
PAIRING TO INTERCONNECT A DEVICE MEA-
SURED PARAMETER WITH AN OUTCOME, now
U.S. Patent Application Publication No. 2019/
0205567;

U.S. patent application Ser. No. 15/940,654, titled SUR-
GICAL HUB SITUATIONAL AWARENESS, now
U.S. Patent Application Publication No. 2019/0201140;

U.S. patent application Ser. No. 15/940,663, titled SUR-
GICAL SYSTEM DISTRIBUTED PROCESSING,
now U.S. Patent Application Publication No. 2019/
0201033;

U.S. patent application Ser. No. 15/940,668, titled
AGGREGATION AND REPORTING OF SURGICAL
HUB DATA, now U.S. Patent Application Publication
No. 2019/0201115;

U.S. patent application Ser. No. 15/940,671, titled SUR-
GICAL HUB SPATIAL AWARENESS TO DETER-
MINE DEVICES IN OPERATING THEATER, now
U.S. Patent Application Publication No. 2019/0201104;

U.S. patent application Ser. No. 15/940,686, titled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, titled STERILE FIELD INTERACTIVE CONTROL DISPLAYS, now U.S. Patent Application Publication No. 2019/0205001;

U.S. patent application Ser. No. 15/940,629, titled COMPUTER IMPLEMENTED INTERACTIVE SURGICAL SYSTEMS, now U.S. Patent Application Publication No. 2019/0201112;

U.S. patent application Ser. No. 15/940,704, titled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No. 2019/0200905; and U.S. patent application Ser. No. 15/940,742, titled DUAL CMOS ARRAY IMAGING, now U.S. Patent Application Publication No. 2019/0200906.

U.S. patent application Ser. No. 15/940,636, titled ADAPTIVE CONTROL PROGRAM UPDATES FOR SURGICAL DEVICES, now U.S. Patent Application Publication No. 2019/0206003;

U.S. patent application Ser. No. 15/940,653, titled ADAPTIVE CONTROL PROGRAM UPDATES FOR SURGICAL HUBS, now U.S. Patent Application Publication No. 2019/0201114;

U.S. patent application Ser. No. 15/940,660, titled CLOUD-BASED MEDICAL ANALYTICS FOR CUSTOMIZATION AND RECOMMENDATIONS TO A USER, now U.S. Patent Application Publication No. 2019/0206555;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Patent Application Publication No. 2019/0201144;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION, now U.S. Patent Application Publication No. 2019/0201119;

U.S. patent application Ser. No. 15/940,634, titled CLOUD-BASED MEDICAL ANALYTICS FOR SECURITY AND AUTHENTICATION TRENDS AND REACTIVE MEASURES, now U.S. Patent Application Publication No. 2019/0201138;

U.S. patent application Ser. No. 15/940,706, titled DATA HANDLING AND PRIORITIZATION IN A CLOUD ANALYTICS NETWORK, now U.S. Patent Application Publication No. 2019/0206561; and U.S. patent application Ser. No. 15/940,675, titled CLOUD INTERFACE FOR COUPLED SURGICAL DEVICES, now U.S. Pat. No. 10,849,697.

U.S. patent application Ser. No. 15/940,627, titled DRIVE ARRANGEMENTS FOR ROBOT-ASSISTED SURGICAL PLATFORMS, now U.S. Patent Application Publication No. 2019/0201111;

U.S. patent application Ser. No. 15/940,637, titled COMMUNICATION ARRANGEMENTS FOR ROBOT- ASSISTED SURGICAL PLATFORMS, now U.S. Patent Application Publication No. 2019/0201139;

U.S. patent application Ser. No. 15/940,642, titled CONTROLS FOR ROBOT-ASSISTED SURGICAL PLATFORMS, now U.S. Patent Application Publication No. 2019/0201113;

U.S. patent application Ser. No. 15/940,676, titled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,680, titled CONTROLLERS FOR ROBOT-ASSISTED SURGICAL PLATFORMS, now U.S. Patent Application Publication No. 2019/0201135;

U.S. patent application Ser. No. 15/940,683, titled COOPERATIVE SURGICAL ACTIONS FOR ROBOT-ASSISTED SURGICAL PLATFORMS, now U.S. Patent Application Publication No. 2019/0201145;

U.S. patent application Ser. No. 15/940,690, titled DISPLAY ARRANGEMENTS FOR ROBOT-ASSISTED SURGICAL PLATFORMS, now U.S. Patent Application Publication No. 2019/0201118; and U.S. patent application Ser. No. 15/940,711, titled SENSING ARRANGEMENTS FOR ROBOT-ASSISTED SURGICAL PLATFORMS, now U.S. Patent Application Publication No. 2019/0201120.

Applicant of the present application owns the following U.S. Provisional patent applications, filed on Mar. 28, 2018, the disclosure of each of which is herein incorporated by reference in its entirety:

U.S. Provisional Patent Application Ser. No. 62/649,302, titled INTERACTIVE SURGICAL SYSTEMS WITH ENCRYPTED COMMUNICATION CAPABILITIES;

U.S. Provisional Patent Application Ser. No. 62/649,294, titled DATA STRIPPING METHOD TO INTERROGATE PATIENT RECORDS AND CREATE ANONYMIZED RECORD;

U.S. Provisional Patent Application Ser. No. 62/649,300, titled SURGICAL HUB SITUATIONAL AWARENESS;

U.S. Provisional Patent Application Ser. No. 62/649,309, titled SURGICAL HUB SPATIAL AWARENESS TO DETERMINE DEVICES IN OPERATING THEATER;

U.S. Provisional Patent Application Ser. No. 62/649,310, titled COMPUTER IMPLEMENTED INTERACTIVE SURGICAL SYSTEMS;

U.S. Provisional Patent Application Ser. No. 62/649,291, titled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, titled ADAPTIVE CONTROL PROGRAM UPDATES FOR SURGICAL DEVICES;

U.S. Provisional Patent Application Ser. No. 62/649,333, titled CLOUD-BASED MEDICAL ANALYTICS FOR CUSTOMIZATION AND RECOMMENDATIONS TO A USER;

U.S. Provisional Patent Application Ser. No. 62/649,327, titled CLOUD-BASED MEDICAL ANALYTICS FOR SECURITY AND AUTHENTICATION TRENDS AND REACTIVE MEASURES;

U.S. Provisional Patent Application Ser. No. 62/649,315, titled DATA HANDLING AND PRIORITIZATION IN A CLOUD ANALYTICS NETWORK;

U.S. Provisional Patent Application Ser. No. 62/649,313, titled CLOUD INTERFACE FOR COUPLED SURGICAL DEVICES;

U.S. Provisional Patent Application Ser. No. 62/649,320, titled DRIVE ARRANGEMENTS FOR ROBOT-ASSISTED SURGICAL PLATFORMS;

U.S. Provisional Patent Application Ser. No. 62/649,307, titled AUTOMATIC TOOL ADJUSTMENTS FOR ROBOT-ASSISTED SURGICAL PLATFORMS; and U.S. Provisional Patent Application Ser. No. 62/649,323, titled SENSING ARRANGEMENTS FOR ROBOT-ASSISTED SURGICAL PLATFORMS.

Applicant of the present application owns the following U.S. Provisional patent applications, filed on Mar. 8, 2018, the disclosure of each of which is herein incorporated by reference in its entirety:

U.S. Provisional Patent Application Ser. No. 62/640,417, titled TEMPERATURE CONTROL IN ULTRASONIC DEVICE AND CONTROL SYSTEM THEREFOR; and U.S. Provisional Patent Application Ser. No. 62/640,415, titled ESTIMATING STATE OF ULTRASONIC END EFFECTOR AND CONTROL SYSTEM THEREFOR.

Applicant of the present application owns the following U.S. Provisional patent applications, filed on Dec. 28, 2017, the disclosure of each of which is herein incorporated by reference in its entirety:

U.S. Provisional patent application Serial No. U.S. Provisional Patent Application Ser. No. 62/611,341, titled INTERACTIVE SURGICAL PLATFORM;

U.S. Provisional Patent Application Ser. No. 62/611,340, titled CLOUD-BASED MEDICAL ANALYTICS; and U.S. Provisional Patent Application Ser. No. 62/611,339, titled ROBOT ASSISTED SURGICAL PLATFORM.

Computer-Implemented Interactive Surgical System

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
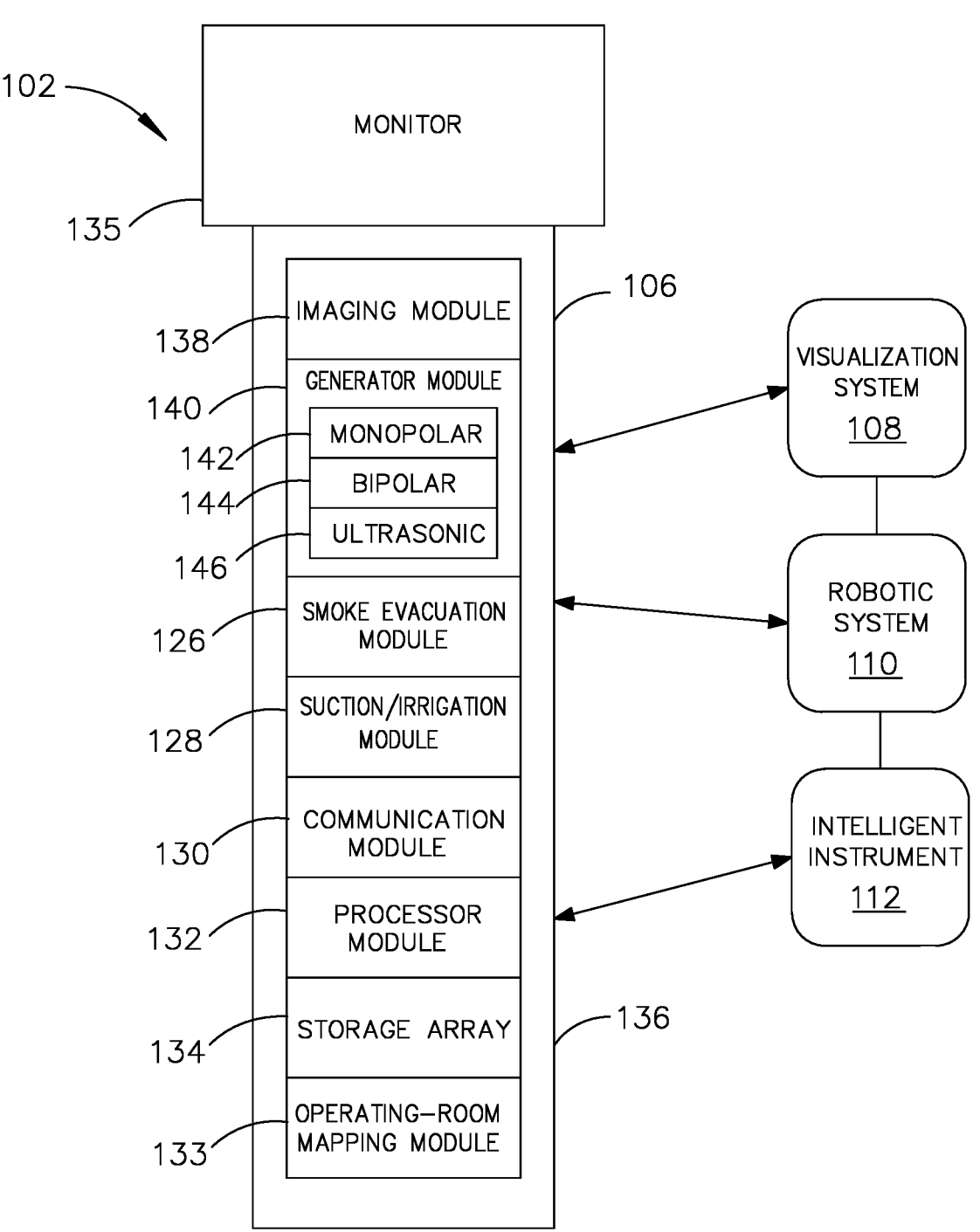
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

In one aspect, the imaging device employs multi-spectrum monitoring to discriminate topography and underlying structures. A multi-spectral image is one that captures image data within specific wavelength ranges across the electro-magnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
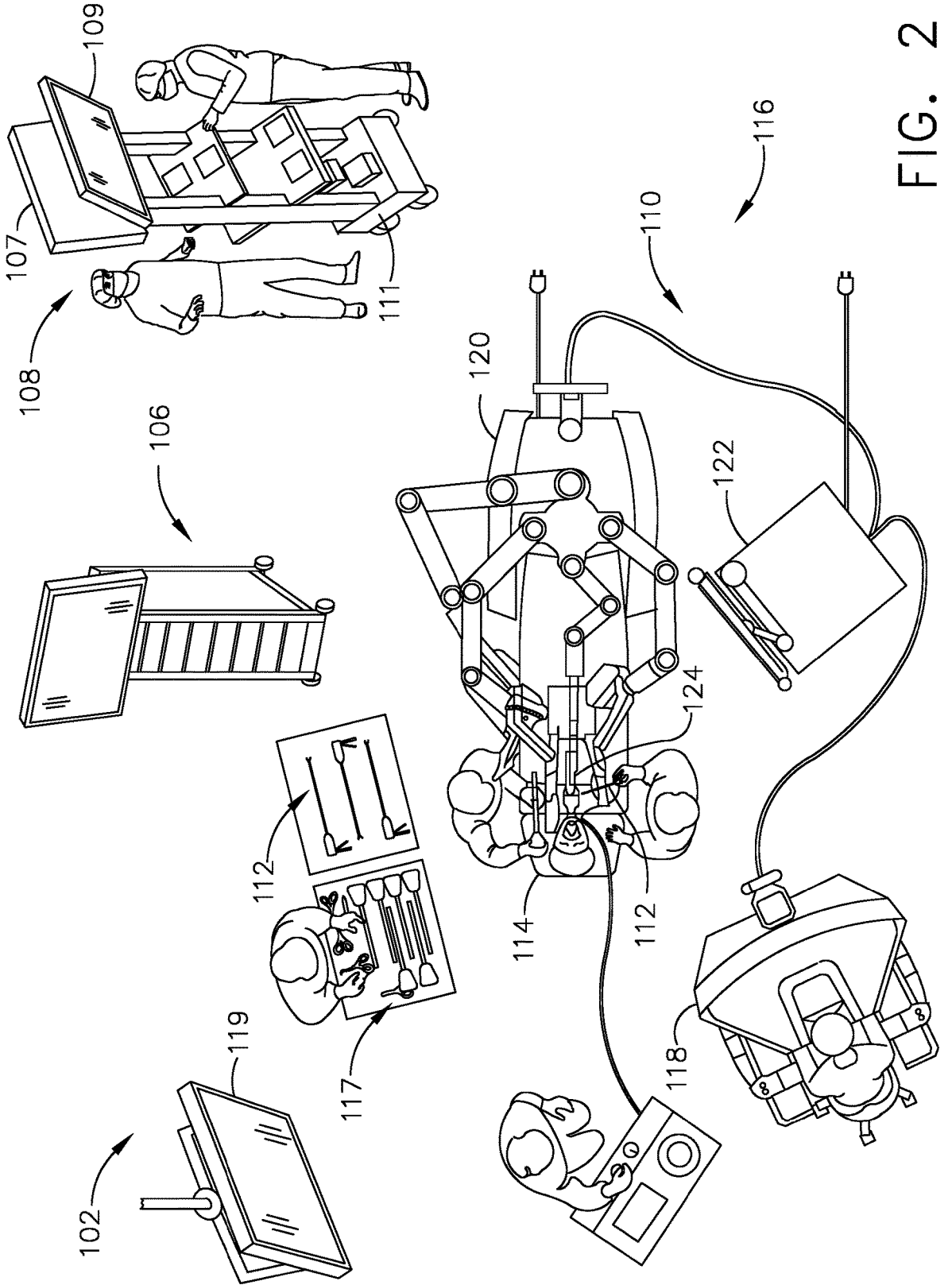
FIG. 2 is a surgical system being used to perform a surgical procedure in an operating room, in accordance with at least one aspect of the present disclosure.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
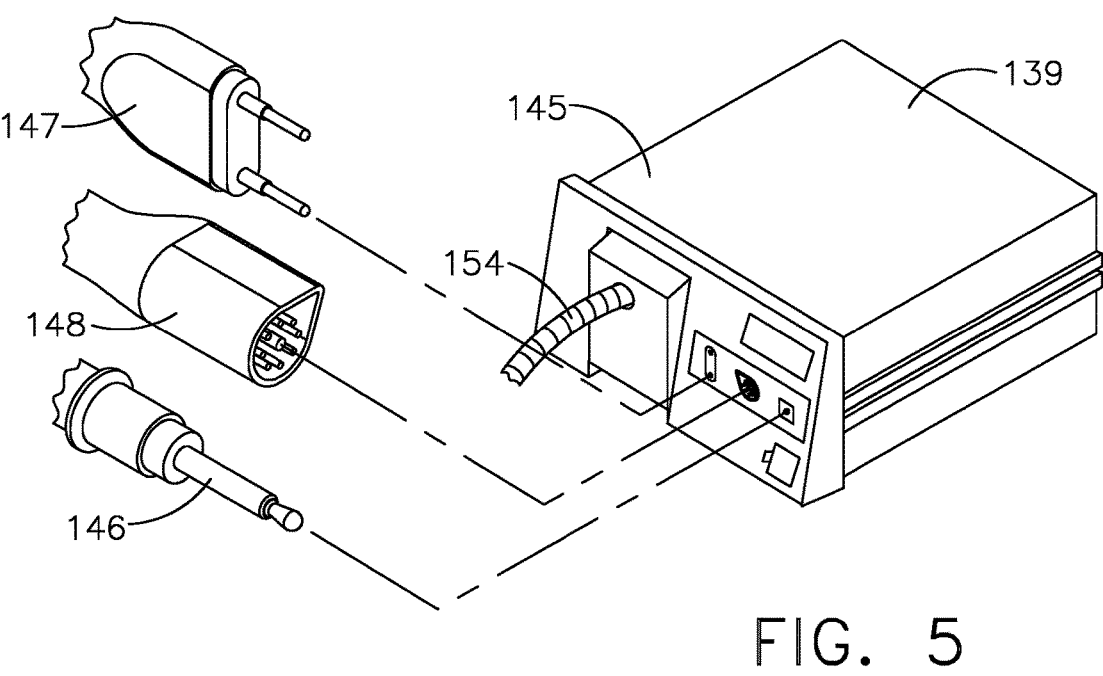
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136.

As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
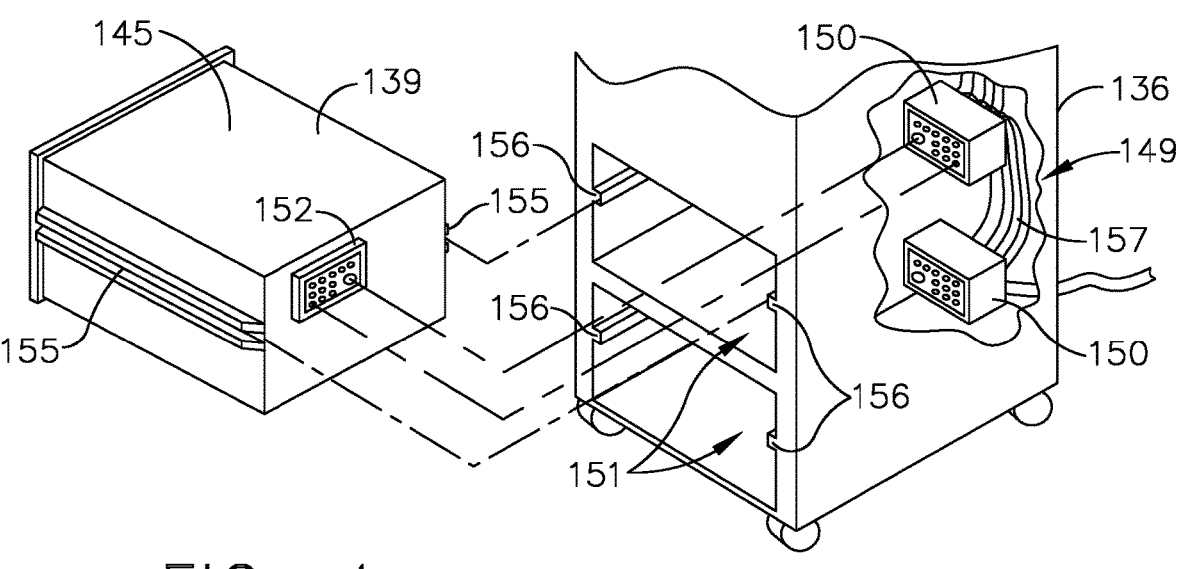
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
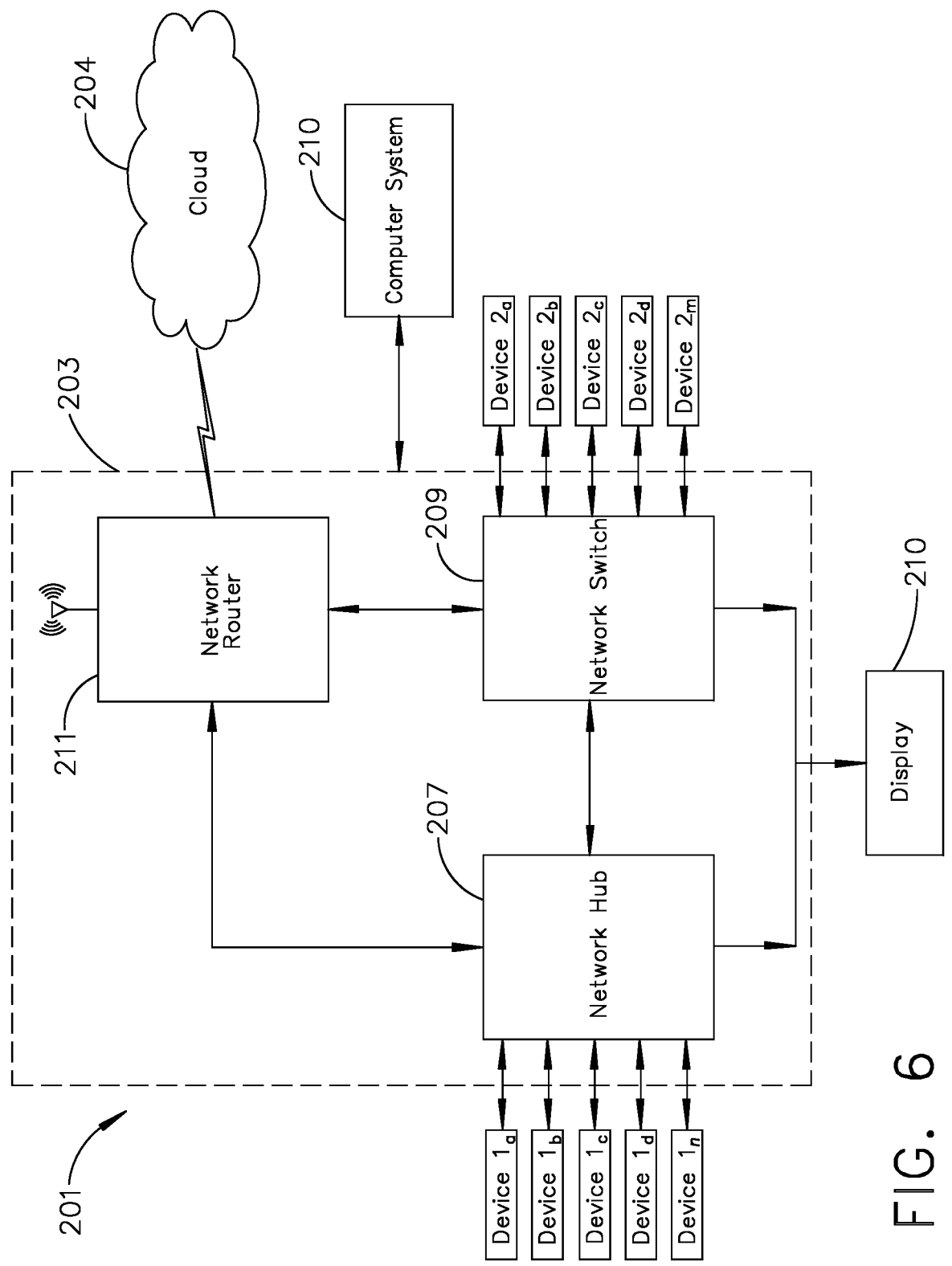
FIG. 6 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 6 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 7) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 7:
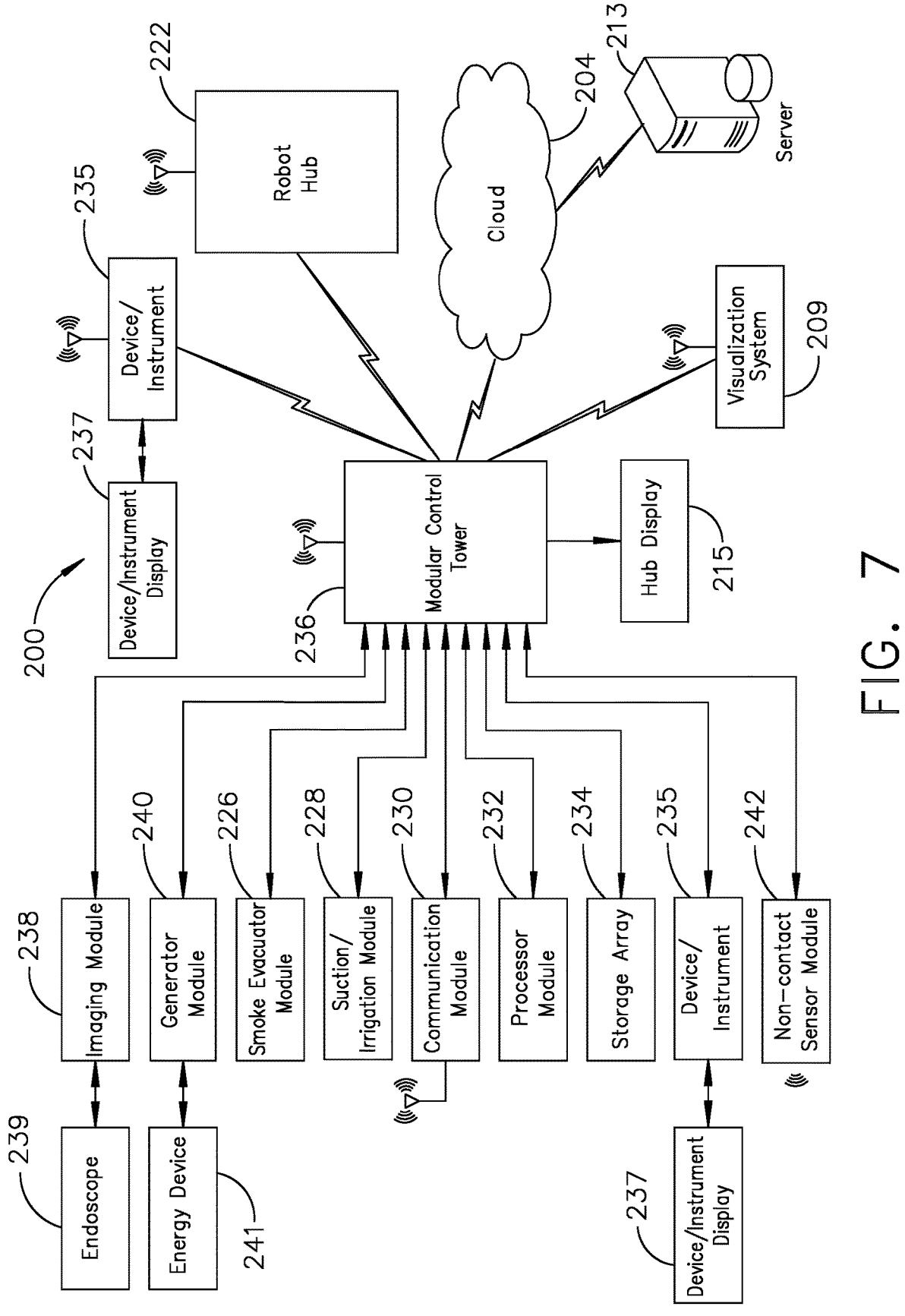
FIG. 7 illustrates a computer-implemented interactive surgical system, in accordance with at least one aspect of the present disclosure.
Figure 8:
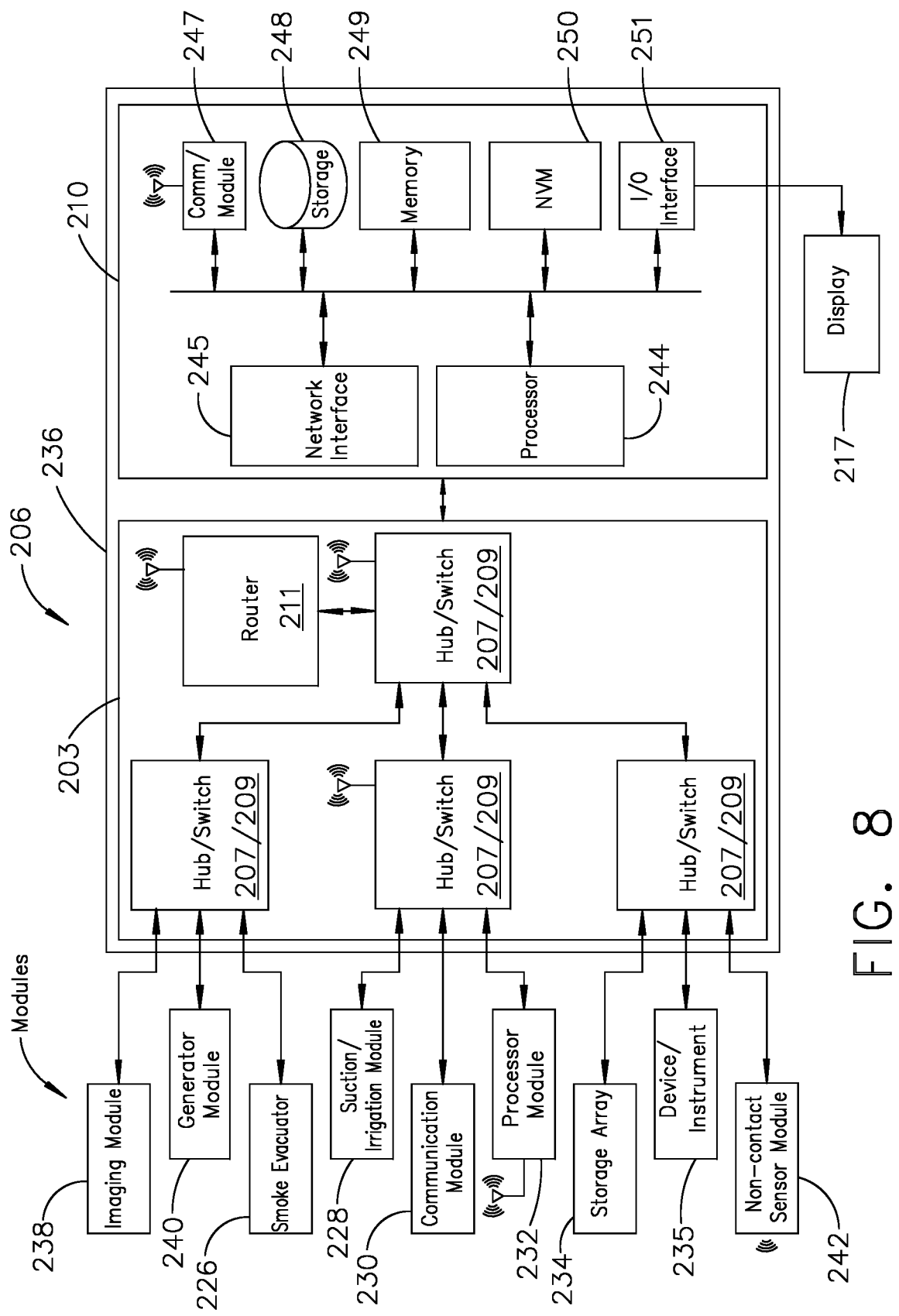
FIG. 8 illustrates a surgical hub comprising a plurality of modules coupled to the modular control tower, in accordance with at least one aspect of the present disclosure.

FIG. 7 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 8, the modular control tower 236 comprises a modular communication hub 203 coupled to a computer system 210. As illustrated in the example of FIG. 7, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 8 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 8, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 8, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

Figure 9:
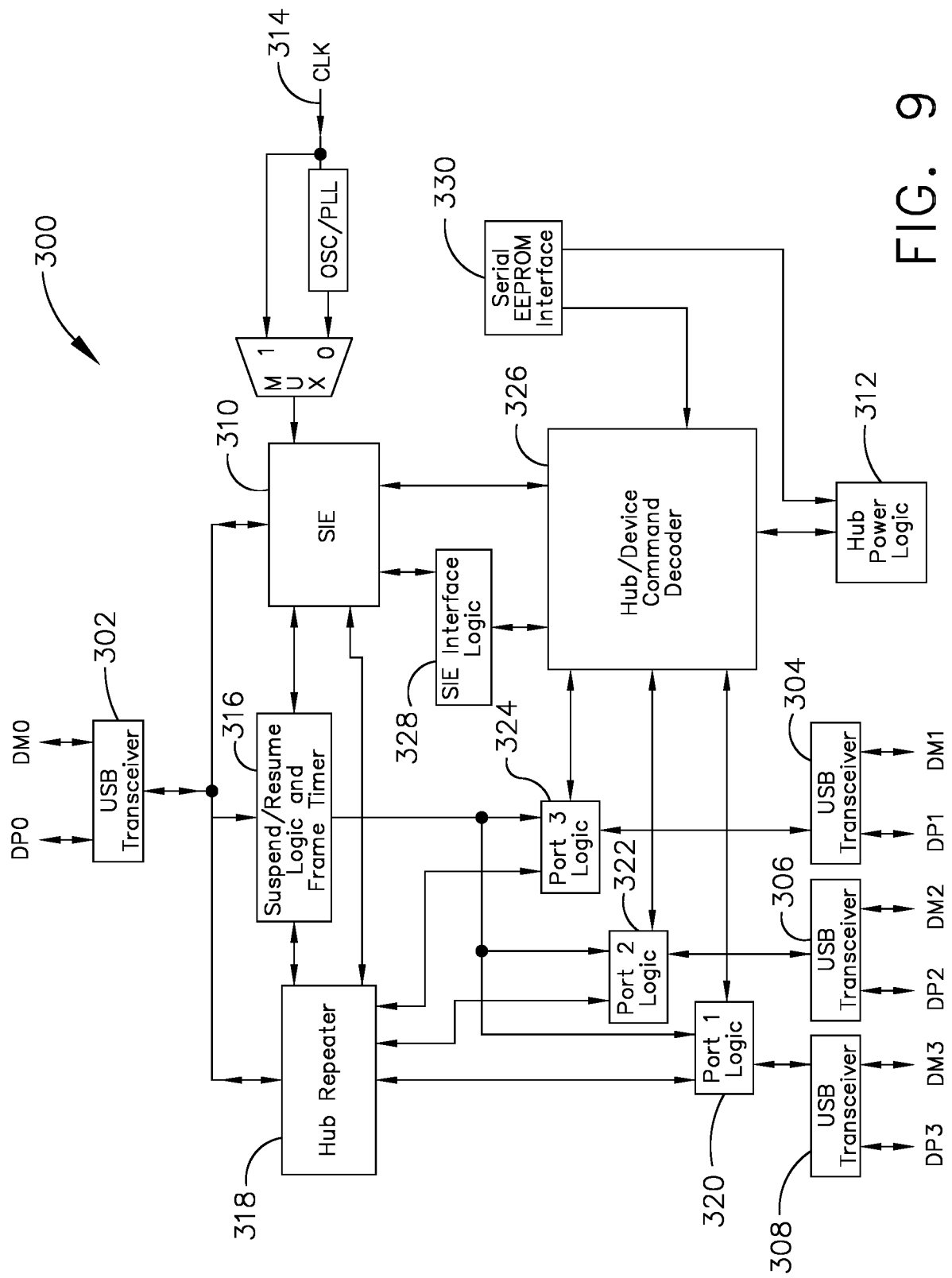
FIG. 9 illustrates one aspect of a Universal Serial Bus (USB) network hub device, in accordance with at least one aspect of the present disclosure.
Figure 10:
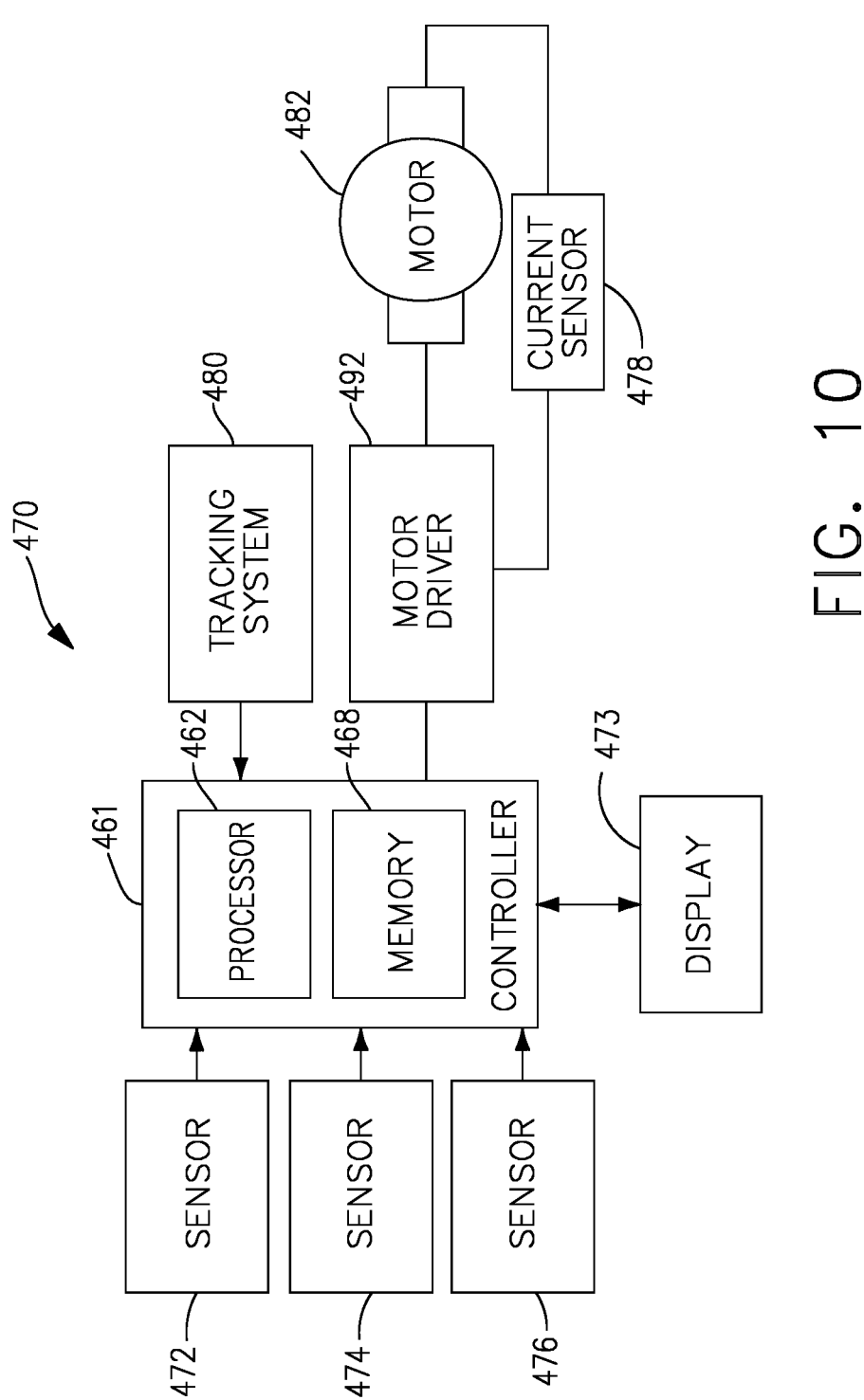
FIG. 10 illustrates a logic diagram of a control system of a surgical instrument or tool, in accordance with at least one aspect of the present disclosure.

In various aspects, the computer system 210 of FIG. 8, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

FIG. 9 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

FIG. 10 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive a clamp arm closure member. A tracking system 480 is configured to determine the position of the longitudinally movable displacement member. The position information is provided to the processor 462, which can be programmed or configured to determine the position of the longitudinally movable drive member as well as the position of the closure member. Additional motors may be provided at the tool driver interface to control closure tube travel, shaft rotation, articulation, or clamp arm closure, or a combination of the above. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife, articulation systems, clamp arm, or a combination of the above. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable battery cells. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a longitudinal displacement member to open and close a clamp arm, which can be adapted and configured to include a rack of drive teeth. In other aspects, the displacement member represents a clamp arm closure member configured to close and to open a clamp arm of a stapler, ultrasonic, or electrosurgical device, or combinations of the above. Accordingly, as used herein, the term displacement member is used generically to refer to any movable member of the surgical instrument or tool such as the drive member, the clamp arm, or any element that can be displaced. Accordingly, the absolute positioning system can, in effect, track the displacement of the clamp arm by tracking the linear displacement of the longitudinally movable drive member.

In other aspects, the absolute positioning system can be configured to track the position of a clamp arm in the process of closing or opening. In various other aspects, the displacement member may be coupled to any position sensor 472 suitable for measuring linear displacement. Thus, the longitudinally movable drive member, or clamp arm, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member to open and close a clamp arm.

A single revolution of the sensor element associated with the position sensor 472 is equivalent to a longitudinal linear displacement $d_1$ of the of the displacement member, where $d_1$ is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement $d_1+d_2+ \ldots d_n$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the micro-controller 461. The position sensor 472 provides 12 or 14 bits of resolution. The position sensor 472 may be an AS5055 chip provided in a small QFN 16-pin 4×4×0.85 mm package.

The tracking system 480 comprising an absolute position-ing system may comprise and/or be programmed to imple-ment a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICK-NESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SEN-SOR SYSTEM, which published on Sep. 18, 2014, which is herein incorporated by reference in its entirety; and U.S. patent application Ser. No. 15/628,175, titled TECH-NIQUES FOR ADAPTIVE CONTROL OF MOTOR VELOCITY OF A SURGICAL STAPLING AND CUT-TING INSTRUMENT, filed Jun. 20, 2017, which is herein incorporated by reference in its entirety. In a digital signal processing system, an absolute positioning system is coupled to a digital data acquisition system where the output of the absolute positioning system will have a finite reso-lution and sampling frequency. The absolute positioning system may comprise a compare-and-combine circuit to combine a computed response with a measured response using algorithms, such as a weighted average and a theo-retical control loop, that drive the computed response towards the measured response. The computed response of the physical system takes into account properties like mass, inertia, viscous friction, inductance resistance, etc., to pre-dict what the states and outputs of the physical system will be by knowing the input.

The absolute positioning system provides an absolute position of the displacement member upon power-up of the instrument, without retracting or advancing the displace-ment member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamp-ing operation, which can be indicative of the closure forces applied to the anvil. The measured strain is converted to a digital signal and provided to the processor 462. Alterna-tively, or in addition to the sensor 474, a sensor 476, such as, for example, a load sensor, can measure the closure force applied by the closure drive system to the anvil in a stapler or a clamp arm in an ultrasonic or electrosurgical instrument. The sensor 476, such as, for example, a load sensor, can measure the firing force applied to a closure member coupled to a clamp arm of the surgical instrument or tool or the force applied by a clamp arm to tissue located in the jaws of an ultrasonic or electrosurgical instrument. Alternatively, a current sensor 478 can be employed to measure the current drawn by the motor 482. The displacement member also may be configured to engage a clamp arm to open or close the clamp arm. The force sensor may be configured to measure the clamping force on tissue. The force required to advance the displacement member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping opera-tion, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A load sensor 476 can measure the force used to operate the clamp arm element, for example, to capture tissue between the clamp arm and an ultrasonic blade or to capture tissue between the clamp arm and a jaw of an electrosurgical instrument. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corre-sponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 11:
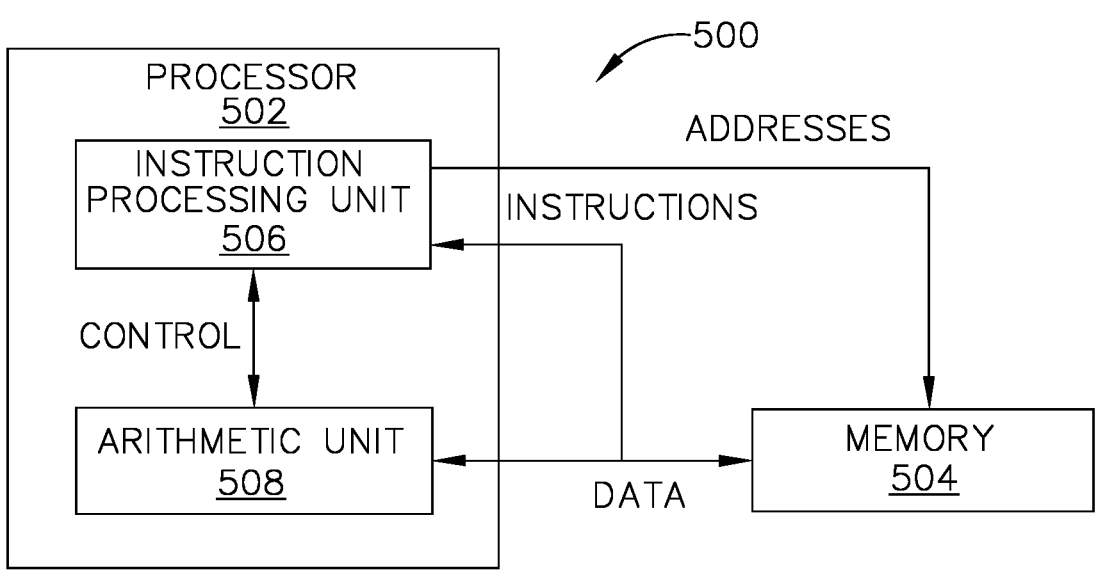
FIG. 11 illustrates a control circuit configured to control aspects of the surgical instrument or tool, in accordance with at least one aspect of the present disclosure.

FIG. 11 illustrates a control circuit 500 configured to control aspects of the surgical instrument or tool according to one aspect of this disclosure. The control circuit 500 can be configured to implement various processes described herein. The control circuit 500 may comprise a microcon-troller comprising one or more processors 502 (e.g., micro-processor, microcontroller) coupled to at least one memory circuit 504. The memory circuit 504 stores machine-execut-able instructions that, when executed by the processor 502, cause the processor 502 to execute machine instructions to implement various processes described herein. The proces-sor 502 may be any one of a number of single-core or multicore processors known in the art. The memory circuit 504 may comprise volatile and non-volatile storage media. The processor 502 may include an instruction processing unit 506 and an arithmetic unit 508. The instruction pro-cessing unit may be configured to receive instructions from the memory circuit 504 of this disclosure.

Figure 12:
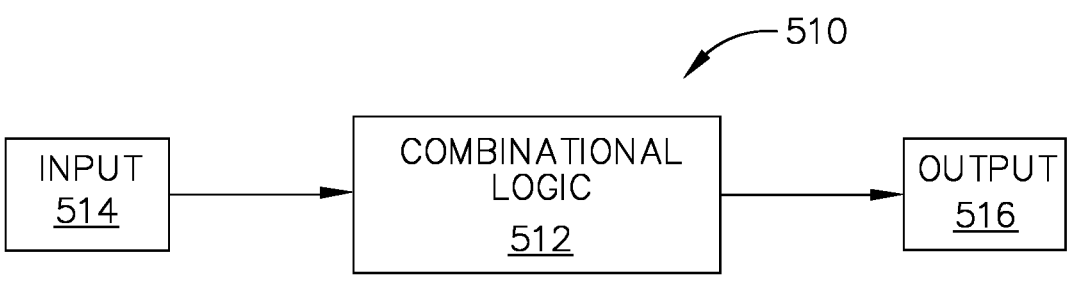
FIG. 12 illustrates a combinational logic circuit configured to control aspects of the surgical instrument or tool, in accordance with at least one aspect of the present disclosure.

FIG. 12 illustrates a combinational logic circuit 510 configured to control aspects of the surgical instrument or tool according to one aspect of this disclosure. The combi-national logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 13:
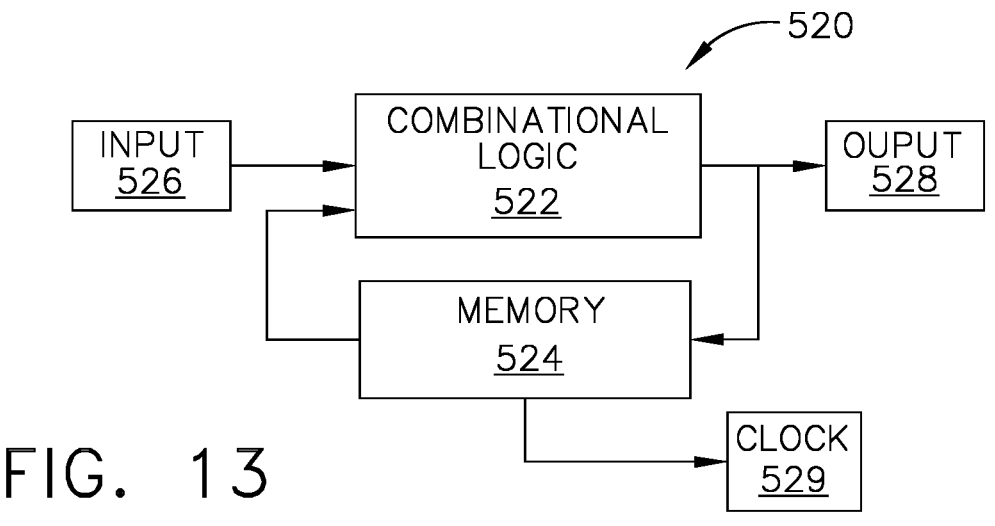
FIG. 13 illustrates a sequential logic circuit configured to control aspects of the surgical instrument or tool, in accordance with at least one aspect of the present disclosure.

FIG. 13 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 11) and a finite state machine to implement various processes herein. In other aspects, the finite state machine may comprise a combination of a combinational logic circuit (e.g., combinational logic circuit 510, FIG. 12) and the sequential logic circuit 520.

Figure 14:
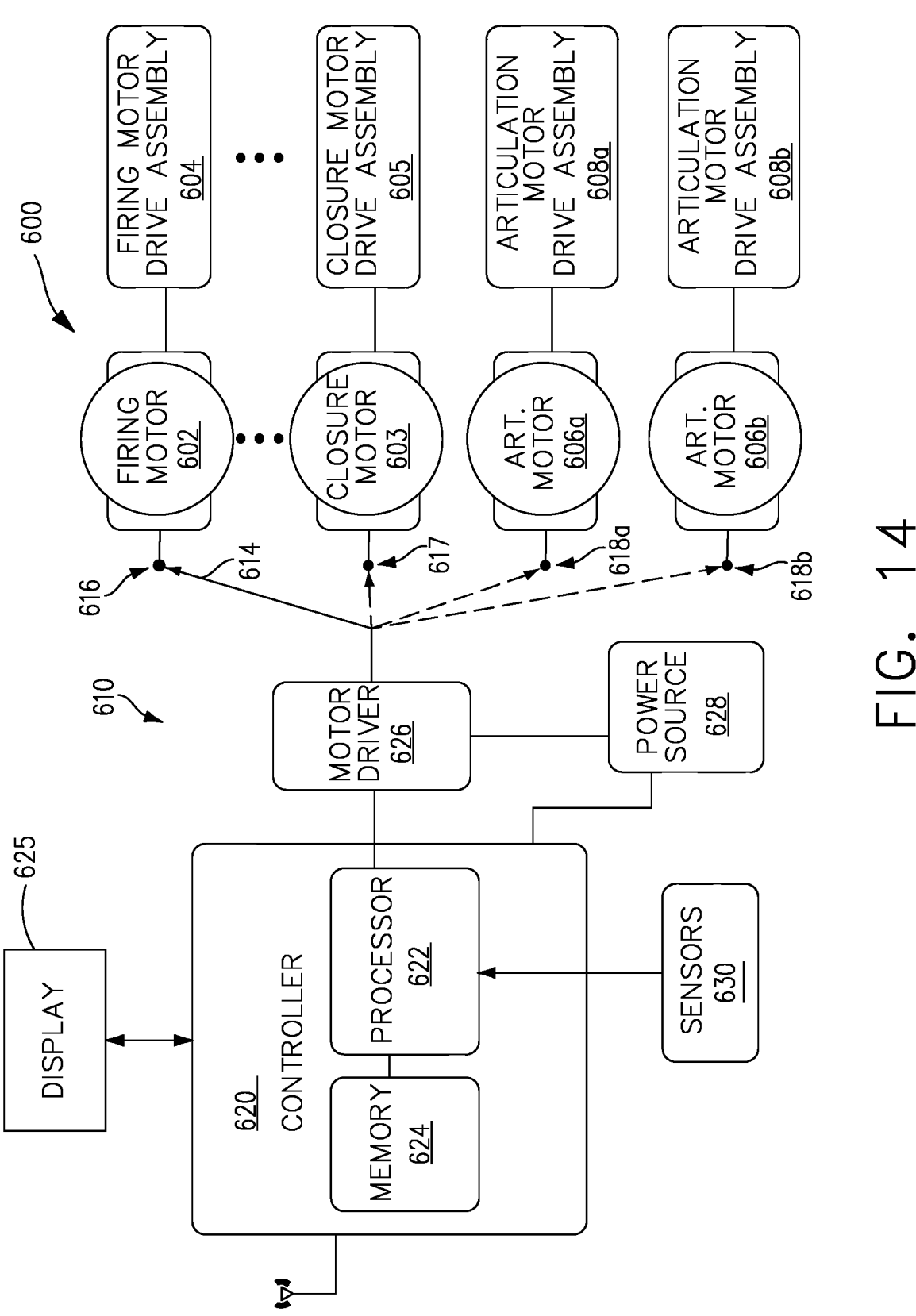
FIG. 14 illustrates a surgical instrument or tool comprising a plurality of motors which can be activated to perform various functions, in accordance with at least one aspect of the present disclosure.

FIG. 14 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the clamp arm closure member. The closure member may be retracted by reversing the direction of the motor 602, which also causes the clamp arm to open.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motor 603 may be operably coupled to a closure motor drive assembly 605 which can be configured to transmit closure motions, generated by the motor 603 to the end effector, in particular to displace a closure tube to close the clamp arm and compress tissue between the clamp arm and either an ultrasonic blade or jaw member of an electrosurgical device. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606*a*, 606*b*, for example. The motors 606*a*, 606*b* may be operably coupled to respective articulation motor drive assemblies 608*a*, 608*b*, which can be configured to transmit articulation motions generated by the motors 606*a*, 606*b* to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606*a*, 606*b* can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube or closure member to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606*a*, 606*b* and operable engagement with either the firing motor 602 or the closure motor 603. In at least one example, as illustrated in FIG. 14, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618*a*, the switch 614 may electrically couple the common control module 610 to the first articulation motor 606*a*; and in a fourth position 618*b*, the switch 614 may electrically couple the common control module 610 to the second articulation motor 606*b*, for example. In certain instances, separate common control modules 610 can be electrically coupled to the firing motor 602, the closure motor 603, and the articulations motor 606*a*, 606*b* at the same time. In certain instances, the switch 614 may be a mechanical switch, an electromechanical switch, a solid-state switch, or any suitable switching mechanism.

Each of the motors 602, 603, 606*a*, 606*b* may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 14, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example. In various aspects, the microcontroller 620 may communicate over a wired or wireless channel, or combinations thereof.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 622 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet.

Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606*a*, 606*b*. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the closure member coupled to the clamp arm of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618*a*, 618*b*.

Figure 15:
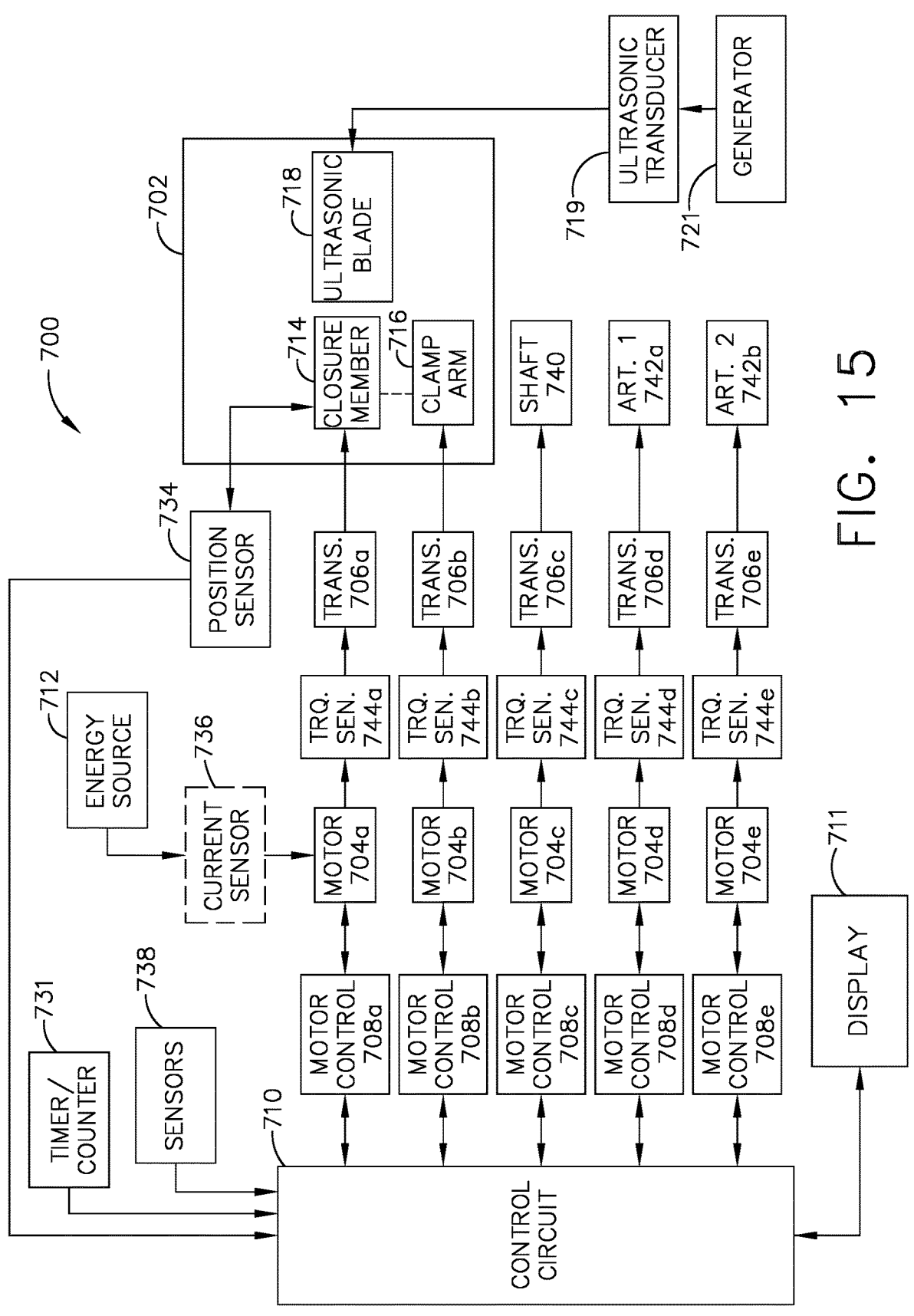
FIG. 15 is a schematic diagram of a robotic surgical instrument configured to operate a surgical tool described herein, in accordance with at least one aspect of the present disclosure.

FIG. 15 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742*a*, 742*b* via a plurality of motors 704*a*-704*e*. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704*a*-704*e*, and a current sensor 736 provides motor current feedback to the control circuit 710. The motors 704*a*-704*e* can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the closure member 714, clamp arm 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708b. In response to the closure signal, the motor 704b advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704*a*-704*e*. The force required to advance any of the movable mechanical elements such as the closure member 714 corresponds to the current drawn by one of the motors 704*a*-704*e*. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, now U.S. Patent Application Publication No. 2019/0000466, which is herein incorporated by reference in its entirety.

Figure 16:
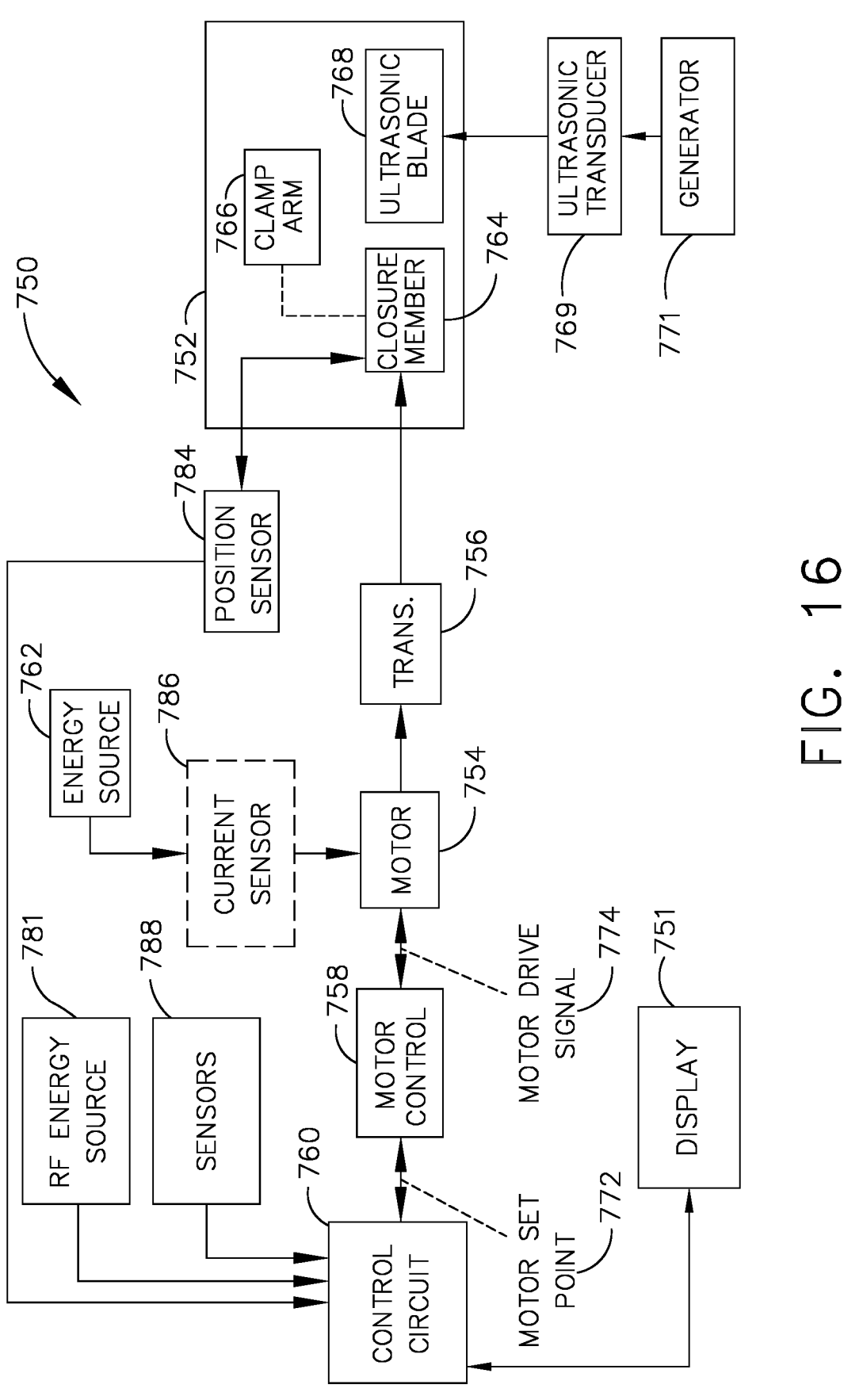
FIG. 16 illustrates a block diagram of a surgical instrument programmed to control the distal translation of a displacement member, in accordance with at least one aspect of the present disclosure.

FIG. 16 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which issued on Aug. 18, 2020 as U.S. Pat. No. 10,743,872, which is herein incorporated by reference in its entirety.

Figure 17:
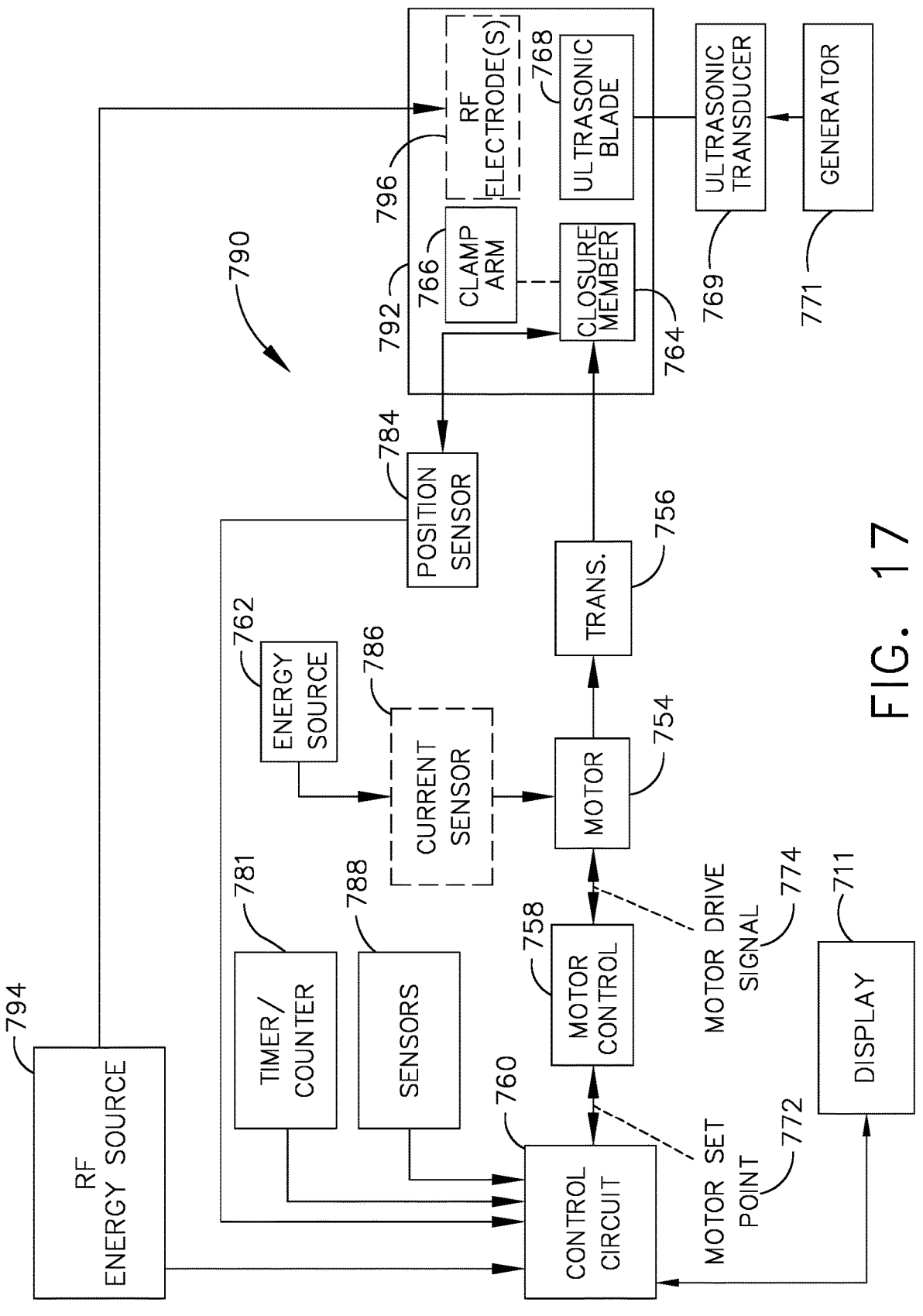
FIG. 17 is a schematic diagram of a surgical instrument configured to control various functions, in accordance with at least one aspect of the present disclosure.

FIG. 17 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOS-FET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, now U.S. Patent Application Publication No. 2019/0000478, which is herein incorporated by reference in its entirety.

Generator Hardware

Adaptive Ultrasonic Blade Control Algorithms

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 1-106, for example. Accordingly, the following description of adaptive ultrasonic blade control algorithms should be read in conjunction with FIGS. 1-106 and the description associated therewith.

Tissue Type Identification And Device Parameter Adjustments

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

Figure 18:
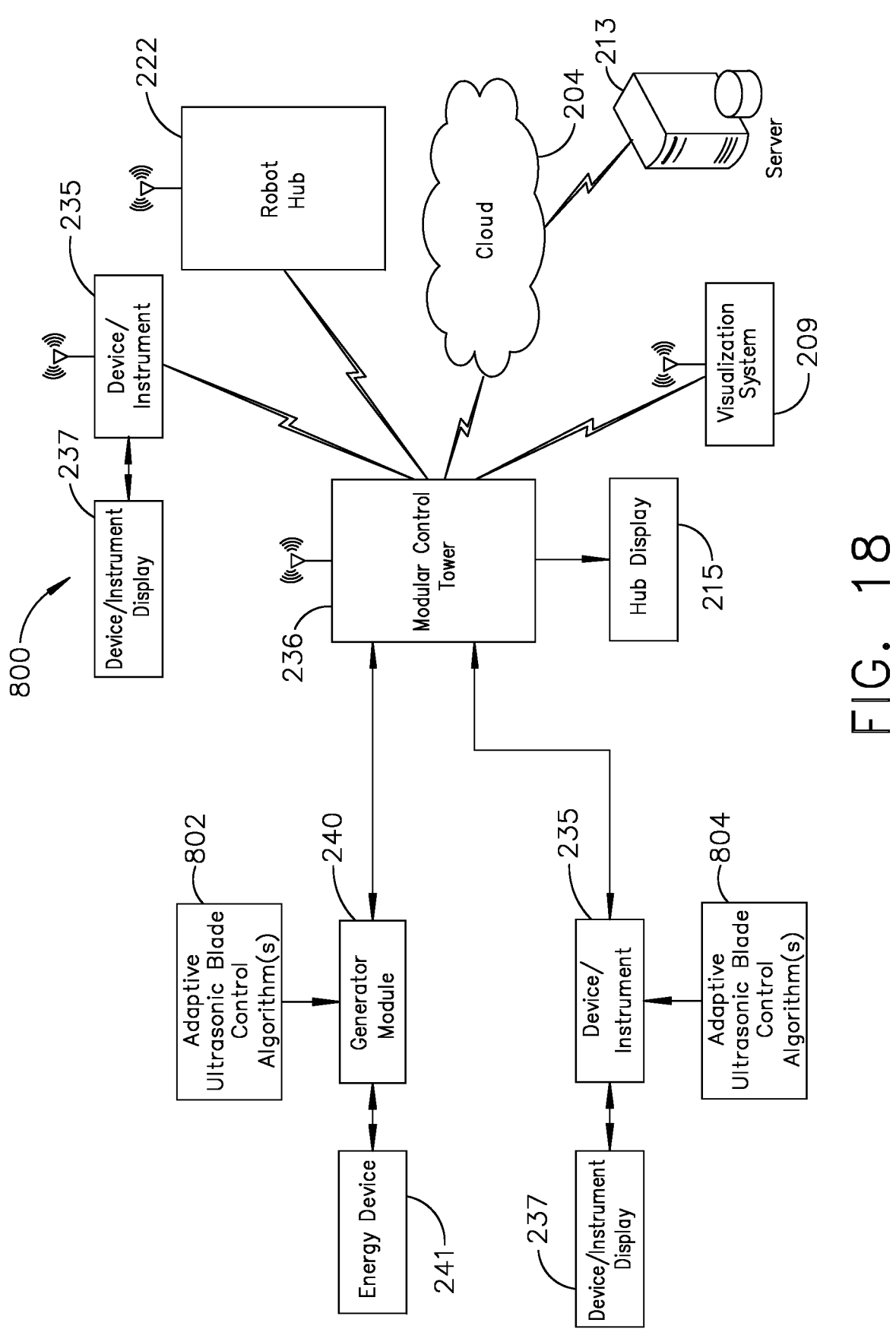
FIG. 18 is a system configured to execute adaptive ultrasonic blade control algorithms in a surgical data network comprising a modular communication hub, in accordance with at least one aspect of the present disclosure.

FIG. 18 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802 as described herein with reference to FIGS. 53-105. In another aspect, the device/instrument 235 is configured to execute the adaptive ultrasonic blade control algorithm(s) 804 as described herein with reference to FIGS. 53-105. In another aspect, both the device/instrument 235 and the device/instrument 235 are configured to execute the adaptive ultrasonic blade control algorithms 802, 804 as described herein with reference to FIGS. 53-105.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 21-25B.

The generator module 240 or the device/instrument 235 or both are coupled to the modular control tower 236 connected to multiple operating theater devices such as, for example, intelligent surgical instruments, robots, and other computerized devices located in the operating theater, as described with reference to FIGS. 8-11, for example.

Figure 19:
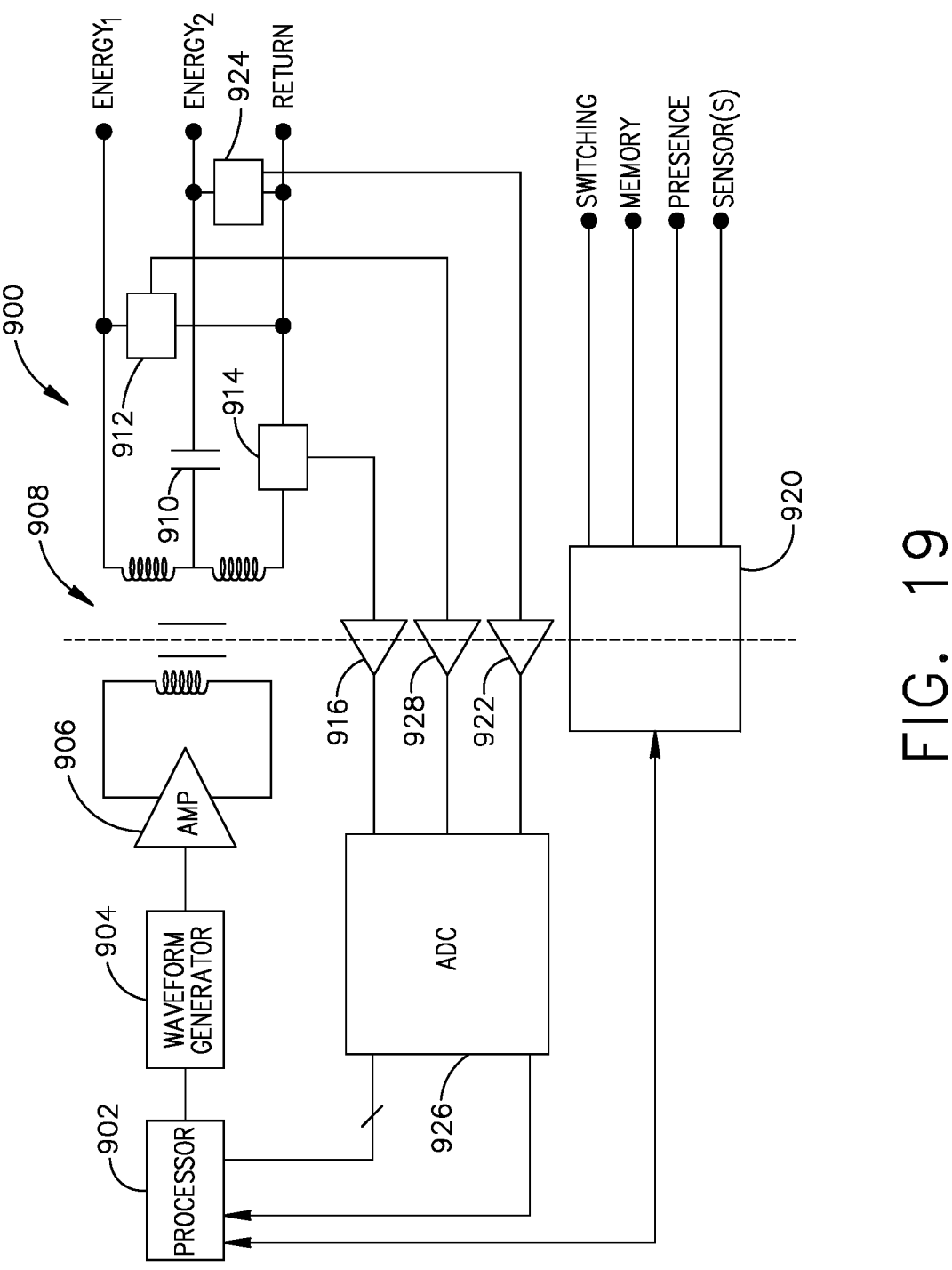
FIG. 19 illustrates an example of a generator, in accordance with at least one aspect of the present disclosure.

FIG. 19 illustrates an example of a generator 900, which is one form of a generator configured to couple to an ultrasonic instrument and further configured to execute adaptive ultrasonic blade control algorithms in a surgical data network comprising a modular communication hub as shown in FIG. 18. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY$_1$ and RETURN. A second signal of a second energy modality is coupled across a capacitor 910 and is provided to the surgical instrument between the terminals labeled ENERGY$_2$ and RETURN. It will be appreciated that more than two energy modalities may be output and thus the subscript "n" may be used to designate that up to n ENERGY$_n$ terminals may be provided, where n is a positive integer greater than 1. It also will be appreciated that up to "n" return paths RETURN$_n$ may be provided without departing from the scope of the present disclosure.

A first voltage sensing circuit 912 is coupled across the terminals labeled ENERGY$_1$ and the RETURN path to measure the output voltage therebetween. A second voltage sensing circuit 924 is coupled across the terminals labeled ENERGY$_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY$_1$/RETURN or the second voltage sensing circuit 924 coupled across the terminals labeled ENERGY$_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY$_1$ may be ultrasonic energy and the second energy modality $ENERGY_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 19 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 19, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 19. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, now U.S. Pat. No. 10,624,691, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 20:
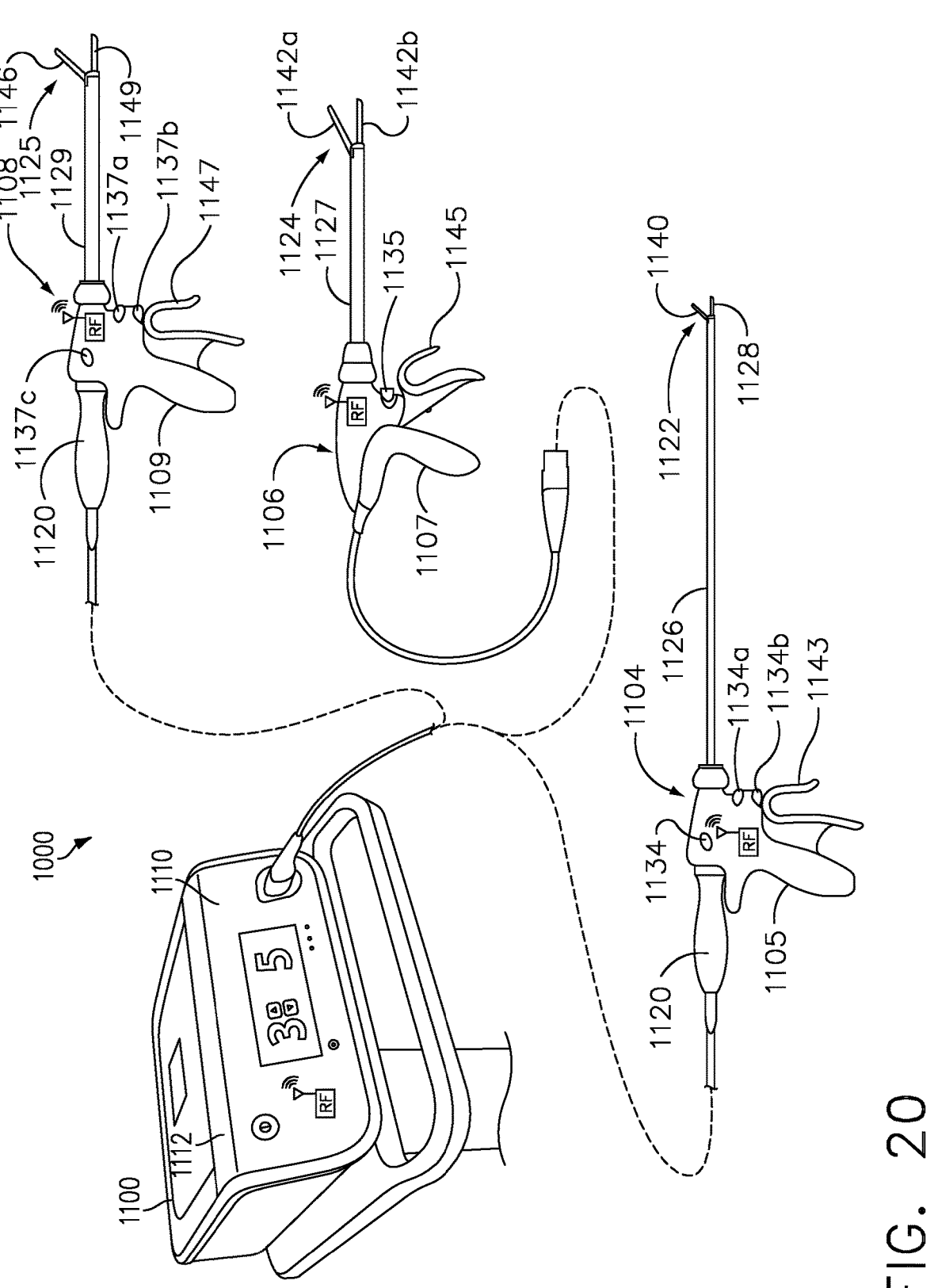
FIG. 20 is a surgical system comprising a generator and various surgical instruments usable therewith, in accordance with at least one aspect of the present disclosure.

FIG. 20 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 20 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134a, 1134b, 1134c to energize and drive the ultrasonic blade 1128 or other function. The toggle buttons 1134a, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142a, 1142b and return through an electrical conductor portion of the shaft 1127. The electrodes are coupled to and energized by a bipolar energy source within the generator 1100. The handpiece 1107 comprises a trigger 1145 to operate the clamp arms 1142a, 1142b and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137a, 1137b, 1137c to energize and drive the ultrasonic blade 1149 or other function. The toggle buttons 1137a, 1137b, 1137c can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 20 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

Figure 21:
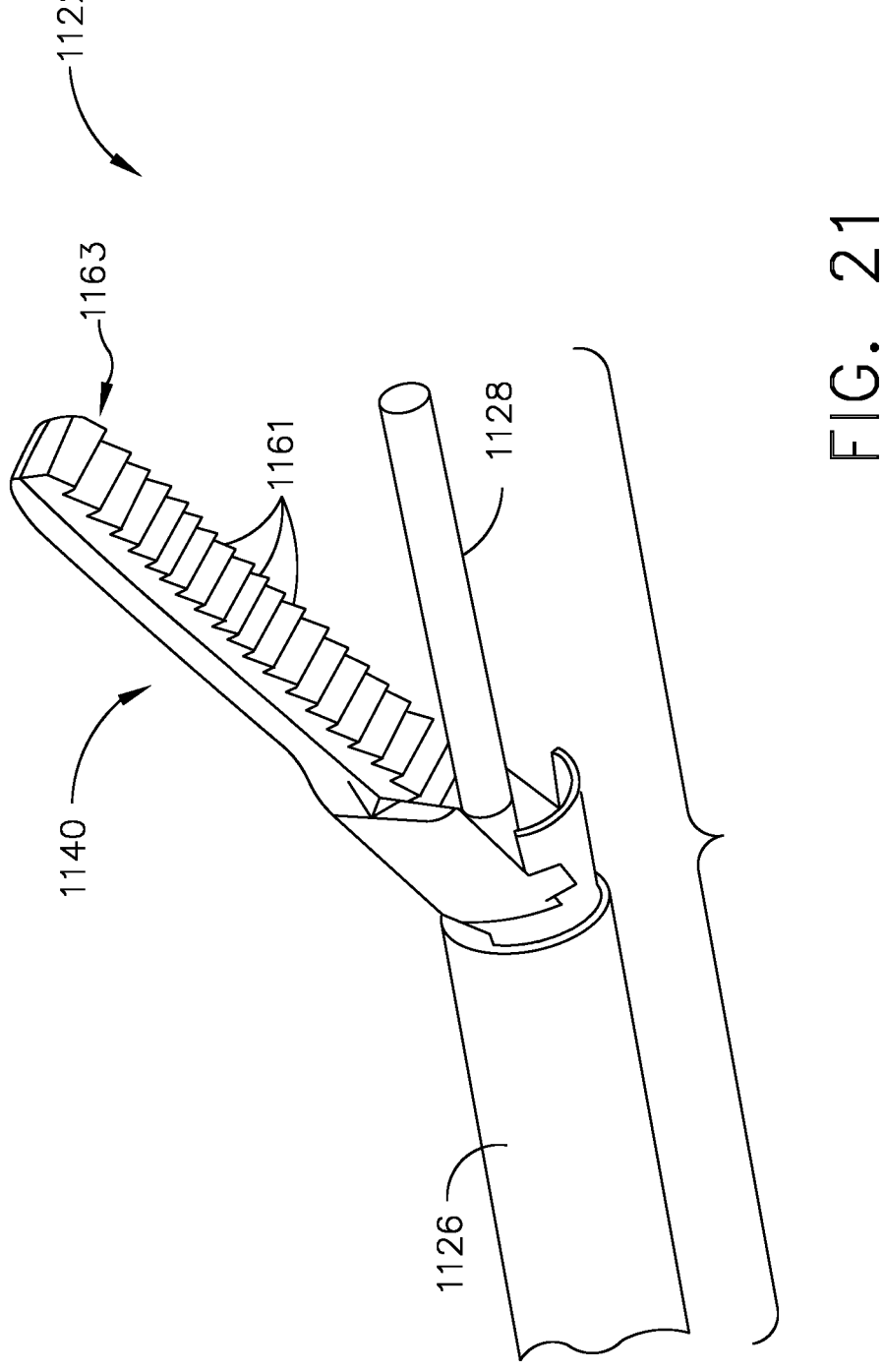
FIG. 21 is an end effector, in accordance with at least one aspect of the present disclosure.

FIG. 21 is an end effector 1122 of the example ultrasonic device 1104, in accordance with at least one aspect of the present disclosure. The end effector 1122 may comprise a blade 1128 that may be coupled to the ultrasonic transducer 1120 via a wave guide. When driven by the ultrasonic transducer 1120, the blade 1128 may vibrate and, when brought into contact with tissue, may cut and/or coagulate the tissue, as described herein. According to various aspects, and as illustrated in FIG. 21, the end effector 1122 may also comprise a clamp arm 1140 that may be configured for cooperative action with the blade 1128 of the end effector 1122. With the blade 1128, the clamp arm 1140 may comprise a set of jaws. The clamp arm 1140 may be pivotally connected at a distal end of a shaft 1126 of the instrument portion 1104. The clamp arm 1140 may include a clamp arm tissue pad 1163, which may be formed from TEFLON® or other suitable low-friction material. The pad 1163 may be mounted for cooperation with the blade 1128, with pivotal movement of the clamp arm 1140 positioning the clamp pad 1163 in substantially parallel relationship to, and in contact with, the blade 1128. By this construction, a tissue bite to be clamped may be grasped between the tissue pad 1163 and the blade 1128. The tissue pad 1163 may be provided with a sawtooth-like configuration including a plurality of axially spaced, proximally extending gripping teeth 1161 to enhance the gripping of tissue in cooperation with the blade 1128. The clamp arm 1140 may transition from the open position shown in FIG. 21 to a closed position (with the clamp arm 1140 in contact with or proximity to the blade 1128) in any suitable manner. For example, the handpiece 1105 may comprise a jaw closure trigger. When actuated by a clinician, the jaw closure trigger may pivot the clamp arm 1140 in any suitable manner.

The generator 1100 may be activated to provide the drive signal to the ultrasonic transducer 1120 in any suitable manner. For example, the generator 1100 may comprise a foot switch 1430 (FIG. 24) coupled to the generator 1100 via a footswitch cable 1432. A clinician may activate the ultrasonic transducer 1120, and thereby the ultrasonic transducer 1120 and blade 1128, by depressing the foot switch 1430. In addition, or instead of the foot switch 1430, some aspects of the device 1104 may utilize one or more switches positioned on the handpiece 1105 that, when activated, may cause the generator 1100 to activate the ultrasonic transducer 1120. In one aspect, for example, the one or more switches may comprise a pair of toggle buttons 1134a, 1134b, 1134c (FIG. 20), for example, to determine an operating mode of the device 1104. When the toggle button 1134a is depressed, for example, the ultrasonic generator 1100 may provide a maximum drive signal to the ultrasonic transducer 1120, causing it to produce maximum ultrasonic energy output. Depressing toggle button 1134b may cause the ultrasonic generator 1100 to provide a user-selectable drive signal to the ultrasonic transducer 1120, causing it to produce less than the maximum ultrasonic energy output. The device 1104 additionally or alternatively may comprise a second switch to, for example, indicate a position of a jaw closure trigger for operating the jaws via the clamp arm 1140 of the end effector 1122. Also, in some aspects, the ultrasonic generator 1100 may be activated based on the position of the jaw closure trigger, (e.g., as the clinician depresses the jaw closure trigger to close the jaws via the clamp arm 1140, ultrasonic energy may be applied).

Additionally or alternatively, the one or more switches may comprise a toggle button 1134c that, when depressed, causes the generator 1100 to provide a pulsed output (FIG. 20). The pulses may be provided at any suitable frequency and grouping, for example. In certain aspects, the power level of the pulses may be the power levels associated with toggle buttons 1134a, 1134b (maximum, less than maximum), for example.

It will be appreciated that a device 1104 may comprise any combination of the toggle buttons 1134a, 1134b, 1134c (FIG. 20). For example, the device 1104 could be configured to have only two toggle buttons: a toggle button 1134a for producing maximum ultrasonic energy output and a toggle button 1134c for producing a pulsed output at either the maximum or less than maximum power level per. In this way, the drive signal output configuration of the generator 1100 could be five continuous signals, or any discrete number of individual pulsed signals (1, 2, 3, 4, or 5). In certain aspects, the specific drive signal configuration may be controlled based upon, for example, EEPROM settings in the generator 1100 and/or user power level selection(s).

In certain aspects, a two-position switch may be provided as an alternative to a toggle button 1134c (FIG. 20). For example, a device 1104 may include a toggle button 1134a for producing a continuous output at a maximum power level and a two-position toggle button 1134b. In a first detented position, toggle button 1134b may produce a continuous output at a less than maximum power level, and in a second detented position the toggle button 1134b may produce a pulsed output (e.g., at either a maximum or less than maximum power level, depending upon the EEPROM settings).

In some aspects, the RF electrosurgical end effector 1124, 1125 (FIG. 20) may also comprise a pair of electrodes. The electrodes may be in communication with the generator 1100, for example, via a cable. The electrodes may be used, for example, to measure an impedance of a tissue bite present between the clamp arm 1142a, 1146 and the blade 1142b, 1149. The generator 1100 may provide a signal (e.g., a non-therapeutic signal) to the electrodes. The impedance of the tissue bite may be found, for example, by monitoring the current, voltage, etc. of the signal.

In accordance with the described aspects, the ultrasonic generator module may produce a drive signal or signals of particular voltages, currents, and frequencies (e.g. 55,500 cycles per second, or Hz). The drive signal or signals may be provided to the ultrasonic device 1104, and specifically to the transducer 1120, which may operate, for example, as described above. In one aspect, the generator 1100 may be configured to produce a drive signal of a particular voltage, current, and/or frequency output signal that can be stepped with high resolution, accuracy, and repeatability.

In accordance with the described aspects, the electrosurgery/RF generator module may generate a drive signal or signals with output power sufficient to perform bipolar electrosurgery using radio frequency (RF) energy. In bipolar electrosurgery applications, the drive signal may be provided, for example, to the electrodes of the electrosurgical device 1106, for example, as described above. Accordingly, the generator 1100 may be configured for therapeutic purposes by applying electrical energy to the tissue sufficient for treating the tissue (e.g., coagulation, cauterization, tissue welding, etc.).

The generator 1100 may comprise an input device 2150 (FIG. 24B) located, for example, on a front panel of the generator 1100 console. The input device 2150 may comprise any suitable device that generates signals suitable for programming the operation of the generator 1100. In operation, the user can program or otherwise control operation of the generator 1100 using the input device 2150. The input device 2150 may comprise any suitable device that generates signals that can be used by the generator (e.g., by one or more processors contained in the generator) to control operation of the generator 1100 (e.g., operation of the ultrasonic generator module and/or electrosurgery/RF generator module). In various aspects, the input device 2150 includes one or more of: buttons, switches, thumbwheels, keyboard, keypad, touch screen monitor, pointing device, remote connection to a general purpose or dedicated computer. In other aspects, the input device 2150 may comprise a suitable user interface, such as one or more user interface screens displayed on a touch screen monitor, for example. Accordingly, by way of the input device 2150, the user can set or program various operating parameters of the generator, such as, for example, current (I), voltage (V), frequency (f), and/or period (T) of a drive signal or signals generated by the ultrasonic generator module and/or electrosurgery/RF generator module.

The generator 1100 may also comprise an output device 2140 (FIG. 24B) located, for example, on a front panel of the generator 1100 console. The output device 2140 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators).

Although certain modules and/or blocks of the generator 1100 may be described by way of example, it can be appreciated that a greater or lesser number of modules and/or blocks may be used and still fall within the scope of the aspects. Further, although various aspects may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one aspect, the ultrasonic generator drive module and electrosurgery/RF drive module 1110 (FIG. 20) may comprise one or more embedded applications implemented as firmware, software, hardware, or any combination thereof. The modules may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one aspect, the modules comprise a hardware component implemented as a processor for executing program instructions for monitoring various measurable characteristics of the devices 1104, 1106, 1108 and generating a corresponding output drive signal or signals for operating the devices 1104, 1106, 1108. In aspects in which the generator 1100 is used in conjunction with the device 1104, the drive signal may drive the ultrasonic transducer 1120 in cutting and/or coagulation operating modes. Electrical characteristics of the device 1104 and/or tissue may be measured and used to control operational aspects of the generator 1100 and/or provided as feedback to the user. In aspects in which the generator 1100 is used in conjunction with the device 1106, the drive signal may supply electrical energy (e.g., RF energy) to the end effector 1124 in cutting, coagulation and/or desiccation modes. Electrical characteristics of the device 1106 and/or tissue may be measured and used to control operational aspects of the generator 1100 and/or provided as feedback to the user. In various aspects, as previously discussed, the hardware components may be implemented as DSP, PLD, ASIC, circuits, and/or registers. In one aspect, the processor may be configured to store and execute computer software program instructions to generate the step function output signals for driving various components of the devices 1104, 1106, 1108, such as the ultrasonic transducer 1120 and the end effectors 1122, 1124, 1125.

An electromechanical ultrasonic system includes an ultrasonic transducer, a waveguide, and an ultrasonic blade. The electromechanical ultrasonic system has an initial resonant frequency defined by the physical properties of the ultrasonic transducer, the waveguide, and the ultrasonic blade. The ultrasonic transducer is excited by an alternating voltage $V_g(t)$ and current $I_g(t)$ signal equal to the resonant frequency of the electromechanical ultrasonic system. When the electromechanical ultrasonic system is at resonance, the phase difference between the voltage $V_g(t)$ and current $I_g(t)$ signals is zero. Stated another way, at resonance the inductive impedance is equal to the capacitive impedance. As the ultrasonic blade heats up, the compliance of the ultrasonic blade (modeled as an equivalent capacitance) causes the resonant frequency of the electromechanical ultrasonic system to shift. Thus, the inductive impedance is no longer equal to the capacitive impedance causing a mismatch between the drive frequency and the resonant frequency of the electromechanical ultrasonic system. The system is now operating "off-resonance." The mismatch between the drive frequency and the resonant frequency is manifested as a phase difference between the voltage $V_g(t)$ and current $I_g(t)$ signals applied to the ultrasonic transducer. The generator electronics can easily monitor the phase difference between the voltage $V_g(t)$ and current $I_g(t)$ signals and can continuously adjust the drive frequency until the phase difference is once again zero. At this point, the new drive frequency is equal to the new resonant frequency of the electromechanical ultrasonic system. The change in phase and/or frequency can be used as an indirect measurement of the ultrasonic blade temperature.

Figure 22:
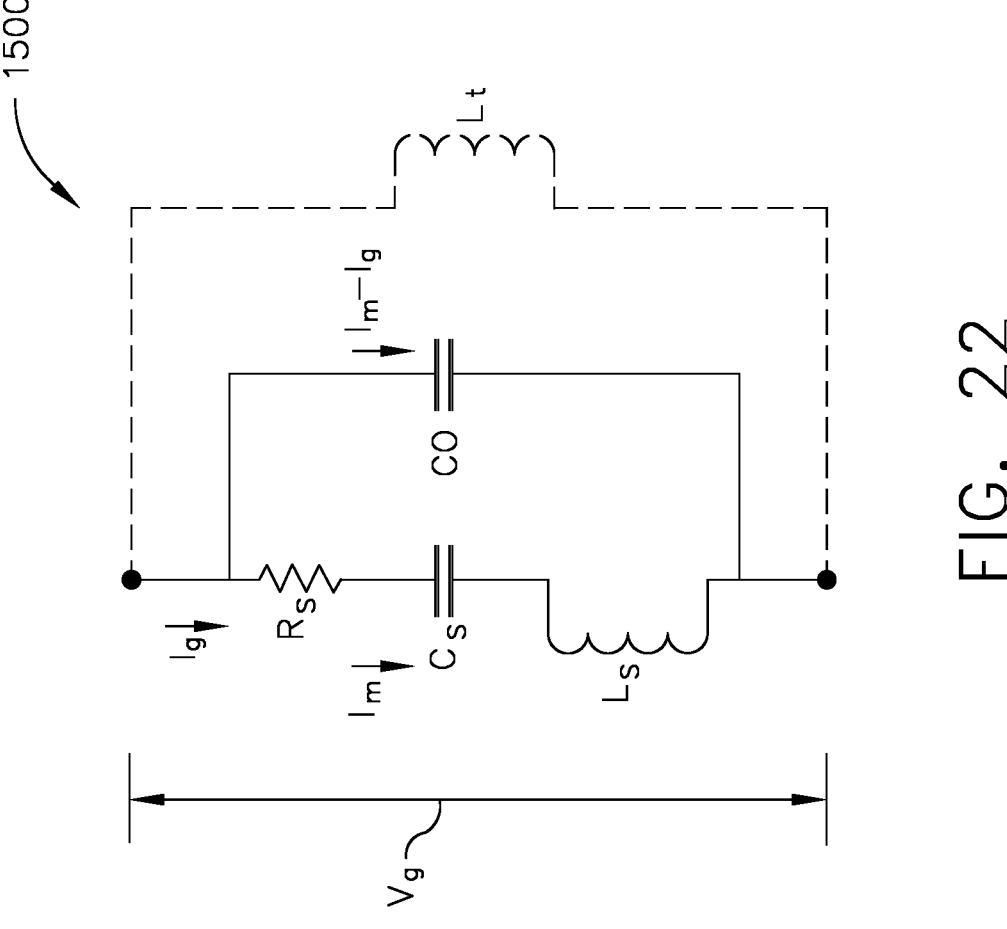
FIG. 22 is a model illustrating motional branch current, in accordance with at least one aspect of the present disclosure.

As shown in FIG. 22, the electromechanical properties of the ultrasonic transducer may be modeled as an equivalent circuit comprising a first branch having a static capacitance and a second "motional" branch having a serially connected inductance, resistance and capacitance that define the electromechanical properties of a resonator. Known ultrasonic generators may include a tuning inductor for tuning out the static capacitance at a resonant frequency so that substantially all of generator's drive signal current flows into the motional branch. Accordingly, by using a tuning inductor, the generator's drive signal current represents the motional branch current, and the generator is thus able to control its drive signal to maintain the ultrasonic transducer's resonant frequency. The tuning inductor may also transform the phase impedance plot of the ultrasonic transducer to improve the generator's frequency lock capabilities. However, the tuning inductor must be matched with the specific static capacitance of an ultrasonic transducer at the operational resonance frequency. In other words, a different ultrasonic transducer having a different static capacitance requires a different tuning inductor.

FIG. 22 illustrates an equivalent circuit 1500 of an ultrasonic transducer, such as the ultrasonic transducer 1120, according to one aspect. The circuit 1500 comprises a first "motional" branch having a serially connected inductance $L_s$, resistance $R_s$ and capacitance $C_s$ that define the electromechanical properties of the resonator, and a second capacitive branch having a static capacitance $C_0$. Drive current $I_g(t)$ may be received from a generator at a drive voltage $V_g(t)$, with motional current $I_m(t)$ flowing through the first branch and current $I_g(t)-I_m(t)$ flowing through the capacitive branch. Control of the electromechanical properties of the ultrasonic transducer may be achieved by suitably controlling $I_g(t)$ and $V_g(t)$. As explained above, known generator architectures may include a tuning inductor $L_t$ (shown in phantom in FIG. 22) in a parallel resonance circuit for tuning out the static capacitance $C_0$ at a resonant frequency so that substantially all of the generator's current output $I_g(t)$ flows through the motional branch. In this way, control of the motional branch current $I_m(t)$ is achieved by controlling the generator current output $I_g(t)$. The tuning inductor $L_t$ is specific to the static capacitance $C_0$ of an ultrasonic transducer, however, and a different ultrasonic transducer having a different static capacitance requires a different tuning inductor $L_t$. Moreover, because the tuning inductor $L_t$ is matched to the nominal value of the static capacitance $C_0$ at a single resonant frequency, accurate control of the motional branch current $I_m(t)$ is assured only at that frequency. As frequency shifts down with transducer temperature, accurate control of the motional branch current is compromised.

Various aspects of the generator 1100 may not rely on a tuning inductor $L_t$ to monitor the motional branch current $I_m(t)$. Instead, the generator 1100 may use the measured value of the static capacitance $C_0$ in between applications of power for a specific ultrasonic surgical device 1104 (along with drive signal voltage and current feedback data) to determine values of the motional branch current $I_m(t)$ on a dynamic and ongoing basis (e.g., in real-time). Such aspects of the generator 1100 are therefore able to provide virtual tuning to simulate a system that is tuned or resonant with any value of static capacitance $C_0$ at any frequency, and not just at a single resonant frequency dictated by a nominal value of the static capacitance $C_0$.

Figure 23:
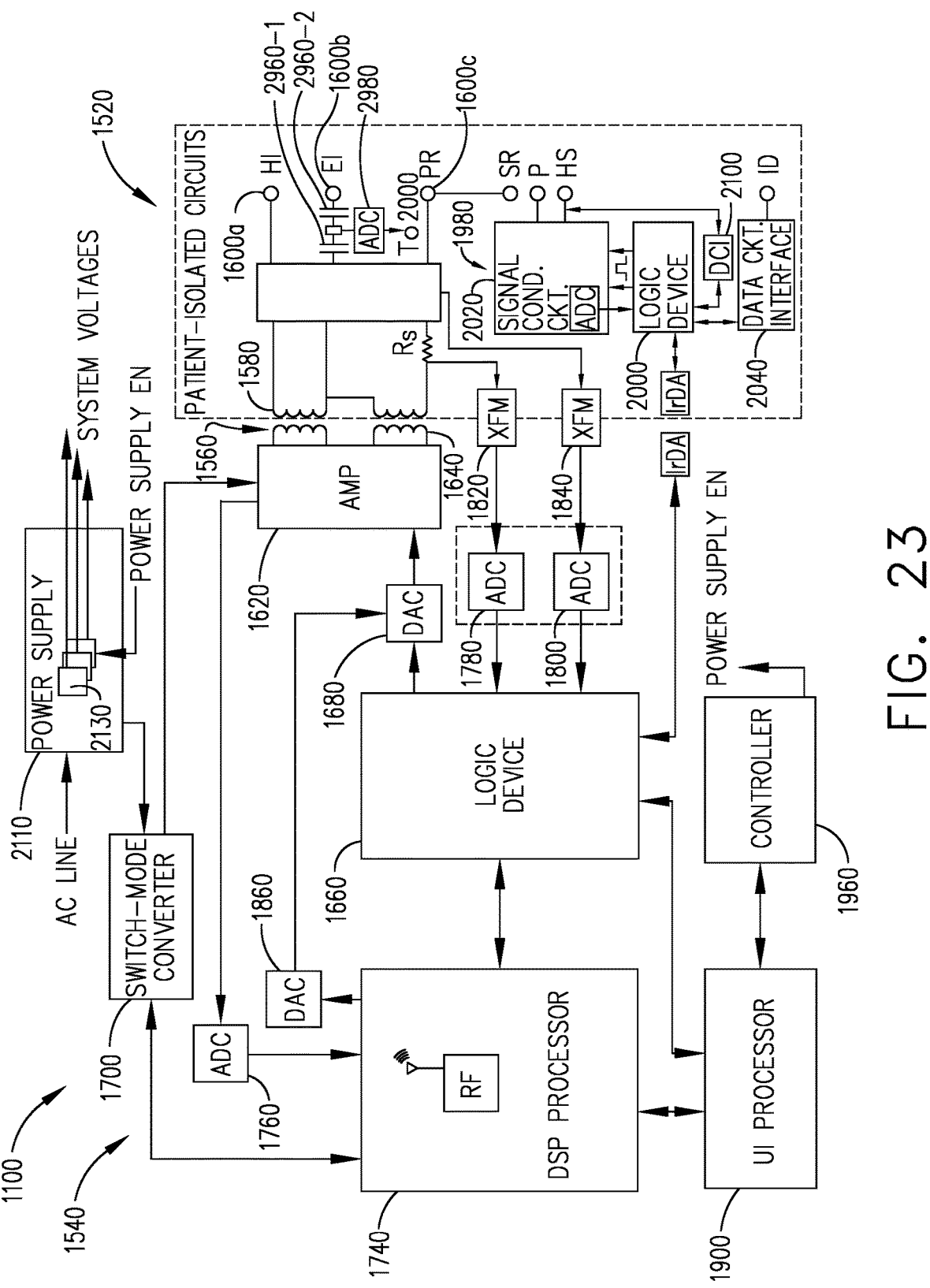
FIG. 23 is a structural view of a generator architecture, in accordance with at least one aspect of the present disclosure.
Figure 24A:
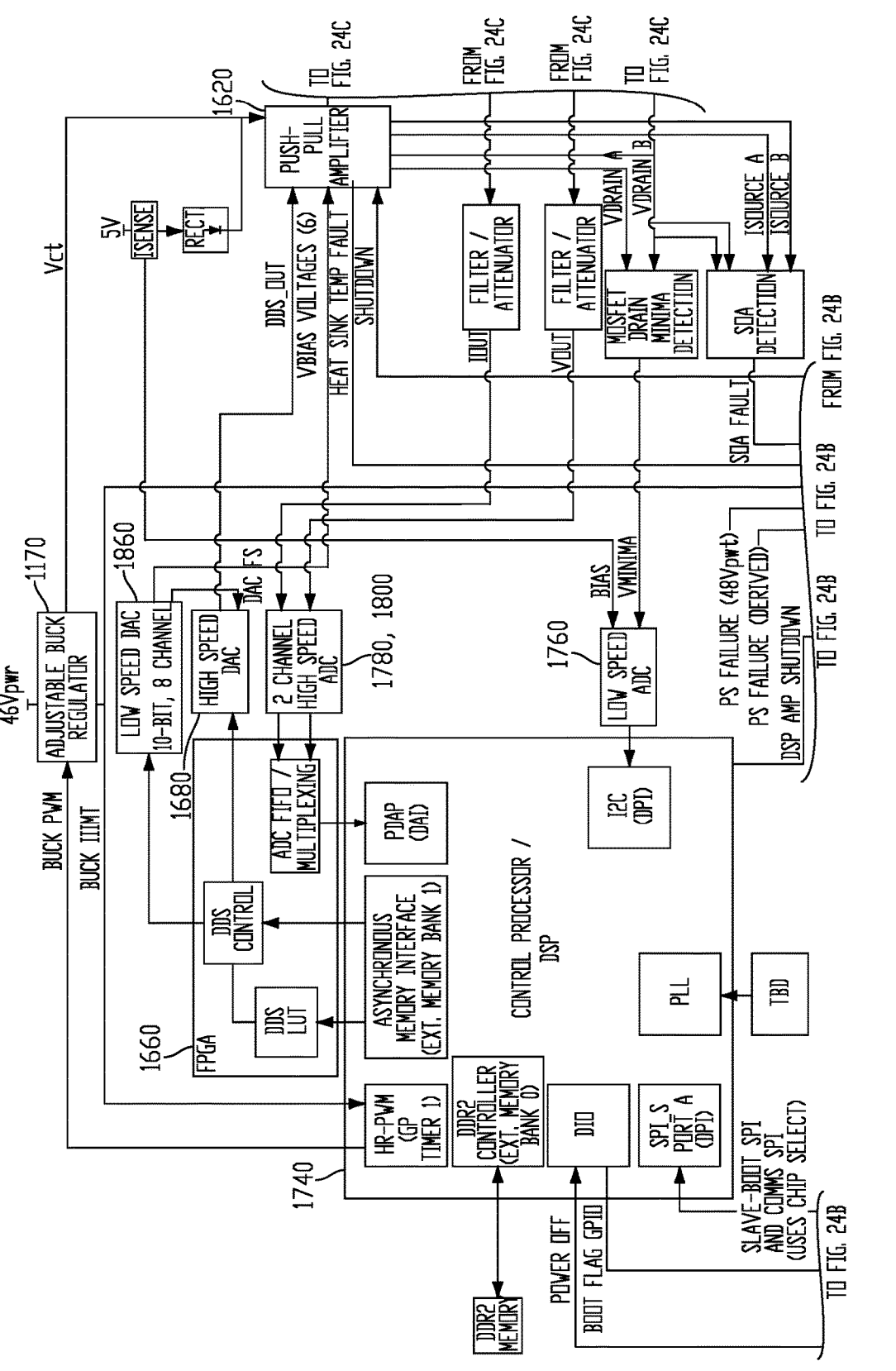
FIGS. 24A-24C are functional views of a generator architecture, in accordance with at least one aspect of the present disclosure.
Figure 24B:
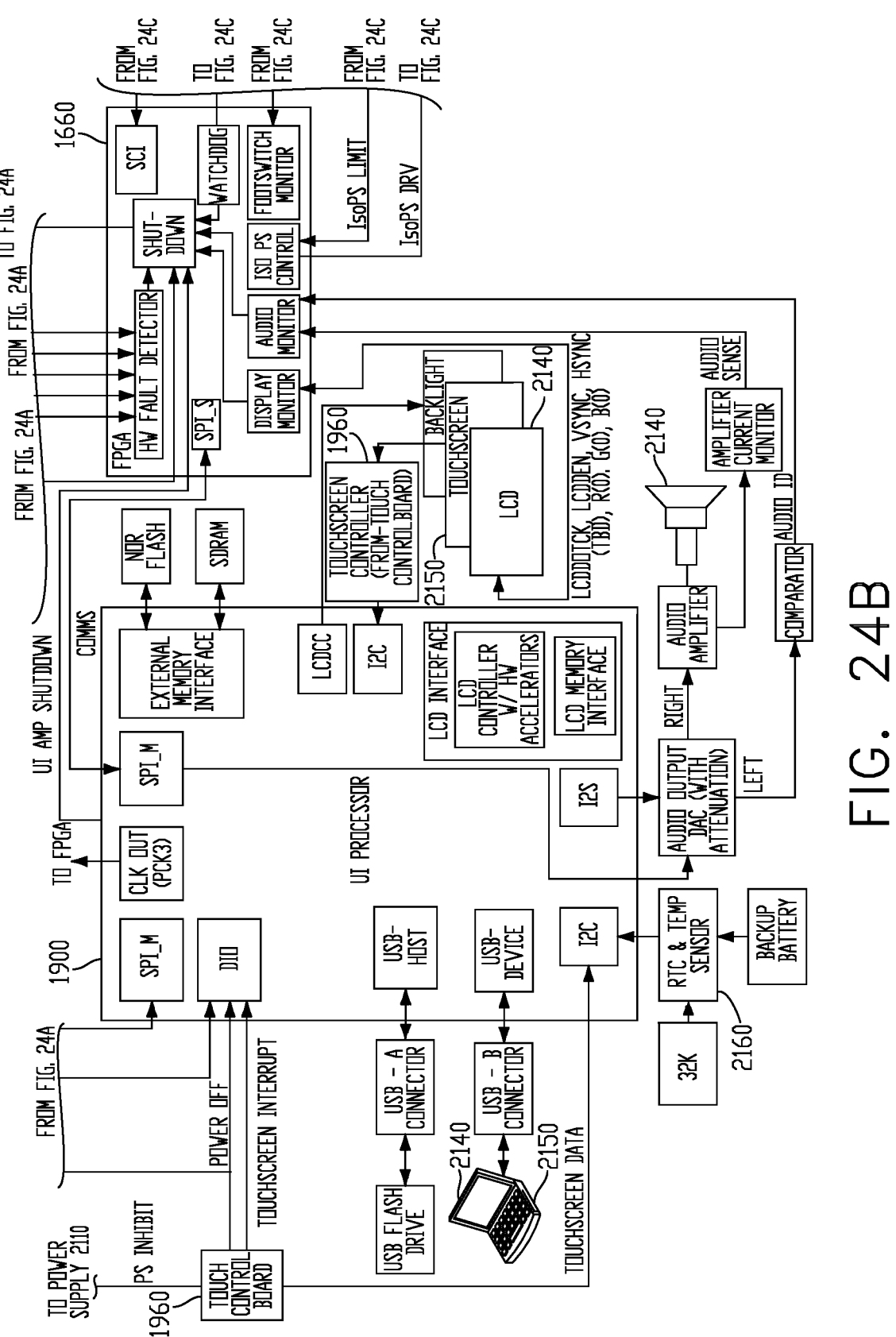
Figure 24C:
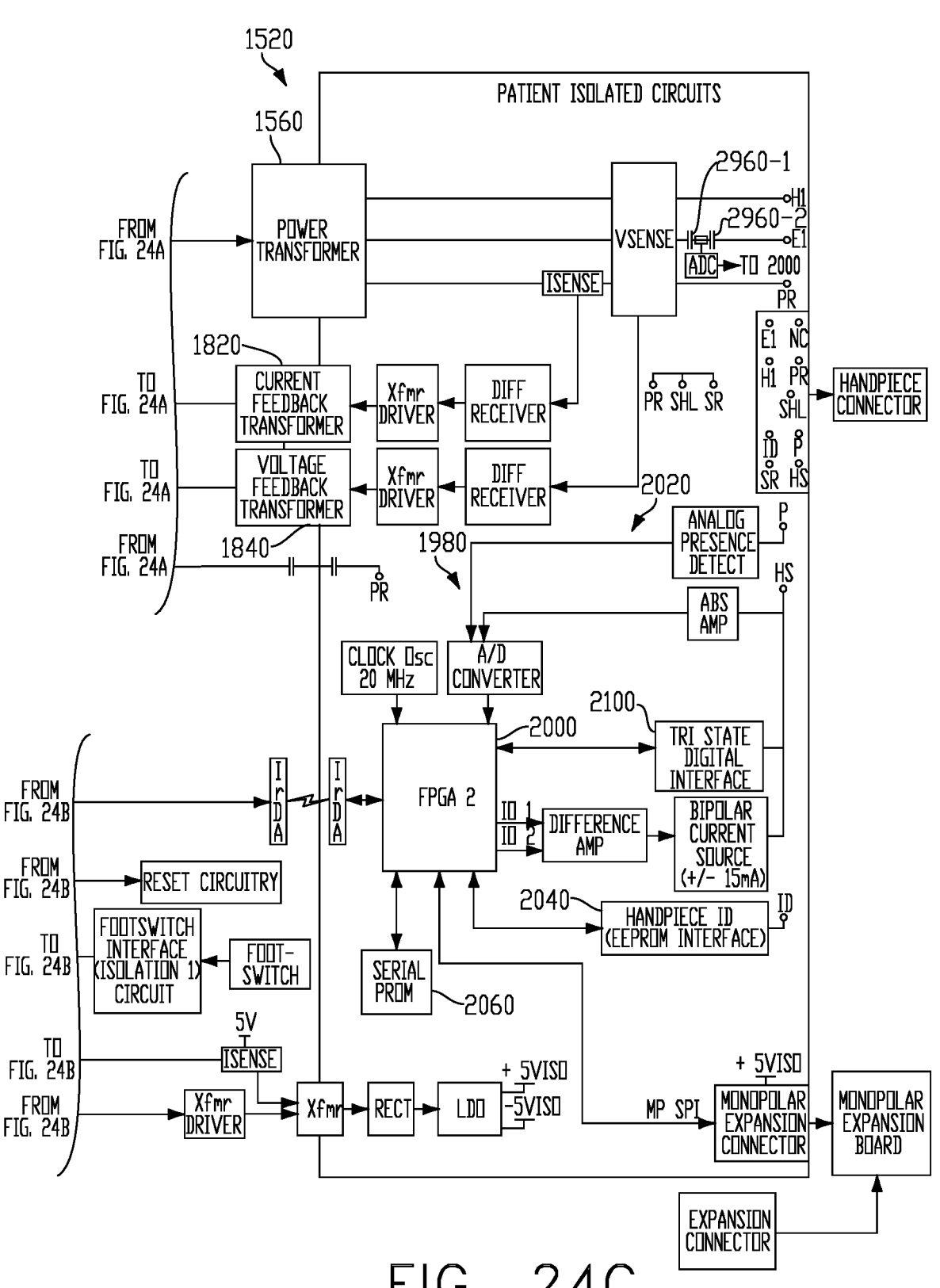

FIG. 23 is a simplified block diagram of one aspect of the generator 1100 for providing inductorless tuning as described above, among other benefits. FIGS. 24A-24C illustrate an architecture of the generator 1100 of FIG. 23 according to one aspect. With reference to FIG. 23, the generator 1100 may comprise a patient isolated stage 1520 in communication with a non-isolated stage 1540 via a power transformer 1560. A secondary winding 1580 of the power transformer 1560 is contained in the isolated stage 1520 and may comprise a tapped configuration (e.g., a center-tapped or non-center tapped configuration) to define drive signal outputs 1600a, 1600b, 1600c for outputting drive signals to different surgical devices, such as, for example, an ultrasonic surgical device 1104 and an electrosurgical device 1106. In particular, drive signal outputs 1600a, 1600b, 1600c may output a drive signal (e.g., a 420V RMS drive signal) to an ultrasonic surgical device 1104, and drive signal outputs 1600a, 1600b, 1600c may output a drive signal (e.g., a 100V RMS drive signal) to an electrosurgical device 1106, with output 1600b corresponding to the center tap of the power transformer 1560. The non-isolated stage 1540 may comprise a power amplifier 1620 having an output connected to a primary winding 1640 of the power transformer 1560. In certain aspects the power amplifier 1620 may comprise a push-pull amplifier, for example. The non-isolated stage 1540 may further comprise a programmable logic device 1660 for supplying a digital output to a digital-to-analog converter (DAC) 1680, which in turn supplies a corresponding analog signal to an input of the power amplifier 1620. In certain aspects the programmable logic device 1660 may comprise a field-programmable gate array (FPGA), for example. The programmable logic device 1660, by virtue of controlling the power amplifier's 1620 input via the DAC 1680, may therefore control any of a number of parameters (e.g., frequency, waveform shape, waveform amplitude) of drive signals appearing at the drive signal outputs 1600a, 1600b, 1600c. In certain aspects and as discussed below, the programmable logic device 1660, in conjunction with a processor (e.g., processor 1740 discussed below), may implement a number of digital signal processing (DSP)-based and/or other control algorithms to control parameters of the drive signals output by the generator 1100.

Power may be supplied to a power rail of the power amplifier 1620 by a switch-mode regulator 1700. In certain aspects the switch-mode regulator 1700 may comprise an adjustable buck regulator, for example. As discussed above, the non-isolated stage 1540 may further comprise a processor 1740, which in one aspect may comprise a DSP processor such as an ADSP-21469 SHARC DSP, available from Analog Devices, Norwood, Mass., for example. In certain aspects the processor 1740 may control operation of the switch-mode power converter 1700 responsive to voltage feedback data received from the power amplifier 1620 by the processor 1740 via an analog-to-digital converter (ADC) 1760. In one aspect, for example, the processor 1740 may receive as input, via the ADC 1760, the waveform envelope of a signal (e.g., an RF signal) being amplified by the power amplifier 1620. The processor 1740 may then control the switch-mode regulator 1700 (e.g., via a pulse-width modulated (PWM) output) such that the rail voltage supplied to the power amplifier 1620 tracks the waveform envelope of the amplified signal. By dynamically modulating the rail voltage of the power amplifier 1620 based on the waveform envelope, the efficiency of the power amplifier 1620 may be significantly improved relative to a fixed rail voltage amplifier scheme. The processor 1740 may be configured for wired or wireless communication.

In certain aspects and as discussed in further detail in connection with FIGS. 25A-25B, the programmable logic device 1660, in conjunction with the processor 1740, may implement a direct digital synthesizer (DDS) control scheme to control the waveform shape, frequency and/or amplitude of drive signals output by the generator 1100. In one aspect, for example, the programmable logic device 1660 may implement a DDS control algorithm 2680 (FIG. 25A) by recalling waveform samples stored in a dynamically-updated look-up table (LUT), such as a RAM LUT which may be embedded in an FPGA. This control algorithm is particularly useful for ultrasonic applications in which an ultrasonic transducer, such as the ultrasonic transducer 1120, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 1100 is impacted by various sources of distortion present in the output drive circuit (e.g., the power transformer 1560, the power amplifier 1620), voltage and current feedback data based on the drive signal may be input into an algorithm, such as an error control algorithm implemented by the processor 1740, which compensates for distortion by suitably pre-distorting or modifying the waveform samples stored in the LUT on a dynamic, ongoing basis (e.g., in real-time). In one aspect, the amount or degree of pre-distortion applied to the LUT samples may be based on the error between a computed motional branch current and a desired current waveform shape, with the error being determined on a sample-by sample basis. In this way, the pre-distorted LUT samples, when processed through the drive circuit, may result in a motional branch drive signal having the desired waveform shape (e.g., sinusoidal) for optimally driving the ultrasonic transducer. In such aspects, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 1540 may further comprise an ADC 1780 and an ADC 1800 coupled to the output of the power transformer 1560 via respective isolation transformers 1820, 1840 for respectively sampling the voltage and current of drive signals output by the generator 1100. In certain aspects, the ADCs 1780, 1800 may be configured to sample at high speeds (e.g., 80 Msps) to enable oversampling of the drive signals. In one aspect, for example, the sampling speed of the ADCs 1780, 1800 may enable approximately 200× (depending on drive frequency) oversampling of the drive signals. In certain aspects, the sampling operations of the ADCs 1780, 1800 may be performed by a single ADC receiving input voltage and current signals via a two-way multiplexer. The use of high-speed sampling in aspects of the generator 1100 may enable, among other things, calculation of the complex current flowing through the motional branch (which may be used in certain aspects to implement DDS-based waveform shape control described above), accurate digital filtering of the sampled signals, and calculation of real power consumption with a high degree of precision. Voltage and current feedback data output by the ADCs 1780, 1800 may be received and processed (e.g., FIFO buffering, multiplexing) by the programmable logic device 1660 and stored in data memory for subsequent retrieval by, for example, the processor 1740. As noted above, voltage and current feedback data may be used as input to an algorithm for pre-distorting or modifying LUT waveform samples on a dynamic and ongoing basis. In certain aspects, this may require each stored voltage and current feedback data pair to be indexed based on, or otherwise associated with, a corresponding LUT sample that was output by the programmable logic device 1660 when the voltage and current feedback data pair was acquired. Synchronization of the LUT samples and the voltage and current feedback data in this manner contributes to the correct timing and stability of the pre-distortion algorithm.

In certain aspects, the voltage and current feedback data may be used to control the frequency and/or amplitude (e.g., current amplitude) of the drive signals. In one aspect, for example, voltage and current feedback data may be used to determine impedance phase, e.g., the phase difference between the voltage and current drive signals. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the processor 1740, for example, with the frequency control signal being supplied as input to a DDS control algorithm implemented by the programmable logic device 1660.

The impedance phase may be determined through Fourier analysis. In one aspect, the phase difference between the generator voltage $V_g(t)$ and generator current $I_g(t)$ driving signals may be determined using the Fast Fourier Transform (FFT) or the Discrete Fourier Transform (DFT) as follows:

$$V_g(t) = A_1 \cos(2\pi f_0 t + \varphi_1)$$

$$I_g(t) = A_2 \cos(2\pi f_0 t + \varphi_2)$$

$$V_g(f) = \frac{A_1}{2}(\delta(f - f_0) + \delta(f + f_0))\exp\left(j2\pi f \frac{\varphi_1}{2\pi f_0}\right)$$

$$I_g(f) = \frac{A_2}{2}(\delta(f - f_0) + \delta(f + f_0))\exp\left(j2\pi f \frac{\varphi_2}{2\pi f_0}\right)$$

Evaluating the Fourier Transform at the frequency of the sinusoid yields:

$$V_g(f_0) = \frac{A_1}{2}\delta(0)\exp(j\varphi_1) \quad \arg V(f_0) = \varphi_1$$

$$I_g(f_0) = \frac{A_2}{2}\delta(0)\exp(j\varphi_2) \quad \arg I(f_0) = \varphi_2$$

Other approaches include weighted least-squares estimation, Kalman filtering, and space-vector-based techniques. Virtually all of the processing in an FFT or DFT technique may be performed in the digital domain with the aid of the 2-channel high speed ADC 1780, 1800, for example. In one technique, the digital signal samples of the voltage and current signals are Fourier transformed with an FFT or a DFT. The phase angle $\varphi$ at any point in time can be calculated by:

$$\varphi = 2\pi f t + \varphi_0$$

Where $\varphi$ is the phase angle, f is the frequency, t is time, and $\varphi_0$ is the phase at t=0.

Another technique for determining the phase difference between the voltage $V_g(t)$ and current $I_g(t)$ signals is the zero-crossing method and produces highly accurate results. For voltage $V_g(t)$ and current $I_g(t)$ signals having the same frequency, each negative to positive zero-crossing of voltage signal $V_g(t)$ triggers the start of a pulse, while each negative to positive zero-crossing of current signal $I_g(t)$ triggers the end of the pulse. The result is a pulse train with a pulse width proportional to the phase angle between the voltage signal and the current signal. In one aspect, the pulse train may be passed through an averaging filter to yield a measure of the phase difference. Furthermore, if the positive to negative zero crossings also are used in a similar manner, and the results averaged, any effects of DC and harmonic components can be reduced. In one implementation, the analog voltage $V_g(t)$ and current $I_g(t)$ signals are converted to digital signals that are high if the analog signal is positive and low if the analog signal is negative. High accuracy phase estimates require sharp transitions between high and low. In one aspect, a Schmitt trigger along with an RC stabilization network may be employed to convert the analog signals into digital signals. In other aspects, an edge triggered RS flip-flop and ancillary circuitry may be employed. In yet another aspect, the zero-crossing technique may employ an eXclusive OR (XOR) gate.

Other techniques for determining the phase difference between the voltage and current signals include Lissajous figures and monitoring the image; methods such as the three-voltmeter method, the crossed-coil method, vector voltmeter and vector impedance methods; and using phase standard instruments, phase-locked loops, and other techniques as described in Phase Measurement, Peter O'Shea, 2000 CRC Press LLC, <http://www.engnetbase.com>, which is incorporated herein by reference.

In another aspect, for example, the current feedback data may be monitored in order to maintain the current amplitude of the drive signal at a current amplitude setpoint. The current amplitude setpoint may be specified directly or determined indirectly based on specified voltage amplitude and power setpoints. In certain aspects, control of the current amplitude may be implemented by control algorithm, such as, for example, a proportional-integral-derivative (PID) control algorithm, in the processor 1740. Variables controlled by the control algorithm to suitably control the current amplitude of the drive signal may include, for example, the scaling of the LUT waveform samples stored in the programmable logic device 1660 and/or the full-scale output voltage of the DAC 1680 (which supplies the input to the power amplifier 1620) via a DAC 1860.

The non-isolated stage 1540 may further comprise a processor 1900 for providing, among other things, user interface (UI) functionality. In one aspect, the processor 1900 may comprise an Atmel AT91 SAM9263 processor having an ARM 926EJ-S core, available from Atmel Corporation, San Jose, Calif., for example. Examples of UI functionality supported by the processor 1900 may include audible and visual user feedback, communication with peripheral devices (e.g., via a Universal Serial Bus (USB) interface), communication with a foot switch 1430, communication with an input device 2150 (e.g., a touch screen display) and communication with an output device 2140 (e.g., a speaker). The processor 1900 may communicate with the processor 1740 and the programmable logic device (e.g., via a serial peripheral interface (SPI) bus). Although the processor 1900 may primarily support UI functionality, it may also coordinate with the processor 1740 to implement hazard mitigation in certain aspects. For example, the processor 1900 may be programmed to monitor various aspects of user input and/or other inputs (e.g., touch screen inputs 2150, foot switch 1430 inputs, temperature sensor inputs 2160) and may disable the drive output of the generator 1100 when an erroneous condition is detected.

In certain aspects, both the processor 1740 (FIG. 23, 24A) and the processor 1900 (FIG. 23, 24B) may determine and monitor the operating state of the generator 1100. For processor 1740, the operating state of the generator 1100 may dictate, for example, which control and/or diagnostic processes are implemented by the processor 1740. For processor 1900, the operating state of the generator 1100 may dictate, for example, which elements of a user interface (e.g., display screens, sounds) are presented to a user. The processors 1740, 1900 may independently maintain the current operating state of the generator 1100 and recognize and evaluate possible transitions out of the current operating state. The processor 1740 may function as the master in this relationship and determine when transitions between operating states are to occur. The processor 1900 may be aware of valid transitions between operating states and may confirm if a particular transition is appropriate. For example, when the processor 1740 instructs the processor 1900 to transition to a specific state, the processor 1900 may verify that the requested transition is valid. In the event that a requested transition between states is determined to be invalid by the processor 1900, the processor 1900 may cause the generator 1100 to enter a failure mode.

The non-isolated stage 1540 may further comprise a controller 1960 (FIG. 23, 24B) for monitoring input devices 2150 (e.g., a capacitive touch sensor used for turning the generator 1100 on and off, a capacitive touch screen). In certain aspects, the controller 1960 may comprise at least one processor and/or other controller device in communication with the processor 1900. In one aspect, for example, the controller 1960 may comprise a processor (e.g., a Mega168 8-bit controller available from Atmel) configured to monitor user input provided via one or more capacitive touch sensors. In one aspect, the controller 1960 may comprise a touch screen controller (e.g., a QT5480 touch screen controller available from Atmel) to control and manage the acquisition of touch data from a capacitive touch screen.

In certain aspects, when the generator 1100 is in a "power off" state, the controller 1960 may continue to receive operating power (e.g., via a line from a power supply of the generator 1100, such as the power supply 2110 (FIG. 23) discussed below). In this way, the controller 1960 may continue to monitor an input device 2150 (e.g., a capacitive touch sensor located on a front panel of the generator 1100) for turning the generator 1100 on and off. When the generator 1100 is in the "power off" state, the controller 1960 may wake the power supply (e.g., enable operation of one or more DC/DC voltage converters 2130 (FIG. 23) of the power supply 2110) if activation of the "on/off" input device 2150 by a user is detected. The controller 1960 may therefore initiate a sequence for transitioning the generator 1100 to a "power on" state. Conversely, the controller 1960 may initiate a sequence for transitioning the generator 1100 to the "power off" state if activation of the "on/off" input device 2150 is detected when the generator 1100 is in the "power on" state. In certain aspects, for example, the controller 1960 may report activation of the "on/off" input device 2150 to the processor 1900, which in turn implements the necessary process sequence for transitioning the generator 1100 to the "power off" state. In such aspects, the controller 1960 may have no independent ability for causing the removal of power from the generator 1100 after its "power on" state has been established.

In certain aspects, the controller 1960 may cause the generator 1100 to provide audible or other sensory feedback for alerting the user that a "power on" or "power off" sequence has been initiated. Such an alert may be provided at the beginning of a "power on" or "power off" sequence and prior to the commencement of other processes associated with the sequence.

In certain aspects, the isolated stage 1520 may comprise an instrument interface circuit 1980 to, for example, provide a communication interface between a control circuit of a surgical device (e.g., a control circuit comprising handpiece switches) and components of the non-isolated stage 1540, such as, for example, the programmable logic device 1660, the processor 1740 and/or the processor 1900. The instrument interface circuit 1980 may exchange information with components of the non-isolated stage 1540 via a communication link that maintains a suitable degree of electrical isolation between the stages 1520, 1540, such as, for example, an infrared (IR)-based communication link. Power may be supplied to the instrument interface circuit 1980 using, for example, a low-dropout voltage regulator powered by an isolation transformer driven from the non-isolated stage 1540.

In one aspect, the instrument interface circuit 1980 may comprise a programmable logic device 2000 (e.g., an FPGA) in communication with a signal conditioning circuit 2020 (FIG. 23 and FIG. 24C). The signal conditioning circuit 2020 may be configured to receive a periodic signal from the programmable logic device 2000 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 1100 to the surgical device) and monitored to determine a state or configuration of the control circuit. For example, the control circuit may comprise a number of switches, resistors and/or diodes to modify one or more characteristics (e.g., amplitude, rectification) of the interrogation signal such that a state or configuration of the control circuit is uniquely discernible based on the one or more characteristics. In one aspect, for example, the signal conditioning circuit 2020 may comprise an ADC for generating samples of a voltage signal appearing across inputs of the control circuit resulting from passage of interrogation signal therethrough. The programmable logic device 2000 (or a component of the non-isolated stage 1540) may then determine the state or configuration of the control circuit based on the ADC samples.

In one aspect, the instrument interface circuit 1980 may comprise a first data circuit interface 2040 to enable information exchange between the programmable logic device 2000 (or other element of the instrument interface circuit 1980) and a first data circuit disposed in or otherwise associated with a surgical device. In certain aspects, for example, a first data circuit 2060 may be disposed in a cable integrally attached to a surgical device handpiece, or in an adaptor for interfacing a specific surgical device type or model with the generator 1100. In certain aspects, the first data circuit may comprise a non-volatile storage device, such as an electrically erasable programmable read-only memory (EEPROM) device. In certain aspects and referring again to FIG. 23, the first data circuit interface 2040 may be implemented separately from the programmable logic device 2000 and comprise suitable circuitry (e.g., discrete logic devices, a processor) to enable communication between the programmable logic device 2000 and the first data circuit. In other aspects, the first data circuit interface 2040 may be integral with the programmable logic device 2000.

In certain aspects, the first data circuit 2060 may store information pertaining to the particular surgical device with which it is associated. Such information may include, for example, a model number, a serial number, a number of operations in which the surgical device has been used, and/or any other type of information. This information may be read by the instrument interface circuit 1980 (e.g., by the programmable logic device 2000), transferred to a component of the non-isolated stage 1540 (e.g., to programmable logic device 1660, processor 1740 and/or processor 1900) for presentation to a user via an output device 2140 and/or for controlling a function or operation of the generator 1100. Additionally, any type of information may be communicated to first data circuit 2060 for storage therein via the first data circuit interface 2040 (e.g., using the programmable logic device 2000). Such information may comprise, for example, an updated number of operations in which the surgical device has been used and/or dates and/or times of its usage.

As discussed previously, a surgical instrument may be detachable from a handpiece (e.g., instrument 1106 may be detachable from handpiece 1107) to promote instrument interchangeability and/or disposability. In such cases, known generators may be limited in their ability to recognize particular instrument configurations being used and to optimize control and diagnostic processes accordingly. The addition of readable data circuits to surgical device instruments to address this issue is problematic from a compatibility standpoint, however. For example, it may be impractical to design a surgical device to maintain backward compatibility with generators that lack the requisite data reading functionality due to, for example, differing signal schemes, design complexity and cost. Other aspects of instruments address these concerns by using data circuits that may be implemented in existing surgical instruments economically and with minimal design changes to preserve compatibility of the surgical devices with current generator platforms.

Additionally, aspects of the generator 1100 may enable communication with instrument-based data circuits. For example, the generator 1100 may be configured to communicate with a second data circuit (e.g., a data circuit) contained in an instrument (e.g., instrument 1104, 1106 or 1108) of a surgical device. The instrument interface circuit 1980 may comprise a second data circuit interface 2100 to enable this communication. In one aspect, the second data circuit interface 2100 may comprise a tri-state digital interface, although other interfaces may also be used. In certain aspects, the second data circuit may generally be any circuit for transmitting and/or receiving data. In one aspect, for example, the second data circuit may store information pertaining to the particular surgical instrument with which it is associated. Such information may include, for example, a model number, a serial number, a number of operations in which the surgical instrument has been used, and/or any other type of information. Additionally or alternatively, any type of information may be communicated to the second data circuit for storage therein via the second data circuit interface 2100 (e.g., using the programmable logic device 2000). Such information may comprise, for example, an updated number of operations in which the instrument has been used and/or dates and/or times of its usage. In certain aspects, the second data circuit may transmit data acquired by one or more sensors (e.g., an instrument-based temperature sensor). In certain aspects, the second data circuit may receive data from the generator 1100 and provide an indication to a user (e.g., an LED indication or other visible indication) based on the received data.

In certain aspects, the second data circuit and the second data circuit interface 2100 may be configured such that communication between the programmable logic device 2000 and the second data circuit can be effected without the need to provide additional conductors for this purpose (e.g., dedicated conductors of a cable connecting a handpiece to the generator 1100). In one aspect, for example, information may be communicated to and from the second data circuit using a one-wire bus communication scheme implemented on existing cabling, such as one of the conductors used transmit interrogation signals from the signal conditioning circuit 2020 to a control circuit in a handpiece. In this way, design changes or modifications to the surgical device that might otherwise be necessary are minimized or reduced. Moreover, because different types of communications can be implemented over a common physical channel (either with or without frequency-band separation), the presence of a second data circuit may be "invisible" to generators that do not have the requisite data reading functionality, thus enabling backward compatibility of the surgical device instrument.

In certain aspects, the isolated stage 1520 may comprise at least one blocking capacitor 2960-1 (FIG. 24C) connected to the drive signal output 1600*b* to prevent passage of DC current to a patient. A single blocking capacitor may be required to comply with medical regulations or standards, for example. While failure in single-capacitor designs is relatively uncommon, such failure may nonetheless have negative consequences. In one aspect, a second blocking capacitor 2960-2 may be provided in series with the blocking capacitor 2960-1, with current leakage from a point between the blocking capacitors 2960-1, 2960-2 being monitored by, for example, an ADC 2980 for sampling a voltage induced by leakage current.

The samples may be received by the programmable logic device 2000, for example. Based on changes in the leakage current (as indicated by the voltage samples in the aspect of FIG. 23), the generator 1100 may determine when at least one of the blocking capacitors 2960-1, 2960-2 has failed. Accordingly, the aspect of FIG. 23 may provide a benefit over single-capacitor designs having a single point of failure.

In certain aspects, the non-isolated stage 1540 may comprise a power supply 2110 for outputting DC power at a suitable voltage and current. The power supply may comprise, for example, a 400 W power supply for outputting a 48 VDC system voltage. As discussed above, the power supply 2110 may further comprise one or more DC/DC voltage converters 2130 for receiving the output of the power supply to generate DC outputs at the voltages and currents required by the various components of the generator 1100. As discussed above in connection with the controller 1960, one or more of the DC/DC voltage converters 2130 may receive an input from the controller 1960 when activation of the "on/off" input device 2150 by a user is detected by the controller 1960 to enable operation of, or wake, the DC/DC voltage converters 2130.

Figure 25A:
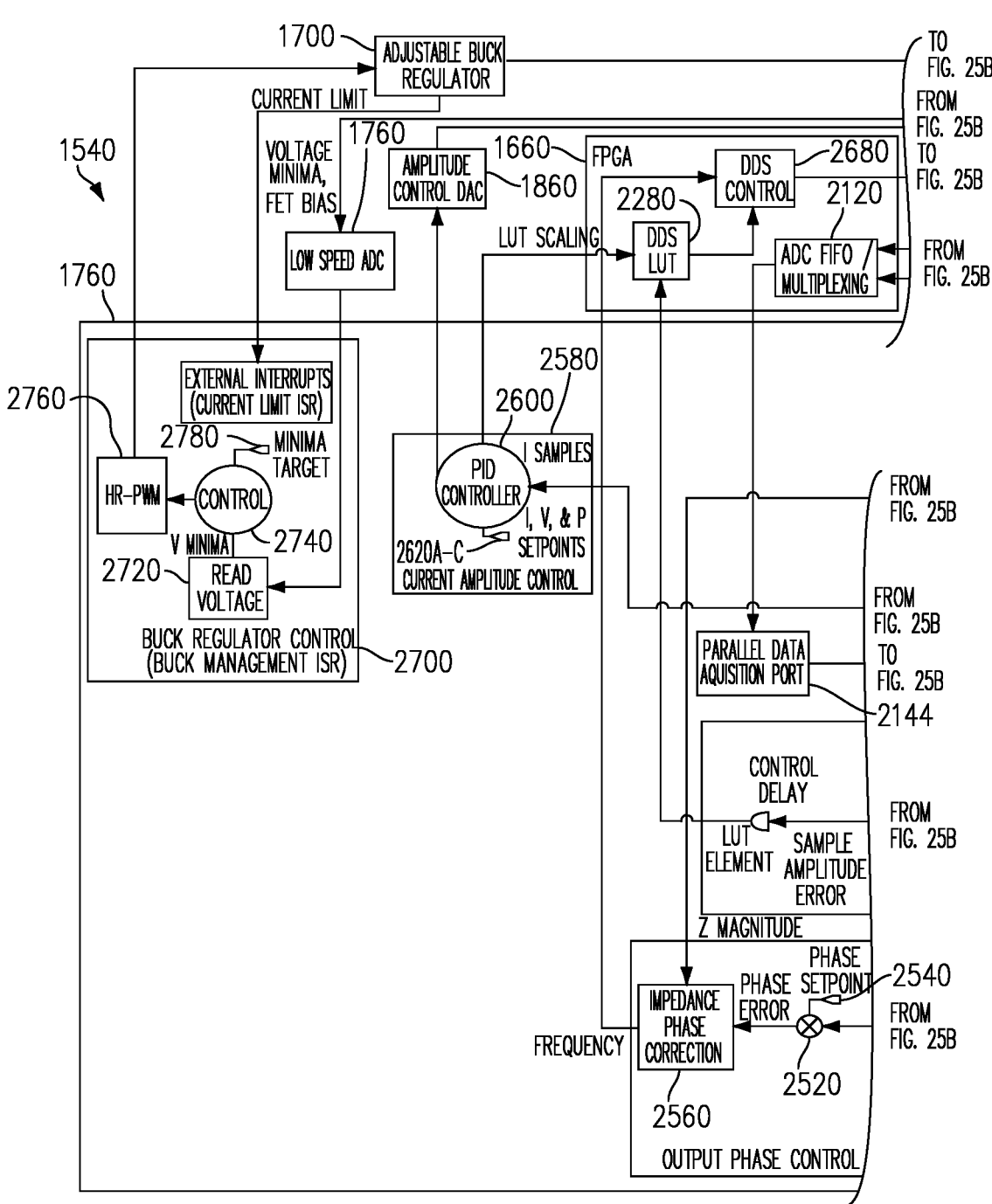
FIGS. 25A-25B are structural and functional aspects of a generator, in accordance with at least one aspect of the present disclosure.
Figure 25B:
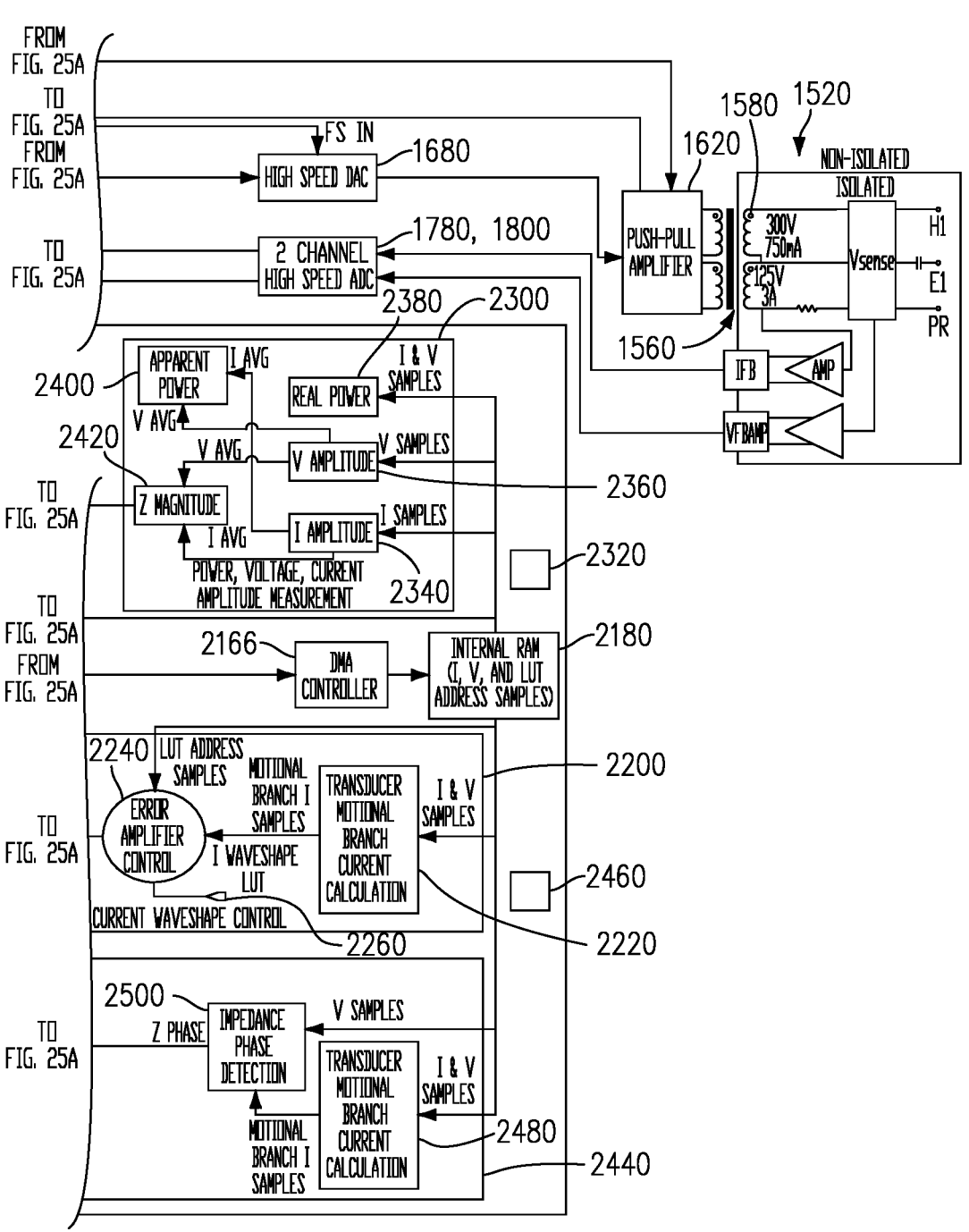

FIGS. 25A-25B illustrate certain functional and structural aspects of one aspect of the generator 1100. Feedback indicating current and voltage output from the secondary winding 1580 of the power transformer 1560 is received by the ADCs 1780, 1800, respectively. As shown, the ADCs 1780, 1800 may be implemented as a 2-channel ADC and may sample the feedback signals at a high speed (e.g., 80 Msps) to enable oversampling (e.g., approximately 200× oversampling) of the drive signals. The current and voltage feedback signals may be suitably conditioned in the analog domain (e.g., amplified, filtered) prior to processing by the ADCs 1780, 1800. Current and voltage feedback samples from the ADCs 1780, 1800 may be individually buffered and subsequently multiplexed or interleaved into a single data stream within block 2120 of the programmable logic device 1660. In the aspect of FIGS. 25A-25B, the programmable logic device 1660 comprises an FPGA.

The multiplexed current and voltage feedback samples may be received by a parallel data acquisition port (PDAP) implemented within block 2144 of the processor 1740. The PDAP may comprise a packing unit for implementing any of a number of methodologies for correlating the multiplexed feedback samples with a memory address. In one aspect, for example, feedback samples corresponding to a particular LUT sample output by the programmable logic device 1660 may be stored at one or more memory addresses that are correlated or indexed with the LUT address of the LUT sample. In another aspect, feedback samples corresponding to a particular LUT sample output by the programmable logic device 1660 may be stored, along with the LUT address of the LUT sample, at a common memory location. In any event, the feedback samples may be stored such that the address of the LUT sample from which a particular set of feedback samples originated may be subsequently ascertained. As discussed above, synchronization of the LUT sample addresses and the feedback samples in this way contributes to the correct timing and stability of the pre-distortion algorithm. A direct memory access (DMA) controller implemented at block 2166 of the processor 1740 may store the feedback samples (and any LUT sample address data, where applicable) at a designated memory location 2180 of the processor 1740 (e.g., internal RAM).

Block 2200 of the processor 1740 may implement a pre-distortion algorithm for pre-distorting or modifying the LUT samples stored in the programmable logic device 1660 on a dynamic, ongoing basis. As discussed above, pre-distortion of the LUT samples may compensate for various sources of distortion present in the output drive circuit of the generator 1100. The pre-distorted LUT samples, when processed through the drive circuit, will therefore result in a drive signal having the desired waveform shape (e.g., sinusoidal) for optimally driving the ultrasonic transducer.

At block 2220 of the pre-distortion algorithm, the current through the motional branch of the ultrasonic transducer is determined. The motional branch current may be determined using Kirchhoff's Current Law based on, for example, the current and voltage feedback samples stored at memory location 2180 (which, when suitably scaled, may be representative of $I_g$ and $V_g$ in the model of FIG. 22 discussed above), a value of the ultrasonic transducer static capacitance $C_0$ (measured or known a priori) and a known value of the drive frequency. A motional branch current sample for each set of stored current and voltage feedback samples associated with a LUT sample may be determined.

At block 2240 of the pre-distortion algorithm, each motional branch current sample determined at block 2220 is compared to a sample of a desired current waveform shape to determine a difference, or sample amplitude error, between the compared samples. For this determination, the sample of the desired current waveform shape may be supplied, for example, from a waveform shape LUT 2260 containing amplitude samples for one cycle of a desired current waveform shape. The particular sample of the desired current waveform shape from the LUT 2260 used for the comparison may be dictated by the LUT sample address associated with the motional branch current sample used in the comparison. Accordingly, the input of the motional branch current to block 2240 may be synchronized with the input of its associated LUT sample address to block 2240. The LUT samples stored in the programmable logic device 1660 and the LUT samples stored in the waveform shape LUT 2260 may therefore be equal in number. In certain aspects, the desired current waveform shape represented by the LUT samples stored in the waveform shape LUT 2260 may be a fundamental sine wave. Other waveform shapes may be desirable. For example, it is contemplated that a fundamental sine wave for driving main longitudinal motion of an ultrasonic transducer superimposed with one or more other drive signals at other frequencies, such as a third order harmonic for driving at least two mechanical resonances for beneficial vibrations of transverse or other modes, could be used.

Each value of the sample amplitude error determined at block 2240 may be transmitted to the LUT of the programmable logic device 1660 (shown at block 2280 in FIG. 25A) along with an indication of its associated LUT address. Based on the value of the sample amplitude error and its associated address (and, optionally, values of sample amplitude error for the same LUT address previously received), the LUT 2280 (or other control block of the programmable logic device 1660) may pre-distort or modify the value of the LUT sample stored at the LUT address such that the sample amplitude error is reduced or minimized. It will be appreciated that such pre-distortion or modification of each LUT sample in an iterative manner across the entire range of LUT addresses will cause the waveform shape of the generator's output current to match or conform to the desired current waveform shape represented by the samples of the waveform shape LUT 2260.

Current and voltage amplitude measurements, power measurements and impedance measurements may be determined at block 2300 of the processor 1740 based on the current and voltage feedback samples stored at memory location 2180. Prior to the determination of these quantities, the feedback samples may be suitably scaled and, in certain aspects, processed through a suitable filter 2320 to remove noise resulting from, for example, the data acquisition process and induced harmonic components. The filtered voltage and current samples may therefore substantially represent the fundamental frequency of the generator's drive output signal. In certain aspects, the filter 2320 may be a finite impulse response (FIR) filter applied in the frequency domain. Such aspects may use the Fast Fourier Transform (FFT) of the output drive signal current and voltage signals. In certain aspects, the resulting frequency spectrum may be used to provide additional generator functionality. In one aspect, for example, the ratio of the second and/or third order harmonic component relative to the fundamental frequency component may be used as a diagnostic indicator.

At block 2340 (FIG. 25B), a root mean square (RMS) calculation may be applied to a sample size of the current feedback samples representing an integral number of cycles of the drive signal to generate a measurement $I_{rms}$ representing the drive signal output current.

At block 2360, a root mean square (RMS) calculation may be applied to a sample size of the voltage feedback samples representing an integral number of cycles of the drive signal to determine a measurement $V_{rms}$ representing the drive signal output voltage.

At block 2380, the current and voltage feedback samples may be multiplied point by point, and a mean calculation is applied to samples representing an integral number of cycles of the drive signal to determine a measurement $P_r$ of the generator's real output power.

At block 2400, measurement $P_a$ of the generator's apparent output power may be determined as the product $V_{rms} \cdot I_{rms}$.

At block 2420, measurement $Z_m$ of the load impedance magnitude may be determined as the quotient $V_{rms}/I_{rms}$.

In certain aspects, the quantities $I_{rms}$, $V_{rms}$, $P_r$, $P_a$ and $Z_m$ determined at blocks 2340, 2360, 2380, 2400 and 2420 may be used by the generator 1100 to implement any of a number of control and/or diagnostic processes. In certain aspects, any of these quantities may be communicated to a user via, for example, an output device 2140 integral with the generator 1100 or an output device 2140 connected to the generator 1100 through a suitable communication interface (e.g., a USB interface). Various diagnostic processes may include, without limitation, handpiece integrity, instrument integrity, instrument attachment integrity, instrument overload, approaching instrument overload, frequency lock failure, over-voltage condition, over-current condition, over-power condition, voltage sense failure, current sense failure, audio indication failure, visual indication failure, short circuit condition, power delivery failure, or blocking capacitor failure, for example.

Block 2440 of the processor 1740 may implement a phase control algorithm for determining and controlling the impedance phase of an electrical load (e.g., the ultrasonic transducer) driven by the generator 1100. As discussed above, by controlling the frequency of the drive signal to minimize or reduce the difference between the determined impedance phase and an impedance phase setpoint (e.g., 0°), the effects of harmonic distortion may be minimized or reduced, and the accuracy of the phase measurement increased.

The phase control algorithm receives as input the current and voltage feedback samples stored in the memory location 2180. Prior to their use in the phase control algorithm, the feedback samples may be suitably scaled and, in certain aspects, processed through a suitable filter 2460 (which may be identical to filter 2320) to remove noise resulting from the data acquisition process and induced harmonic components, for example. The filtered voltage and current samples may therefore substantially represent the fundamental frequency of the generator's drive output signal.

At block 2480 of the phase control algorithm, the current through the motional branch of the ultrasonic transducer is determined. This determination may be identical to that described above in connection with block 2220 of the pre-distortion algorithm. The output of block 2480 may thus be, for each set of stored current and voltage feedback samples associated with a LUT sample, a motional branch current sample.

At block 2500 of the phase control algorithm, impedance phase is determined based on the synchronized input of motional branch current samples determined at block 2480 and corresponding voltage feedback samples. In certain aspects, the impedance phase is determined as the average of the impedance phase measured at the rising edge of the waveforms and the impedance phase measured at the falling edge of the waveforms.

At block 2520 of the of the phase control algorithm, the value of the impedance phase determined at block 2220 is compared to phase setpoint 2540 to determine a difference, or phase error, between the compared values.

At block 2560 (FIG. 25A) of the phase control algorithm, based on a value of phase error determined at block 2520 and the impedance magnitude determined at block 2420, a frequency output for controlling the frequency of the drive signal is determined. The value of the frequency output may be continuously adjusted by the block 2560 and transferred to a DDS control block 2680 (discussed below) in order to maintain the impedance phase determined at block 2500 at the phase setpoint (e.g., zero phase error). In certain aspects, the impedance phase may be regulated to a 0° phase setpoint. In this way, any harmonic distortion will be centered about the crest of the voltage waveform, enhancing the accuracy of phase impedance determination.

Block 2580 of the processor 1740 may implement an algorithm for modulating the current amplitude of the drive signal in order to control the drive signal current, voltage and power in accordance with user specified setpoints, or in accordance with requirements specified by other processes or algorithms implemented by the generator 1100. Control of these quantities may be realized, for example, by scaling the LUT samples in the LUT 2280 and/or by adjusting the full-scale output voltage of the DAC 1680 (which supplies the input to the power amplifier 1620) via a DAC 1860. Block 2600 (which may be implemented as a PID controller in certain aspects) may receive, as input, current feedback samples (which may be suitably scaled and filtered) from the memory location 2180. The current feedback samples may be compared to a "current demand" Id value dictated by the controlled variable (e.g., current, voltage or power) to determine if the drive signal is supplying the necessary current. In aspects in which drive signal current is the control variable, the current demand Id may be specified directly by a current setpoint 2620A ($I_{sp}$). For example, an RMS value of the current feedback data (determined as in block 2340) may be compared to user-specified RMS current setpoint $I_{sp}$ to determine the appropriate controller action. If, for example, the current feedback data indicates an RMS value less than the current setpoint $I_{sp}$, LUT scaling and/or the full-scale output voltage of the DAC 1680 may be adjusted by the block 2600 such that the drive signal current is increased. Conversely, block 2600 may adjust LUT scaling and/or the full-scale output voltage of the DAC 1680 to decrease the drive signal current when the current feedback data indicates an RMS value greater than the current setpoint $I_{sp}$.

In aspects in which the drive signal voltage is the control variable, the current demand $I_d$ may be specified indirectly, for example, based on the current required to maintain a desired voltage setpoint 2620B ($V_{sp}$) given the load impedance magnitude $Z_m$ measured at block 2420 (e.g. $I_d = V_{sp}/Z_m$). Similarly, in aspects in which drive signal power is the control variable, the current demand Id may be specified indirectly, for example, based on the current required to maintain a desired power setpoint 2620C ($P_{sp}$) given the voltage $V_{rms}$ measured at blocks 2360 (e.g. $I_d = P_{sp}/V_{rms}$).

Block 2680 (FIG. 25A) may implement a DDS control algorithm for controlling the drive signal by recalling LUT samples stored in the LUT 2280. In certain aspects, the DDS control algorithm may be a numerically-controlled oscillator (NCO) algorithm for generating samples of a waveform at a fixed clock rate using a point (memory location)-skipping technique. The NCO algorithm may implement a phase accumulator, or frequency-to-phase converter, that functions as an address pointer for recalling LUT samples from the LUT 2280. In one aspect, the phase accumulator may be a D step size, modulo N phase accumulator, where D is a positive integer representing a frequency control value, and N is the number of LUT samples in the LUT 2280. A frequency control value of D=1, for example, may cause the phase accumulator to sequentially point to every address of the LUT 2280, resulting in a waveform output replicating the waveform stored in the LUT 2280. When D>1, the phase accumulator may skip addresses in the LUT 2280, resulting in a waveform output having a higher frequency. Accordingly, the frequency of the waveform generated by the DDS control algorithm may therefore be controlled by suitably varying the frequency control value. In certain aspects, the frequency control value may be determined based on the output of the phase control algorithm implemented at block 2440. The output of block 2680 may supply the input of DAC 1680, which in turn supplies a corresponding analog signal to an input of the power amplifier 1620.

Block 2700 of the processor 1740 may implement a switch-mode converter control algorithm for dynamically modulating the rail voltage of the power amplifier 1620 based on the waveform envelope of the signal being amplified, thereby improving the efficiency of the power amplifier 1620. In certain aspects, characteristics of the waveform envelope may be determined by monitoring one or more signals contained in the power amplifier 1620. In one aspect, for example, characteristics of the waveform envelope may be determined by monitoring the minima of a drain voltage (e.g., a MOSFET drain voltage) that is modulated in accordance with the envelope of the amplified signal. A minima voltage signal may be generated, for example, by a voltage minima detector coupled to the drain voltage. The minima voltage signal may be sampled by ADC 1760, with the output minima voltage samples being received at block 2720 of the switch-mode converter control algorithm. Based on the values of the minima voltage samples, block 2740 may control a PWM signal output by a PWM generator 2760, which, in turn, controls the rail voltage supplied to the power amplifier 1620 by the switch-mode regulator 1700. In certain aspects, as long as the values of the minima voltage samples are less than a minima target 2780 input into block 2720, the rail voltage may be modulated in accordance with the waveform envelope as characterized by the minima voltage samples. When the minima voltage samples indicate low envelope power levels, for example, block 2740 may cause a low rail voltage to be supplied to the power amplifier 1620, with the full rail voltage being supplied only when the minima voltage samples indicate maximum envelope power levels. When the minima voltage samples fall below the minima target 2780, block 2740 may cause the rail voltage to be maintained at a minimum value suitable for ensuring proper operation of the power amplifier 1620.

Figure 26:
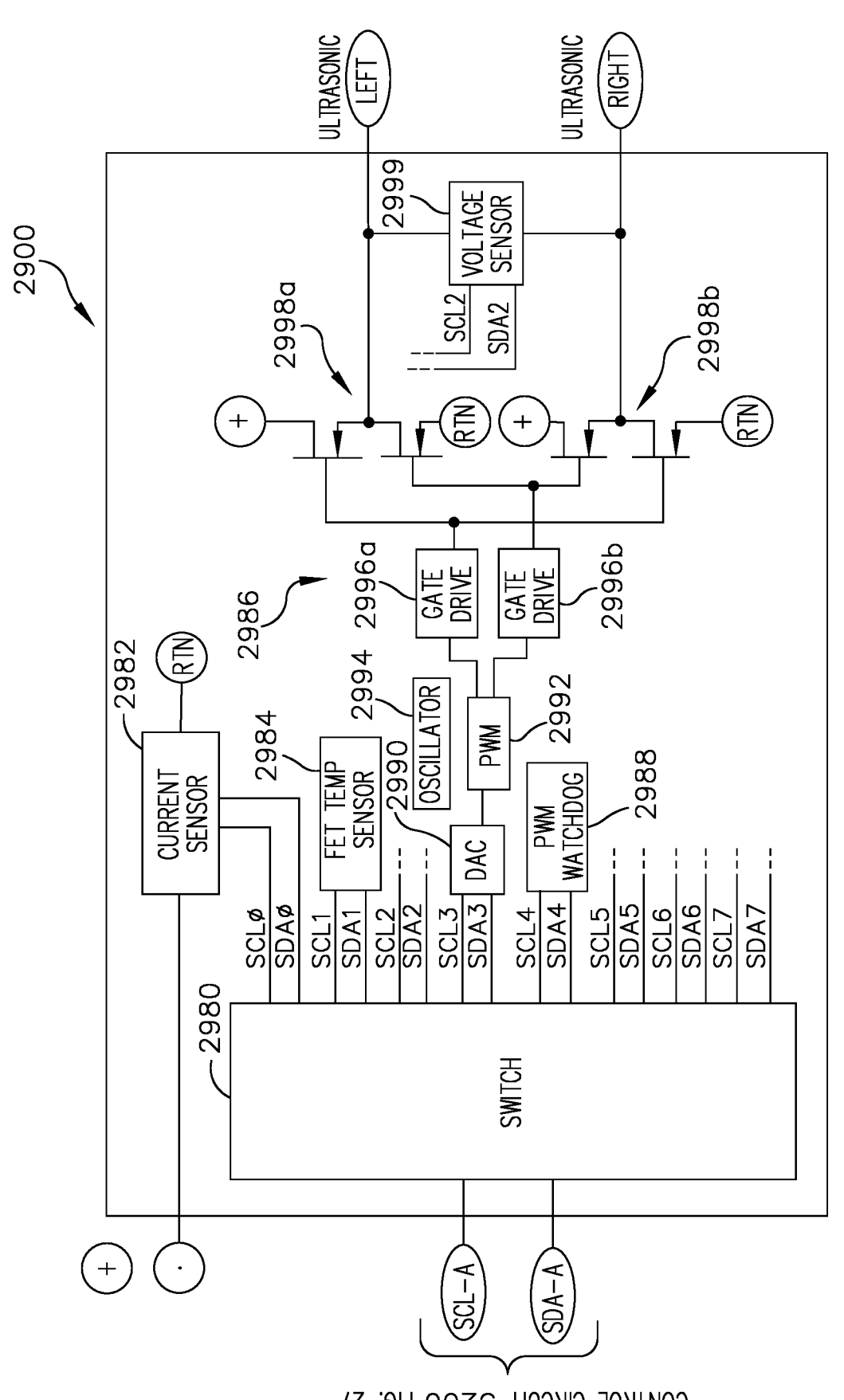
FIG. 26 is a schematic diagram of one aspect of an ultrasonic drive circuit.

FIG. 26 is a schematic diagram of one aspect of an electrical circuit 2900, suitable for driving an ultrasonic transducer, such as ultrasonic transducer 1120, in accordance with at least one aspect of the present disclosure. The electrical circuit 2900 comprises an analog multiplexer 2980. The analog multiplexer 2980 multiplexes various signals from the upstream channels SCL-A, SDA-A such as ultrasonic, battery, and power control circuit. A current sensor 2982 is coupled in series with the return or ground leg of the power supply circuit to measure the current supplied by the power supply. A field effect transistor (FET) temperature sensor 2984 provides the ambient temperature. A pulse width modulation (PWM) watchdog timer 2988 automatically generates a system reset if the main program neglects to periodically service it. It is provided to automatically reset the electrical circuit 2900 when it hangs or freezes because of a software or hardware fault. It will be appreciated that the electrical circuit 2900 may be configured as an RF driver circuit for driving the ultrasonic transducer or for driving RF electrodes such as the electrical circuit 3600 shown in FIG. 31, for example. Accordingly, with reference now back to FIG. 26, the electrical circuit 2900 can be used to drive both ultrasonic transducers and RF electrodes interchangeably. If driven simultaneously, filter circuits may be provided in the corresponding first stage circuits 3404 (FIG. 29) to select either the ultrasonic waveform or the RF waveform. Such filtering techniques are described in commonly owned U.S. Pat. Pub. No. US-2017-0086910-A1, titled TECHNIQUES FOR CIRCUIT TOPOLOGIES FOR COMBINED GENERATOR, which is herein incorporated by reference in its entirety.

Figure 27:
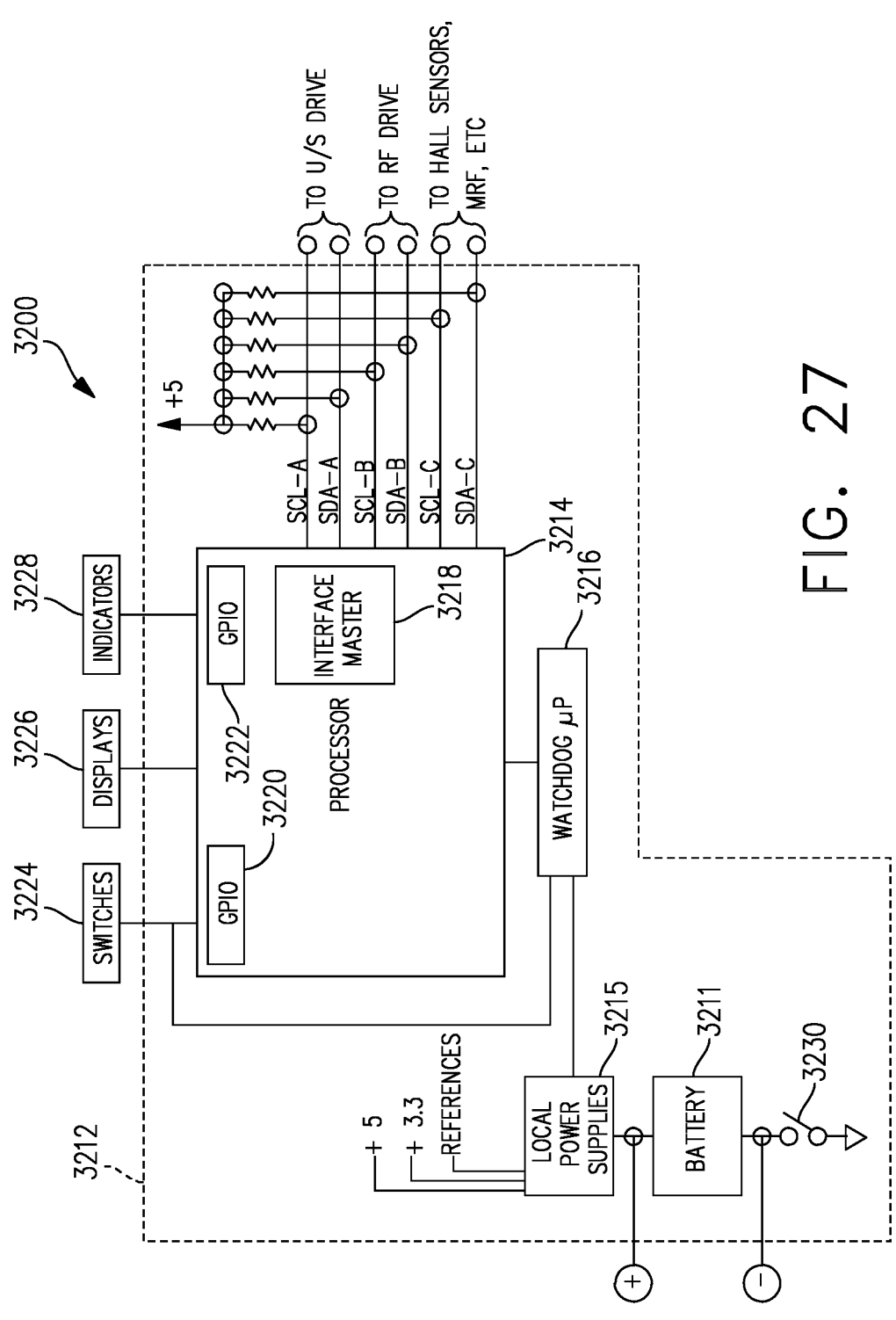
FIG. 27 is a schematic diagram of a control circuit, in accordance with at least one aspect of the present disclosure.
Figures 40, 41:
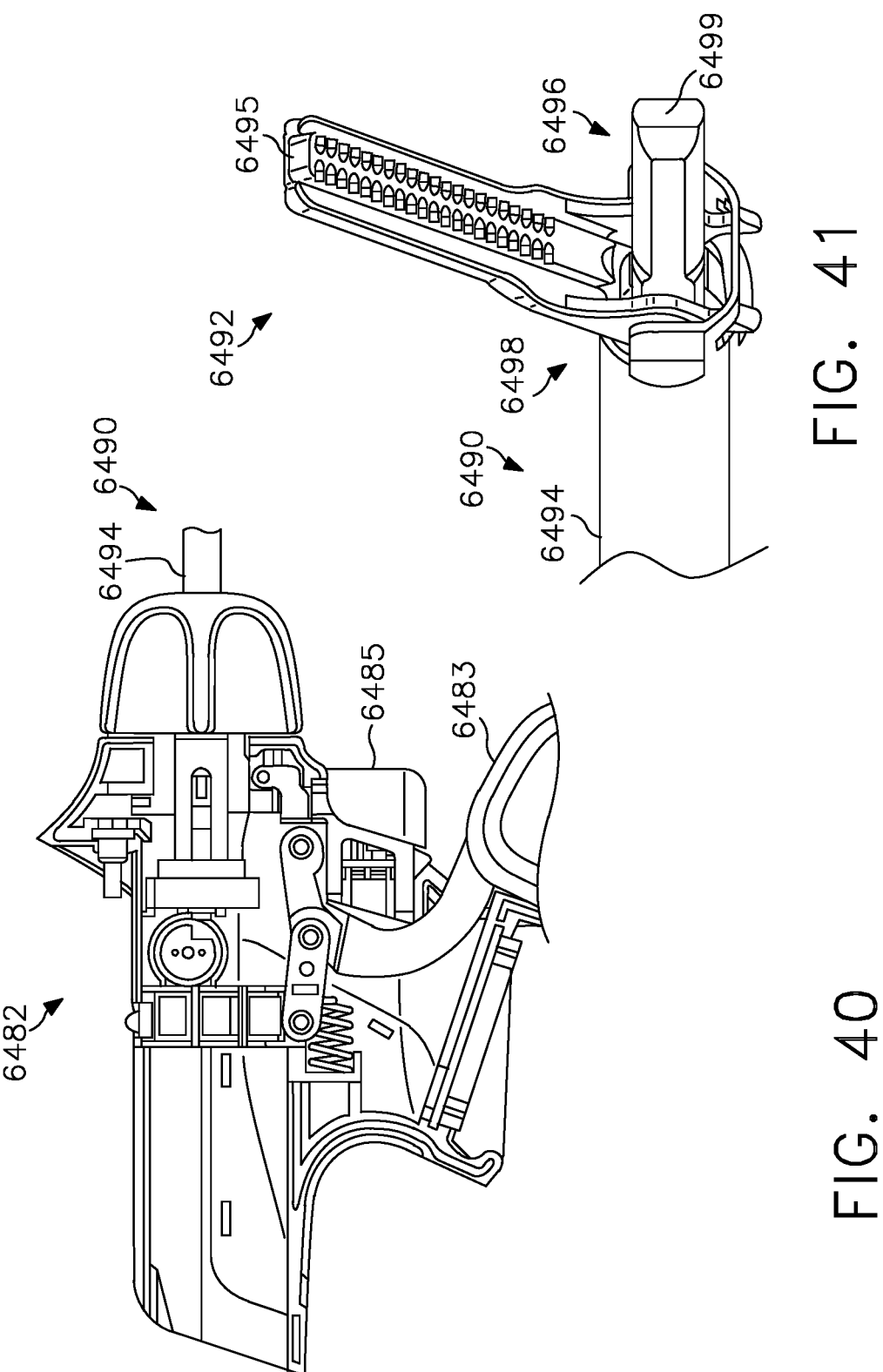
FIG. 40 is a detail view of a trigger portion and switch of the ultrasonic surgical instrument shown in FIG. 39, in accordance with at least one aspect of the present disclosure.
FIG. 41 is a fragmentary, enlarged perspective view of an end effector from a distal end with a jaw member in an open position, in accordance with at least one aspect of the present disclosure.
Figure 42:
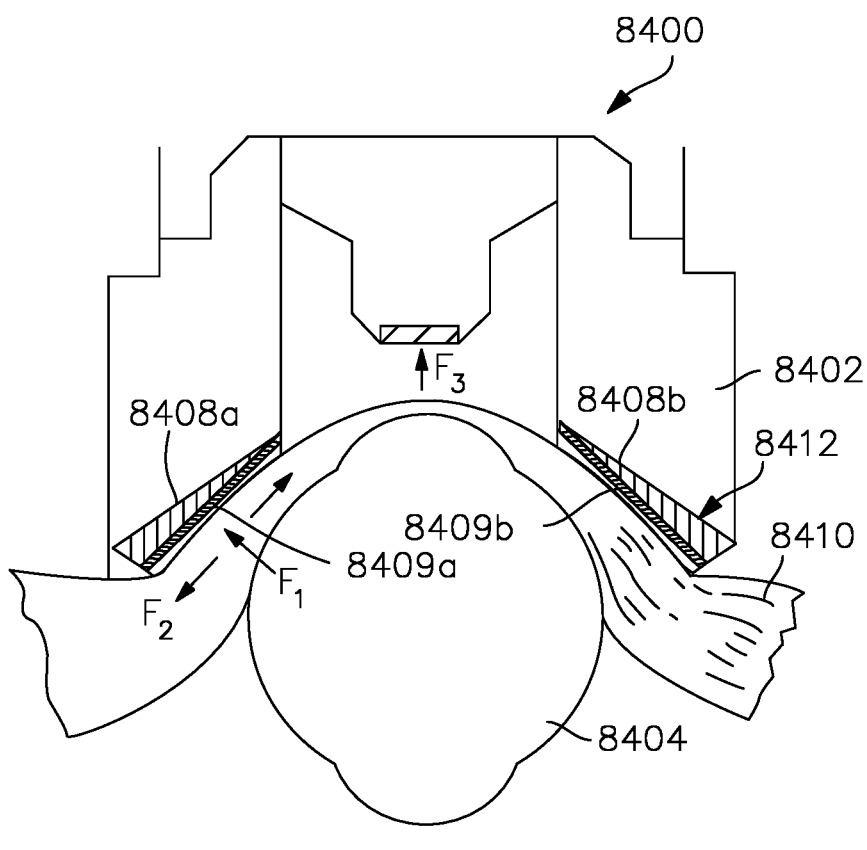
FIG. 42 illustrates one aspect of an end effector comprising RF data sensors located on the jaw member, in accordance with at least one aspect of the present disclosure.

A drive circuit 2986 provides left and right ultrasonic energy outputs. A digital signal that represents the signal waveform is provided to the SCL-A, SDA-A inputs of the analog multiplexer 2980 from a control circuit, such as the control circuit 3200 (FIG. 27). A digital-to-analog converter 2990 (DAC) converts the digital input to an analog output to drive a PWM circuit 2992 coupled to an oscillator 2994. The PWM circuit 2992 provides a first signal to a first gate drive circuit 2996a coupled to a first transistor output stage 2998a to drive a first Ultrasonic (LEFT) energy output. The PWM circuit 2992 also provides a second signal to a second gate drive circuit 2996b coupled to a second transistor output stage 2998b to drive a second Ultrasonic (RIGHT) energy output. A voltage sensor 2999 is coupled between the Ultrasonic LEFT/RIGHT output terminals to measure the output voltage. The drive circuit 2986, the first and second drive circuits 2996a, 2996b, and the first and second transistor output stages 2998a, 2998b define a first stage amplifier circuit. In operation, the control circuit 3200 (FIG. 27) generates a digital waveform 4300 (FIG. 36) employing circuits such as direct digital synthesis (DDS) circuits 4100, 4200 (FIGS. 41 and 42). The DAC 2990 receives the digital waveform 4300 and converts it into an analog waveform, which is received and amplified by the first stage amplifier circuit.

FIG. 27 is a schematic diagram of a control circuit 3200, such as control circuit 3212, in accordance with at least one aspect of the present disclosure. The control circuit 3200 is located within a housing of the battery assembly. The battery assembly is the energy source for a variety of local power supplies 3215. The control circuit comprises a main processor 3214 coupled via an interface master 3218 to various downstream circuits by way of outputs SCL-A and SDA-A, SCL-B and SDA-B, SCL-C and SDA-C, for example. In one aspect, the interface master 3218 is a general purpose serial interface such as an I²C serial interface. The main processor 3214 also is configured to drive switches 3224 through general purposes input/output (GPIO) 3220, a display 3226 (e.g., and LCD display), and various indicators 3228 through GPIO 3222. A watchdog processor 3216 is provided to control the main processor 3214. A switch 3230 is provided in series with a battery 3211 to activate the control circuit 3212 upon insertion of the battery assembly into a handle assembly of a surgical instrument.

In one aspect, the main processor 3214 is coupled to the electrical circuit 2900 (FIG. 26) by way of output terminals SCL-A, SDA-A. The main processor 3214 comprises a memory for storing tables of digitized drive signals or waveforms that are transmitted to the electrical circuit 2900 for driving the ultrasonic transducer 1120, for example. In other aspects, the main processor 3214 may generate a digital waveform and transmit it to the electrical circuit 2900 or may store the digital waveform for later transmission to the electrical circuit 2900. The main processor 3214 also may provide RF drive by way of output terminals SCL-B, SDA-B and various sensors (e.g., Hall-effect sensors, mag-neto-rheological fluid (MRF) sensors, etc.) by way of output terminals SCL-C, SDA-C. In one aspect, the main processor 3214 is configured to sense the presence of ultrasonic drive circuitry and/or RF drive circuitry to enable appropriate software and user interface functionality.

In one aspect, the main processor 3214 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with Stellar-isWare® software, 2 KB electrically erasable programmable read-only memory (EEPROM), one or more pulse width modulation (PWM) modules, one or more quadrature encoder inputs (QED analog, one or more 12-bit Analog-to-Digital Converters (ADC) with 12 analog input channels, among other features that are readily available from the product datasheet. Other processors may be readily substi-tuted and, accordingly, the present disclosure should not be limited in this context.

Figure 28:
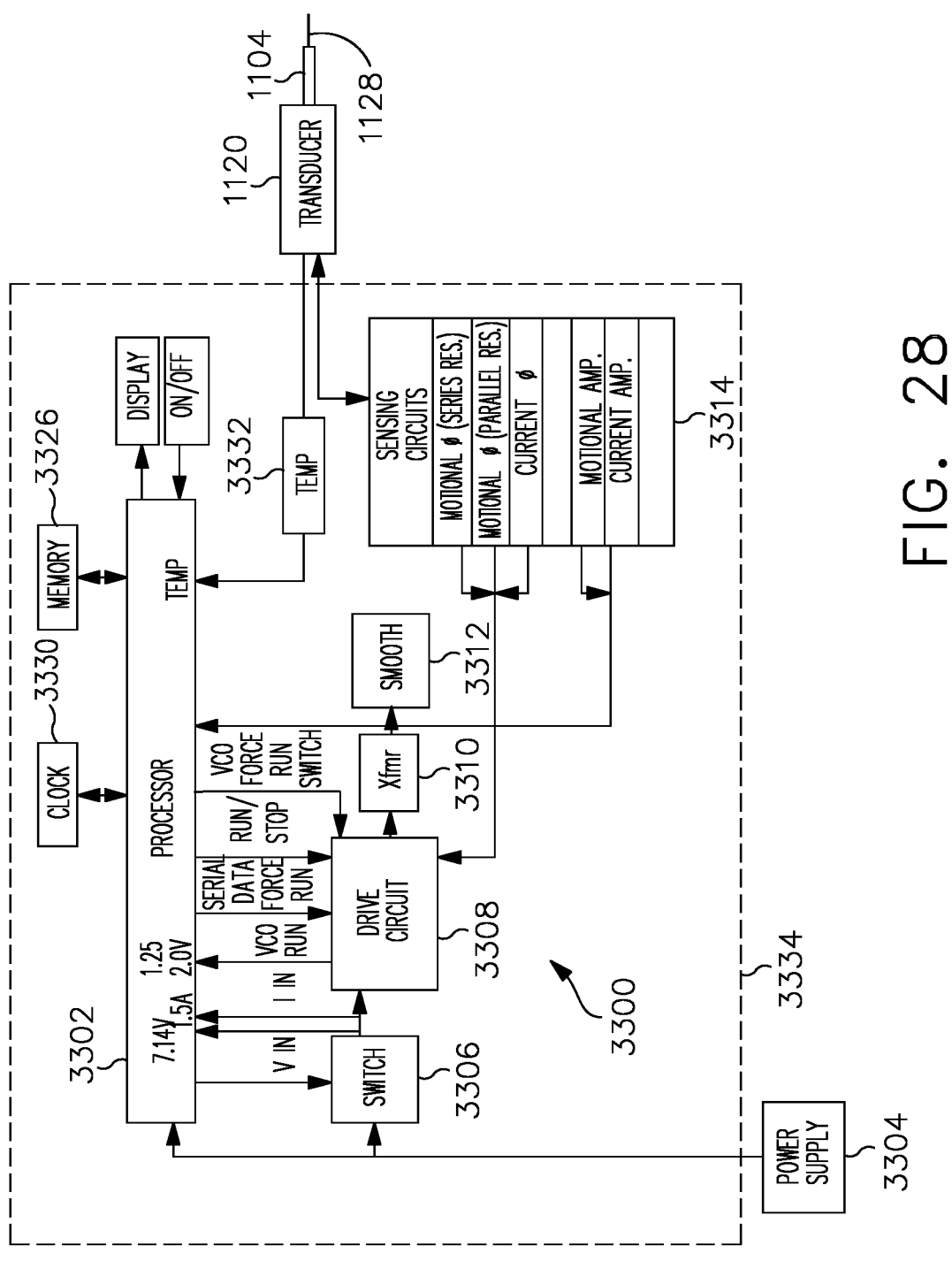
FIG. 28 shows a simplified block circuit diagram illustrating another electrical circuit contained within a modular ultrasonic surgical instrument, in accordance with at least one aspect of the present disclosure.

FIG. 28 shows a simplified block circuit diagram illus-trating another electrical circuit 3300 contained within a modular ultrasonic surgical instrument 3334, in accordance with at least one aspect of the present disclosure. The electrical circuit 3300 includes a processor 3302, a clock 3330, a memory 3326, a power supply 3304 (e.g., a battery), a switch 3306, such as a metal-oxide semiconductor field effect transistor (MOSFET) power switch, a drive circuit 3308 (PLL), a transformer 3310, a signal smoothing circuit 3312 (also referred to as a matching circuit and can be, for example, a tank circuit), a sensing circuit 3314, a transducer 1120, and a shaft assembly (e.g. shaft assembly 1126, 1129) comprising an ultrasonic transmission waveguide that ter-minates at an ultrasonic blade (e.g. ultrasonic blade 1128, 1149) which may be referred to herein simply as the wave-guide.

One feature of the present disclosure that severs depen-dency on high voltage (120 VAC) input power (a charac-teristic of general ultrasonic cutting devices) is the utiliza-tion of low-voltage switching throughout the wave-forming process and the amplification of the driving signal only directly before the transformer stage. For this reason, in one aspect of the present disclosure, power is derived from only a battery, or a group of batteries, small enough to fit either within a handle assembly. State-of-the-art battery technol-ogy provides powerful batteries of a few centimeters in height and width and a few millimeters in depth. By com-bining the features of the present disclosure to provide a self-contained and self-powered ultrasonic device, a reduc-tion in manufacturing cost may be achieved.

The output of the power supply 3304 is fed to and powers the processor 3302. The processor 3302 receives and outputs signals and, as will be described below, functions according to custom logic or in accordance with computer programs that are executed by the processor 3302. As discussed above, the electrical circuit 3300 can also include a memory 3326, preferably, random access memory (RAM), that stores com-puter-readable instructions and data.

The output of the power supply 3304 also is directed to the switch 3306 having a duty cycle controlled by the processor 3302. By controlling the on-time for the switch 3306, the processor 3302 is able to dictate the total amount of power that is ultimately delivered to the transducer 1120. In one aspect, the switch 3306 is a MOSFET, although other switches and switching configurations are adaptable as well. The output of the switch 3306 is fed to a drive circuit 3308 that contains, for example, a phase detecting phase-locked loop (PLL) and/or a low-pass filter and/or a voltage-con-trolled oscillator. The output of the switch 3306 is sampled by the processor 3302 to determine the voltage and current of the output signal ($V_{IN}$ and $I_{IN}$, respectively). These values are used in a feedback architecture to adjust the pulse width modulation of the switch 3306. For instance, the duty cycle of the switch 3306 can vary from about 20% to about 80%, depending on the desired and actual output from the switch 3306.

The drive circuit 3308, which receives the signal from the switch 3306, includes an oscillatory circuit that turns the output of the switch 3306 into an electrical signal having an ultrasonic frequency, e.g., 55 kHz (VCO). As explained above, a smoothed-out version of this ultrasonic waveform is ultimately fed to the ultrasonic transducer 1120 to produce a resonant sine wave along an ultrasonic transmission wave-guide.

At the output of the drive circuit 3308 is a transformer 3310 that is able to step up the low voltage signal(s) to a higher voltage. It is noted that upstream switching, prior to the transformer 3310, is performed at low (e.g., battery driven) voltages, something that, to date, has not been possible for ultrasonic cutting and cautery devices. This is at least partially due to the fact that the device advantageously uses low on-resistance MOSFET switching devices. Low on-resistance MOSFET switches are advantageous, as they produce lower switching losses and less heat than a tradi-tional MOSFET device and allow higher current to pass through. Therefore, the switching stage (pre-transformer) can be characterized as low voltage/high current. To ensure the lower on-resistance of the amplifier MOSFET(s), the MOSFET(s) are run, for example, at 10 V. In such a case, a separate 10 VDC power supply can be used to feed the MOSFET gate, which ensures that the MOSFET is fully on and a reasonably low on resistance is achieved. In one aspect of the present disclosure, the transformer 3310 steps up the battery voltage to 120 V root-mean-square (RMS). Trans-formers are known in the art and are, therefore, not explained here in detail.

In the circuit configurations described, circuit component degradation can negatively impact the circuit performance of the circuit. One factor that directly affects component performance is heat. Known circuits generally monitor switching temperatures (e.g., MOSFET temperatures). However, because of the technological advancements in MOSFET designs, and the corresponding reduction in size, MOSFET temperatures are no longer a valid indicator of circuit loads and heat. For this reason, in accordance with at least one aspect of the present disclosure, the sensing circuit 3314 senses the temperature of the transformer 3310. This temperature sensing is advantageous as the transformer 3310 is run at or very close to its maximum temperature during use of the device. Additional temperature will cause the core material, e.g., the ferrite, to break down and permanent damage can occur. The present disclosure can respond to a maximum temperature of the transformer 3310 by, for example, reducing the driving power in the transformer 3310, signaling the user, turning the power off, pulsing the power, or other appropriate responses.

In one aspect of the present disclosure, the processor 3302 is communicatively coupled to the end effector (e.g. 1122, 1125), which is used to place material in physical contact with the ultrasonic blade (e.g. 1128, 1149). Sensors are provided that measure, at the end effector, a clamping force value (existing within a known range) and, based upon the received clamping force value, the processor 3302 varies the motional voltage $V_M$. Because high force values combined with a set motional rate can result in high blade temperatures, a temperature sensor 3332 can be communicatively coupled to the processor 3302, where the processor 3302 is operable to receive and interpret a signal indicating a current temperature of the blade from the temperature sensor 3336 and to determine a target frequency of blade movement based upon the received temperature. In another aspect, force sensors such as strain gages or pressure sensors may be coupled to the trigger (e.g. 1143, 1147) to measure the force applied to the trigger by the user. In another aspect, force sensors such as strain gages or pressure sensors may be coupled to a switch button such that displacement intensity corresponds to the force applied by the user to the switch button.

In accordance with at least one aspect of the present disclosure, the PLL portion of the drive circuit 3308, which is coupled to the processor 3302, is able to determine a frequency of waveguide movement and communicate that frequency to the processor 3302. The processor 3302 stores this frequency value in the memory 3326 when the device is turned off. By reading the clock 3330, the processor 3302 is able to determine an elapsed time after the device is shut off and retrieve the last frequency of waveguide movement if the elapsed time is less than a predetermined value. The device can then start up at the last frequency, which, presumably, is the optimum frequency for the current load.

Modular Battery Powered Handheld Surgical Instrument with Multistage Generator Circuits In another aspect, the present disclosure provides a modular battery powered handheld surgical instrument with multistage generator circuits. Disclosed is a surgical instrument that includes a battery assembly, a handle assembly, and a shaft assembly where the battery assembly and the shaft assembly are configured to mechanically and electrically connect to the handle assembly. The battery assembly includes a control circuit configured to generate a digital waveform. The handle assembly includes a first stage circuit configured to receive the digital waveform, convert the digital waveform into an analog waveform, and amplify the analog waveform. The shaft assembly includes a second stage circuit coupled to the first stage circuit to receive, amplify, and apply the analog waveform to a load.

In one aspect, the present disclosure provides a surgical instrument, comprising: a battery assembly, comprising a control circuit comprising a battery, a memory coupled to the battery, and a processor coupled to the memory and the battery, wherein the processor is configured to generate a digital waveform; a handle assembly comprising a first stage circuit coupled to the processor, the first stage circuit comprising a digital-to-analog (DAC) converter and a first stage amplifier circuit, wherein the DAC is configured to receive the digital waveform and convert the digital waveform into an analog waveform, wherein the first stage amplifier circuit is configured to receive and amplify the analog waveform; and a shaft assembly comprising a second stage circuit coupled to the first stage amplifier circuit to receive the analog waveform, amplify the analog waveform, and apply the analog waveform to a load; wherein the battery assembly and the shaft assembly are configured to mechanically and electrically connect to the handle assembly.

The load may comprise any one of an ultrasonic transducer, an electrode, or a sensor, or any combinations thereof. The first stage circuit may comprise a first stage ultrasonic drive circuit and a first stage high-frequency current drive circuit. The control circuit may be configured to drive the first stage ultrasonic drive circuit and the first stage high-frequency current drive circuit independently or simultaneously. The first stage ultrasonic drive circuit may be configured to couple to a second stage ultrasonic drive circuit. The second stage ultrasonic drive circuit may be configured to couple to an ultrasonic transducer. The first stage high-frequency current drive circuit may be configured to couple to a second stage high-frequency drive circuit. The second stage high-frequency drive circuit may be configured to couple to an electrode.

The first stage circuit may comprise a first stage sensor drive circuit. The first stage sensor drive circuit may be configured to a second stage sensor drive circuit. The second stage sensor drive circuit may be configured to couple to a sensor.

In another aspect, the present disclosure provides a surgical instrument, comprising: a battery assembly, comprising a control circuit comprising a battery, a memory coupled to the battery, and a processor coupled to the memory and the battery, wherein the processor is configured to generate a digital waveform; a handle assembly comprising a common first stage circuit coupled to the processor, the common first stage circuit comprising a digital-to-analog (DAC) converter and a common first stage amplifier circuit, wherein the DAC is configured to receive the digital waveform and convert the digital waveform into an analog waveform, wherein the common first stage amplifier circuit is configured to receive and amplify the analog waveform; and a shaft assembly comprising a second stage circuit coupled to the common first stage amplifier circuit to receive the analog waveform, amplify the analog waveform, and apply the analog waveform to a load; wherein the battery assembly and the shaft assembly are configured to mechanically and electrically connect to the handle assembly.

The load may comprise any one of an ultrasonic transducer, an electrode, or a sensor, or any combinations thereof. The common first stage circuit may be configured to drive ultrasonic, high-frequency current, or sensor circuits. The common first stage drive circuit may be configured to couple to a second stage ultrasonic drive circuit, a second stage high-frequency drive circuit, or a second stage sensor drive circuit. The second stage ultrasonic drive circuit may be configured to couple to an ultrasonic transducer, the second stage high-frequency drive circuit is configured to couple to an electrode, and the second stage sensor drive circuit is configured to couple to a sensor.

In another aspect, the present disclosure provides a surgical instrument, comprising a control circuit comprising a memory coupled to a processor, wherein the processor is configured to generate a digital waveform; a handle assembly comprising a common first stage circuit coupled to the processor, the common first stage circuit configured to receive the digital waveform, convert the digital waveform into an analog waveform, and amplify the analog waveform; and a shaft assembly comprising a second stage circuit coupled to the common first stage circuit to receive and amplify the analog waveform; wherein the shaft assembly is configured to mechanically and electrically connect to the handle assembly.

The common first stage circuit may be configured to drive ultrasonic, high-frequency current, or sensor circuits. The common first stage drive circuit may be configured to couple to a second stage ultrasonic drive circuit, a second stage high-frequency drive circuit, or a second stage sensor drive circuit. The second stage ultrasonic drive circuit may be configured to couple to an ultrasonic transducer, the second stage high-frequency drive circuit is configured to couple to an electrode, and the second stage sensor drive circuit is configured to couple to a sensor.

Figure 29:
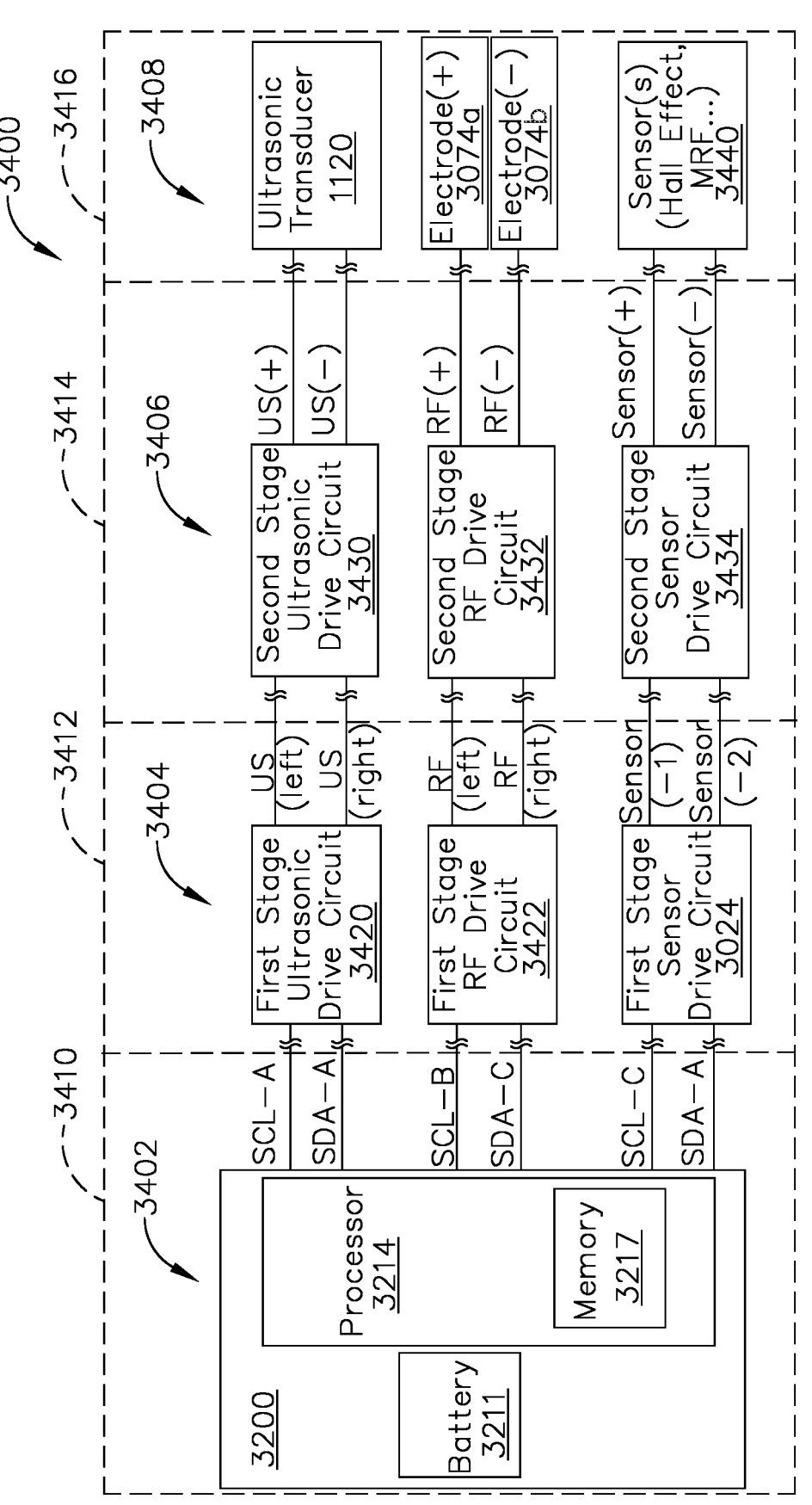
FIG. 29 illustrates a generator circuit partitioned into multiple stages, in accordance with at least one aspect of the present disclosure.

FIG. 29 illustrates a generator circuit 3400 partitioned into a first stage circuit 3404 and a second stage circuit 3406, in accordance with at least one aspect of the present disclosure. In one aspect, the surgical instruments of surgical system 1000 described herein may comprise a generator circuit 3400 partitioned into multiple stages. For example, surgical instruments of surgical system 1000 may comprise the generator circuit 3400 partitioned into at least two circuits: the first stage circuit 3404 and the second stage circuit 3406 of amplification enabling operation of RF energy only, ultrasonic energy only, and/or a combination of RF energy and ultrasonic energy. A combination modular shaft assembly 3414 may be powered by the common first stage circuit 3404 located within a handle assembly 3412 and the modular second stage circuit 3406 integral to the modular shaft assembly 3414. As previously discussed throughout this description in connection with the surgical instruments of surgical system 1000, a battery assembly 3410 and the shaft assembly 3414 are configured to mechanically and electrically connect to the handle assembly 3412. The end effector assembly is configured to mechanically and electrically connect the shaft assembly 3414.

Turning now to FIG. 29, the generator circuit 3400 is partitioned into multiple stages located in multiple modular assemblies of a surgical instrument, such as the surgical instruments of surgical system 1000 described herein. In one aspect, a control stage circuit 3402 may be located in the battery assembly 3410 of the surgical instrument. The control stage circuit 3402 is a control circuit 3200 as described in connection with FIG. 27. The control circuit 3200 comprises a processor 3214, which includes internal memory 3217 (FIG. 29) (e.g., volatile and non-volatile memory), and is electrically coupled to a battery 3211. The battery 3211 supplies power to the first stage circuit 3404, the second stage circuit 3406, and a third stage circuit 3408, respectively. As previously discussed, the control circuit 3200 generates a digital waveform 4300 (FIG. 36) using circuits and techniques described in connection with FIGS. 41 and 42. Returning to FIG. 29, the digital waveform 4300 may be configured to drive an ultrasonic transducer, high-frequency (e.g., RF) electrodes, or a combination thereof either independently or simultaneously. If driven simultaneously, filter circuits may be provided in the corresponding first stage circuits 3404 to select either the ultrasonic waveform or the RF waveform. Such filtering techniques are described in commonly owned U.S. Patent Application Publication No. 2017/0086910, titled TECHNIQUES FOR CIRCUIT TOPOLOGIES FOR COMBINED GENERATOR, which issued on Apr. 7, 2020 as U.S. Pat. No. 10,610,286, which is herein incorporated by reference in its entirety.

The first stage circuits 3404 (e.g., the first stage ultrasonic drive circuit 3420, the first stage RF drive circuit 3422, and the first stage sensor drive circuit 3424) are located in a handle assembly 3412 of the surgical instrument. The control circuit 3200 provides the ultrasonic drive signal to the first stage ultrasonic drive circuit 3420 via outputs SCL-A, SDA-A of the control circuit 3200. The first stage ultrasonic drive circuit 3420 is described in detail in connection with FIG. 26. The control circuit 3200 provides the RF drive signal to the first stage RF drive circuit 3422 via outputs SCL-B, SDA-B of the control circuit 3200. The first stage RF drive circuit 3422 is described in detail in connection with FIG. 31. The control circuit 3200 provides the sensor drive signal to the first stage sensor drive circuit 3424 via outputs SCL-C, SDA-C of the control circuit 3200. Generally, each of the first stage circuits 3404 includes a digital-to-analog (DAC) converter and a first stage amplifier section to drive the second stage circuits 3406. The outputs of the first stage circuits 3404 are provided to the inputs of the second stage circuits 3406.

The control circuit 3200 is configured to detect which modules are plugged into the control circuit 3200. For example, the control circuit 3200 is configured to detect whether the first stage ultrasonic drive circuit 3420, the first stage RF drive circuit 3422, or the first stage sensor drive circuit 3424 located in the handle assembly 3412 is connected to the battery assembly 3410. Likewise, each of the first stage circuits 3404 can detect which second stage circuits 3406 are connected thereto and that information is provided back to the control circuit 3200 to determine the type of signal waveform to generate. Similarly, each of the second stage circuits 3406 can detect which third stage circuits 3408 or components are connected thereto and that information is provided back to the control circuit 3200 to determine the type of signal waveform to generate.

In one aspect, the second stage circuits 3406 (e.g., the ultrasonic drive second stage circuit 3430, the RF drive second stage circuit 3432, and the sensor drive second stage circuit 3434) are located in the shaft assembly 3414 of the surgical instrument. The first stage ultrasonic drive circuit 3420 provides a signal to the second stage ultrasonic drive circuit 3430 via outputs US-Left/US-Right. The second stage ultrasonic drive circuit 3430 is described in detail in connection with FIGS. 30 and 31. In addition to a transformer (FIGS. 30 and 31), the second stage ultrasonic drive circuit 3430 also may include filter, amplifier, and signal conditioning circuits. The first stage high-frequency (RF) current drive circuit 3422 provides a signal to the second stage RF drive circuit 3432 via outputs RF-Left/RF-Right. In addition to a transformer and blocking capacitors, the second stage RF drive circuit 3432 also may include filter, amplifier, and signal conditioning circuits. The first stage sensor drive circuit 3424 provides a signal to the second stage sensor drive circuit 3434 via outputs Sensor-1/Sensor-2. The second stage sensor drive circuit 3434 may include filter, amplifier, and signal conditioning circuits depending on the type of sensor. The outputs of the second stage circuits 3406 are provided to the inputs of the third stage circuits 3408.

In one aspect, the third stage circuits 3408 (e.g., the ultrasonic transducer 1120, the RF electrodes 3074a, 3074b, and the sensors 3440) may be located in various assemblies 3416 of the surgical instruments. In one aspect, the second stage ultrasonic drive circuit 3430 provides a drive signal to the ultrasonic transducer 1120 piezoelectric stack. In one aspect, the ultrasonic transducer 1120 is located in the ultrasonic transducer assembly of the surgical instrument. In other aspects, however, the ultrasonic transducer 1120 may be located in the handle assembly 3412, the shaft assembly 3414, or the end effector. In one aspect, the second stage RF drive circuit 3432 provides a drive signal to the RF electrodes 3074a, 3074b, which are generally located in the end effector portion of the surgical instrument. In one aspect, the second stage sensor drive circuit 3434 provides a drive signal to various sensors 3440 located throughout the surgical instrument.

Figure 30:
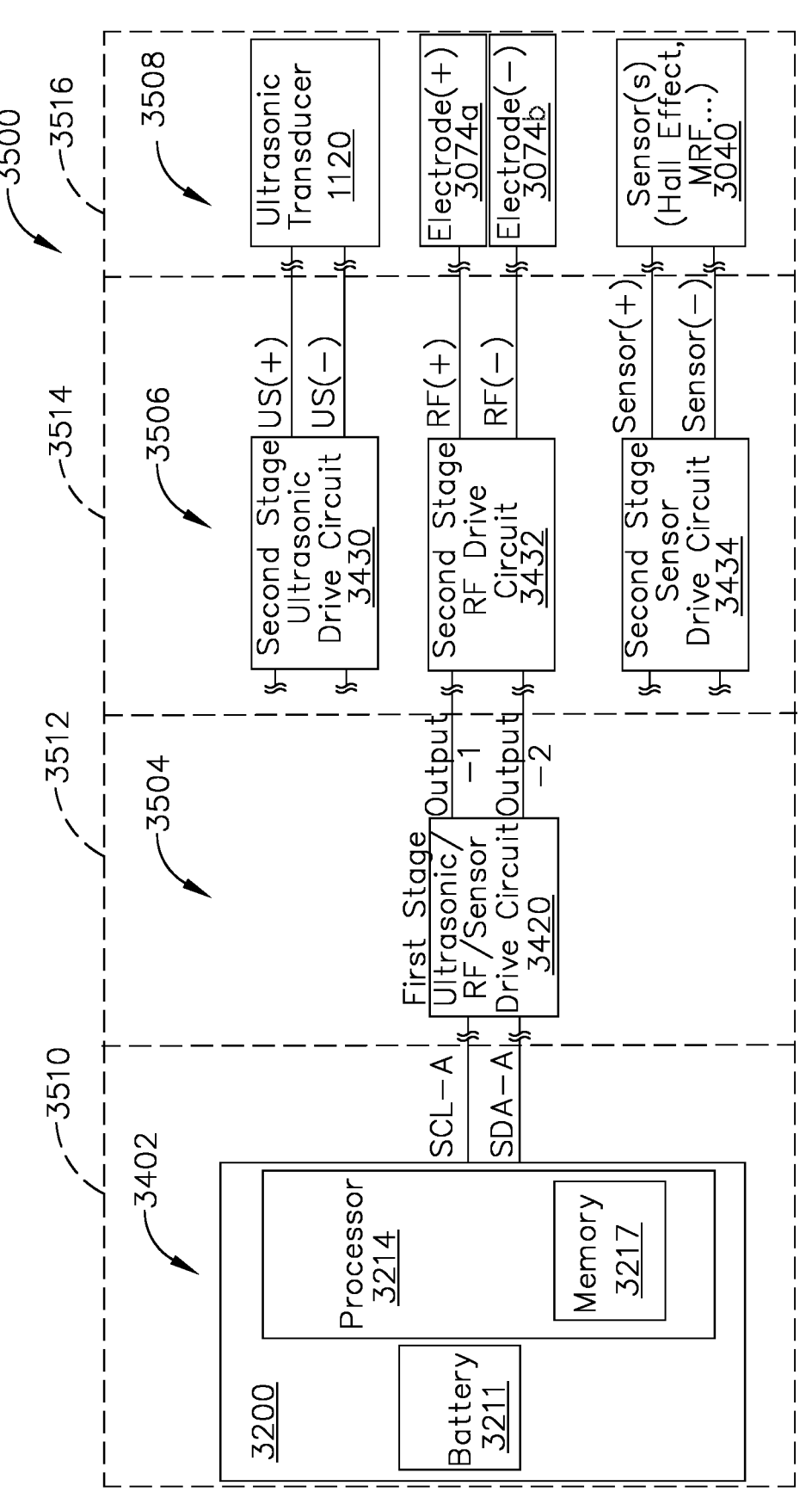
FIG. 30 illustrates a generator circuit partitioned into multiple stages where a first stage circuit is common to the second stage circuit, in accordance with at least one aspect of the present disclosure.

FIG. 30 illustrates a generator circuit 3500 partitioned into multiple stages where a first stage circuit 3504 is common to the second stage circuit 3506, in accordance with at least one aspect of the present disclosure. In one aspect, the surgical instruments of surgical system 1000 described herein may comprise generator circuit 3500 partitioned into multiple stages. For example, the surgical instruments of surgical system 1000 may comprise the generator circuit 3500 partitioned into at least two circuits: the first stage circuit 3504 and the second stage circuit 3506 of amplification enabling operation of high-frequency (RF) energy only, ultrasonic energy only, and/or a combination of RF energy and ultrasonic energy. A combination modular shaft assembly 3514 may be powered by a common first stage circuit 3504 located within the handle assembly 3512 and a modular second stage circuit 3506 integral to the modular shaft assembly 3514. As previously discussed throughout this description in connection with the surgical instruments of surgical system 1000, a battery assembly 3510 and the shaft assembly 3514 are configured to mechanically and electrically connect to the handle assembly 3512. The end effector assembly is configured to mechanically and electrically connect the shaft assembly 3514.

As shown in the example of FIG. 30, the battery assembly 3510 portion of the surgical instrument comprises a first control circuit 3502, which includes the control circuit 3200 previously described. The handle assembly 3512, which connects to the battery assembly 3510, comprises a common first stage drive circuit 3420. As previously discussed, the first stage drive circuit 3420 is configured to drive ultrasonic, high-frequency (RF) current, and sensor loads. The output of the common first stage drive circuit 3420 can drive any one of the second stage circuits 3506 such as the second stage ultrasonic drive circuit 3430, the second stage high-frequency (RF) current drive circuit 3432, and/or the second stage sensor drive circuit 3434. The common first stage drive circuit 3420 detects which second stage circuit 3506 is located in the shaft assembly 3514 when the shaft assembly 3514 is connected to the handle assembly 3512. Upon the shaft assembly 3514 being connected to the handle assembly 3512, the common first stage drive circuit 3420 determines which one of the second stage circuits 3506 (e.g., the second stage ultrasonic drive circuit 3430, the second stage RF drive circuit 3432, and/or the second stage sensor drive circuit 3434) is located in the shaft assembly 3514. The information is provided to the control circuit 3200 located in the handle assembly 3512 in order to supply a suitable digital waveform 4300 (FIG. 36) to the second stage circuit 3506 to drive the appropriate load, e.g., ultrasonic, RF, or sensor. It will be appreciated that identification circuits may be included in various assemblies 3516 in third stage circuit 3508 such as the ultrasonic transducer 1120, the electrodes 3074a, 3074b, or the sensors 3440. Thus, when a third stage circuit 3508 is connected to a second stage circuit 3506, the second stage circuit 3506 knows the type of load that is required based on the identification information.

Figure 31:
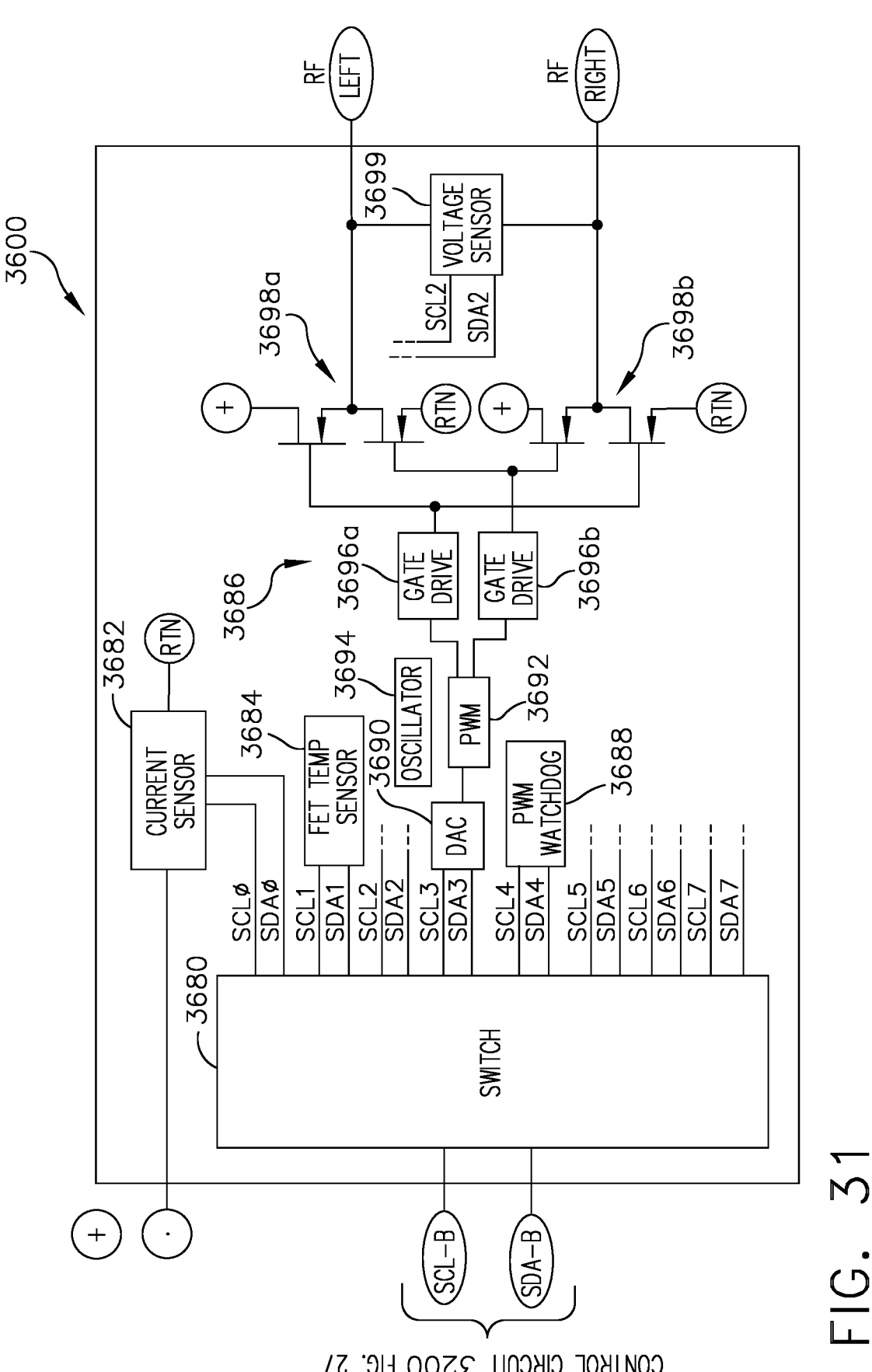
FIG. 31 is a schematic diagram of one aspect of a drive circuit configured for driving a high-frequency current (RF), in accordance with at least one aspect of the present disclosure.

FIG. 31 is a schematic diagram of one aspect of an electrical circuit 3600 configured to drive a high-frequency current (RF), in accordance with at least one aspect of the present disclosure. The electrical circuit 3600 comprises an analog multiplexer 3680. The analog multiplexer 3680 multiplexes various signals from the upstream channels SCL-A, SDA-A such as RF, battery, and power control circuit. A current sensor 3682 is coupled in series with the return or ground leg of the power supply circuit to measure the current supplied by the power supply. A field effect transistor (FET) temperature sensor 3684 provides the ambient temperature. A pulse width modulation (PWM) watchdog timer 3688 automatically generates a system reset if the main program neglects to periodically service it. It is provided to automatically reset the electrical circuit 3600 when it hangs or freezes because of a software or hardware fault. It will be appreciated that the electrical circuit 3600 may be configured for driving RF electrodes or for driving the ultrasonic transducer 1120 as described in connection with FIG. 26, for example. Accordingly, with reference now back to FIG. 31, the electrical circuit 3600 can be used to drive both ultrasonic and RF electrodes interchangeably.

A drive circuit 3686 provides Left and Right RF energy outputs. A digital signal that represents the signal waveform is provided to the SCL-A, SDA-A inputs of the analog multiplexer 3680 from a control circuit, such as the control circuit 3200 (FIG. 27). A digital-to-analog converter 3690 (DAC) converts the digital input to an analog output to drive a PWM circuit 3692 coupled to an oscillator 3694. The PWM circuit 3692 provides a first signal to a first gate drive circuit 3696a coupled to a first transistor output stage 3698a to drive a first RF+ (Left) energy output. The PWM circuit 3692 also provides a second signal to a second gate drive circuit 3696b coupled to a second transistor output stage 3698b to drive a second RF− (Right) energy output. A voltage sensor 3699 is coupled between the RF Left/RF output terminals to measure the output voltage. The drive circuit 3686, the first and second drive circuits 3696a, 3696b, and the first and second transistor output stages 3698a, 3698b define a first stage amplifier circuit. In operation, the control circuit 3200 (FIG. 27) generates a digital waveform 4300 (FIG. 36) employing circuits such as direct digital synthesis (DDS) circuits 4100, 4200 (FIGS. 41 and 42). The DAC 3690 receives the digital waveform 4300 and converts it into an analog waveform, which is received and amplified by the first stage amplifier circuit.

Figure 32:
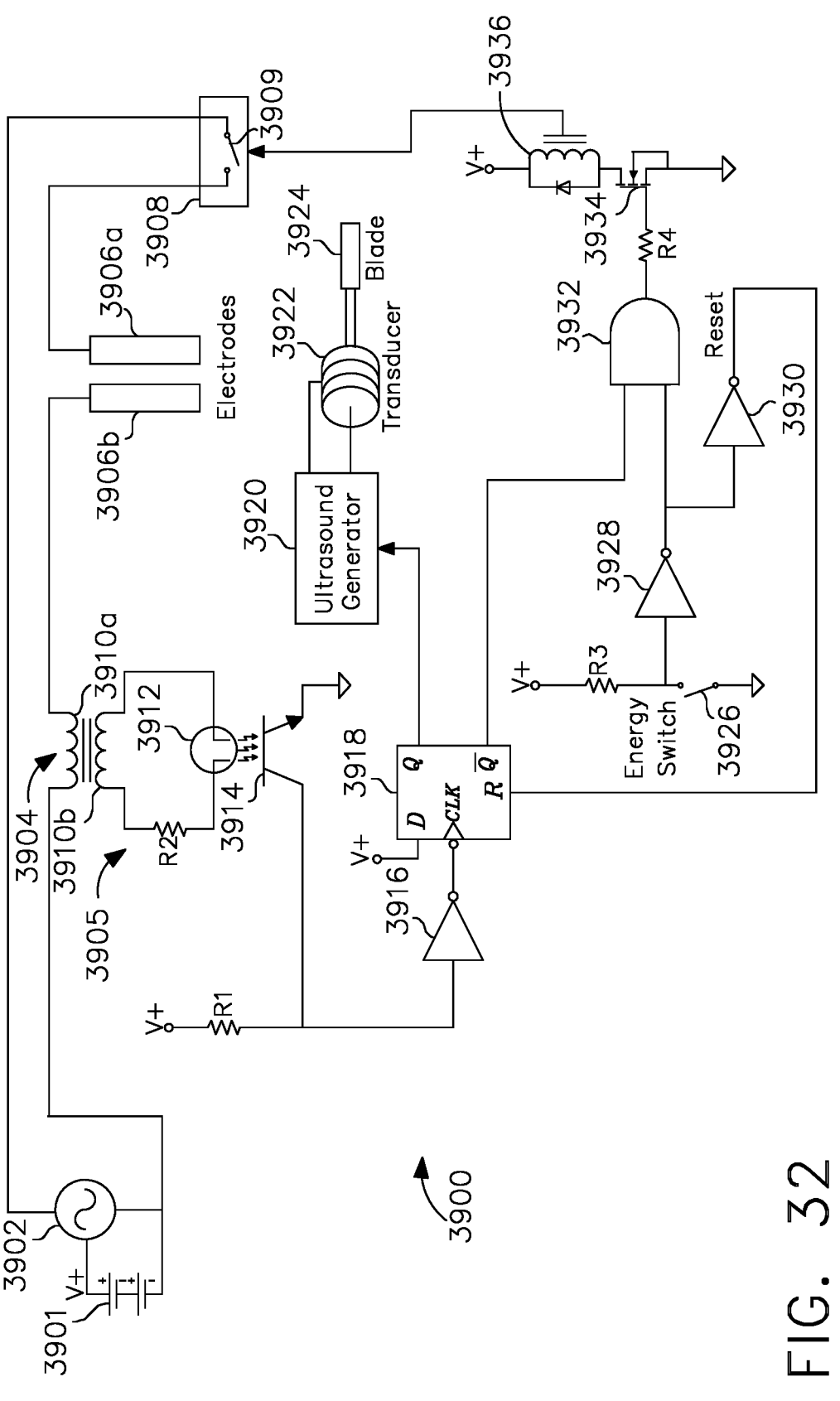
FIG. 32 illustrates a control circuit that allows a dual generator system to switch between the RF generator and the ultrasonic generator energy modalities for a surgical instrument.

FIG. 32 illustrates the control circuit 3900 that allows a dual generator system to switch between the RF generator circuit 3902 and the ultrasonic generator circuit 3920 energy modalities for a surgical instrument of the surgical system 1000. In one aspect, a current threshold in an RF signal is detected. When the impedance of the tissue is low the high-frequency current through tissue is high when RF energy is used as the treatment source for the tissue. According to one aspect, a visual indicator 3912 or light located on the surgical instrument of surgical system 1000 may be configured to be in an on-state during this high current period. When the current falls below a threshold, the visual indicator 3912 is in an off-state. Accordingly, a phototransistor 3914 may be configured to detect the transition from an on-state to an off-state and disengages the RF energy as shown in the control circuit 3900 shown in FIG. 32. Therefore, when the energy button is released and an energy switch 3926 is opened, the control circuit 3900 is reset and both the RF and ultrasonic generator circuits 3902, 3920 are held off.

Figure 39:
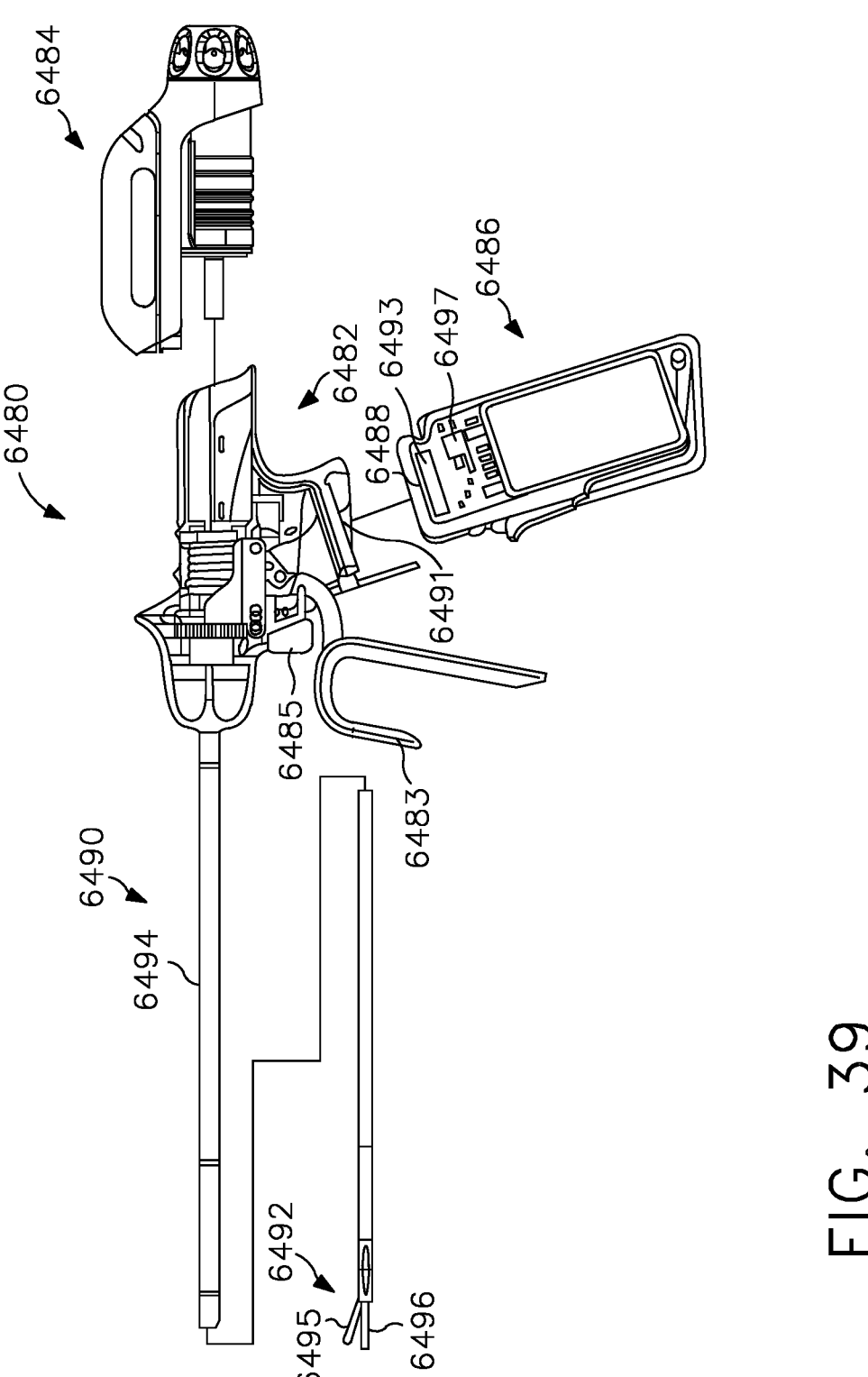
FIG. 39 is an elevational exploded view of modular handheld ultrasonic surgical instrument showing the left shell half removed from a handle assembly exposing a device identifier communicatively coupled to the multi-lead handle terminal assembly in accordance with one aspect of the present disclosure.

With reference to FIG. 39, in one aspect, a method of managing an RF generator circuit 3902 and ultrasound generator circuit 3920 is provided. The RF generator circuit 3902 and/or the ultrasound generator circuit 3920 may be located in the handle assembly 1109, the ultrasonic transducer/RF generator assembly 1120, the battery assembly, the shaft assembly 1129, and/or the nozzle, of the multifunction electrosurgical instrument 1108, for example. The control circuit 3900 is held in a reset state if the energy switch 3926 is off (e.g., open). Thus, when the energy switch 3926 is opened, the control circuit 3900 is reset and both the RF and ultrasonic generator circuits 3902, 3920 are turned off. When the energy switch 3926 is squeezed and the energy switch 3926 is engaged (e.g., closed), RF energy is delivered to the tissue and the visual indicator 3912 operated by a current sensing step-up transformer 3904 will be lit while the tissue impedance is low. The light from the visual indicator 3912 provides a logic signal to keep the ultrasonic generator circuit 3920 in the off state. Once the tissue impedance increases above a threshold and the high-frequency current through the tissue decreases below a threshold, the visual indicator 3912 turns off and the light transitions to an off-state. A logic signal generated by this transition turns off a relay 3908, whereby the RF generator circuit 3902 is turned off and the ultrasonic generator circuit 3920 is turned on, to complete the coagulation and cut cycle.

Still with reference to FIG. 39, in one aspect, the dual generator circuit configuration employs the on-board RF generator circuit 3902, which is battery 3901 powered, for one modality and a second, on-board ultrasound generator circuit 3920, which may be on-board in the handle assembly 1109, battery assembly, shaft assembly 1129, nozzle, and/or the ultrasonic transducer/RF generator assembly 1120 of the multifunction electrosurgical instrument 1108, for example. The ultrasonic generator circuit 3920 also is battery 3901 operated. In various aspects, the RF generator circuit 3902 and the ultrasonic generator circuit 3920 may be an integrated or separable component of the handle assembly 1109. According to various aspects, having the dual RF/ultrasonic generator circuits 3902, 3920 as part of the handle assembly 1109 may eliminate the need for complicated wiring. The RF/ultrasonic generator circuits 3902, 3920 may be configured to provide the full capabilities of an existing generator while utilizing the capabilities of a cordless generator system simultaneously.

Either type of system can have separate controls for the modalities that are not communicating with each other. The surgeon activates the RF and Ultrasonic separately and at their discretion. Another approach would be to provide fully integrated communication schemes that share buttons, tissue status, instrument operating parameters (such as jaw closure, forces, etc.) and algorithms to manage tissue treatment. Various combinations of this integration can be implemented to provide the appropriate level of function and performance.

As discussed above, in one aspect, the control circuit 3900 includes the battery 3901 powered RF generator circuit 3902 comprising a battery as an energy source. As shown, RF generator circuit 3902 is coupled to two electrically conductive surfaces referred to herein as electrodes 3906a, 3906b (i.e., active electrode 3906a and return electrode 3906b) and is configured to drive the electrodes 3906a, 3906b with RF energy (e.g., high-frequency current). A first winding 3910a of the step-up transformer 3904 is connected in series with one pole of the bipolar RF generator circuit 3902 and the return electrode 3906b. In one aspect, the first winding 3910a and the return electrode 3906b are connected to the negative pole of the bipolar RF generator circuit 3902. The other pole of the bipolar RF generator circuit 3902 is connected to the active electrode 3906a through a switch contact 3909 of the relay 3908, or any suitable electromagnetic switching device comprising an armature which is moved by an electromagnet 3936 to operate the switch contact 3909. The switch contact 3909 is closed when the electromagnet 3936 is energized and the switch contact 3909 is open when the electromagnet 3936 is de-energized. When the switch contact is closed, RF current flows through conductive tissue (not shown) located between the electrodes 3906a, 3906b. It will be appreciated, that in one aspect, the active electrode 3906a is connected to the positive pole of the bipolar RF generator circuit 3902.

A visual indicator circuit 3905 comprises the step-up transformer 3904, a series resistor R2, and the visual indicator 3912. The visual indicator 3912 can be adapted for use with the surgical instrument 1108 and other electrosurgical systems and tools, such as those described herein. The first winding 3910a of the step-up transformer 3904 is connected in series with the return electrode 3906b and the second winding 3910b of the step-up transformer 3904 is connected in series with the resistor R2 and the visual indicator 3912 comprising a type NE-2 neon bulb, for example.

In operation, when the switch contact 3909 of the relay 3908 is open, the active electrode 3906a is disconnected from the positive pole of the bipolar RF generator circuit 3902 and no current flows through the tissue, the return electrode 3906b, and the first winding 3910a of the step-up transformer 3904. Accordingly, the visual indicator 3912 is not energized and does not emit light. When the switch contact 3909 of the relay 3908 is closed, the active electrode 3906a is connected to the positive pole of the bipolar RF generator circuit 3902 enabling current to flow through tissue, the return electrode 3906b, and the first winding 3910a of the step-up transformer 3904 to operate on tissue, for example cut and cauterize the tissue.

A first current flows through the first winding 3910a as a function of the impedance of the tissue located between the active and return electrodes 3906a, 3906b providing a first voltage across the first winding 3910a of the step-up transformer 3904. A stepped up second voltage is induced across the second winding 3910b of the step-up transformer 3904. The secondary voltage appears across the resistor R2 and energizes the visual indicator 3912 causing the neon bulb to light when the current through the tissue is greater than a predetermined threshold. It will be appreciated that the circuit and component values are illustrative and not limited thereto. When the switch contact 3909 of the relay 3908 is closed, current flows through the tissue and the visual indicator 3912 is turned on.

Turning now to the energy switch 3926 portion of the control circuit 3900, when the energy switch 3926 is open position, a logic high is applied to the input of a first inverter 3928 and a logic low is applied of one of the two inputs of the AND gate 3932. Thus, the output of the AND gate 3932 is low and a transistor 3934 is off to prevent current from flowing through the winding of the electromagnet 3936. With the electromagnet 3936 in the de-energized state, the switch contact 3909 of the relay 3908 remains open and prevents current from flowing through the electrodes 3906a, 3906b. The logic low output of the first inverter 3928 also is applied to a second inverter 3930 causing the output to go high and resetting a flip-flop 3918 (e.g., a D-Type flip-flop).

At which time, the Q output goes low to turn off the ultrasound generator circuit 3920 circuit and the $\overline{Q}$ output goes high and is applied to the other input of the AND gate 3932.

When the user presses the energy switch 3926 on the instrument handle to apply energy to the tissue between the electrodes 3906a, 3906b, the energy switch 3926 closes and applies a logic low at the input of the first inverter 3928, which applies a logic high to other input of the AND gate 3932 causing the output of the AND gate 3932 to go high and turns on the transistor 3934. In the on state, the transistor 3934 conducts and sinks current through the winding of the electromagnet 3936 to energize the electromagnet 3936 and close the switch contact 3909 of the relay 3908. As discussed above, when the switch contact 3909 is closed, current can flow through the electrodes 3906a, 3906b and the first winding 3910a of the step-up transformer 3904 when tissue is located between the electrodes 3906a, 3906b.

As discussed above, the magnitude of the current flowing through the electrodes 3906a, 3906b depends on the impedance of the tissue located between the electrodes 3906a, 3906b. Initially, the tissue impedance is low and the magnitude of the current high through the tissue and the first winding 3910a. Consequently, the voltage impressed on the second winding 3910b is high enough to turn on the visual indicator 3912. The light emitted by the visual indicator 3912 turns on the phototransistor 3914, which pulls the input of an inverter 3916 low and causes the output of the inverter 3916 to go high. A high input applied to the CLK of the flip-flop 3918 has no effect on the Q or the $\overline{Q}$ outputs of the flip-flop 3918 and Q output remains low and the $\overline{Q}$ output remains high. Accordingly, while the visual indicator 3912 remains energized, the ultrasound generator circuit 3920 is turned OFF and an ultrasonic transducer 3922 and an ultrasonic blade 3924 of the multifunction electrosurgical instrument are not activated.

As the tissue between the electrodes 3906a, 3906b dries up, due to the heat generated by the current flowing through the tissue, the impedance of the tissue increases and the current therethrough decreases. When the current through the first winding 3910a decreases, the voltage across the second winding 3910b also decreases and when the voltage drops below a minimum threshold required to operate the visual indicator 3912, the visual indicator 3912 and the phototransistor 3914 turn off. When the phototransistor 3914 turns off, a logic high is applied to the input of the inverter 3916 and a logic low is applied to the CLK input of the flip-flop 3918 to clock a logic high to the Q output and a logic low to the $\overline{Q}$ output. The logic high at the Q output turns on the ultrasound generator circuit 3920 to activate the ultrasonic transducer 3922 and the ultrasonic blade 3924 to initiate cutting the tissue located between the electrodes 3906a, 3906a. Simultaneously or near simultaneously with the ultrasound generator circuit 3920 turning on, the $\overline{Q}$ output of the flip-flop 3918 goes low and causes the output of the AND gate 3932 to go low and turn off the transistor 3934, thereby de-energizing the electromagnet 3936 and opening the switch contact 3909 of the relay 3908 to cut off the flow of current through the electrodes 3906a, 3906b.

While the switch contact 3909 of the relay 3908 is open, no current flows through the electrodes 3906a, 3906b, tissue, and the first winding 3910a of the step-up transformer 3904. Therefore, no voltage is developed across the second winding 3910b and no current flows through the visual indicator 3912.

The state of the Q and the $\overline{Q}$ outputs of the flip-flop 3918 remain the same while the user squeezes the energy switch 3926 on the instrument handle to maintain the energy switch 3926 closed. Thus, the ultrasonic blade 3924 remains activated and continues cutting the tissue between the jaws of the end effector while no current flows through the electrodes 3906a, 3906b from the bipolar RF generator circuit 3902. When the user releases the energy switch 3926 on the instrument handle, the energy switch 3926 opens and the output of the first inverter 3928 goes low and the output of the second inverter 3930 goes high to reset the flip-flop 3918 causing the Q output to go low and turn off the ultrasound generator circuit 3920. At the same time, the $\overline{Q}$ output goes high and the circuit is now in an off state and ready for the user to actuate the energy switch 3926 on the instrument handle to close the energy switch 3926, apply current to the tissue located between the electrodes 3906a, 3906b, and repeat the cycle of applying RF energy to the tissue and ultrasonic energy to the tissue as described above.

Figure 33:
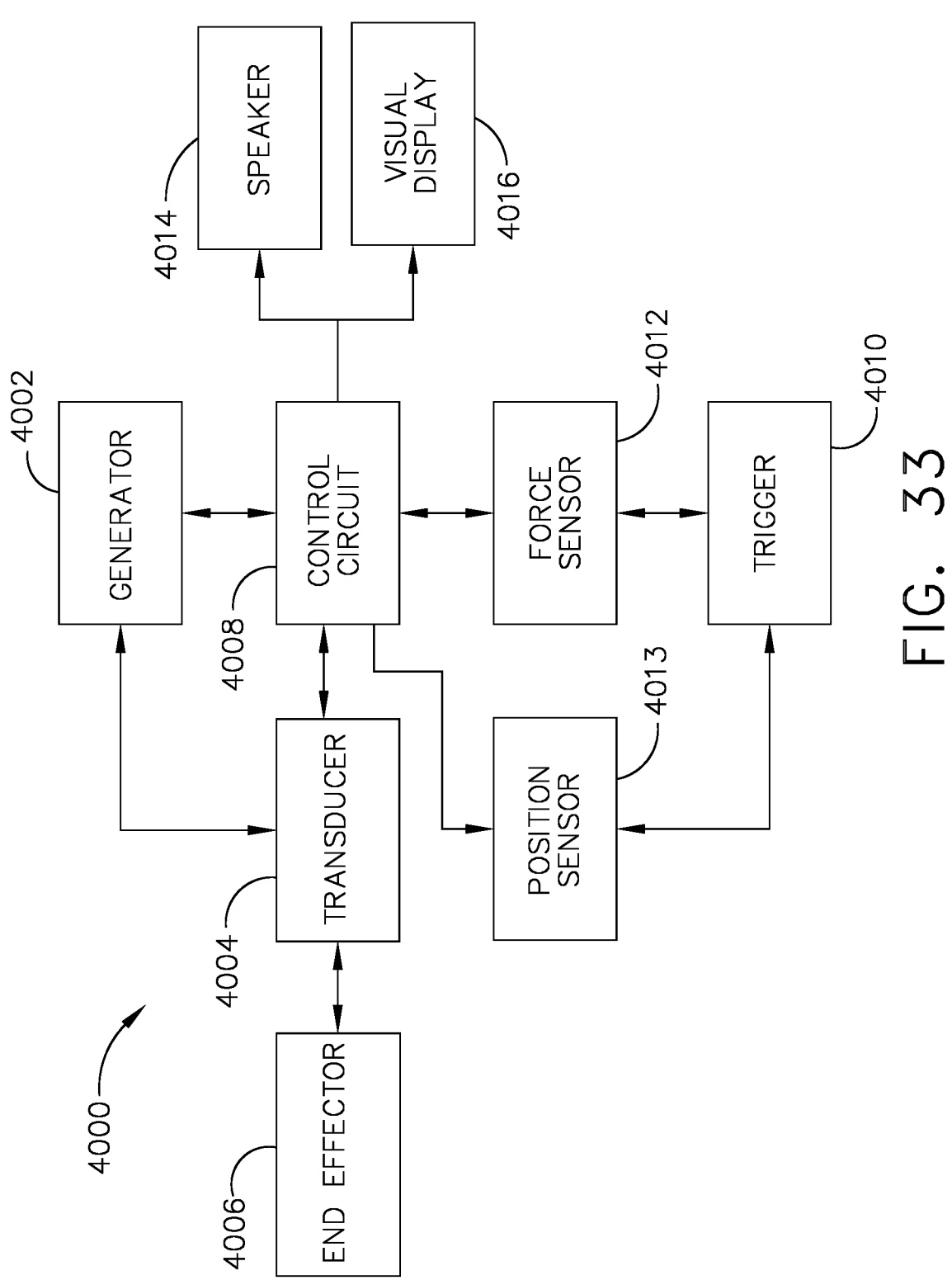
FIG. 33 illustrates a diagram of one aspect of a surgical instrument comprising a feedback system for use with a surgical instrument, according to one aspect of the resent disclosure.

FIG. 33 illustrates a diagram of a surgical system 4000, which represents one aspect of the surgical system 1000, comprising a feedback system for use with any one of the surgical instruments of surgical system 1000, which may include or implement many of the features described herein. The surgical system 4000 may include a generator 4002 coupled to a surgical instrument that includes an end effector 4006, which may be activated when a clinician operates a trigger 4010. In various aspects, the end effector 4006 may include an ultrasonic blade to deliver ultrasonic vibration to carry out surgical coagulation/cutting treatments on living tissue. In other aspects the end effector 4006 may include electrically conductive elements coupled to an electrosurgical high-frequency current energy source to carry out surgical coagulation or cauterization treatments on living tissue and either a mechanical knife with a sharp edge or an ultrasonic blade to carry out cutting treatments on living tissue. When the trigger 4010 is actuated, a force sensor 4012 may generate a signal indicating the amount of force being applied to the trigger 4010. In addition to, or instead of a force sensor 4012, the surgical instrument may include a position sensor 4013, which may generate a signal indicating the position of the trigger 4010 (e.g., how far the trigger has been depressed or otherwise actuated). In one aspect, the position sensor 4013 may be a sensor positioned with an outer tubular sheath or reciprocating tubular actuating member located within the outer tubular sheath of the surgical instrument. In one aspect, the sensor may be a Hall-effect sensor or any suitable transducer that varies its output voltage in response to a magnetic field. The Hall-effect sensor may be used for proximity switching, positioning, speed detection, and current sensing applications. In one aspect, the Hall-effect sensor operates as an analog transducer, directly returning a voltage. With a known magnetic field, its distance from the Hall plate can be determined.

A control circuit 4008 may receive the signals from the sensors 4012 and/or 4013. The control circuit 4008 may include any suitable analog or digital circuit components. The control circuit 4008 also may communicate with the generator 4002 and/or a transducer 4004 to modulate the power delivered to the end effector 4006 and/or the generator level or ultrasonic blade amplitude of the end effector 4006 based on the force applied to the trigger 4010 and/or the position of the trigger 4010 and/or the position of the outer tubular sheath described above relative to a reciprocating tubular actuating member located within an outer tubular sheath (e.g., as measured by a Hall-effect sensor and magnet combination). For example, as more force is applied to the trigger 4010, more power and/or higher ultrasonic blade amplitude may be delivered to the end effector 4006.

According to various aspects, the force sensor 4012 may be replaced by a multi-position switch.

According to various aspects, the end effector 4006 may include a clamp or clamping mechanism. When the trigger 4010 is initially actuated, the clamping mechanism may close, clamping tissue between a clamp arm and the end effector 4006. As the force applied to the trigger increases (e.g., as sensed by force sensor 4012) the control circuit 4008 may increase the power delivered to the end effector 4006 by the transducer 4004 and/or the generator level or ultrasonic blade amplitude brought about in the end effector 4006. In one aspect, trigger position, as sensed by position sensor 4013 or clamp or clamp arm position, as sensed by position sensor 4013 (e.g., with a Hall-effect sensor), may be used by the control circuit 4008 to set the power and/or amplitude of the end effector 4006. For example, as the trigger is moved further towards a fully actuated position, or the clamp or clamp arm moves further towards the ultrasonic blade (or end effector 4006), the power and/or amplitude of the end effector 4006 may be increased.

According to various aspects, the surgical instrument of the surgical system 4000 also may include one or more feedback devices for indicating the amount of power delivered to the end effector 4006. For example, a speaker 4014 may emit a signal indicative of the end effector power. According to various aspects, the speaker 4014 may emit a series of pulse sounds, where the frequency of the sounds indicates power. In addition to, or instead of the speaker 4014, the surgical instrument may include a visual display 4016. The visual display 4016 may indicate end effector power according to any suitable method. For example, the visual display 4016 may include a series of LEDs, where end effector power is indicated by the number of illuminated LEDs. The speaker 4014 and/or visual display 4016 may be driven by the control circuit 4008. According to various aspects, the surgical instrument may include a ratcheting device connected to the trigger 4010. The ratcheting device may generate an audible sound as more force is applied to the trigger 4010, providing an indirect indication of end effector power. The surgical instrument may include other features that may enhance safety. For example, the control circuit 4008 may be configured to prevent power from being delivered to the end effector 4006 in excess of a predetermined threshold. Also, the control circuit 4008 may implement a delay between the time when a change in end effector power is indicated (e.g., by speaker 4014 or visual display 4016), and the time when the change in end effector power is delivered. In this way, a clinician may have ample warning that the level of ultrasonic power that is to be delivered to the end effector 4006 is about to change.

Figure 34:
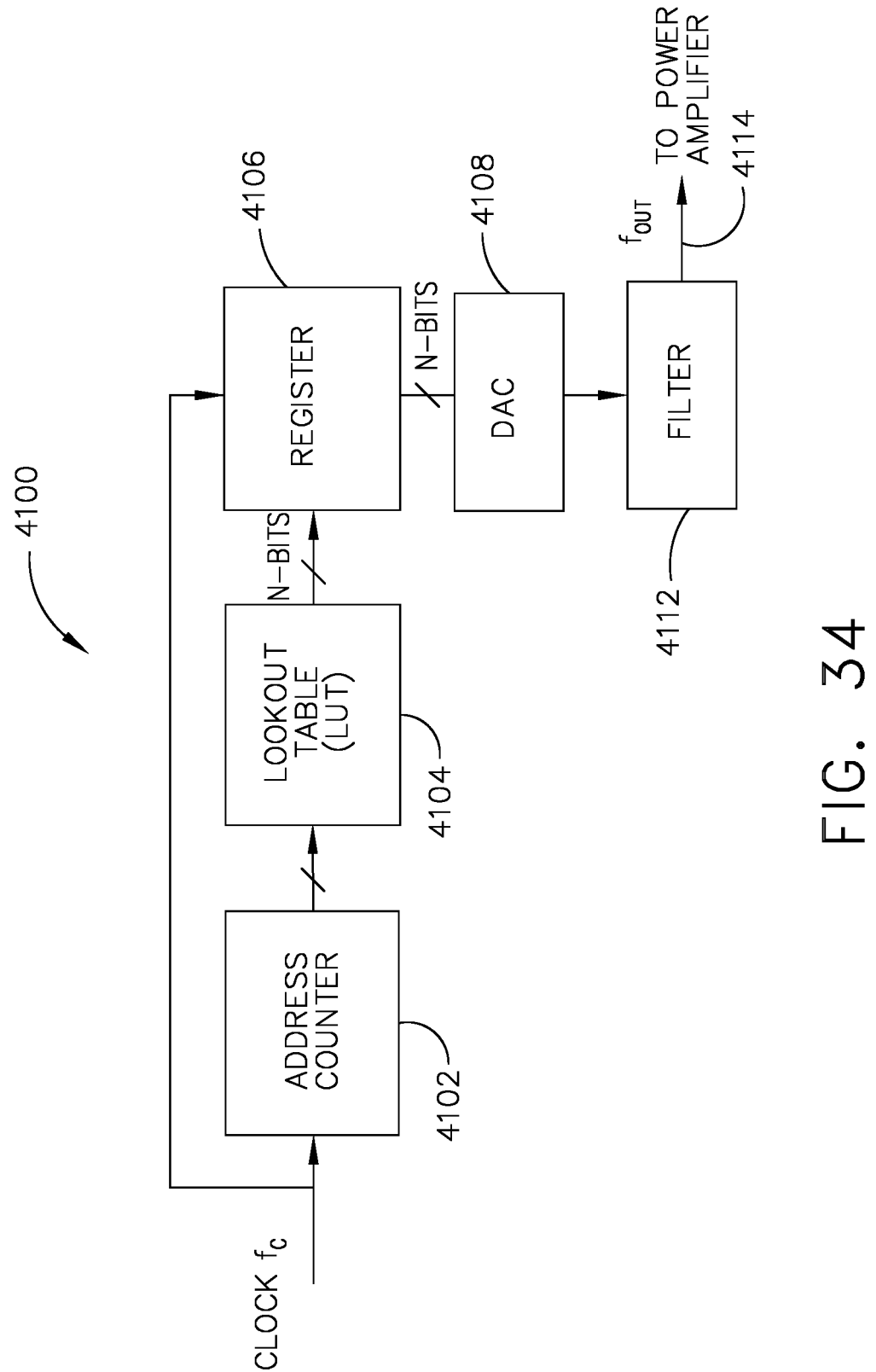
FIG. 34 illustrates one aspect of a fundamental architecture for a digital synthesis circuit such as a direct digital synthesis (DDS) circuit configured to generate a plurality of wave shapes for the electrical signal waveform for use in a surgical instrument, in accordance with at least one aspect of the present disclosure.

In one aspect, the ultrasonic or high-frequency current generators of the surgical system 1000 may be configured to generate the electrical signal waveform digitally such that the desired using a predetermined number of phase points stored in a lookup table to digitize the wave shape. The phase points may be stored in a table defined in a memory, a field programmable gate array (FPGA), or any suitable non-volatile memory. FIG. 34 illustrates one aspect of a fundamental architecture for a digital synthesis circuit such as a direct digital synthesis (DDS) circuit 4100 configured to generate a plurality of wave shapes for the electrical signal waveform. The generator software and digital controls may command the FPGA to scan the addresses in the lookup table 4104 which in turn provides varying digital input values to a DAC circuit 4108 that feeds a power amplifier. The addresses may be scanned according to a frequency of interest. Using such a lookup table 4104 enables generating various types of wave shapes that can be fed into tissue or into a transducer, an RF electrode, multiple transducers simultaneously, multiple RF electrodes simultaneously, or a combination of RF and ultrasonic instruments. Furthermore, multiple lookup tables 4104 that represent multiple wave shapes can be created, stored, and applied to tissue from a generator.

The waveform signal may be configured to control at least one of an output current, an output voltage, or an output power of an ultrasonic transducer and/or an RF electrode, or multiples thereof (e.g. two or more ultrasonic transducers and/or two or more RF electrodes). Further, where the surgical instrument comprises an ultrasonic components, the waveform signal may be configured to drive at least two vibration modes of an ultrasonic transducer of the at least one surgical instrument. Accordingly, a generator may be configured to provide a waveform signal to at least one surgical instrument wherein the waveform signal corresponds to at least one wave shape of a plurality of wave shapes in a table. Further, the waveform signal provided to the two surgical instruments may comprise two or more wave shapes. The table may comprise information associated with a plurality of wave shapes and the table may be stored within the generator. In one aspect or example, the table may be a direct digital synthesis table, which may be stored in an FPGA of the generator. The table may be addressed by anyway that is convenient for categorizing wave shapes. According to one aspect, the table, which may be a direct digital synthesis table, is addressed according to a frequency of the waveform signal. Additionally, the information associated with the plurality of wave shapes may be stored as digital information in the table.

The analog electrical signal waveform may be configured to control at least one of an output current, an output voltage, or an output power of an ultrasonic transducer and/or an RF electrode, or multiples thereof (e.g., two or more ultrasonic transducers and/or two or more RF electrodes). Further, where the surgical instrument comprises ultrasonic components, the analog electrical signal waveform may be configured to drive at least two vibration modes of an ultrasonic transducer of the at least one surgical instrument. Accordingly, the generator circuit may be configured to provide an analog electrical signal waveform to at least one surgical instrument wherein the analog electrical signal waveform corresponds to at least one wave shape of a plurality of wave shapes stored in a lookup table 4104. Further, the analog electrical signal waveform provided to the two surgical instruments may comprise two or more wave shapes. The lookup table 4104 may comprise information associated with a plurality of wave shapes and the lookup table 4104 may be stored either within the generator circuit or the surgical instrument. In one aspect or example, the lookup table 4104 may be a direct digital synthesis table, which may be stored in an FPGA of the generator circuit or the surgical instrument. The lookup table 4104 may be addressed by anyway that is convenient for categorizing wave shapes. According to one aspect, the lookup table 4104, which may be a direct digital synthesis table, is addressed according to a frequency of the desired analog electrical signal waveform. Additionally, the information associated with the plurality of wave shapes may be stored as digital information in the lookup table 4104.

With the widespread use of digital techniques in instrumentation and communications systems, a digitally-controlled method of generating multiple frequencies from a reference frequency source has evolved and is referred to as direct digital synthesis. The basic architecture is shown in FIG. 34. In this simplified block diagram, a DDS circuit is coupled to a processor, controller, or a logic device of the generator circuit and to a memory circuit located in the generator circuit of the surgical system 1000. The DDS circuit 4100 comprises an address counter 4102, lookup table 4104, a register 4106, a DAC circuit 4108, and a filter 4112. A stable clock $f_c$ is received by the address counter 4102 and the register 4106 drives a programmable-read-only-memory (PROM) which stores one or more integral number of cycles of a sinewave (or other arbitrary wave-form) in a lookup table 4104. As the address counter 4102 steps through memory locations, values stored in the lookup table 4104 are written to the register 4106, which is coupled to the DAC circuit 4108. The corresponding digital ampli-tude of the signal at the memory location of the lookup table 4104 drives the DAC circuit 4108, which in turn generates an analog output signal 4110. The spectral purity of the analog output signal 4110 is determined primarily by the DAC circuit 4108. The phase noise is basically that of the reference clock $f_c$. The first analog output signal 4110 output from the DAC circuit 4108 is filtered by the filter 4112 and a second analog output signal 4114 output by the filter 4112 is provided to an amplifier having an output coupled to the output of the generator circuit. The second analog output signal has a frequency $f_{out}$.

Because the DDS circuit 4100 is a sampled data system, issues involved in sampling must be considered: quantiza-tion noise, aliasing, filtering, etc. For instance, the higher order harmonics of the DAC circuit 4108 output frequencies fold back into the Nyquist bandwidth, making them unfil-terable, whereas, the higher order harmonics of the output of phase-locked-loop (PLL) based synthesizers can be filtered. The lookup table 4104 contains signal data for an integral number of cycles. The final output frequency $f_{out}$ can be changed changing the reference clock frequency $f_c$ or by reprogramming the PROM.

The DDS circuit 4100 may comprise multiple lookup tables 4104 where the lookup table 4104 stores a waveform represented by a predetermined number of samples, wherein the samples define a predetermined shape of the waveform. Thus multiple waveforms having a unique shape can be stored in multiple lookup tables 4104 to provide different tissue treatments based on instrument settings or tissue feedback. Examples of waveforms include high crest factor RF electrical signal waveforms for surface tissue coagula-tion, low crest factor RF electrical signal waveform for deeper tissue penetration, and electrical signal waveforms that promote efficient touch-up coagulation. In one aspect, the DDS circuit 4100 can create multiple wave shape lookup tables 4104 and during a tissue treatment procedure (e.g., "on-the-fly" or in virtual real time based on user or sensor inputs) switch between different wave shapes stored in separate lookup tables 4104 based on the tissue effect desired and/or tissue feedback.

Figure 36:
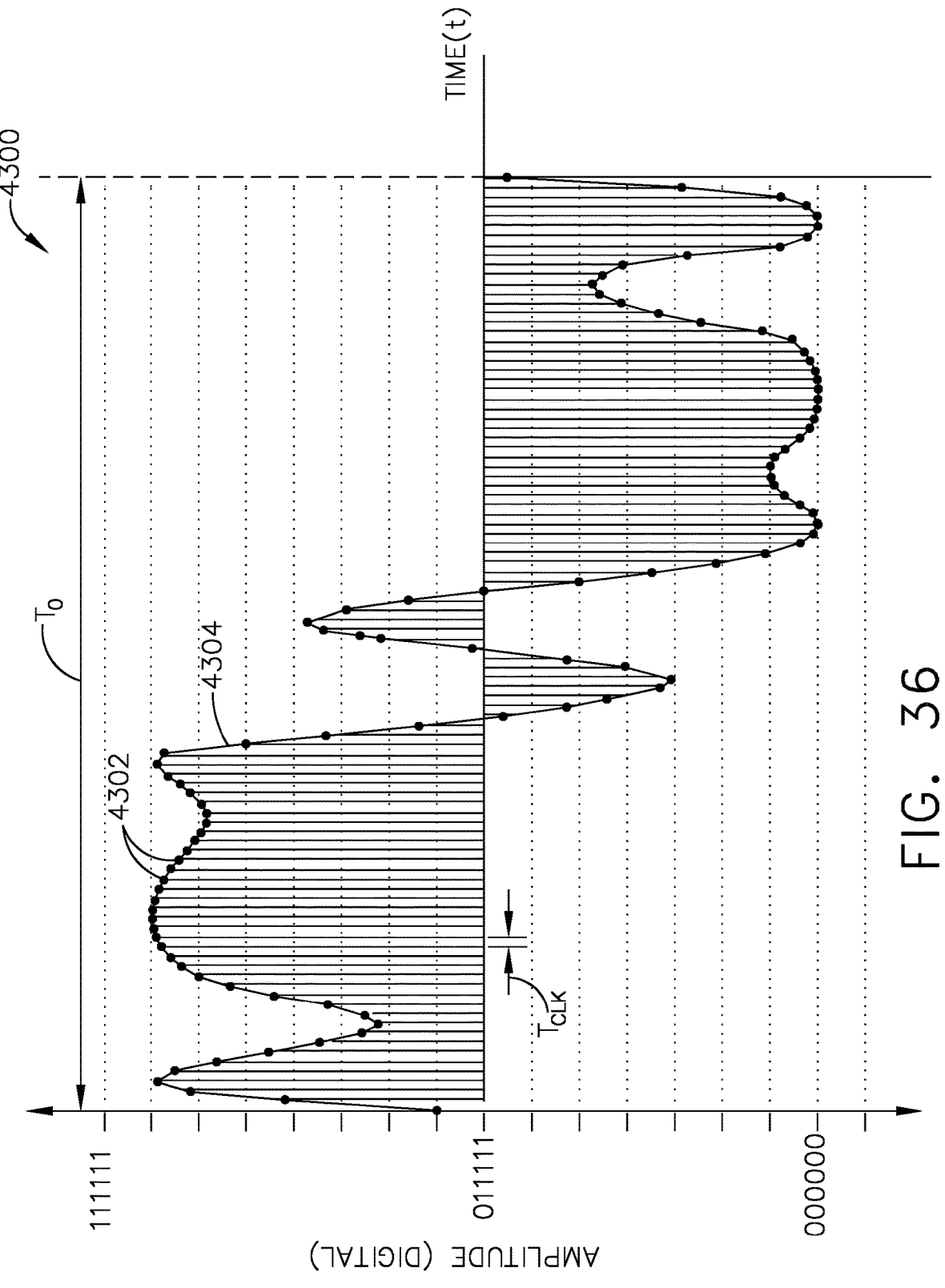
FIG. 36 illustrates one cycle of a discrete time digital electrical signal waveform, in accordance with at least one aspect of the present disclosure of an analog waveform (shown superimposed over a discrete time digital electrical signal waveform for comparison purposes), in accordance with at least one aspect of the present disclosure.

Accordingly, switching between wave shapes can be based on tissue impedance and other factors, for example. In other aspects, the lookup tables 4104 can store electrical signal waveforms shaped to maximize the power delivered into the tissue per cycle (i.e., trapezoidal or square wave). In other aspects, the lookup tables 4104 can store wave shapes synchronized in such way that they make maximizing power delivery by the multifunction surgical instrument of surgical system 1000 while delivering RF and ultrasonic drive sig-nals. In yet other aspects, the lookup tables 4104 can store electrical signal waveforms to drive ultrasonic and RF therapeutic, and/or sub-therapeutic, energy simultaneously while maintaining ultrasonic frequency lock. Custom wave shapes specific to different instruments and their tissue effects can be stored in the non-volatile memory of the generator circuit or in the non-volatile memory (e.g., EEPROM) of the surgical system 1000 and be fetched upon connecting the multifunction surgical instrument to the generator circuit. An example of an exponentially damped sinusoid, as used in many high crest factor "coagulation" waveforms is shown in FIG. 36.

Figure 35:
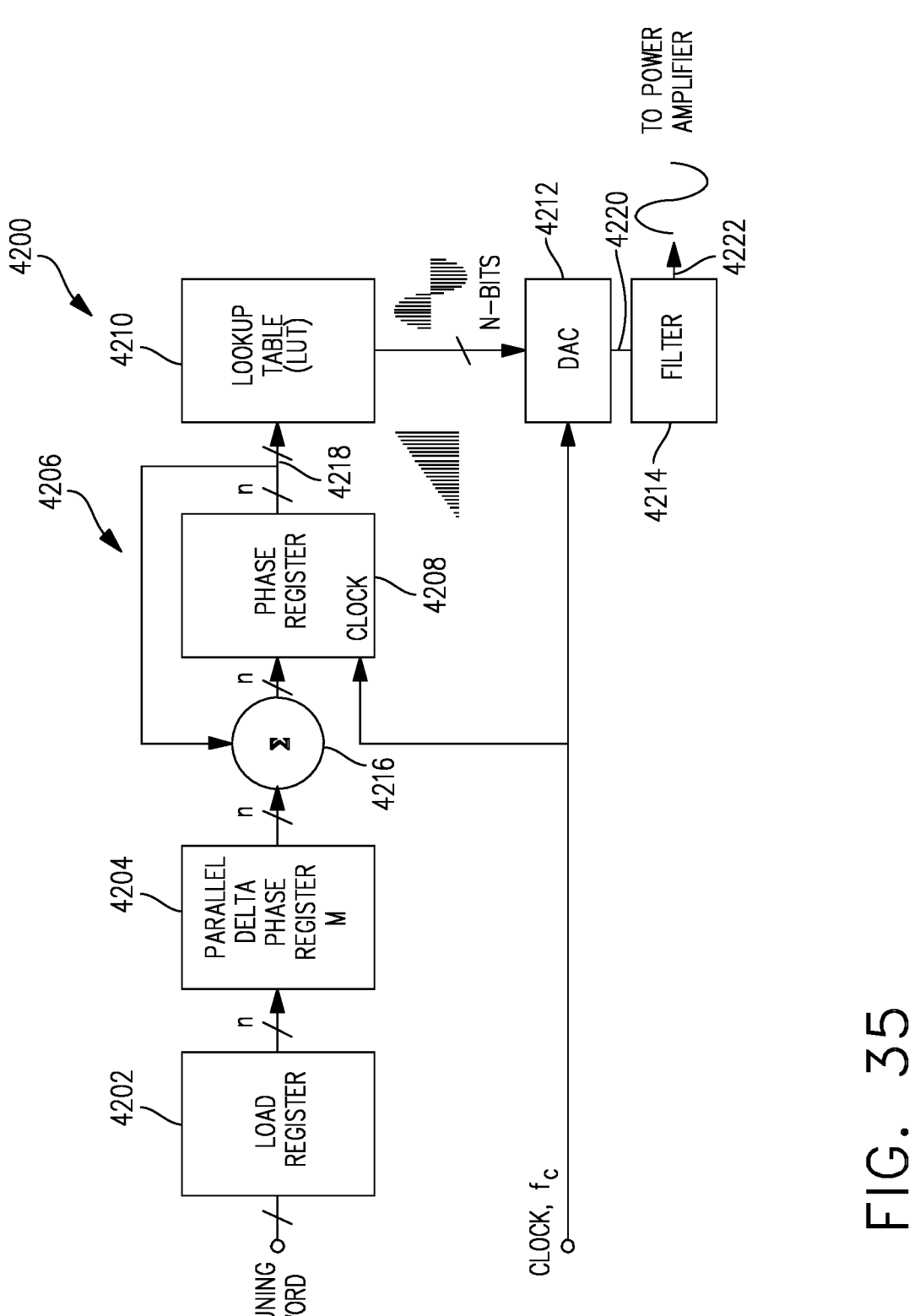
FIG. 35 illustrates one aspect of direct digital synthesis (DDS) circuit configured to generate a plurality of wave shapes for the electrical signal waveform for use in surgical instrument, in accordance with at least one aspect of the present disclosure.

A more flexible and efficient implementation of the DDS circuit 4100 employs a digital circuit called a Numerically Controlled Oscillator (NCO). A block diagram of a more flexible and efficient digital synthesis circuit such as a DDS circuit 4200 is shown in FIG. 35. In this simplified block diagram, a DDS circuit 4200 is coupled to a processor, controller, or a logic device of the generator and to a memory circuit located either in the generator or in any of the surgical instruments of surgical system 1000. The DDS circuit 4200 comprises a load register 4202, a parallel delta phase register 4204, an adder circuit 4216, a phase register 4208, a lookup table 4210 (phase-to-amplitude converter), a DAC circuit 4212, and a filter 4214. The adder circuit 4216 and the phase register 4208 form part of a phase accumulator 4206. A clock frequency $f_c$ is applied to the phase register 4208 and a DAC circuit 4212. The load register 4202 receives a tuning word that specifies output frequency as a fraction of the reference clock frequency signal $f_c$. The output of the load register 4202 is provided to the parallel delta phase register 4204 with a tuning word M.

The DDS circuit 4200 includes a sample clock that generates the clock frequency $f_c$, the phase accumulator 4206, and the lookup table 4210 (e.g., phase to amplitude converter). The content of the phase accumulator 4206 is updated once per clock cycle $f_c$. When time the phase accumulator 4206 is updated, the digital number, M, stored in the parallel delta phase register 4204 is added to the number in the phase register 4208 by the adder circuit 4216. Assuming that the number in the parallel delta phase register 4204 is 00 . . . 01 and that the initial contents of the phase accumulator 4206 is 00 . . . 00. The phase accumulator 4206 is updated by 00 . . . 01 per clock cycle. If the phase accumulator 4206 is 32-bits wide, 232 clock cycles (over 4 billion) are required before the phase accumulator 4206 returns to 00 . . . 00, and the cycle repeats.

A truncated output 4218 of the phase accumulator 4206 is provided to a phase-to amplitude converter lookup table 4210 and the output of the lookup table 4210 is coupled to a DAC circuit 4212. The truncated output 4218 of the phase accumulator 4206 serves as the address to a sine (or cosine) lookup table. An address in the lookup table corresponds to a phase point on the sinewave from 0° to 360°. The lookup table 4210 contains the corresponding digital amplitude information for one complete cycle of a sinewave. The lookup table 4210 therefore maps the phase information from the phase accumulator 4206 into a digital amplitude word, which in turn drives the DAC circuit 4212. The output of the DAC circuit is a first analog signal 4220 and is filtered by a filter 4214. The output of the filter 4214 is a second analog signal 4222, which is provided to a power amplifier coupled to the output of the generator circuit.

In one aspect, the electrical signal waveform may be digitized into 1024 ($2^{10}$) phase points, although the wave shape may be digitized is any suitable number of $2n$ phase points ranging from 256 ($2^8$) to 281,474,976,710,656 ($2^{48}$), where n is a positive integer, as shown in TABLE 1. The electrical signal waveform may be expressed as $A_n(\theta_n)$, where a normalized amplitude $A_n$ at a point n is represented by a phase angle $\theta_n$ is referred to as a phase point at point n. The number of discrete phase points n determines the tuning resolution of the DDS circuit 4200 (as well as the DDS circuit 4100 shown in FIG. 34).

TABLE 1 specifies the electrical signal waveform digitized into a number of phase points.

TABLE 1

| N | Number of Phase Points $2^n$ |
|---|---|
| 8 | 256 |
| 10 | 1,024 |
| 12 | 4,096 |
| 14 | 16,384 |
| 16 | 65,536 |
| 18 | 262,144 |
| 20 | 1,048,576 |
| 22 | 4,194,304 |
| 24 | 16,777,216 |
| 26 | 67,108,864 |
| 28 | 268,435,456 |
| . . . | . . . |
| 32 | 4,294,967,296 |
| . . . | . . . |
| 48 | 281,474,976,710,656 |
| . . . | . . . |

The generator circuit algorithms and digital control circuits scan the addresses in the lookup table 4210, which in turn provides varying digital input values to the DAC circuit 4212 that feeds the filter 4214 and the power amplifier. The addresses may be scanned according to a frequency of interest. Using the lookup table enables generating various types of shapes that can be converted into an analog output signal by the DAC circuit 4212, filtered by the filter 4214, amplified by the power amplifier coupled to the output of the generator circuit, and fed to the tissue in the form of RF energy or fed to an ultrasonic transducer and applied to the tissue in the form of ultrasonic vibrations which deliver energy to the tissue in the form of heat. The output of the amplifier can be applied to an RF electrode, multiple RF electrodes simultaneously, an ultrasonic transducer, multiple ultrasonic transducers simultaneously, or a combination of RF and ultrasonic transducers, for example. Furthermore, multiple wave shape tables can be created, stored, and applied to tissue from a generator circuit.

With reference back to FIG. 34, for n=32, and M=1, the phase accumulator 4206 steps through 232 possible outputs before it overflows and restarts. The corresponding output wave frequency is equal to the input clock frequency divided by 232. If M=2, then the phase register 1708 "rolls over" twice as fast, and the output frequency is doubled. This can be generalized as follows.

For a phase accumulator 4206 configured to accumulate n-bits (n generally ranges from 24 to 32 in most DDS systems, but as previously discussed n may be selected from a wide range of options), there are $2^n$ possible phase points. The digital word in the delta phase register, M, represents the amount the phase accumulator is incremented per clock cycle. If $f_c$ is the clock frequency, then the frequency of the output sinewave is equal to:

$$f_0 = \frac{M \cdot f_c}{2^n}$$

The above equation is known as the DDS "tuning equation." Note that the frequency resolution of the system is equal to $$\frac{f_0}{2^n}.$$

For n=32, the resolution is greater than one part in four billion. In one aspect of the DDS circuit 4200, not all of the bits out of the phase accumulator 4206 are passed on to the lookup table 4210, but are truncated, leaving only the first 13 to 15 most significant bits (MSBs), for example. This reduces the size of the lookup table 4210 and does not affect the frequency resolution. The phase truncation only adds a small but acceptable amount of phase noise to the final output.

The electrical signal waveform may be characterized by a current, voltage, or power at a predetermined frequency. Further, where any one of the surgical instruments of surgical system 1000 comprises ultrasonic components, the electrical signal waveform may be configured to drive at least two vibration modes of an ultrasonic transducer of the at least one surgical instrument. Accordingly, the generator circuit may be configured to provide an electrical signal waveform to at least one surgical instrument wherein the electrical signal waveform is characterized by a predetermined wave shape stored in the lookup table 4210 (or lookup table 4104 FIG. 34). Further, the electrical signal waveform may be a combination of two or more wave shapes. The lookup table 4210 may comprise information associated with a plurality of wave shapes. In one aspect or example, the lookup table 4210 may be generated by the DDS circuit 4200 and may be referred to as a direct digital synthesis table. DDS works by first storing a large repetitive waveform in onboard memory. A cycle of a waveform (sine, triangle, square, arbitrary) can be represented by a predetermined number of phase points as shown in TABLE 1 and stored into memory. Once the waveform is stored into memory, it can be generated at very precise frequencies. The direct digital synthesis table may be stored in a non-volatile memory of the generator circuit and/or may be implemented with a FPGA circuit in the generator circuit. The lookup table 4210 may be addressed by any suitable technique that is convenient for categorizing wave shapes. According to one aspect, the lookup table 4210 is addressed according to a frequency of the electrical signal waveform. Additionally, the information associated with the plurality of wave shapes may be stored as digital information in a memory or as part of the lookup table 4210.

In one aspect, the generator circuit may be configured to provide electrical signal waveforms to at least two surgical instruments simultaneously. The generator circuit also may be configured to provide the electrical signal waveform, which may be characterized two or more wave shapes, via an output channel of the generator circuit to the two surgical instruments simultaneously. For example, in one aspect the electrical signal waveform comprises a first electrical signal to drive an ultrasonic transducer (e.g., ultrasonic drive signal), a second RF drive signal, and/or a combination thereof. In addition, an electrical signal waveform may comprise a plurality of ultrasonic drive signals, a plurality of RF drive signals, and/or a combination of a plurality of ultrasonic and RF drive signals.

In addition, a method of operating the generator circuit according to the present disclosure comprises generating an electrical signal waveform and providing the generated electrical signal waveform to any one of the surgical instruments of surgical system 1000, where generating the electrical signal waveform comprises receiving information associated with the electrical signal waveform from a memory. The generated electrical signal waveform comprises at least one wave shape. Furthermore, providing the generated electrical signal waveform to the at least one surgical instrument comprises providing the electrical signal waveform to at least two surgical instruments simultaneously.

The generator circuit as described herein may allow for the generation of various types of direct digital synthesis tables. Examples of wave shapes for RF/Electrosurgery signals suitable for treating a variety of tissue generated by the generator circuit include RF signals with a high crest factor (which may be used for surface coagulation in RF mode), a low crest factor RF signals (which may be used for deeper tissue penetration), and waveforms that promote efficient touch-up coagulation. The generator circuit also may generate multiple wave shapes employing a direct digital synthesis lookup table 4210 and, on the fly, can switch between particular wave shapes based on the desired tissue effect. Switching may be based on tissue impedance and/or other factors.

In addition to traditional sine/cosine wave shapes, the generator circuit may be configured to generate wave shape(s) that maximize the power into tissue per cycle (i.e., trapezoidal or square wave). The generator circuit may provide wave shape(s) that are synchronized to maximize the power delivered to the load when driving RF and ultrasonic signals simultaneously and to maintain ultrasonic frequency lock, provided that the generator circuit includes a circuit topology that enables simultaneously driving RF and ultrasonic signals. Further, custom wave shapes specific to instruments and their tissue effects can be stored in a non-volatile memory (NVM) or an instrument EEPROM and can be fetched upon connecting any one of the surgical instruments of surgical system 1000 to the generator circuit.

The DDS circuit 4200 may comprise multiple lookup tables 4104 where the lookup table 4210 stores a waveform represented by a predetermined number of phase points (also may be referred to as samples), wherein the phase points define a predetermined shape of the waveform. Thus multiple waveforms having a unique shape can be stored in multiple lookup tables 4210 to provide different tissue treatments based on instrument settings or tissue feedback. Examples of waveforms include high crest factor RF electrical signal waveforms for surface tissue coagulation, low crest factor RF electrical signal waveform for deeper tissue penetration, and electrical signal waveforms that promote efficient touch-up coagulation. In one aspect, the DDS circuit 4200 can create multiple wave shape lookup tables 4210 and during a tissue treatment procedure (e.g., "on-the-fly" or in virtual real time based on user or sensor inputs) switch between different wave shapes stored in different lookup tables 4210 based on the tissue effect desired and/or tissue feedback.

Accordingly, switching between wave shapes can be based on tissue impedance and other factors, for example. In other aspects, the lookup tables 4210 can store electrical signal waveforms shaped to maximize the power delivered into the tissue per cycle (i.e., trapezoidal or square wave). In other aspects, the lookup tables 4210 can store wave shapes synchronized in such way that they make maximizing power delivery by any one of the surgical instruments of surgical system 1000 when delivering RF and ultrasonic drive signals. In yet other aspects, the lookup tables 4210 can store electrical signal waveforms to drive ultrasonic and RF therapeutic, and/or sub-therapeutic, energy simultaneously while maintaining ultrasonic frequency lock. Generally, the output wave shape may be in the form of a sine wave, cosine wave, pulse wave, square wave, and the like. Nevertheless, the more complex and custom wave shapes specific to different instruments and their tissue effects can be stored in the non-volatile memory of the generator circuit or in the non-volatile memory (e.g., EEPROM) of the surgical instrument and be fetched upon connecting the surgical instrument to the generator circuit. One example of a custom wave shape is an exponentially damped sinusoid as used in many high crest factor "coagulation" waveforms, as shown in FIG. 36.

FIG. 36 illustrates one cycle of a discrete time digital electrical signal waveform 4300, in accordance with at least one aspect of the present disclosure of an analog waveform 4304 (shown superimposed over the discrete time digital electrical signal waveform 4300 for comparison purposes). The horizontal axis represents Time (t) and the vertical axis represents digital phase points. The digital electrical signal waveform 4300 is a digital discrete time version of the desired analog waveform 4304, for example. The digital electrical signal waveform 4300 is generated by storing an amplitude phase point 4302 that represents the amplitude per clock cycle $T_{clk}$ over one cycle or period $T_0$. The digital electrical signal waveform 4300 is generated over one period $T_0$ by any suitable digital processing circuit. The amplitude phase points are digital words stored in a memory circuit. In the example illustrated in FIGS. 41, 42, the digital word is a six-bit word that is capable of storing the amplitude phase points with a resolution of 26 or 64 bits. It will be appreciated that the examples shown in FIGS. 41, 42 is for illustrative purposes and in actual implementations the resolution can be much higher. The digital amplitude phase points 4302 over one cycle $T_0$ are stored in the memory as a string of string words in a lookup table 4104, 4210 as described in connection with FIGS. 41, 42, for example. To generate the analog version of the analog waveform 4304, the amplitude phase points 4302 are read sequentially from the memory from 0 to $T_0$ per clock cycle $T_{clk}$ and are converted by a DAC circuit 4108, 4212, also described in connection with FIGS. 41, 42. Additional cycles can be generated by repeatedly reading the amplitude phase points 4302 of the digital electrical signal waveform 4300 the from 0 to $T_0$ for as many cycles or periods as may be desired. The smooth analog version of the analog waveform 4304 is achieved by filtering the output of the DAC circuit 4108, 4212 by a filter 4112, 4214 (FIGS. 41 and 42). The filtered analog output signal 4114, 4222 (FIGS. 41 and 42) is applied to the input of a power amplifier.

Figures 37, 38:
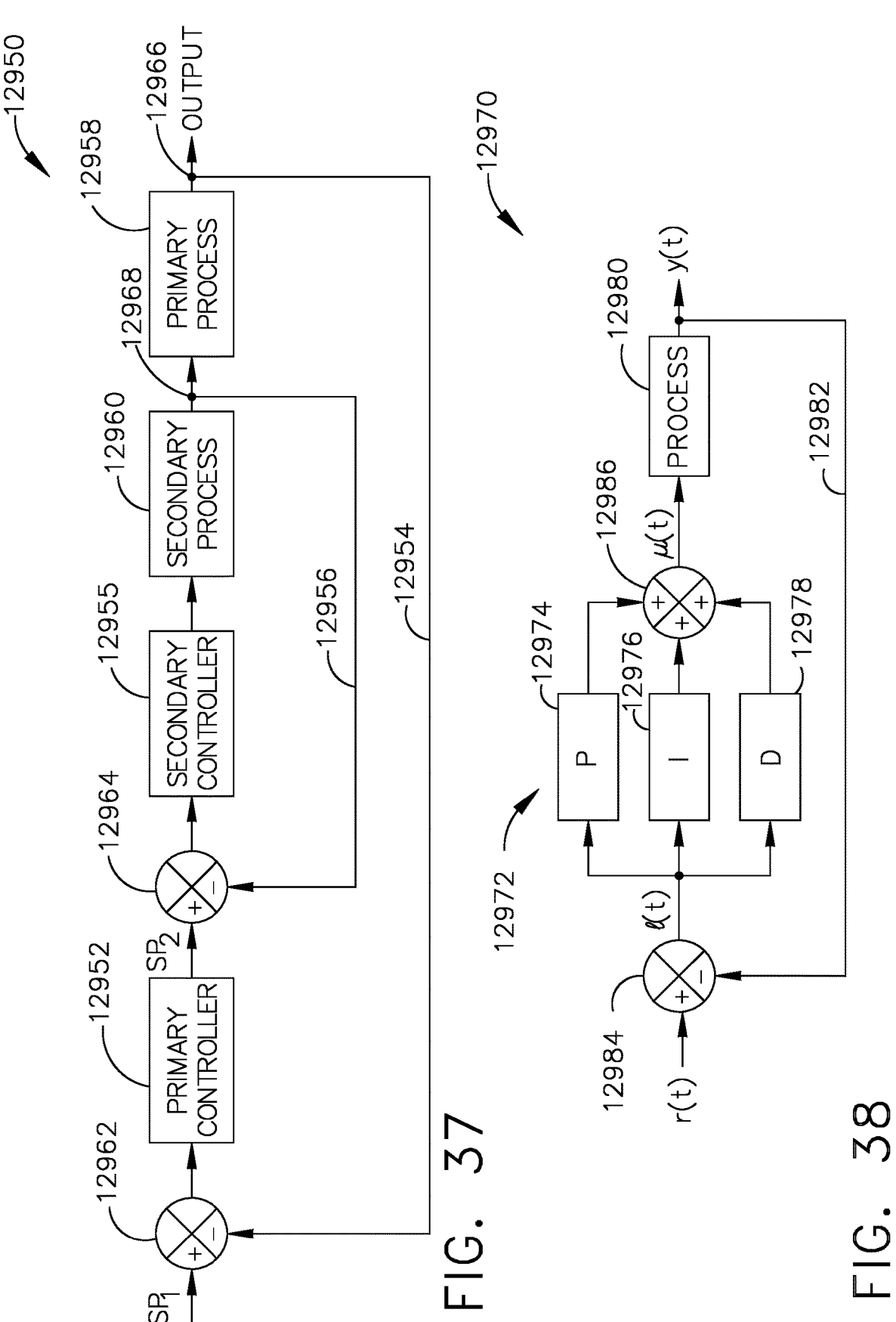
FIG. 37 is a diagram of a control system configured to provide progressive closure of a closure member as it advances distally to close the clamp arm to apply a closure force load at a desired rate according to one aspect of this disclosure.
FIG. 38 illustrates a proportional-integral-derivative (PID) controller feedback control system according to one aspect of this disclosure.

FIG. 37 is a diagram of a control system 12950 configured to provide progressive closure of a closure member (e.g., closure tube) when the displacement member advances distally and couples into a clamp arm (e.g., anvil) to lower the closure force load on the closure member at a desired rate and decrease the firing force load on the firing member according to one aspect of this disclosure. In one aspect, the control system 12950 may be implemented as a nested PID feedback controller. A PID controller is a control loop feedback mechanism (controller) to continuously calculate an error value as the difference between a desired set point and a measured process variable and applies a correction based on proportional, integral, and derivative terms (sometimes denoted P, I, and D respectively). The nested PID controller feedback control system 12950 includes a primary controller 12952, in a primary (outer) feedback loop 12954 and a secondary controller 12955 in a secondary (inner) feedback loop 12956. The primary controller 12952 may be a PID controller 12972 as shown in FIG. 38, and the secondary controller 12955 also may be a PID controller 12972 as shown in FIG. 38. The primary controller 12952 controls a primary process 12958 and the secondary controller 12955 controls a secondary process 12960. The output 12966 of the primary process 12958 is subtracted from a primary set point $SP_1$ by a first summer 12962. The first summer 12962 produces a single sum output signal which is applied to the primary controller 12952. The output of the primary controller 12952 is the secondary set point $SP_2$. The output 12968 of the secondary process 12960 is subtracted from the secondary set point $SP_2$ by a second summer 12964.

In the context of controlling the displacement of a closure tube, the control system 12950 may be configured such that the primary set point $SP_1$ is a desired closure force value and the primary controller 12952 is configured to receive the closure force from a torque sensor coupled to the output of a closure motor and determine a set point $SP_2$ motor velocity for the closure motor. In other aspects, the closure force may be measured with strain gauges, load cells, or other suitable force sensors. The closure motor velocity set point $SP_2$ is compared to the actual velocity of the closure tube, which is determined by the secondary controller 12955. The actual velocity of the closure tube may be measured by comparing measuring the displacement of the closure tube with the position sensor and measuring elapsed time with a timer/counter. Other techniques, such as linear or rotary encoders may be employed to measure displacement of the closure tube. The output 12968 of the secondary process 12960 is the actual velocity of the closure tube. This closure tube velocity output 12968 is provided to the primary process 12958 which determines the force acting on the closure tube and is fed back to the adder 12962, which subtracts the measured closure force from the primary set point $SP_1$. The primary set point $SP_1$ may be an upper threshold or a lower threshold. Based on the output of the adder 12962, the primary controller 12952 controls the velocity and direction of the closure motor. The secondary controller 12955 controls the velocity of the closure motor based on the actual velocity of closure tube measured by the secondary process 12960 and the secondary set point $SP_2$, which is based on a comparison of the actual firing force and the firing force upper and lower thresholds.

FIG. 38 illustrates a PID feedback control system 12970 according to one aspect of this disclosure. The primary controller 12952 or the secondary controller 12955, or both, may be implemented as a PID controller 12972. In one aspect, the PID controller 12972 may comprise a proportional element 12974 (P), an integral element 12976 (I), and a derivative element 12978 (D). The outputs of the P, I, D elements 12974, 12976, 12978 are summed by a summer 12986, which provides the control variable p(t) to the process 12980. The output of the process 12980 is the process variable y(t). A summer 12984 calculates the difference between a desired set point r(t) and a measured process variable y(t). The PID controller 12972 continuously calculates an error value e(t) (e.g., difference between closure force threshold and measured closure force) as the difference between a desired set point r(t) (e.g., closure force threshold) and a measured process variable y(t) (e.g., velocity and direction of closure tube) and applies a correction based on the proportional, integral, and derivative terms calculated by the proportional element 12974 (P), integral element 12976 (I), and derivative element 12978 (D), respectively. The PID controller 12972 attempts to minimize the error e(t) over time by adjustment of the control variable p(t) (e.g., velocity and direction of the closure tube).

In accordance with the PID algorithm, the "P" element 12974 accounts for present values of the error. For example, if the error is large and positive, the control output will also be large and positive. In accordance with the present disclosure, the error term e(t) is the different between the desired closure force and the measured closure force of the closure tube. The "I" element 12976 accounts for past values of the error. For example, if the current output is not sufficiently strong, the integral of the error will accumulate over time, and the controller will respond by applying a stronger action. The "D" element 12978 accounts for possible future trends of the error, based on its current rate of change. For example, continuing the P example above, when the large positive control output succeeds in bringing the error closer to zero, it also puts the process on a path to large negative error in the near future. In this case, the derivative turns negative and the D module reduces the strength of the action to prevent this overshoot.

It will be appreciated that other variables and set points may be monitored and controlled in accordance with the feedback control systems 12950, 12970. For example, the adaptive closure member velocity control algorithm described herein may measure at least two of the following parameters: firing member stroke location, firing member load, displacement of cutting element, velocity of cutting element, closure tube stroke location, closure tube load, among others.

Ultrasonic surgical devices, such as ultrasonic scalpels, are finding increasingly widespread applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device may comprise a handpiece containing an ultrasonic transducer, and an instrument coupled to the ultrasonic transducer having a distally-mounted end effector (e.g., a blade tip) to cut and seal tissue. In some cases, the instrument may be permanently affixed to the handpiece. In other cases, the instrument may be detachable from the handpiece, as in the case of a disposable instrument or an interchangeable instrument. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures and can be transmitted to the end effector by an ultrasonic generator in communication with the handpiece. Vibrating at high frequencies (e.g., 55,500 cycles per second), the ultrasonic blade denatures protein in the tissue to form a sticky coagulum. Pressure exerted on tissue by the blade surface collapses blood vessels and allows the coagulum to form a hemostatic seal. A surgeon can control the cutting speed and coagulation by the force applied to the tissue by the end effector, the time over which the force is applied, and the selected excursion level of the end effector.

The ultrasonic transducer may be modeled as an equivalent circuit comprising a first branch having a static capacitance and a second "motional" branch having a serially connected inductance, resistance and capacitance that define the electromechanical properties of a resonator. Known ultrasonic generators may include a tuning inductor for tuning out the static capacitance at a resonant frequency so that substantially all of a generator's drive signal current flows into the motional branch. Accordingly, by using a tuning inductor, the generator's drive signal current represents the motional branch current, and the generator is thus able to control its drive signal to maintain the ultrasonic transducer's resonant frequency. The tuning inductor may also transform the phase impedance plot of the ultrasonic transducer to improve the generator's frequency lock capabilities. However, the tuning inductor must be matched with the specific static capacitance of an ultrasonic transducer at the operational resonant frequency. In other words, a different ultrasonic transducer having a different static capacitance requires a different tuning inductor.

Additionally, in some ultrasonic generator architectures, the generator's drive signal exhibits asymmetrical harmonic distortion that complicates impedance magnitude and phase measurements. For example, the accuracy of impedance phase measurements may be reduced due to harmonic distortion in the current and voltage signals.

Moreover, electromagnetic interference in noisy environments decreases the ability of the generator to maintain lock on the ultrasonic transducer's resonant frequency, increasing the likelihood of invalid control algorithm inputs.

Electrosurgical devices for applying electrical energy to tissue in order to treat and/or destroy the tissue are also finding increasingly widespread applications in surgical procedures. An electrosurgical device may comprise a handpiece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

Electrical energy applied by an electrosurgical device can be transmitted to the instrument by a generator in communication with the handpiece. The electrical energy may be in the form of radio frequency (RF) energy. RF energy is a form of electrical energy that may be in the frequency range of 300 kHz to 1 MHz, as described in EN60601-2-2:2009+A11:2011, Definition 201.3.218—HIGH FREQUENCY. For example, the frequencies in monopolar RF applications are typically restricted to less than 5 MHz. However, in bipolar RF applications, the frequency can be almost any value. Frequencies above 200 kHz are typically used for monopolar applications in order to avoid the unwanted stimulation of nerves and muscles which would result from the use of low frequency current. Lower frequencies may be used for bipolar techniques if a risk analysis shows the possibility of neuromuscular stimulation has been mitigated to an acceptable level. Normally, frequencies above 5 MHz are not used in order to minimize the problems associated with high frequency leakage currents. It is generally recognized that 10 mA is the lower threshold of thermal effects on tissue.

During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

Due to their unique drive signal, sensing and feedback needs, ultrasonic and electrosurgical devices have generally required different generators. Additionally, in cases where the instrument is disposable or interchangeable with a handpiece, ultrasonic and electrosurgical generators are limited in their ability to recognize the particular instrument configuration being used and to optimize control and diagnostic processes accordingly. Moreover, capacitive coupling between the non-isolated and patient-isolated circuits of the generator, especially in cases where higher voltages and frequencies are used, may result in exposure of a patient to unacceptable levels of leakage current.

Furthermore, due to their unique drive signal, sensing and feedback needs, ultrasonic and electrosurgical devices have generally required different user interfaces for the different generators. In such conventional ultrasonic and electrosurgical devices, one user interface is configured for use with an ultrasonic instrument whereas a different user interface may be configured for use with an electrosurgical instrument. Such user interfaces include hand and/or foot activated user interfaces such as hand activated switches and/or foot activated switches. As various aspects of combined generators for use with both ultrasonic and electrosurgical instruments are contemplated in the subsequent disclosure, additional user interfaces that are configured to operate with both ultrasonic and/or electrosurgical instrument generators also are contemplated.

Additional user interfaces for providing feedback, whether to the user or other machine, are contemplated within the subsequent disclosure to provide feedback indicating an operating mode or status of either an ultrasonic and/or electrosurgical instrument. Providing user and/or machine feedback for operating a combination ultrasonic and/or electrosurgical instrument will require providing sensory feedback to a user and electrical/mechanical/electromechanical feedback to a machine. Feedback devices that incorporate visual feedback devices (e.g., an LCD display screen, LED indicators), audio feedback devices (e.g., a speaker, a buzzer) or tactile feedback devices (e.g., haptic actuators) for use in combined ultrasonic and/or electrosurgical instruments are contemplated in the subsequent disclosure.

Other electrical surgical instruments include, without limitation, irreversible and/or reversible electroporation, and/or microwave technologies, among others. Accordingly, the techniques disclosed herein are applicable to ultrasonic, bipolar or monopolar RF (electrosurgical), irreversible and/or reversible electroporation, and/or microwave based surgical instruments, among others.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Aspects of the generator utilize high-speed analog-to-digital sampling (e.g., approximately 200× oversampling, depending on frequency) of the generator drive signal current and voltage, along with digital signal processing, to provide a number of advantages and benefits over known generator architectures. In one aspect, for example, based on current and voltage feedback data, a value of the ultrasonic transducer static capacitance, and a value of the drive signal frequency, the generator may determine the motional branch current of an ultrasonic transducer. This provides the benefit of a virtually tuned system, and simulates the presence of a system that is tuned or resonant with any value of the static capacitance (e.g., $C_O$ in FIG. 22) at any frequency. Accordingly, control of the motional branch current may be realized by tuning out the effects of the static capacitance without the need for a tuning inductor. Additionally, the elimination of the tuning inductor may not degrade the generator's frequency lock capabilities, as frequency lock can be realized by suitably processing the current and voltage feedback data.

High-speed analog-to-digital sampling of the generator drive signal current and voltage, along with digital signal processing, may also enable precise digital filtering of the samples. For example, aspects of the generator may utilize a low-pass digital filter (e.g., a finite impulse response (FIR) filter) that rolls off between a fundamental drive signal frequency and a second-order harmonic to reduce the asymmetrical harmonic distortion and EMI-induced noise in current and voltage feedback samples. The filtered current and voltage feedback samples represent substantially the fundamental drive signal frequency, thus enabling a more accurate impedance phase measurement with respect to the fundamental drive signal frequency and an improvement in the generator's ability to maintain resonant frequency lock. The accuracy of the impedance phase measurement may be further enhanced by averaging falling edge and rising edge phase measurements, and by regulating the measured impedance phase to 0°.

Various aspects of the generator may also utilize the high-speed analog-to-digital sampling of the generator drive signal current and voltage, along with digital signal processing, to determine real power consumption and other quantities with a high degree of precision. This may allow the generator to implement a number of useful algorithms, such as, for example, controlling the amount of power delivered to tissue as the impedance of the tissue changes and controlling the power delivery to maintain a constant rate of tissue impedance increase. Some of these algorithms are used to determine the phase difference between the generator drive signal current and voltage signals. At resonance, the phase difference between the current and voltage signals is zero. The phase changes as the ultrasonic system goes off-resonance. Various algorithms may be employed to detect the phase difference and adjust the drive frequency until the ultrasonic system returns to resonance, i.e., the phase difference between the current and voltage signals goes to zero. The phase information also may be used to infer the conditions of the ultrasonic blade. As discussed with particularity below, the phase changes as a function of the temperature of the ultrasonic blade. Therefore, the phase information may be employed to control the temperature of the ultrasonic blade. This may be done, for example, by reducing the power delivered to the ultrasonic blade when the ultrasonic blade runs too hot and increasing the power delivered to the ultrasonic blade when the ultrasonic blade runs too cold.

Various aspects of the generator may have a wide frequency range and increased output power necessary to drive both ultrasonic surgical devices and electrosurgical devices. The lower voltage, higher current demand of electrosurgical devices may be met by a dedicated tap on a wideband power transformer, thereby eliminating the need for a separate power amplifier and output transformer. Moreover, sensing and feedback circuits of the generator may support a large dynamic range that addresses the needs of both ultrasonic and electrosurgical applications with minimal distortion.

Various aspects may provide a simple, economical means for the generator to read from, and optionally write to, a data circuit (e.g., a single-wire bus device, such as a one-wire protocol EEPROM known under the trade name "1-Wire") disposed in an instrument attached to the handpiece using existing multi-conductor generator/handpiece cables. In this way, the generator is able to retrieve and process instrument-specific data from an instrument attached to the handpiece. This may enable the generator to provide better control and improved diagnostics and error detection. Additionally, the ability of the generator to write data to the instrument makes possible new functionality in terms of, for example, tracking instrument usage and capturing operational data. Moreover, the use of frequency band permits the backward compatibility of instruments containing a bus device with existing generators.

Disclosed aspects of the generator provide active cancellation of leakage current caused by unintended capacitive coupling between non-isolated and patient-isolated circuits of the generator. In addition to reducing patient risk, the reduction of leakage current may also lessen electromagnetic emissions.

These and other benefits of aspects of the present disclosure will be apparent from the description to follow.

It will be appreciated that the terms "proximal" and "distal" are used herein with reference to a clinician gripping a handpiece. Thus, an end effector is distal with respect to the more proximal handpiece. It will be further appreciated that, for convenience and clarity, spatial terms such as "top" and "bottom" may also be used herein with respect to the clinician gripping the handpiece. However, surgical devices are used in many orientations and positions, and these terms are not intended to be limiting and absolute.

FIG. 39 is an elevational exploded view of modular handheld ultrasonic surgical instrument 6480 showing the left shell half removed from a handle assembly 6482 exposing a device identifier communicatively coupled to the multi-lead handle terminal assembly in accordance with one aspect of the present disclosure. In additional aspects of the present disclosure, an intelligent or smart battery is used to power the modular handheld ultrasonic surgical instrument 6480. However, the smart battery is not limited to the modular handheld ultrasonic surgical instrument 6480 and, as will be explained, can be used in a variety of devices, which may or may not have power requirements (e.g., current and voltage) that vary from one another. The smart battery assembly 6486, in accordance with one aspect of the present disclosure, is advantageously able to identify the particular device to which it is electrically coupled. It does this through encrypted or unencrypted identification methods. For instance, a smart battery assembly 6486 can have a connection portion, such as connection portion 6488. The handle assembly 6482 can also be provided with a device identifier communicatively coupled to the multi-lead handle terminal assembly 6491 and operable to communicate at least one piece of information about the handle assembly 6482. This information can pertain to the number of times the handle assembly 6482 has been used, the number of times an ultrasonic transducer/generator assembly 6484 (presently disconnected from the handle assembly 6482) has been used, the number of times a waveguide shaft assembly 6490 (presently connected to the handle assembly 6482) has been used, the type of the waveguide shaft assembly 6490 that is presently connected to the handle assembly 6482, the type or identity of the ultrasonic transducer/generator assembly 6484 that is presently connected to the handle assembly 6482, and/or many other characteristics. When the smart battery assembly 6486 is inserted in the handle assembly 6482, the connection portion 6488 within the smart battery assembly 6486 makes communicating contact with the device identifier of the handle assembly 6482. The handle assembly 6482, through hardware, software, or a combination thereof, is able to transmit information to the smart battery assembly 6486 (whether by self-initiation or in response to a request from the smart battery assembly 6486). This communicated identifier is received by the connection portion 6488 of the smart battery assembly 6486. In one aspect, once the smart battery assembly 6486 receives the information, the communication portion is operable to control the output of the smart battery assembly 6486 to comply with the device's specific power requirements.

In one aspect, the communication portion includes a processor 6493 and a memory 6497, which may be separate or a single component. The processor 6493, in combination with the memory, is able to provide intelligent power management for the modular handheld ultrasonic surgical instrument 6480. This aspect is particularly advantageous because an ultrasonic device, such as the modular handheld ultrasonic surgical instrument 6480, has a power requirement (frequency, current, and voltage) that may be unique to the modular handheld ultrasonic surgical instrument 6480. In fact, the modular handheld ultrasonic surgical instrument 6480 may have a particular power requirement or limitation for one dimension or type of outer tube 6494 and a second different power requirement for a second type of waveguide having a different dimension, shape, and/or configuration.

A smart battery assembly 6486, in accordance with at least one aspect of the present disclosure, therefore, allows a battery assembly to be used amongst several surgical instruments. Because the smart battery assembly 6486 is able to identify to which device it is attached and is able to alter its output accordingly, the operators of various different surgical instruments utilizing the smart battery assembly 6486 no longer need be concerned about which power source they are attempting to install within the electronic device being used. This is particularly advantageous in an operating environment where a battery assembly needs to be replaced or interchanged with another surgical instrument in the middle of a complex surgical procedure.

In a further aspect of the present disclosure, the smart battery assembly 6486 stores in a memory 6497 a record of each time a particular device is used. This record can be useful for assessing the end of a device's useful or permitted life. For instance, once a device is used 20 times, such batteries in the smart battery assembly 6486 connected to the device will refuse to supply power thereto—because the device is defined as a "no longer reliable" surgical instrument. Reliability is determined based on a number of factors. One factor can be wear, which can be estimated in a number of ways including the number of times the device has been used or activated. After a certain number of uses, the parts of the device can become worn and tolerances between parts exceeded. For instance, the smart battery assembly 6486 can sense the number of button pushes received by the handle assembly 6482 and can determine when a maximum number of button pushes has been met or exceeded. The smart battery assembly 6486 can also monitor an impedance of the button mechanism which can change, for instance, if the handle gets contaminated, for example, with saline.

This wear can lead to an unacceptable failure during a procedure. In some aspects, the smart battery assembly 6486 can recognize which parts are combined together in a device and even how many uses a part has experienced. For instance, if the smart battery assembly 6486 is a smart battery according to the present disclosure, it can identify the handle assembly 6482, the waveguide shaft assembly 6490, as well as the ultrasonic transducer/generator assembly 6484, well before the user attempts use of the composite device. The memory 6497 within the smart battery assembly 6486 can, for example, record a time when the ultrasonic transducer/generator assembly 6484 is operated, and how, when, and for how long it is operated. If the ultrasonic transducer/generator assembly 6484 has an individual identifier, the smart battery assembly 6486 can keep track of uses of the ultrasonic transducer/generator assembly 6484 and refuse to supply power to that the ultrasonic transducer/generator assembly 6484 once the handle assembly 6482 or the ultrasonic transducer/generator assembly 6484 exceeds its maximum number of uses. The ultrasonic transducer/generator assembly 6484, the handle assembly 6482, the waveguide shaft assembly 6490, or other components can include a memory chip that records this information as well. In this way, any number of smart batteries in the smart battery assembly 6486 can be used with any number of ultrasonic transducer/generator assemblies 6484, staplers, vessel sealers, etc. and still be able to determine the total number of uses, or the total time of use (through use of the clock), or the total number of actuations, etc. of the ultrasonic transducer/generator assembly 6484, the stapler, the vessel sealer, etc. or charge or discharge cycles. Smart functionality may reside outside the battery assembly 6486 and may reside in the handle assembly 6482, the ultrasonic transducer/generator assembly 6484, and/or the shaft assembly 6490, for example.

When counting uses of the ultrasonic transducer/generator assembly 6484, to intelligently terminate the life of the ultrasonic transducer/generator assembly 6484, the surgical instrument accurately distinguishes between completion of an actual use of the ultrasonic transducer/generator assembly 6484 in a surgical procedure and a momentary lapse in actuation of the ultrasonic transducer/generator assembly 6484 due to, for example, a battery change or a temporary delay in the surgical procedure. Therefore, as an alternative to simply counting the number of activations of the ultrasonic transducer/generator assembly 6484, a real-time clock (RTC) circuit can be implemented to keep track of the amount of time the ultrasonic transducer/generator assembly 6484 actually is shut down. From the length of time measured, it can be determined through appropriate logic if the shutdown was significant enough to be considered the end of one actual use or if the shutdown was too short in time to be considered the end of one use. Thus, in some applications, this method may be a more accurate determination of the useful life of the ultrasonic transducer/generator assembly 6484 than a simple "activations-based" algorithm, which for example, may provide that ten "activations" occur in a surgical procedure and, therefore, ten activations should indicate that the counter is incremented by one. Generally, this type and system of internal clocking will prevent misuse of the device that is designed to deceive a simple "activations-based" algorithm and will prevent incorrect logging of a complete use in instances when there was only a simple de-mating of the ultrasonic transducer/generator assembly 6484 or the smart battery assembly 6486 that was required for legitimate reasons.

Although the ultrasonic transducer/generator assemblies 6484 of the surgical instrument 6480 are reusable, in one aspect a finite number of uses may be set because the surgical instrument 6480 is subjected to harsh conditions during cleaning and sterilization. More specifically, the battery pack is configured to be sterilized. Regardless of the material employed for the outer surfaces, there is a limited expected life for the actual materials used. This life is determined by various characteristics which could include, for example, the amount of times the pack has actually been sterilized, the time from which the pack was manufactured, and the number of times the pack has been recharged, to name a few. Also, the life of the battery cells themselves is limited. Software of the present disclosure incorporates inventive algorithms that verify the number of uses of the ultrasonic transducer/generator assembly 6484 and smart battery assembly 6486 and disables the device when this number of uses has been reached or exceeded. Analysis of the battery pack exterior in each of the possible sterilizing methods can be performed. Based on the harshest steriliza- tion procedure, a maximum number of permitted steriliza- tions can be defined and that number can be stored in a memory of the smart battery assembly 6486. If it is assumed that a charger is non-sterile and that the smart battery assembly 6486 is to be used after it is charged, then the charge count can be defined as being equal to the number of sterilizations encountered by that particular pack.

In one aspect, the hardware in the battery pack may be to disabled to minimize or eliminate safety concerns due to continuous drain in from the battery cells after the pack has been disabled by software. A situation can exist where the battery's internal hardware is incapable of disabling the battery under certain low voltage conditions. In such a situation, in an aspect, the charger can be used to "kill" the battery. Due to the fact that the battery microcontroller is OFF while the battery is in its charger, a non-volatile, System Management Bus (SMB) based electrically erasable programmable read only memory (EEPROM) can be used to exchange information between the battery microcontroller and the charger. Thus, a serial EEPROM can be used to store information that can be written and read even when the battery microcontroller is OFF, which is very beneficial when trying to exchange information with the charger or other peripheral devices. This example EEPROM can be configured to contain enough memory registers to store at least (a) a use-count limit at which point the battery should be disabled (Battery Use Count), (b) the number of proce- dures the battery has undergone (Battery Procedure Count), and/or (c) a number of charges the battery has undergone (Charge Count), to name a few. Some of the information stored in the EEPROM, such as the Use Count Register and Charge Count Register are stored in write-protected sections of the EEPROM to prevent users from altering the infor- mation. In an aspect, the use and counters are stored with corresponding bit-inverted minor registers to detect data corruption.

Any residual voltage in the SMBus lines could damage the microcontroller and corrupt the SMBus signal. There- fore, to ensure that the SMBus lines of a battery controller do not carry a voltage while the microcontroller is OFF, relays are provided between the external SM Bus lines and the battery microcontroller board.

During charging of the smart battery assembly 6486, an "end-of-charge" condition of the batteries within the smart battery assembly 6486 is determined when, for example, the current flowing into the battery falls below a given threshold in a tapering manner when employing a constant-current/ constant-voltage charging scheme. To accurately detect this "end-of-charge" condition, the battery microcontroller and buck boards are powered down and turned OFF during charging of the battery to reduce any current drain that may be caused by the boards and that may interfere with the tapering current detection. Additionally, the microcontroller and buck boards are powered down during charging to prevent any resulting corruption of the SM Bus signal.

With regard to the charger, in one aspect the smart battery assembly 6486 is prevented from being inserted into the charger in any way other than the correct insertion position. Accordingly, the exterior of the smart battery assembly 6486 is provided with charger-holding features. A cup for holding the smart battery assembly 6486 securely in the charger is configured with a contour-matching taper geometry to pre- vent the accidental insertion of the smart battery assembly 6486 in any way other than the correct (intended) way. It is further contemplated that the presence of the smart battery assembly 6486 may be detectable by the charger itself. For example, the charger may be configured to detect the pres- ence of the SMBus transmission from the battery protection circuit, as well as resistors that are located in the protection board. In such case, the charger would be enabled to control the voltage that is exposed at the charger's pins until the smart battery assembly 6486 is correctly seated or in place at the charger. This is because an exposed voltage at the charger's pins would present a hazard and a risk that an electrical short could occur across the pins and cause the charger to inadvertently begin charging.

In some aspects, the smart battery assembly 6486 can communicate to the user through audio and/or visual feed- back. For example, the smart battery assembly 6486 can cause the LEDs to light in a pre-set way. In such a case, even though the microcontroller in the ultrasonic transducer/ generator assembly 6484 controls the LEDs, the microcon- troller receives instructions to be carried out directly from the smart battery assembly 6486.

In yet a further aspect of the present disclosure, the microcontroller in the ultrasonic transducer/generator assembly 6484, when not in use for a predetermined period of time, goes into a sleep mode. Advantageously, when in the sleep mode, the clock speed of the microcontroller is reduced, cutting the current drain significantly. Some current continues to be consumed because the processor continues pinging waiting to sense an input. Advantageously, when the microcontroller is in this power-saving sleep mode, the microcontroller and the battery controller can directly con- trol the LEDs. For example, a decoder circuit could be built into the ultrasonic transducer/generator assembly 6484 and connected to the communication lines such that the LEDs can be controlled independently by the processor 6493 while the ultrasonic transducer/generator assembly 6484 micro- controller is "OFF" or in a "sleep mode." This is a power- saving feature that eliminates the need for waking up the microcontroller in the ultrasonic transducer/generator assembly 6484. Power is conserved by allowing the gen- erator to be turned off while still being able to actively control the user-interface indicators.

Another aspect slows down one or more of the micro- controllers to conserve power when not in use. For example, the clock frequencies of both microcontrollers can be reduced to save power. To maintain synchronized operation, the microcontrollers coordinate the changing of their respective clock frequencies to occur at about the same time, both the reduction and, then, the subsequent increase in frequency when full speed operation is required. For example, when entering the idle mode, the clock frequencies are decreased and, when exiting the idle mode, the frequencies are increased.

In an additional aspect, the smart battery assembly 6486 is able to determine the amount of usable power left within its cells and is programmed to only operate the surgical instrument to which it is attached if it determines there is enough battery power remaining to predictably operate the device throughout the anticipated procedure. For example, the smart battery assembly 6486 is able to remain in a non-operational state if there is not enough power within the cells to operate the surgical instrument for 20 seconds. According to one aspect, the smart battery assembly 6486 determines the amount of power remaining within the cells at the end of its most recent preceding function, e.g., a surgical cutting. In this aspect, therefore, the smart battery assembly 6486 would not allow a subsequent function to be carried out if, for example, during that procedure, it determines that the cells have insufficient power. Alternatively, if the smart battery assembly 6486 determines that there is sufficient power for a subsequent procedure and goes below that threshold during the procedure, it would not interrupt the ongoing procedure and, instead, will allow it to finish and thereafter prevent additional procedures from occurring.

The following explains an advantage to maximizing use of the device with the smart battery assembly 6486 of the present disclosure. In this example, a set of different devices have different ultrasonic transmission waveguides. By definition, the waveguides could have a respective maximum allowable power limit where exceeding that power limit overstresses the waveguide and eventually causes it to fracture. One waveguide from the set of waveguides will naturally have the smallest maximum power tolerance. Because prior-art batteries lack intelligent battery power management, the output of prior-art batteries must be limited by a value of the smallest maximum allowable power input for the smallest/thinnest/most-frail waveguide in the set that is envisioned to be used with the device/battery. This would be true even though larger, thicker waveguides could later be attached to that handle and, by definition, allow a greater force to be applied. This limitation is also true for maximum battery power. For example, if one battery is designed to be used in multiple devices, its maximum output power will be limited to the lowest maximum power rating of any of the devices in which it is to be used. With such a configuration, one or more devices or device configurations would not be able to maximize use of the battery because the battery does not know the particular device's specific limits.

In one aspect, the smart battery assembly 6486 may be employed to intelligently circumvent the above-mentioned ultrasonic device limitations. The smart battery assembly 6486 can produce one output for one device or a particular device configuration and the same smart battery assembly 6486 can later produce a different output for a second device or device configuration. This universal smart battery surgical system lends itself well to the modern operating room where space and time are at a premium. By having a smart battery pack operate many different devices, the nurses can easily manage the storage, retrieval, and inventory of these packs. Advantageously, in one aspect the smart battery system according to the present disclosure may employ one type of charging station, thus increasing ease and efficiency of use and decreasing cost of surgical room charging equipment.

In addition, other surgical instruments, such as an electric stapler, may have a different power requirement than that of the modular handheld ultrasonic surgical instrument 6480. In accordance with various aspects of the present disclosure, a smart battery assembly 6486 can be used with any one of a series of surgical instruments and can be made to tailor its own power output to the particular device in which it is installed. In one aspect, this power tailoring is performed by controlling the duty cycle of a switched mode power supply, such as buck, buck-boost, boost, or other configuration, integral with or otherwise coupled to and controlled by the smart battery assembly 6486. In other aspects, the smart battery assembly 6486 can dynamically change its power output during device operation. For instance, in vessel sealing devices, power management provides improved tissue sealing. In these devices, large constant current values are needed. The total power output needs to be adjusted dynamically because, as the tissue is sealed, its impedance changes. Aspects of the present disclosure provide the smart battery assembly 6486 with a variable maximum current limit. The current limit can vary from one application (or device) to another, based on the requirements of the application or device.

FIG. 40 is a detail view of a trigger 6483 portion and switch of the ultrasonic surgical instrument 6480 shown in FIG. 39, in accordance with at least one aspect of the present disclosure. The trigger 6483 is operably coupled to the jaw member 6495 of the end effector 6492. The ultrasonic blade 6496 is energized by the ultrasonic transducer/generator assembly 6484 upon activating the activation switch 6485. Continuing now with FIG. 39 and also looking to FIG. 40, the trigger 6483 and the activation switch 6485 are shown as components of the handle assembly 6482. The trigger 6483 activates the end effector 6492, which has a cooperative association with the ultrasonic blade 6496 of the waveguide shaft assembly 6490 to enable various kinds of contact between the end effector jaw member 6495 and the ultrasonic blade 6496 with tissue and/or other substances. The jaw member 6495 of the end effector 6492 is usually a pivoting jaw that acts to grasp or clamp onto tissue disposed between the jaw and the ultrasonic blade 6496. In one aspect, an audible feedback is provided in the trigger that clicks when the trigger is fully depressed. The noise can be generated by a thin metal part that the trigger snaps over while closing. This feature adds an audible component to user feedback that informs the user that the jaw is fully compressed against the waveguide and that sufficient clamping pressure is being applied to accomplish vessel sealing. In another aspect, force sensors such as strain gages or pressure sensors may be coupled to the trigger 6483 to measure the force applied to the trigger 6483 by the user. In another aspect, force sensors such as strain gages or pressure sensors may be coupled to the switch 6485 button such that displacement intensity corresponds to the force applied by the user to the switch 6485 button.

The activation switch 6485, when depressed, places the modular handheld ultrasonic surgical instrument 6480 into an ultrasonic operating mode, which causes ultrasonic motion at the waveguide shaft assembly 6490. In one aspect, depression of the activation switch 6485 causes electrical contacts within a switch to close, thereby completing a circuit between the smart battery assembly 6486 and the ultrasonic transducer/generator assembly 6484 so that electrical power is applied to the ultrasonic transducer, as previously described. In another aspect, depression of the activation switch 6485 closes electrical contacts to the smart battery assembly 6486. Of course, the description of closing electrical contacts in a circuit is, here, merely an example general description of switch operation. There are many alternative aspects that can include opening contacts or processor-controlled power delivery that receives information from the switch and directs a corresponding circuit reaction based on the information.

FIG. 41 is a fragmentary, enlarged perspective view of an end effector 6492, in accordance with at least one aspect of the present disclosure, from a distal end with a jaw member 6495 in an open position. Referring to FIG. 41, a perspective partial view of the distal end 6498 of the waveguide shaft assembly 6490 is shown. The waveguide shaft assembly 6490 includes an outer tube 6494 surrounding a portion of the waveguide. The ultrasonic blade 6496 portion of the waveguide 6499 protrudes from the distal end 6498 of the outer tube 6494. It is the ultrasonic blade 6496 portion that contacts the tissue during a medical procedure and transfers its ultrasonic energy to the tissue. The waveguide shaft assembly 6490 also includes a jaw member 6495 that is coupled to the outer tube 6494 and an inner tube (not visible in this view). The jaw member 6495, together with the inner and outer tubes and the ultrasonic blade 6496 portion of the waveguide 6499, can be referred to as an end effector 6492. As will be explained below, the outer tube 6494 and the non-illustrated inner tube slide longitudinally with respect to each other. As the relative movement between the outer tube 6494 and the non-illustrated inner tube occurs, the jaw member 6495 pivots upon a pivot point, thereby causing the jaw member 6495 to open and close. When closed, the jaw member 6495 imparts a pinching force on tissue located between the jaw member 6495 and the ultrasonic blade 6496, insuring positive and efficient blade-to-tissue contact.

Turning now to FIG. 42, the end effector 8400 comprises RF data sensors 8406, 8408*a*, 8408*b* located on the jaw member 8402. The end effector 8400 comprises a jaw member 8402 and an ultrasonic blade 8404. The jaw member 8402 is shown clamping tissue 8410 located between the jaw member 8402 and the ultrasonic blade 8404. A first sensor 8406 is located in a center portion of the jaw member 8402. Second and third sensors 8408*a*, 8408*b* are located on lateral portions of the jaw member 8402. The sensors 8406, 8408*a*, 8408*b* are mounted or formed integrally with a flexible circuit 8412 (shown more particularly in FIG. 52) configured to be fixedly mounted to the jaw member 8402.

The end effector 8400 is an example end effector for a surgical instrument. The sensors 8406, 8408*a*, 8408*b* are electrically connected to a control circuit such as the control circuit 7400 (FIG. 63) via interface circuits. The sensors 8406, 8408*a*, 8408*b* are battery powered and the signals generated by the sensors 8406, 8408*a*, 8408*b* are provided to analog and/or digital processing circuits of the control circuit.

In one aspect, the first sensor 8406 is a force sensor to measure a normal force F3 applied to the tissue 8410 by the jaw member 8402. The second and third sensors 8408*a*, 8408*b* include one or more elements to apply RF energy to the tissue 8410, measure tissue impedance, down force F1, transverse forces F2, and temperature, among other parameters. Electrodes 8409*a*, 8409*b* are electrically coupled to an energy source and apply RF energy to the tissue 8410. In one aspect, the first sensor 8406 and the second and third sensors 8408*a*, 8408*b* are strain gauges to measure force or force per unit area. It will be appreciated that the measurements of the down force F1, the lateral forces F2, and the normal force F3 may be readily converted to pressure by determining the surface area upon which the force sensors 8406, 8408*a*, 8408*b* are acting upon. Additionally, as described with particularity herein, the flexible circuit 8412 may comprise temperature sensors embedded in one or more layers of the flexible circuit 8412. The one or more temperature sensors may be arranged symmetrically or asymmetrically and provide tissue 8410 temperature feedback to control circuits of an ultrasonic drive circuit and an RF drive circuit.

Ultrasonic spectroscopy smart blade algorithm techniques may be employed for estimating the state of the jaw (clamp arm pad burn through, staples, broken blade, bone in jaw, tissue in jaw, back-cutting with jaw closed, etc.) based on the impedance $$Z_g(t) = \frac{V_g(t)}{I_g(t)}$$

of an ultrasonic transducer configured to drive an ultrasonic transducer blade, in accordance with at least one aspect of the present disclosure. The impedance $Z_g(t)$, magnitude |Z|, and phase $\varphi$ are plotted as a function of frequency f.

Dynamic mechanical analysis (DMA), also known as dynamic mechanical spectroscopy or simply mechanical spectroscopy, is a technique used to study and characterize materials. A sinusoidal stress is applied to a material, and the strain in the material is measured, allowing the determination of the complex modulus of the material. The spectroscopy as applied to ultrasonic devices includes exciting the tip of the ultrasonic blade with a sweep of frequencies (compound signals or traditional frequency sweeps) and measuring the resulting complex impedance at each frequency. The complex impedance measurements of the ultrasonic transducer across a range of frequencies are used in a classifier or model to infer the characteristics of the ultrasonic end effector. In one aspect, the present disclosure provides a technique for determining the state of an ultrasonic end effector (clamp arm, jaw) to drive automation in the ultrasonic device (such as disabling power to protect the device, executing adaptive algorithms, retrieving information, identifying tissue, etc.).

Figure 43:
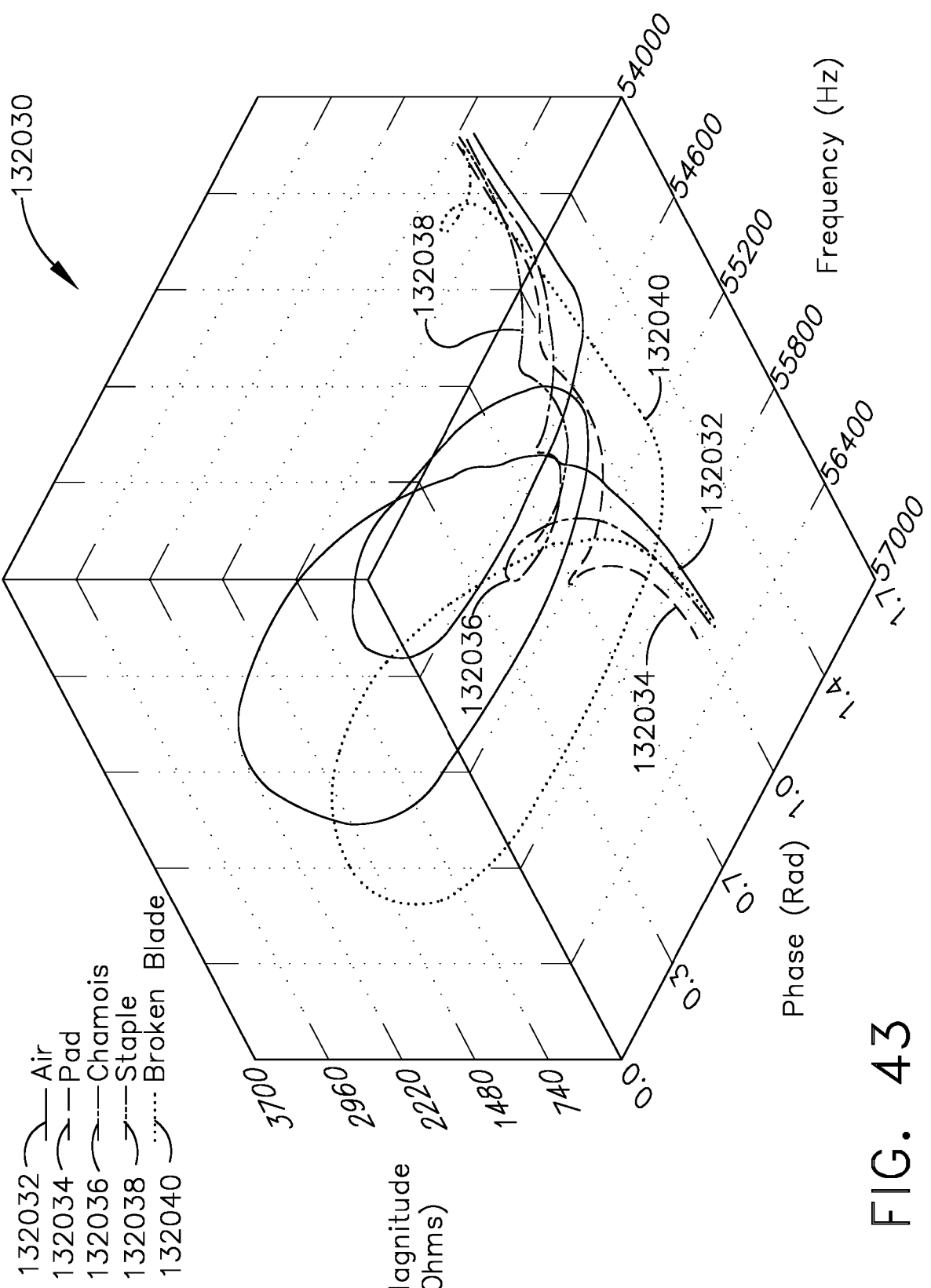
FIG. 43 is a spectra of the same ultrasonic device with a variety of different states and conditions of the end effector where phase and magnitude of the impedance of an ultrasonic transducer are plotted as a function of frequency, in accordance with at least one aspect of the present disclosure.

FIG. 43 is a spectra 132030 of an ultrasonic device with a variety of different states and conditions of the end effector where the impedance $Z_g(t)$, magnitude |Z|, and phase $\varphi$ are plotted as a function of frequency f, in accordance with at least one aspect of the present disclosure. The spectra 132030 is plotted in three-dimensional space where frequency (Hz) is plotted along the x-axis, phase (Rad) is plotted along the y-axis, and magnitude (Ohms) is plotted along the z-axis.

Spectral analysis of different jaw bites and device states produces different complex impedance characteristic patterns (fingerprints) across a range of frequencies for different conditions and states. Each state or condition has a different characteristic pattern in 3D space when plotted. These characteristic patterns can be used to estimate the condition and state of the end effector. FIG. 43 shows the spectra for air 132032, clamp arm pad 132034, chamois 132036, staple 132038, and broken blade 132040. The chamois 132036 may be used to characterize different types of tissue.

The spectra 132030 can be evaluated by applying a low-power electrical signal across the ultrasonic transducer to produce a non-therapeutic excitation of the ultrasonic blade. The low-power electrical signal can be applied in the form of a sweep or a compound Fourier series to measure the impedance $$Z_g(t) = \frac{V_g(t)}{I_g(t)}$$

across the ultrasonic transducer at a range of frequencies in series (sweep) or in parallel (compound signal) using an FFT.

Figure 44:
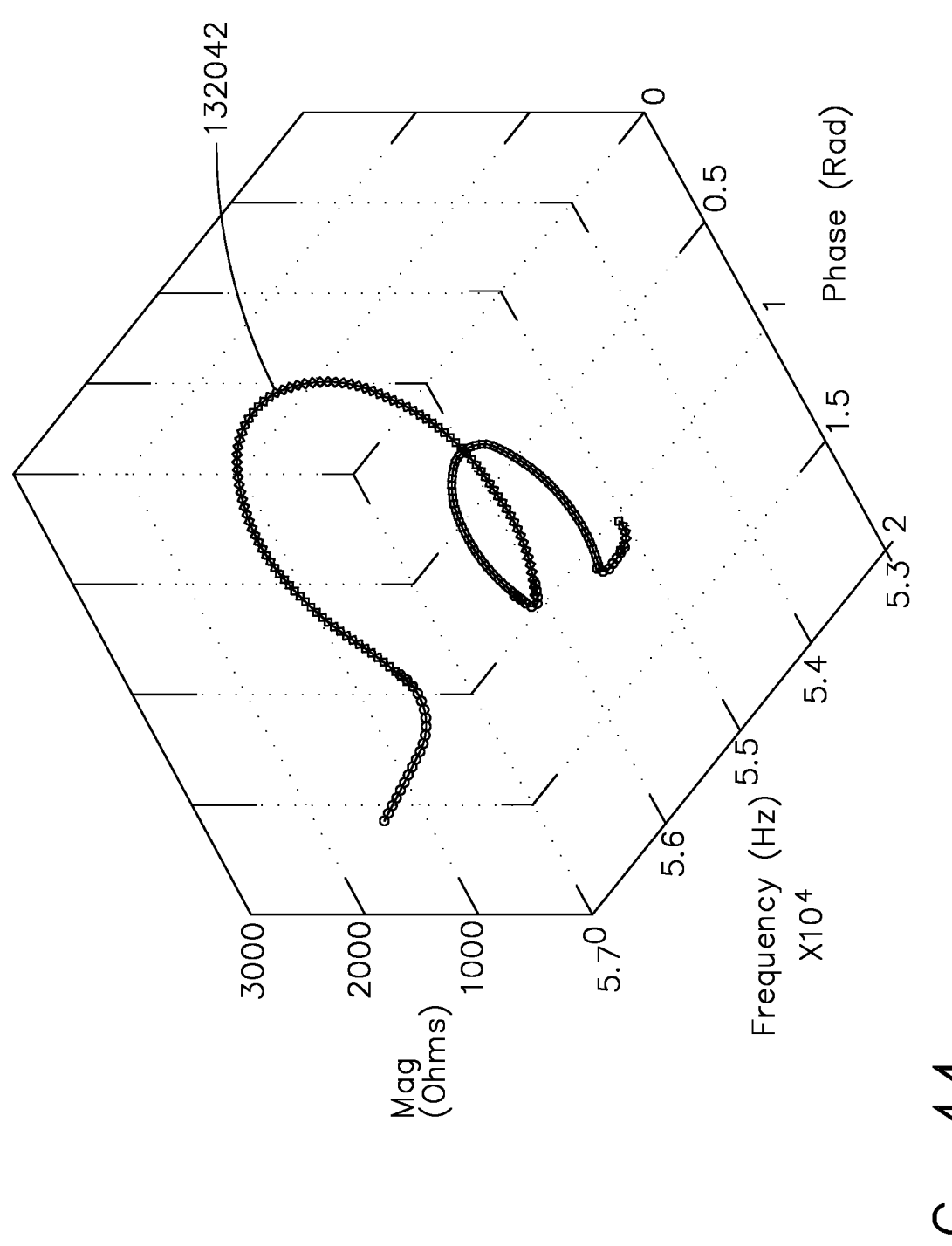
FIG. 44 is a graphical representation of a plot of a set of 3D training data S, where ultrasonic transducer impedance magnitude and phase are plotted as a function of frequency, in accordance with at least one aspect of the present disclosure.

FIG. 44 is a graphical representation of a plot 132042 of a set of 3D training data set (S), where ultrasonic transducer impedance $Z_g(t)$, magnitude |Z|, and phase $\varphi$ are plotted as a function of frequency f, in accordance with at least one aspect of the present disclosure. The 3D training data set (S) plot 132042 is graphically depicted in three-dimensional space where phase (Rad) is plotted along the x-axis, frequency (Hz) is plotted along the y-axis, magnitude (Ohms) is plotted along the z-axis, and a parametric Fourier series is fit to the 3D training data set (S). A methodology for classifying data is based on the 3D training data set (S0 is used to generate the plot 132042).

The parametric Fourier series fit to the 3D training data set (S) is given by:

$$\vec{p} = \vec{a}_0 + \sum_{n=1}^{\infty} \left( \vec{a}_n \cos\frac{n\pi t}{L} + \vec{b}_n \sin\frac{n\pi t}{L} \right)$$

For a new point $\vec{z}$, the perpendicular distance from $\vec{p}$ to $\vec{z}$ is found by:

$$D = \|\vec{p} - \vec{z}\|$$

When:

$$\frac{\partial D}{\partial T} = 0$$

Then:

$$D = D_{\perp}$$

A probability distribution of D can be used to estimate the probability of a data point $\vec{z}$ belonging to the group S.

Adjustment of Compression Force Applied to Tissue Based on Proportion of Energy Modalities Aspects of the present disclosure are presented for a surgical instrument that is situationally aware. The surgical instrument may be any suitable surgical instrument described in the present disclosure. For the sake of clarity, surgical instrument 112 is referenced. In particular, the surgical instrument 112 may be a bipolar combination surgical instrument 112 which may automatically adjust a compression force applied by the end effector of the surgical instrument 112 based on a selected energy modality. In one aspect, the bipolar combination surgical instrument 112 may be configured to deliver energy according to a bipolar radio frequency (RF) and an ultrasonic energy modality. More specifically, the automatic adjustment may be based on a proportion of two different selected energy modalities. This automatic adjustment of the compression force is an example of a situational awareness characteristic of the surgical instrument 112 that may improve the efficacy and quality of a surgical procedure performed with the surgical instrument 112. The clamp pressure applied by the end effector can be indicative of the compression force applied to tissue being treated. As discussed above, selectable energy modalities include ultrasonic, bipolar or monopolar radio frequency (electrosurgical), irreversible or reversible electroporation, and microwave energy modality implemented by a generator of the surgical instrument 112. In one aspect, the two selected energy modalities are bipolar RF energy and ultrasonic energy. Additionally or alternatively to adjusting the compression force applied to tissue based on the selected energy modality, the compression force may also be adjusted based on a power parameter. The power parameter may refer to the relative proportion of total energy applied during a surgical procedure that is allocated between bipolar RF and ultrasonic energy, respectively, for example.

In general, the compression force adjustment may be actively performed during performance of a surgical procedure. Such active adjustment can mean that the clinician operating the surgical instrument 112 does not need to manually adjust the clamp arm, waveguide or ultrasonic blade, or end effector to modify the compression force applied to tissue being treated in the jaws of the end effector. As described below in further detail, a control circuit or generator of the situationally aware surgical instrument 112 may automatically adjust tissue compression force by executing an algorithm. The algorithm is executable to determine an appropriate compression force by considering the particular proportion or blend of the selected energy modalities. For example, the relative proportion of time spent applying each energy modality can be considered in determining suitable tissue compression forces to be applied during the course of the performed surgical procedure. The relative amplitudes of each energy modality could be considered as well. Also, each type of energy modality can correspond to a certain pressure or range of pressures, which could also change depending on other parameters such as the power and timing of the delivered energy modality. This energy-pressure relationship can also be understood as energy delivered and pressure existing on a spectrum together. That is, the more compression pressure that is applied, the more effective the application of energy to treat tissue will be. Consequently, less energy may be required when more compression pressure is applied. Energy is delivered according to the selected energy modality.

The selected energy modalities could be applied simultaneously to tissue. Alternatively, the generator may switch between providing a drive output signal according to a first energy modality such as bipolar RF and providing the drive output signal according to a second energy modality such as ultrasonic. That is, the delivery of RF can follow ultrasonic and vice versa. The extent of switching may be used in the algorithm to determine a suitable automatic adjustment to tissue compression force. For example, when the generator switches from delivering ultrasonic energy to bipolar RF energy, the applied tissue compression force may be increased. When multiple energy modalities are applied simultaneously, the relative proportion of the energy modalities may be used to determine the compression force adjustment. For example, the control circuit could the proportion of ultrasonic drive signals to RF drive signals provided by the generator. As described further below, electrical or mechanical methods of adjusting tissue compression may be used and such methods may or may not involve control by the processor, control circuit, or generator as appropriate. In some aspects, the tissue compression adjustment algorithm may be stored in memory and may be updated by an algorithm program update transmitted from the corresponding surgical hub (e.g., surgical hub 106, 206) to the surgical instrument 112. In turn, the hub may receive this algorithm program update from a cloud computing system (e.g. cloud 104, 204). The hub may also store the update locally in a memory device of the hub. Additionally or alternatively, the control circuit or generator of the surgical instrument 112 can modify the algorithm as suitable, such as by a clinician changing the parameters of the algorithm through a user interface of the surgical instrument 112.

Mechanical methods of adjusting tissue compression force include adjusting the waveguide or ultrasonic blade and adjusting the clamp arm linkage mechanism (e.g., linkage components of the transmissions 706a-706e) of the surgical instrument 112. The ultrasonic blade can be for example, an offset oval ultrasonic blade where the end effector clamp arm and offset ultrasonic blade are rotatable relative to each other to define a tissue gap distance between the end effector jaws. By adjusting the tissue gap distance, various tissue compression forces are possible. In this way, the ultrasonic blade is adjustable to generate a smaller tissue gap (and thus relatively higher compression force) when the RF energy modality is selected and to generate a larger tissue gap (and thus relatively lower compression force) when the ultrasonic energy modality is selected. The end effector jaw members can also be adjusted for a desired tissue gap size independently of the wave guide. For example, in one aspect, a clamp arm linkage mechanism is provided to change the clamp arm actuator rod stroke according to the selected energy modality. The clamp arm actuator rod (e.g., articulation actuator such as via output shaft of the motor 704a, 704b coupled to moveable mechanical elements of transmissions 706a, 706b) is coupled to a linkage pivot, which in turn is operationally coupled to a mechanical selector of a surgical instrument 112.

The mechanical selector may be a mechanically actuated switch such as a momentary-action manual switch, mechanical-bail switch, capacitive touch switch, membrane switch, or other suitable mechanical switch. The mechanical switch may be controlled by the control circuit or generator to change the linkage pivot or linkage mechanism coupled to the end effector clamp arm such that the clamp arm exerts different compression force according to the selected energy modality. As such, in one position of the mechanical switch, the clamp arm may be linked so that when the actuator rod is actuated, relatively high compressive forces are applied. In a second position of the mechanical switch, the clamp arm may be linked so that when the actuator rod is actuated, relatively low compressive forces are applied. In one aspect, the first position corresponds to the ultrasonic energy modality, while the second position corresponds to the bipolar RF energy modality.

Electrical methods of adjusting tissue compression force are also possible. For example, compression force can be automatically adjusted by the situationally aware surgical instrument 112 with the use of an electroactive polymer (EAP). The EAP can be, for example an electric EAP (e.g., ferroelectric polymer), ionic EAP (e.g., ionomeric polymer-metal composite), non-ionic EAP, conductive polymer or other suitable EAP. The EAP can be arranged in parallel with an RF energy circuit of the surgical instrument 112, where the RF energy circuit is configured to implement the delivery of RF energy. Accordingly, the selection of an RF energy modality would cause current to flow through the RF energy circuit as RF energy is being delivered, which would also cause the EAP to expand. Upon expansion of the EAP, the tissue gap size decreases and results in the application of greater compression force.

Additionally or alternatively, multiple sets of electrodes (e.g. electrodes 796, 3074a, 3074b) may be provided and activated according to a particular sequence. This type of surgical treatment can be called hybrid activation. In hybrid activation, multiple different electrodes in the end effector are provided to perform different surgical functions. For example, a first set of electrodes may be used for the sealing surgical stage and a second set of electrodes may be used for the cutting surgical stage. To this end, a switch, filter, or other suitable wiring is provided to route the drive signal delivered by the generator to one or more appropriate electrodes in the end effector. For example, the situationally aware surgical instrument 112 may determine that an end effector electrode is configured for sealing rather than cutting. Consequently, an RF drive signal of relatively low voltage and high current may be driven through the output port of the generator to the pre-defined sealing electrodes for sealing. Similarly, an RF drive signal of greater power than the one used for sealing may be driven to different pre-defined cutting electrodes. The surgical instrument 112 may determine when the shift from the sealing electrodes to the cutting electrodes should occur based on a measured impedance threshold. When the impedance threshold is reached, the surgical instrument 112 may determine that a sufficiently secure seal has been created and that the cutting stage of the surgical procedure may begin. In general, the drive signal from the generator output port is routed appropriately to the corresponding electrode. Thus, drive signals can be routed to the appropriate treatment electrodes based on the appropriate stage of the surgical operation being performed. Also, the tissue compression force can be adjusted to a suitable level based on the power, time, or proportion of the drive signal or signals that are delivered to the tissue.

In some aspects, the automatic adjustment of jaw clamp pressure may be based on an algorithm implemented by a control circuit of the surgical instrument 112. As described above, the control circuit is configured to set and change various control parameters of the surgical instrument 112, including clamp pressure, power delivered to treat tissue, and amplitude and frequency of waveform/drive signal output by the generator. Each energy modality may generally correspond to a compression force. For example, the RF (whether bipolar or monopolar) energy modality generally requires a higher extent of tissue pressure compared to the ultrasonic energy modality. The high tissue compression forces used for low operating temperature RF energy may be advantageous for treating soft and connective tissue. Bipolar RF energy may require even higher tissue compression forces as opposed to those used in monopolar RF energy applications. In one aspect, the compression force adjustment algorithm may be adjusted based on a proportion of two or more different energy modalities. That is, two energy modalities could be applied during a surgical procedure and the proportion of time spent on each modality could be used in an algorithm to calculate suitable tissue compression forces to be applied during the surgical procedure. Energy according to the blended multiple energy modalities could be delivered simultaneously or substantially simultaneously. The situationally aware compression force adjustment algorithm may also be dynamically modified or updated via the surgical instrument 112 receiving an update from a corresponding surgical hub or the cloud.

Figure 45:
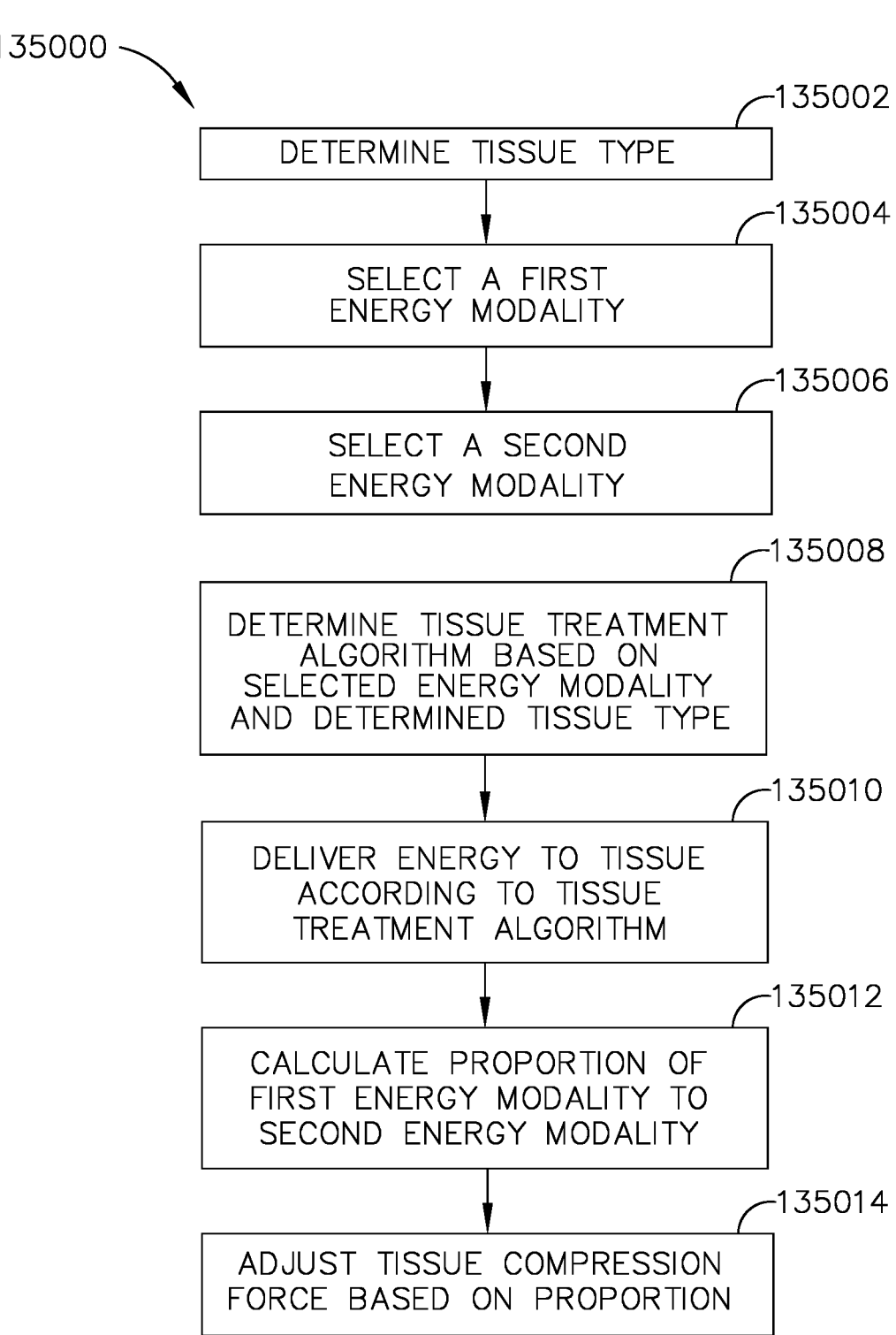
FIG. 45 is a logic flow diagram depicting a control program or a logic configuration to adjust compression force applied to tissue, based on one or more selected energy modalities, according to a least one aspect of the present disclosure.

FIG. 45 is a logic flow diagram 135000 depicting a control program or a logic configuration to adjust compression force applied to tissue, based on one or more selected energy modalities, according to a least one aspect of the present disclosure. The compression force is adjustable for a surgical procedure performed with a surgical instrument 112. A control circuit or processor of the surgical instrument 112 (FIGS. 10-17) or hub 106 (e.g., processor 244 FIG. 8) determines 135002 a type of tissue (which includes any tissue described herein, but is referred to as tissue 8410 for the sake of clarity) being treated by the surgical instrument 112. Tissue types include, for example, connective tissue (e.g., blood vessels), muscular tissue, and bronchus tissue. Tissue types could be detected or determined in a number of ways, such as by using spectral analysis of tissue bites. As discussed above, spectral analysis of different jaw bites and device states produces different complex impedance characteristic patterns (fingerprint) across a range of frequencies for different conditions and states. Spectroscopy may be applied to surgical instrument 112 by exciting the tip of the ultrasonic blade of the surgical instrument 112 with a sweep of frequencies, for example. The complex impedance characteristic patterns across a range of frequencies could be used in a model or classifier to infer tissue types.

Aside from inferring tissue type, tissue characteristics such as tissue thickness and stiffness may be determined, for example. The determination or inference of tissue type and tissue characteristics may be performed by the control circuit, including control circuit 500, 710, 760, 3200, 3300, 3402, 3502, 3686, 3900. For the sake of clarity, control circuit 3900 is referenced in this portion of the present disclosure. Control circuit 3900 may comprise the processors described above, as appropriate, including processors 822, 1740, 1900, 3214, 3302. In one aspect, the control circuit 3900 may cause the generator to apply a non-therapeutic signal to the end effector over a range of frequencies. Subsequently, the control circuit 3900 can determine the tissue impedance based on the impedance characteristic pattern derived from spectral analysis of the non-therapeutic signal, as discussed above. For the sake of clarity, generator 1100 is referred to in this portion although the generator may be any generator described here, including generator 800, 900, 1100, 4002. Also for the sake of clarity, end effector 8400 is referenced in this portion although the end effector may be any end effector described above, including end effector 702, 752, 792, 1122. In some aspects, the generator 1100 comprises the control circuit 3900; that is, the control circuit 3900 can be a component of the generator 1100.

Based on the tissue type and characteristic determination the situationally aware surgical instrument 112 might infer 135002 a type of surgical procedure or tissue treatment. Alternatively, a suitable surgical procedure could be manually determined or input by the clinician using the surgical instrument 112. Based on the surgical procedure to be performed, a first energy modality is selected 135004 by the control circuit 3900 so that energy may be delivered by the generator 1100 to tissue 8410 grasped by the end effector 8400. Delivering energy may comprise outputting drive signals according to the selected energy modality (e.g., ultrasonic drive signals) or electrical signal waveforms (e.g., current waveform determined based on LUT 2260 and used to drive the ultrasonic transducer 1120 or digital waveform 4300). As described above, the drive signal may have the waveform shape of the waveform generated by the generator 1100 or control circuit 3900. Based on the surgical procedure, a second energy modality is selected 135006 by the control circuit 3900. More than two energy modalities could also be selected by the control circuit 3900. The control circuit 3900 or generator 1100 may then generate signal waveforms according to or based on the selected energy modalities or a tissue treatment algorithm, which could be received from the corresponding hub 106, 206 or cloud 104, 204. As discussed above, energy modalities include ultrasonic, bipolar or monopolar RF, irreversible and/or reversible electroporation, and/or microwave energy, among others. Energy modalities can be selected depending on the type of treatment of tissue being performed. For example, the first and second energy modalities could be the ultrasonic energy modality and bipolar RF energy modality, respectively.

A tissue treatment algorithm is determined 135008. As discussed above, the surgical instrument 112 may receive 112 may receive the tissue treatment algorithm from an external source. Additionally or alternatively, the control circuit 3900 may determine the tissue treatment algorithm or an adjustment to the received algorithm based on the determined tissue type and selected energy modalities from steps 135002, 135004, 135006. In particular, the tissue treatment algorithm may define parameters of the surgical treatment such as the power and timing of the drive signal and the proportion of the energy modalities. Such parameters also may be dynamically adjusted by control circuit 3900 or generator 1100 during performance of the surgical procedure. In general, the tissue treatment algorithm could be inferred by the surgical instrument 112, received by the surgical instrument 112 through the corresponding surgical hub or cloud, or manually set by the clinician. The generator 1100 may infer what energy modality to apply based on feedback conditions or other sensed data received by the generator. For example, undeformed tissue thickness could be detected via a contact sensor 738 and could be used as one example characteristic in the inference of tissue type. As discussed above, different energy modalities may be advantageous for different tissue types and treatments. For example, ultrasonic energy may be well suited for treating smaller tissue 8410 (e.g., a small blood vessel). In particular, treatment with an ultrasonic blade may be appropriate for ultrasonic coagulation of a small vessel.

In contrast, RF energy may be more suitable for cauterization of larger tissue. To this end, as discussed above, the generator 1100 may deliver energy with higher voltage and lower current to drive an ultrasonic transducer, with lower voltage and higher current to drive RF electrodes for sealing tissue 8410, or with a coagulation waveform for spot coagulation using either monopolar or bipolar RF electrosurgical electrodes. In one aspect, the treatment tissue algorithm may specify the times during a surgical procedure that a particular energy modality is applied (e.g., RF versus ultrasonic). For example, the algorithm may define that a mixture of RF and ultrasonic energy are delivered during the sealing stage of the surgical procedure and only ultrasonic energy is delivered during the cutting stage. To this end, the generator 1100 may deliver ultrasonic and electrosurgical RF energy simultaneously from its output port to provide the desired output drive signal. The mixture of RF and ultrasonic could be applied simultaneously or substantially simultaneously as a blended energy modality or the generator 1100 could be configured to switch between delivering energy according to the RF and ultrasonic energy modalities (e.g., by switching between RF generator circuit 3902 and the ultrasonic generator circuit 3920 energy modalities). The treatment tissue algorithm may also specify the power at which the energy modalities are applied. For example, as discussed above, the waveform generator 904 and processor 902 of the generator 1100 are configured to generate signal waveforms of various amplitudes (the power parameter could be set by controlling the input of the power amplifier 1620 to set a particular waveform amplitude). The treatment tissue algorithm can also define how the amplitude, frequency and shape of the waveforms output by the generator 1100 changes over the course of the surgical procedure being performed.

The generator 1100 delivers 135010 energy to the tissue 8410 according to the desired tissue treatment algorithm. It may be possible to change the tissue treatment algorithm during performance of the surgical procedure, such as via manual input by the clinician or data transmitted by the corresponding hub 106, 206 or cloud 104, 204. Also, as discussed above, tissue compression force and energy delivered to the tissue 8410 can vary inversely. As such, in some situations when the amplitude of the waveform output by the generator 1100 increases, the compression force may be decreased. Similarly, when the amplitude decreases, the compression force may be increased. In other situations, the compression force may stay the same even as the amplitude changes. Similarly, the compression force may change even as the amplitude stays constant. The situationally aware surgical instrument 112 may determine the proportion of the first energy modality versus the second energy modality. For example, a clock generator (e.g., clock 3330) may produce a clock signal used to track the duration that RF waveforms are applied and the duration that ultrasonic waveforms are applied during a surgical operation. Accordingly, the control circuit 3900 calculates 135012 the proportion of the first energy modality to the second energy modality. The control circuit 3900 may calculate 135012 the proportion based on a time or duration of the respective waveforms/drive signals of the selected energy modalities are applied as well as a frequency or amplitude of the respective waveforms. The proportion of additional energy modalities (e.g., a third energy modality) may also be calculated 135012 if such additional modalities are used.

In one aspect, the compression force corresponding to one energy modality is relatively higher. That is, a range of compression force at which RF energy is applied may be greater than the range of compression force at which ultrasonic energy is applied. The proportion of energy modalities may be used to determine an appropriate level to set the pressure exerted by the end effector 8400. In other words, the proportion may be used to determine an appropriate tissue gap size of the end effector 8400 jaws. For some surgical instruments 112, the jaws of the end effector 8400 may be considered the clamp arm and the ultrasonic blade or waveguide. For the sake of clarity, clamp arm 716 is referenced in this portion although the clamp arm may be any clamp arm described in the present disclosure, including clamp arm 716, 766, 1140, 1142*a*, 1142*b*. Similarly, ultrasonic blade 718 is referenced in this portion of the present disclosure although the ultrasonic blade may be any ultrasonic blade described here, including ultrasonic blade 718, 768, 1128. When trigger such as trigger 4010 is actuated, the end effector 8400 closes such as tissue 8410 is clamped between the clamp arm 716 and ultrasonic blade 718. In one aspect, the first energy modality such as the ultrasonic energy modality corresponds to a higher level of compression force while the second energy modality such as the RF energy modality corresponds to a lower level of compression force. The processor or control circuit may adjust 135014 tissue compression based on the calculated 135012 proportion. For example, a surgical procedure in which more ultrasonic energy and less RF energy are delivered may result in an overall algorithmic adjustment to greater tissue compression force. Similarly, a procedure in which less ultrasonic energy and more RF energy are delivered may result in an overall algorithmic adjustment to lesser tissue compression force.

When ultrasonic energy and RF energy are delivered simultaneously or substantially simultaneously, the overall proportion of ultrasonic to RF energy may be used to determine the appropriate compression force. More generally, the proportion of selected energy modalities is useable by the control circuit 3900 to determine the adjustment. In one example, a lower proportion of ultrasonic to RF energy would correspond to a higher compression force compared to the compression force corresponding to a higher proportion. Also, the timing and power parameter of the delivered energy modalities during the surgical procedure may be considered for the adjustment 135014 by the control circuit 3900. For example, if relatively high power RF energy is delivered at the sealing stage, then this may result in a smaller increase or adjustment to compression force than compared to a situation in which relatively high power RF energy is delivered at the cutting stage. Moreover, the tissue compression force adjustment may be made for only a discrete portion of the surgical procedure being performed. The timing and duration of the compression force adjustment can be determined based on the calculated proportion, selected tissue treatment algorithm, and tissue type and characteristics, among other possible considerations. As discussed in further detail below, both mechanical and electrical methods are provided to adjust the tissue gap size and consequently the applied pressure/compression force. That is, the control circuit 3900 may use the disclosed mechanical or electrical methods to adjust the size of the gap defined between the clamp arm 716 and ultrasonic blade 718. Audible feedback could be provided in the trigger 4010, for example, to indicate that the applied compression force was adjusted. Also, the amount of the adjustment could be displayed in a display of the surgical instrument 112, based on the control circuit 3900 assessing the compression forces applied to the clamp arm 716. The logic flow diagram 135000 of FIG. 45 could also be performed by a control circuit or processor the generator 1100.

Figure 46:
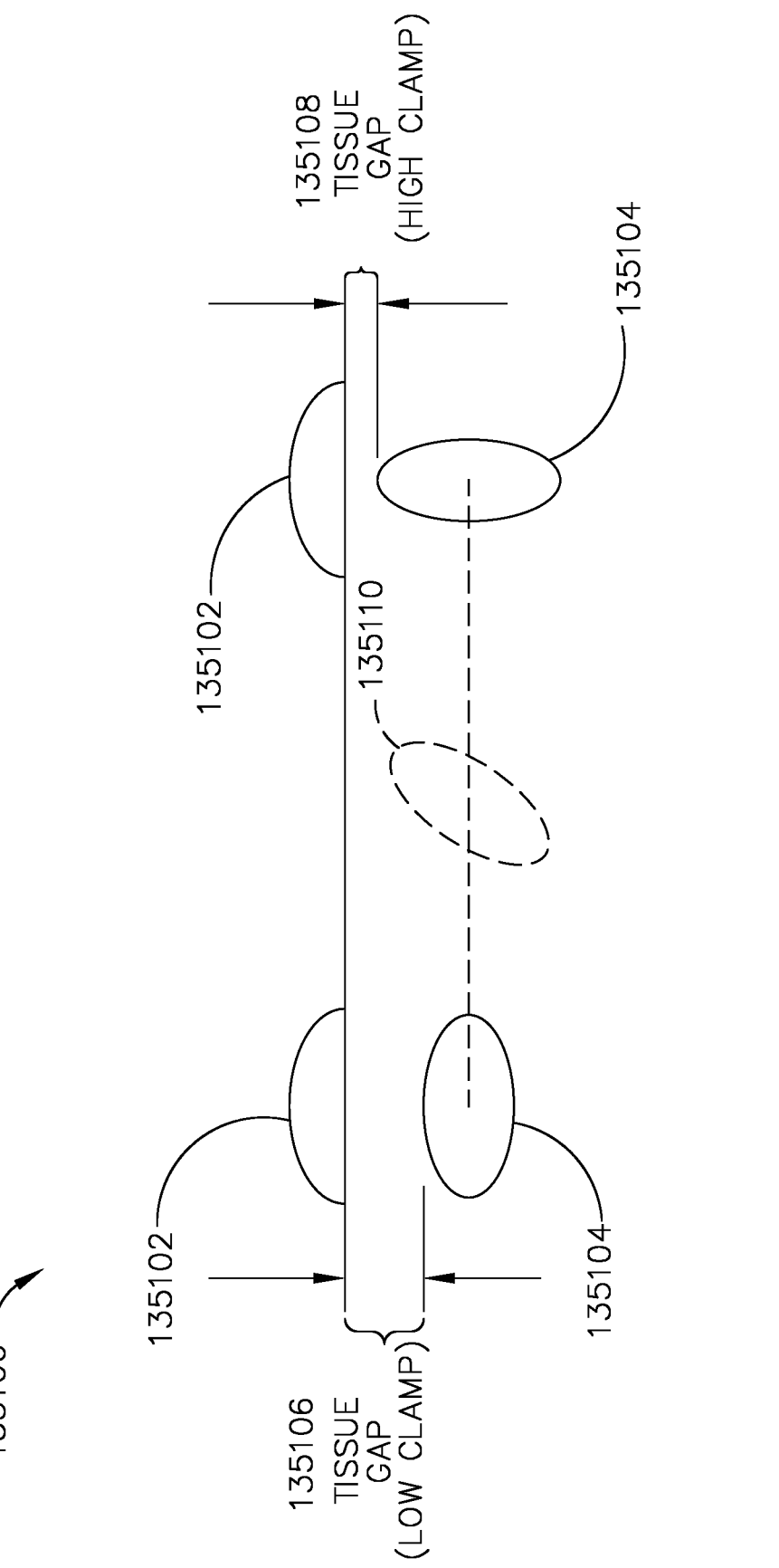
FIG. 46 illustrates a mechanical method of adjusting compression force applied by an end effector for different treatment types, in accordance with at least one aspect of the present disclosure.
Figures 47A, 47B:
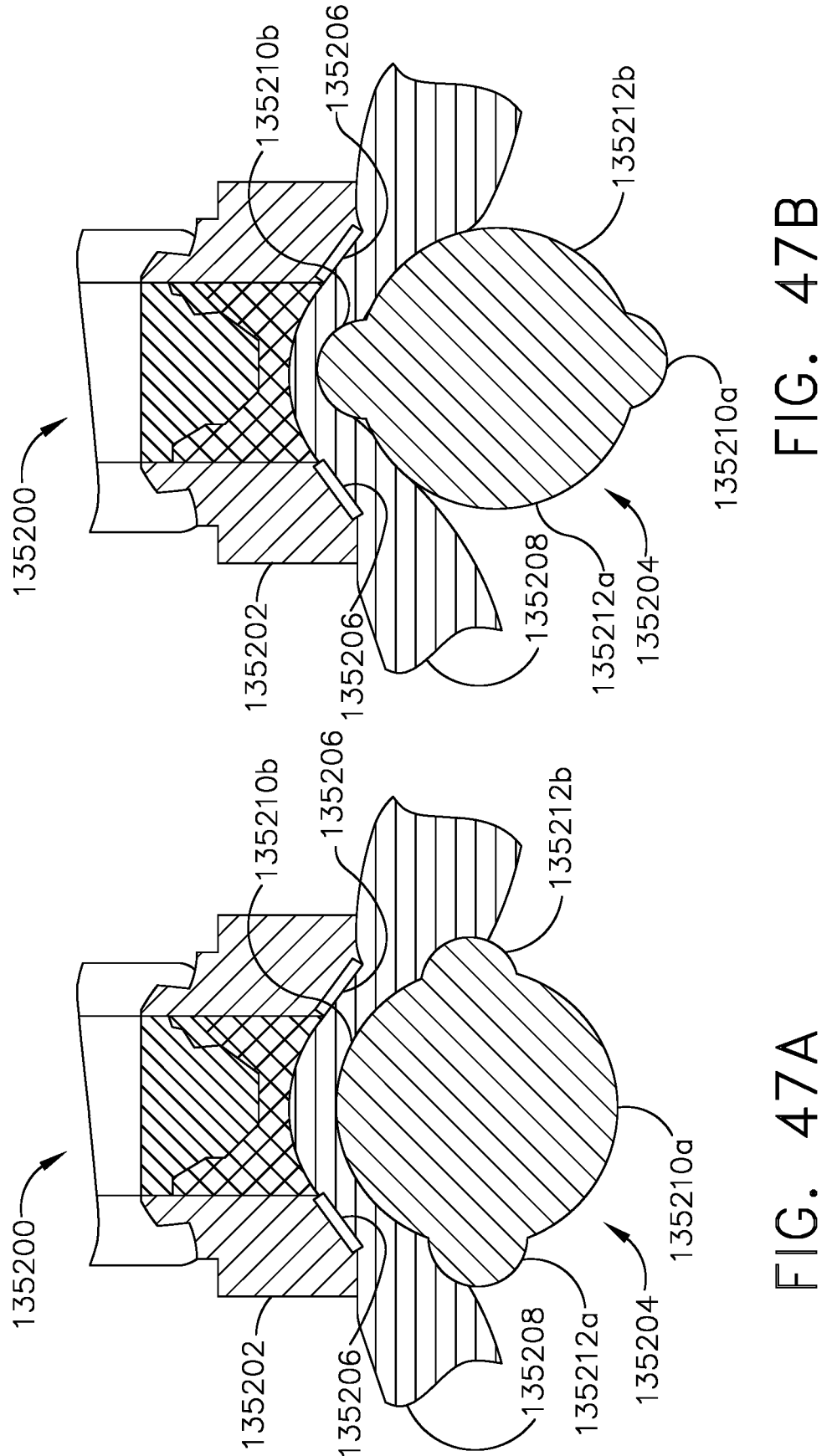
FIGS. 47A-47B illustrate a mechanical method of adjusting compression force applied by an end effector for different treatment types, by rotating an ultrasonic blade, in accordance with at least one aspect of the present disclosure.

FIG. 46 illustrates a mechanical method of adjusting compression force applied by an end effector 135100 for different treatment types, according to one aspect of the present disclosure. End effector 135100 of the surgical instrument 112 is the same as or similar to other end effectors described above, such as end effector 702, 752, 792, 1122, 8400. Accordingly, end effector 135100 may comprise two jaw members. In various aspects, the jaw members are a clamp arm 135102 and a waveguide or blade 135104. The clamp arm 135102, which is the same or similar to clamp arm 716, 766, 1140, 1142*a*, 1142*b*, and the blade 135104, which is the same or similar to ultrasonic blade 718, 768, 1128, can be configured to rotate. For example, as shown in FIG. 46-47B, the ultrasonic blade 135104 is rotatable three hundred and sixty degrees. Additionally or alternatively, the clamp arm 135102 is also rotatable three hundred and sixty degrees. In this way, as illustrated in FIG. 46, the ultrasonic blade 135104 can be transitioned between a horizontal or landscape orientation to a vertical or portrait orientation, including intermediate positions, which may be in between the horizontal and vertical orientations or may exceed ninety degrees.

Stated differently, the ultrasonic blade 135104 has a zero degree orientation corresponding to a horizontal orientation and a ninety degree orientation corresponding to a vertical orientation. With the clamp arm 135102 held in a constant or substantially constant position (shown in FIG. 46), the ultrasonic blade 135104 is rotatable to define a spectrum of clamp pressure. An opposite configuration is also possible such that the ultrasonic blade 135104 is the constant jaw member rather than the clamp arm 135102. In one aspect, as the ultrasonic blade 135104 rotates from zero degrees to ninety degrees, the tissue compression force increases from a low force to a high force. The tissue gap resulting from the zero degree orientation may be called low clamp 135106 while the tissue gap resulting from ninety degrees orientation may be called high clamp 135108. Various orientations of ultrasonic blade 135104 correspond to the same level of compression pressure. For example, zero degrees and one hundred and eighty degrees both correspond to low clamp 135106. FIG. 46 depicts the low clamp 135106, high clamp 135108, and a third orientation 135110. The third orientation 135110 depicted in FIG. 46 is slightly greater than ninety degrees, such as a one hundred and twenty degree orientation. Consequently, this third orientation 135110 defines a tissue gap size that is slightly smaller than the tissue gap corresponding to high clamp 135108.

In the horizontal orientation (low clamp) 135106, the ultrasonic blade 135104 may be configured for tissue sealing (e.g., coagulation or cauterization). In the vertical orientation (high clamp) 135108, the ultrasonic blade 135104 may be configured for tissue cutting or dissection. As discussed above, the RF energy modality may generally correspond to a greater tissue compression force. Accordingly, in one aspect, the horizontal orientation 135106 corresponds to the ultrasonic energy modality while the vertical orientation 135108 corresponds to the RF energy modality. Other intermediate positions, including third orientation 135110, may be used as appropriate during the surgical operation. For example, an RF waveform of relatively high power and an intermediate orientation such as 60 degrees may be used when surgical treatment initially commences. Furthermore, the ultrasonic blade 135104 orientation may change throughout a performed surgical procedure according to the selected 135008 tissue treatment algorithm, for example. In another aspect, the ultrasonic blade 135104 may be an oval shape and offset relative to the clamp arm 135102.

Other mechanical methods of adjusting compression force are disclosed. For example, the clamp arm 135102 or ultrasonic blade 135104 may be moveable such that the end effector 135100 is configurable between a closed configuration, an open configuration, and intermediate positions in between to define various clamp pressures. In one aspect, a mechanical switch such as a momentary-action manual switch, mechanical-bail switch, capacitive touch switch, membrane switch, or other suitable mechanical switch of the surgical instrument 112 can transition between two positions. The control circuit 3900 may control operation of the mechanical switch. The first and second positions may correspond to a first and second compression force level, which in turn may correspond to a first and second energy modality, respectively. Thus, for example, in the first position, the mechanical switch could cause an adjustment to the stroke or longitudinal movement of an actuator rod. The actuator rod may refer to a suitable end effector 135100 actuation mechanism, such as the linkage components of transmissions 706a-706e to couple motors 704a-704e.

In particular, the actuator rod may comprise linkage elements similar to or the same as transmissions 706a-706e used to transmit mechanical energy from the motors 704a-704b to actuate or close closure member 714 and clamp arm 716, respectfully. The actuation stroke of the actuator rod could be adjusted by the control circuit 3900 to achieve the different compression forces of the end effector 1351000.

With the adjustment caused by the first position of the mechanical switch, actuation of the actuator rod may result in a clamp arm 135102 orientation corresponding to a relatively large tissue gap. Conversely, in the second position, the mechanical switch could cause a different adjustment such that actuation of the actuator rod may result in a clamp arm 135102 orientation corresponding to a relatively small tissue gap. The first position could correspond to the delivery of energy according to the ultrasonic modality while the second position could correspond to the delivery of energy according to the RF modality. In one aspect, by shifting between the first and second position, the mechanical switch shifts the pivotal linkage or coupling between the actuator rod and the clamp arm 135102. In this way, the control circuit 3900 can control the mechanical switch to implement adjustments to actuator stroke which in turn results in various clamp arm 135102 configurations (between and including open and closed configurations) that correspond to different tissue compression forces. Other suitable mechanical means of adjusting the actuator stroke or clamp arm configuration are also possible.

FIGS. 47A-47B illustrate a mechanical method of adjusting compression force applied by an end effector 135200 for different treatment types, by rotating an ultrasonic blade 135204, according to aspects of the present disclosure. End effector 135200 and ultrasonic blade 135204 are the same as or similar to end effector 135100 and ultrasonic blade 135104, respectively. The ultrasonic blade 135204 is rotatable between a vertical and a horizontal configuration, as shown in FIGS. 47A-47B. In one aspect, the end effector 135200 comprises a jaw member 135202 (e.g., clamp arm 135102, 716), flexible circuit 135206 and the ultrasonic blade 135204. Additionally or alternatively, the jaw member 135202 may be rotatable as well. FIG. 47A depicts tissue 135208 located between the jaw member 135202 and the ultrasonic blade 135204. In the horizontal orientation shown, the ultrasonic blade 135204 is at or substantially at a zero degree orientation. Accordingly, relatively low compression force is applied to the tissue 135208. In one aspect, the ultrasonic blade 135204 is configured for tissue sealing (e.g., cauterization) in the horizontal orientation. The ultrasonic blade 135204 also comprises side lobe sections 135210a, 135210b to enhance tissue dissection and uniform sections 135212a, 135212b to enhance tissue sealing. As discussed above, the control circuit 3900 may control rotation of the jaw member 135202 or ultrasonic blade 135204.

FIG. 47B depicts the vertical orientation in which the ultrasonic blade 135204 is at or substantially at a ninety degree orientation. In another aspect, the ultrasonic blade 135204 is configured for tissue dissection in the vertical orientation. The flexible circuit 135206 may include electrodes such that when a RF energy modality is selected, the electrodes are configured to deliver high-frequency RF current to the tissue 135208. The electrodes may be the same or similar to electrodes described in the present disclosure, such as electrodes 796, 3074a, 3074b, 3906a, 3906b. Lower-frequency RF current is also possible. When the RF energy modality is selected, the ultrasonic blade 135204 may act as the electrical ground for the RF waveform output from the generator 1100. That is, the RF electrodes (e.g., RF electrodes 796) could be coupled to the positive pole while the ultrasonic blade 135204 is coupled to the negative or return pole. In some configurations, the polarity may be reversed such that the RF electrodes 796 are coupled to the negative pole and the ultrasonic blade 135204 is coupled to the positive pole. In one aspect, when both the RF and ultrasonic energy modalities are selected, the RF current conducted by the electrodes 796 is used to seal the tissue 135208 and the ultrasonic blade 135204 is used to dissect tissue based on ultrasonic vibrations propagating through ultrasonic blade 135204. As discussed above with respect to FIG. 40, other intermediate orientations of the rotatable ultrasonic blade 135204 may also be possible, so that additional levels of different compression forces may be adjusted and applied to tissue 135208 as appropriate.

Electrical methods of adjusting compression force between treatment types are also disclosed. For example, a suitable EAP may be used as an electrostatic actuator for changing tissue gap size. EAPs are voltage activated elastomers which can be electronic EAPs such as electrostrictive elastomers and dielectric electroactive polymers (DEAPs) or ionic EAPs such as ionic polymer metal composites (IP-MCs). EAPs have an electromechanical thickness or other strain that is induced by electrostatic forces. Stated differently, when a voltage is applied to an EAP, the EAP bends, contracts, or expands. An EAP actuator may be used in the surgical instrument 112 to change the tissue gap size for changing the applied compression forces based on application of a voltage potential to the EAP. The EAP actuator may be controlled by the control circuit 3900. For example, the EAP may be configured to expand, which causes the application of more pressure on the blade 135204 or electrodes 796 positioned in the end effector 135200. To this end, the EAP may be positioned in the end effector 135200 between the power source (e.g., generator) and RF electrodes 796. For example, the EAP could be part of the flexible circuit 135206. In this way, as an RF waveform is output from the generator 1100, voltage is applied to the EAP, which causes the EAP to expand and apply a force on the RF electrodes such that the tissue gap size decreases. In general, the EAP may expand as the generator 1100 delivers energy according to the selected energy modalities.

Additionally or alternatively, when the EAP expands, this causes a force to be applied to the blade 135200 such that the tissue gap size decreases. Conversely, the EAP may be positioned and configured such that electrostatic actuation causes the EAP to contract, which reduces the compression force applied to the tissue. The change in the size of the EAP may be proportional to the voltage used for EAP actuation and the adjustment to compression force that results. In one aspect, the EAP may also be positioned in the shaft of the surgical instrument 112, for example, such that electrostatic actuation causes the EAP to exert further force on the clamp arm 135102 or the end effector 135200. Similarly, the EAP could be configured to remove or reduce force applied by the clamp arm 135102. In this way, the EAP actuator may be employed to change the end effector configuration, which spans between the open and closed configurations. In general, the EAP could be provided such that the control circuit 3900 can increase compression force as a greater proportion of energy is delivered according to the RF energy modality. Similarly, the EAP could be used to adjust pressure as another energy modality such as the ultrasonic energy modality is selected. The EAP could be part of the flexible circuit 135206, for example.

In general, the end effector 135200 of the surgical instrument 112 may comprise an ultrasonic blade 135200 and a clamp arm 135102, which may function as the first and second jaws of the end effector 135200. The end effector 135200 is configured to clamp tissue therebetween the jaws, fire fasteners through the clamped tissue 135208, sever the clamped tissue 135208, and grasp tissue 135208 for application of energy according to the selected energy modality. Moreover, the force applied to the tissue 135208 by the end effector 135200 may be measured by the strain gauge sensor 474, such as by measuring the amplitude or magnitude of the strain exerted on a jaw member of the end effector 135200 during a clamping operation. As discussed above, energy may be delivered according to multiple energy modalities such as RF and ultrasonic energy, in conjunction to achieve surgical sealing, cutting, and coagulation functions. Although energy from the generator 1100 could be delivered simultaneously such as through simultaneously delivering or outputting waveforms from the generator 1100 to the RF electrodes 796 and the ultrasonic transducer 1120 in conjunction, such energy delivery can also switch between different energy modalities.

Figure 48:
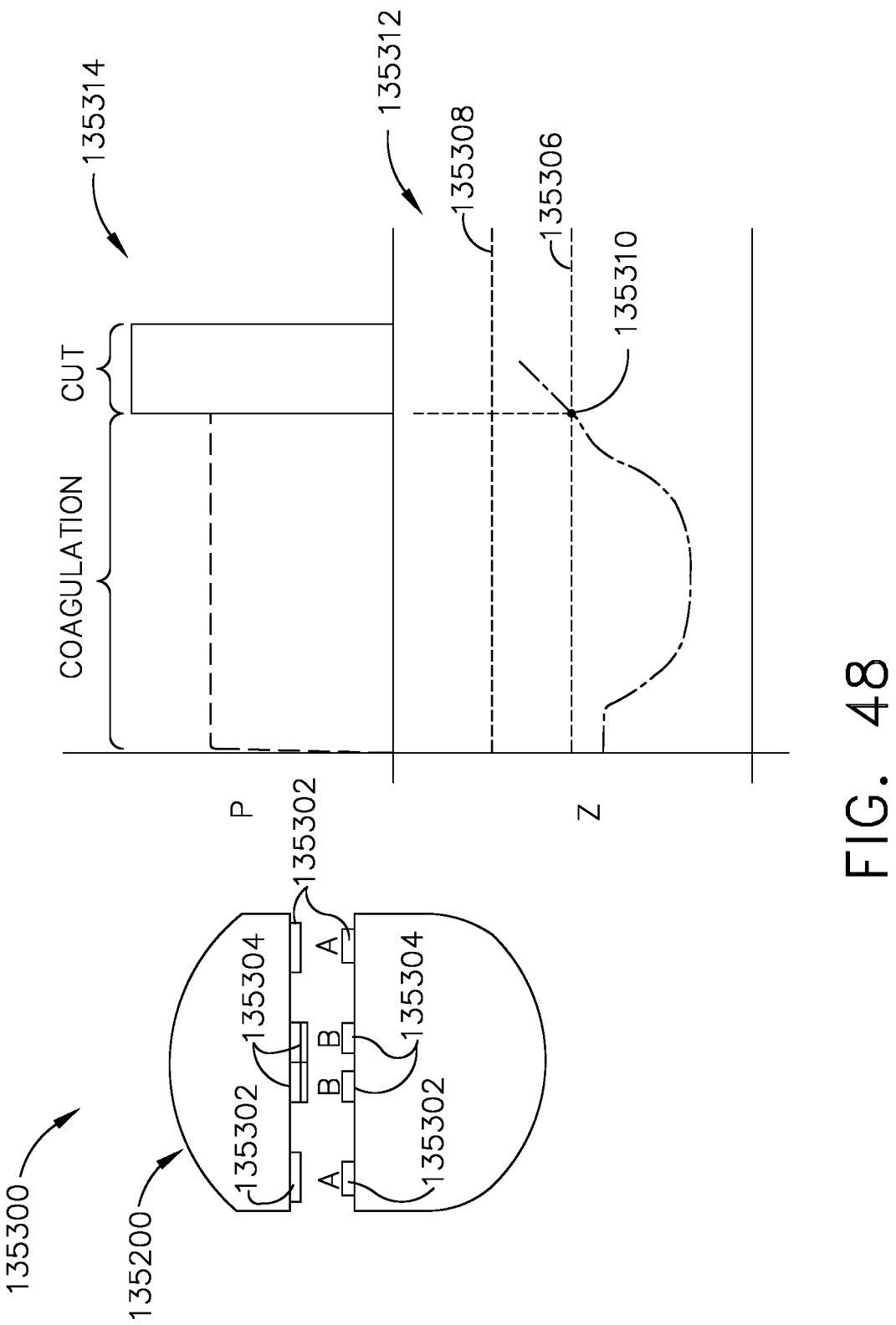
FIG. 48 shows a diagram illustrating switching between active electrodes of an end effector, in accordance with at least one aspect of the present disclosure.

FIG. 48 shows a diagram 135300 illustrating switching between active electrodes of an end effector 135200 according to one aspect of the present disclosure. Again, the electrodes may be the same or similar to electrodes 796, 3074a, 3074b, 3906a, 3906b. As discussed above, the situationally aware surgical instrument 112 may infer or determine an appropriate tissue treatment algorithm for the surgical procedure being performed. The tissue compression force adjustment is made based on this algorithm and the proportion of selected energy modalities. In addition, the tissue compression force adjustment may be made based on switching from a passive electrode to an active electrode for treatment, as shown in FIG. 48. For example, the situationally aware surgical instrument 112 may detect a selected function of the surgical instrument 112 such as sealing or cutting. Based on the selected function, a switch, filter, or other suitable wiring such as a relay or transistor may be provided to control routing the waveform (e.g., waveform 4300) output by the generator 1100 to an appropriate electrode. FIG. 49 depicts the end effector 135200 with a first set of two treatment electrodes "A" 135302 and a second set of two treatment electrodes "B" 135304, both of which may alternate between active or passive states. The two sets of treatment electrodes 135302, 135304 are provided on both jaws of the end effector 135200. Based on which treatment electrode is active or passive, the applied compression force may be adjusted.

In one aspect, the "A" electrodes 135302 are configured for the sealing stage and the "B" electrodes 135304 are configured for the cutting stage. These configurations could be used by the surgical instrument 112 to determine if and what compression force adjustment is required when an energy modality is selected. For example, when the "A" electrodes 135302 become passive while the "B" electrodes 135304 become active, the surgical instrument 112 may adjust the compression force. This could be an adjustment to decrease the compression force, such as because the additional power delivered during the cutting stage might not require as much corresponding compression force. The extent of the adjustment can depend on the proportion of one energy modality (e.g., RF) to another (e.g., ultrasonic) as calculated throughout the duration of the performed surgical operation. In one aspect, the switch is configured to route the output energy by the generator 1100 to the sealing electrodes "A" 135302 while the surgical instrument 112 is used for coagulation. Multiple impedance thresholds 135306, 135308 may be provided, which are indicated on the impedance graph (Z) 135312 in FIG. 48 as dotted lines. FIG. 48 shows that when threshold 135306 is crossed at point 135310, the crossing may indicate when optimal tissue coagulation is complete. That is, when the measured tissue impedance reaches point 135310, it may be determined that a sufficiently secure tissue seal has formed.

As discussed above, impedance may be measured by dividing the output of the voltage sensing circuit and the current sensing circuit or by using spectral analysis, for example. When coagulation is complete, the switch may transition to a second position to route a different waveform from the generator 1100, in which the amplitude of the different waveform is raised relative to the waveform used for coagulation. The different waveform may be applied for surgical cutting rather than for coagulation. Accordingly, the switch may route this different waveform to the "B" electrodes 135304. As can be seen in the power graph 135314 of FIG. 48, the amplitude of the waveform is greater than the amplitude of the coagulation waveform. Although the power levels shown in power graph 135314 are constant, dynamic power levels may be used as well. As discussed above, the increase in power from "A" electrodes 135302 to "B" electrodes 135304 may trigger an adjustment to tissue compression, which may be determined based on the proportion of one selected energy modality to another. In another aspect, the surgical cutting achieved via the "B" electrodes 135304 is a knifeless cutting. Although the energy modality selected for the tissue treatment illustrated in FIG. 49 may be RF, other energy modalities may be used for such treatment and over the course of a performed surgical operation.

Situational Awareness

Referring now to FIG. 49, a timeline 5200 depicting situational awareness of a hub, such as the surgical hub 106 or 206, for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step S202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step S204, the staff members scan the incoming medical supplies for the procedure. The surgical hub 106,

206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step S206, the medical personnel scan the patient band via a scanner that is communicably connected to the surgical hub 106, 206. The surgical hub 106, 206 can then confirm the patient's identity based on the scanned data.

Fourth step S208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step S210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step S212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step S212, the pre-operative portion of the lung segmentectomy procedure is completed and the operative portion begins.

Seventh step S214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step S216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step S218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step S220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step S222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step S224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step S224, the incisions are closed up and the post-operative portion of the procedure begins.

Thirteenth step S226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step S228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/611,341, titled INTERACTIVE SURGICAL PLATFORM, filed Dec. 28, 2017, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 102.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP).

The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect.

Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein under the heading "ADJUSTMENT OF COMPRESSION FORCE APPLIED TO TISSUE BASED ON PROPORTION OF ENERGY MODALITIES" are set out in the following examples:

Example 1. A method of adjusting a compression force applied by a surgical instrument, wherein the surgical instrument comprises an end effector and a clamp arm configured to receive energy modalities from a generator configured to deliver a plurality of energy modalities to the surgical instrument. The method comprises determining, by a control circuit, tissue impedance of tissue in contact with an end effector of the surgical instrument; determining, by the control circuit, a tissue type based on the tissue impedance; selecting, by the control circuit, a first energy modality of the plurality of energy modalities to deliver to the surgical instrument; generating, by the control circuit, a first signal waveform based on the first energy modality; selecting, by the control circuit, a second energy modality of the plurality of energy modalities to deliver to the surgical instrument; generating, by the control circuit, a second signal waveform based on the second energy modality; outputting, by the generator, the first and second signal waveform to deliver energy to the end effector; and adjusting, by the control circuit, a compression force applied by the end effector by changing a size of a gap between the tissue and the clamp arm based on a proportion of the first signal waveform to the second signal waveform.

Example 2. The method of Example 1, wherein the first energy modality is a radio frequency (RF) energy modality and the second energy modality is an ultrasonic energy modality.

Example 3. The method of Example 1 or 2, wherein determining the tissue impedance comprises: applying, by the generator, a non-therapeutic electrical signal to the end effector over a range of frequencies; and determining, by the control circuit, an impedance characteristic pattern based on spectral analysis of the non-therapeutic electrical signal.

Example 4. The method of any one of Examples 1-3, wherein the proportion is determined by the control circuit based on a time that each of the first and second signal waveform is applied during a surgical treatment cycle or amplitude of each of the first and second signal waveform or a combination thereof.

Example 5. The method of any one of Examples 1-4, wherein adjusting the compression force comprises actuating a mechanical switch coupled to the clamp arm, wherein a first position of the mechanical switch corresponds to a first actuation of the clamp arm resulting in high compression force, and wherein a second position of the mechanical switch corresponds to a second actuation of the clamp arm resulting in low compression force.

Example 6. The method of any one of Examples 1-5, wherein adjusting the compression force comprises expanding an electroactive polymer coupled to the clamp arm, and wherein expanding the electroactive polymer based on applying the first and second signal waveform to the end effector.

Example 7. A surgical instrument comprises a control circuit. The control circuit is configured to communicatively couple to a generator configured to deliver a plurality of energy modalities to an end effector of the surgical instrument, wherein the control circuit is further configured to: determine tissue impedance of tissue in contact with an end effector of the surgical instrument; determine a tissue type of based on the tissue impedance; select a first energy modality of the plurality of energy modalities; generate a first signal waveform based on the first energy modality; select a second energy modality of the plurality of energy modalities; generate a second signal waveform based on the second energy modality; and adjust a compression force applied by an end effector to tissue by changing a gap between tissue and an end effector based on a proportion of the first signal waveform to the second signal waveform.

Example 8. The surgical instrument of Example 7, further comprising an end effector coupled to the control circuit, wherein the end effector comprises a clamp arm and an ultrasonic blade.

Example 9. The surgical instrument of Example 7 or 8, further comprising a generator coupled to the control circuit.

Example 10. The surgical instrument of any one of Examples 7-10, wherein the control circuit determines proportion based on a time that each of the first and second signal waveform are applied during a surgical treatment cycle or amplitude of each of the first and second signal waveform or a combination thereof.

Example 11. The surgical instrument of any one of Examples 7-10, wherein the control circuit adjusts the compression force based on actuating a mechanical switch coupled to the clamp arm, wherein a first position of the mechanical switch corresponds to a first actuation of the clamp arm resulting in high compression force, and wherein a second position of the mechanical switch corresponds to a second actuation of the clamp arm resulting in low compression force.

Example 12. The surgical instrument of any one of Examples 7-11, wherein the control circuit adjusts the compression force based on expansion of an electroactive polymer coupled to the clamp arm, and wherein the electroactive polymer expands based on applying the first and second signal waveform to the end effector.

Example 13. A surgical system comprises a surgical hub configured to receive a tissue treatment algorithm transmitted from a cloud computing system, wherein the surgical hub is communicatively coupled to the cloud computing system; and a surgical instrument communicatively coupled to the surgical hub, wherein the surgical instrument comprises: an end effector comprising: a clamp arm; and a ultrasonic blade; a generator configured to deliver a plurality of energy modalities to the end effector; a control circuit communicatively coupled to the end effector and the generator, wherein the control circuit is configured to treat tissue, and wherein the control circuit is configured to: determine tissue impedance of tissue in contact with the end effector; determine tissue type based on the tissue impedance; select a first energy modality of the plurality of energy modalities; generate a first signal waveform based on the first energy modality; select a second energy modality of the plurality of energy modalities; generate a second signal waveform based on the second energy modality; apply the first and second signal waveform to the end effector; and adjust a compression force applied by the end effector by changing a size of a gap between the tissue and the waveguide based on a proportion of the first signal waveform to the second signal waveform.

Example 14. The surgical instrument of Example 13, wherein the first energy modality is a radio frequency (RF) energy modality and the second energy modality is an ultrasonic energy modality.

Example 15. The surgical instrument of Example 13 or 14, wherein to determine the tissue impedance, the control circuit is configured: apply a non-therapeutic electrical signal to the end effector over a range of frequencies; and determine an impedance characteristic pattern based on spectral analysis of the non-therapeutic electrical signal.

Example 16. The surgical instrument of any one of Examples 13-15, wherein the control circuit determines the proportion based on a time that each of the first and second signal waveform are applied during a surgical treatment cycle or an amplitude of each of the first and second signal waveform or a combination thereof.

Example 17. The surgical instrument of any one of Examples 13-16, wherein to adjust the compression force, the control circuit is configured to actuate a mechanical switch coupled to the clamp arm, wherein a first position of the mechanical switch corresponds to a first actuation of the clamp arm resulting in high compression force, and wherein a second position of the mechanical switch corresponds to a second actuation of the clamp arm resulting in low compression force.

Example 18. The surgical instrument of any one of Examples 13-17, wherein to adjust the compression force, the control circuit is configured to expand an electroactive polymer coupled to the clamp arm, and to expand the electroactive polymer based on the first and second signal waveforms applied to the end effector.

Example 19. The surgical instrument of any one of Examples 14-18, wherein the RF energy modality corresponds to a first range of compression force and the ultrasonic energy modality to a second range of compression force, and wherein the first range of compression force is greater than the second range of compression force.

Example 20. The surgical instrument of any one of Examples 13-19, wherein the surgical instrument comprises a passive electrode and an active electrode.

The invention claimed is:

1. A surgical system, comprising:
one or more modular devices; and
a surgical hub configured to serve as a central connection for a surgical operating theater, wherein the one or more modular devices are operably coupled to the surgical hub, wherein the surgical hub comprises a processor and a memory communicatively coupled to the processor, and wherein the memory stores instructions executable by the processor to:
receive data from data sources;
infer a type of surgical procedure to be performed based on the received data;
receive additional data from one or more of the data sources or additional data sources;
continuously infer a current step of the surgical procedure throughout the surgical procedure as the additional data is received; and
adjust the one or more modular devices based on the current step of the surgical procedure.

2. The surgical system of claim 1, further comprising a plurality of auxiliary equipment, and wherein the received data comprises which equipment of the plurality of auxiliary equipment has been activated.

3. The surgical system of claim 1, wherein the memory further stores instructions executable by the processor to retrieve steps associated with the type of surgical procedure from a memory.

4. The surgical system of claim 3, wherein the received data comprises data from medical devices in the surgical operating theater.

5. The surgical system of claim 3, wherein the memory further stores instructions executable by the processor to record data pertaining to the surgical procedure being performed.

6. The surgical system of claim 1, wherein the surgical system further comprises a monitoring device, wherein the received data comprises data from the monitoring device, and wherein the memory further stores instructions executable by the processor to infer a location of a patient relative to the surgical operating theater based on the received data.

7. The surgical system of claim 1, wherein the one or more modular devices are mounted to a robotic arm of a robotic surgical system.

8. The surgical system of claim 1, wherein the memory further stores instructions executable by the processor to adjust the one or more modular devices by adjusting a field of view of one or more modular devices.

9. The surgical system of claim 1, wherein the one or more modular devices further comprise an electrosurgical instrument, and wherein the memory further stores instructions executable by the processor to adjust the one or more modular devices by adjusting an energy level of the electrosurgical instrument.

10. The surgical system of claim 1, wherein the one or more modular devices comprise a handheld surgical instrument.

11. The surgical system of claim 1, wherein the one or more modular devices comprise a surgical stapler, wherein the received additional data comprises data associated with a type of staple cartridge being utilized by the surgical stapler, and wherein the memory further stores instructions executable by the processor to infer a type of tissue being stapled based on the received additional data.

12. The surgical system of claim 1, wherein the received data comprises scanned medical supplies.

13. A surgical system, comprising:
one or more surgical instruments; and
a surgical hub operable coupled to the one or more surgical instruments, wherein the surgical hub is configured to serve as a central connection for a surgical operating theater, and wherein the surgical hub comprises a processor and a memory communicatively coupled to the processor, and wherein the memory stores instructions executable by the processor to:

receive data from data sources within the surgical operating theater;

infer a type of surgical procedure to be performed based on the received data;

receive additional data from one or more of the data sources or additional data sources;

continuously infer a current step of the surgical procedure throughout the surgical procedure as the additional data is received; and adjust the one or more surgical instruments based on the current step of the surgical procedure.

14. The surgical system of claim 13, wherein the one or more surgical instruments comprise an electrosurgical instrument, and wherein the memory further stores instructions executable by the processor to adjust the one or more surgical instruments by adjusting an energy level of the electrosurgical instrument.

15. A surgical hub configured to serve as a central connection for a surgical operating theater, wherein the surgical hub comprises a processor and a memory communicatively coupled to the processor, and wherein the memory stores instructions executable by the processor to:

receive data from data sources within the surgical operating theater;

infer a type of surgical procedure to be performed based on the received data;

receive additional data from one or more of the data sources or additional data sources;

continuously infer a current step of the surgical procedure throughout the surgical procedure as the additional data is received; and adjust one or more modular devices operably coupled to the surgical hub based on the current step of the surgical procedure.

16. The surgical hub of claim 15, wherein the received data comprises data associated with which equipment of a plurality of auxiliary equipment has been activated.

17. The surgical hub of claim 15, wherein the memory further stores instructions executable by the processor to retrieve steps associated with the type of surgical procedure from a memory.

18. The surgical hub of claim 15, wherein the memory further stores instructions executable by the processor to retrieve steps associated with the type of surgical procedure from a cloud-based system.

19. The surgical hub of claim 15, wherein the one or more modular devices comprise an electrosurgical instrument, and wherein the memory further stores instructions executable by the processor to adjust the one or more modular devices by adjusting an energy level of the electrosurgical instrument.

* * * * *